United States Patent
Kim et al.

(10) Patent No.: US 12,157,724 B2
(45) Date of Patent: Dec. 3, 2024

(54) COMPOUND AND ORGANIC LIGHT EMITTING DEVICE COMPRISING THE SAME

(71) Applicant: LG CHEM, LTD., Seoul (KR)

(72) Inventors: Young Seok Kim, Daejeon (KR); Kongkyeom Kim, Daejeon (KR); Ki Dong Koo, Daejeon (KR); Joongsuk Oh, Daejeon (KR); Mina Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 989 days.

(21) Appl. No.: 17/050,328

(22) PCT Filed: Sep. 4, 2019

(86) PCT No.: PCT/KR2019/011397
§ 371 (c)(1),
(2) Date: Oct. 23, 2020

(87) PCT Pub. No.: WO2020/050623
PCT Pub. Date: Mar. 12, 2020

(65) Prior Publication Data
US 2021/0130295 A1    May 6, 2021

(30) Foreign Application Priority Data
Sep. 4, 2018 (KR) .................. 10-2018-0105513

(51) Int. Cl.
*H01L 51/50* (2006.01)
*C07C 211/61* (2006.01)
(Continued)

(52) U.S. Cl.
CPC .......... *C07D 209/86* (2013.01); *C07C 211/61* (2013.01); *C07D 307/79* (2013.01);
(Continued)

(58) Field of Classification Search
None
See application file for complete search history.

(56) References Cited

U.S. PATENT DOCUMENTS

| 7,274,141 B2 | 9/2007 | Leo et al. |
| 2016/0072064 A1 | 3/2016 | Tada et al. |

(Continued)

FOREIGN PATENT DOCUMENTS

| CN | 110467536 | 11/2009 |
| CN | 105190930 A | 12/2015 |

(Continued)

OTHER PUBLICATIONS

Shu et al., Synthesis and characterization of spiro(adamantane-2,9-fluorene)-based triaryldiamines: thermally stable hole-transporting materials; 2004, Synthetic Metals 143 (2004) 215-220 (Year: 2004).*

(Continued)

*Primary Examiner* — Gregory D Clark
(74) *Attorney, Agent, or Firm* — Bryan Cave Leighton Paisner LLP

(57) ABSTRACT

A compound of Chemical Formula 1, and an organic light emitting device comprising the same.

[Chemical Formula 1]

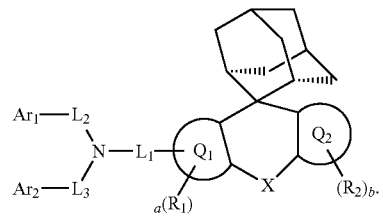

9 Claims, 1 Drawing Sheet

(51) Int. Cl.
    *C07D 209/86*     (2006.01)
    *C07D 307/79*     (2006.01)
    *C07D 333/54*     (2006.01)
    *H10K 85/60*      (2023.01)

(52) U.S. Cl.
    CPC ......... *C07D 333/54* (2013.01); *H10K 85/633* (2023.02); *H10K 85/6572* (2023.02); *H10K 85/6574* (2023.02); *H10K 85/6576* (2023.02)

(56) References Cited

U.S. PATENT DOCUMENTS

| | | | |
|---|---|---|---|
| 2016/0372678 A1 | 12/2016 | Arai et al. | |
| 2019/0016666 A1 | 1/2019 | Jeong et al. | |
| 2020/0395544 A1* | 12/2020 | Ma ...................... | C07D 405/12 |

FOREIGN PATENT DOCUMENTS

| | | | | |
|---|---|---|---|---|
| CN | 107459466 A | | 12/2017 | |
| CN | 110128279 A | | 8/2019 | |
| KR | 1020000051826 A | | 8/2000 | |
| KR | 1020080071723 A | | 8/2008 | |
| KR | 1020150139969 A | | 12/2015 | |
| KR | 1020160032020 A | | 3/2016 | |
| KR | 1020170080432 A | | 7/2017 | |
| KR | 107459466 A | * | 12/2017 | ............ H01L 51/54 |
| KR | 1020170136980 A | | 12/2017 | |
| KR | 1020180078177 A | | 7/2018 | |
| KR | 1020180082710 A | | 7/2018 | |
| WO | 2003012890 A2 | | 8/2003 | |

OTHER PUBLICATIONS

International Search Report from PCT/KR2019/011397, dated Dec. 20, 2019.
Written Opinion of the ISA from PCT/KR2019/011397, dated Dec. 20, 2019.
Chen, C.-H. et al., "Synthesis and characterization of spiro (adamantane-2, 9'-fluorene)-based triaryldiamines: thermally stable hole-transporting materials", Synthetic metals, 2004, vol. 143-2, pp. 215-220.

* cited by examiner

【FIG. 1】
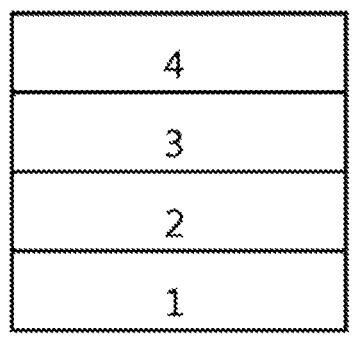
【FIG. 2】
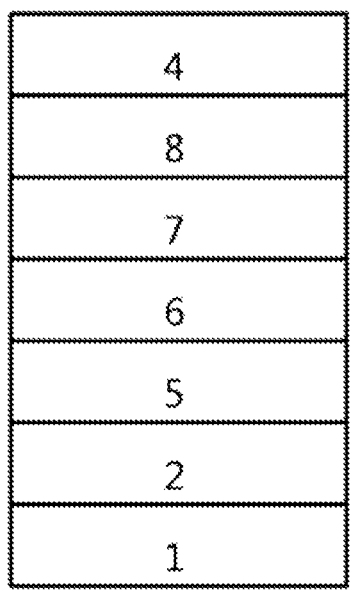

COMPOUND AND ORGANIC LIGHT EMITTING DEVICE COMPRISING THE SAME

CROSS-REFERENCE TO RELATED APPLICATION(S)

This application is the National Stage of International Application No. PCT/KR2019/011397, filed on Sep. 4, 2019, which claims the benefit of Korean Patent Application No. 10-2018-0105513 filed on Sep. 4, 2018 with the Korean Intellectual Property Office, the disclosures of which are incorporated herein by reference in its entirety.

FIELD OF THE INVENTION

The present disclosure relates to a novel compound and an organic light emitting device comprising the same.

BACKGROUND OF THE INVENTION

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

(Patent Literature 0001) Korean Unexamined Patent Publication No. 10-2000-0051826

SUMMARY OF THE INVENTION

Technical Problem

It is an object of the present disclosure to provide a novel compound and an organic light emitting device comprising the same.

Technical Solution

According to an aspect of the present disclosure, there is provided a compound of the following Chemical Formula 1:

[Chemical Formula 1]

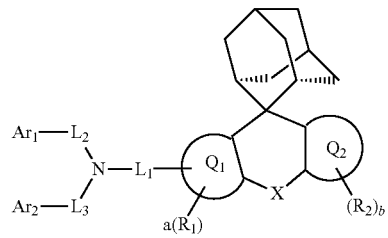

in the Chemical Formula 1,
$Q_1$ and $Q_2$ are each independently a $C_{6-30}$ aromatic ring;
a and b are each independently an integer of 0 to 3;
X is a single bond; $CR_3R_4$; $SiR_5R_6$; $NR_7$; O; S; $SO_2$; or a substituent group of the following Chemical Formula 2,

[Chemical Formula 2]

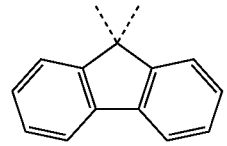

$R_1$ to $R_7$ are each independently hydrogen; deuterium; a substituted or unsubstituted $C_{1-60}$ alkyl; a substituted or unsubstituted $C_{1-60}$ alkoxy; a substituted or unsubstituted $C_{6-60}$ aryl; a substituted or unsubstituted $C_{5-60}$ heteroaryl containing one or more heteroatoms selected from the group consisting of N, O and S; or may be bonded to adjacent groups to form a ring, $L_1$ to $L_3$ are each independently a single bond; a substituted or unsubstituted $C_{6-60}$ arylene; or a substituted or unsubstituted $C_{2-60}$ heteroarylene containing any one or more heteroatoms selected from the group consisting of N, O and S, and $Ar_1$ and $Ar_2$ are each independently a substituted or unsubstituted $C_{6-60}$ aryl; a substituted or unsubstituted $C_{2-60}$ heteroaryl containing one or more heteroatoms selected from the group consisting of N, O and S; a substituted or unsubstituted $C_{1-30}$ alkyl silyl; or a substituted or unsubstituted $C_{5-30}$ aryl silyl, provided that diphenylfluorene is excluded.

According to another aspect of the present disclosure, there is provided an organic light emitting device comprising: a first electrode; a second electrode that is provided opposite to the first electrode; and one or more organic material layers that are provided between the first electrode and the second electrode, wherein one or more layers of the organic material layers include the above-mentioned compound of Chemical Formula 1.

Advantageous Effects

The above-mentioned compound of Chemical Formula 1 can be used as a material of an organic material layer of an organic light emitting device, and can improve the efficiency, achieve low driving voltage and/or improve lifetime characteristics in the organic light emitting device. In particular, the compound of Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, embodiments of the present disclosure will be described in more detail to facilitate understanding of the invention.

The present disclosure provides the compound of Chemical Formula 1.

As used herein, the notation

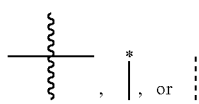

means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

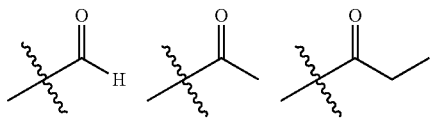

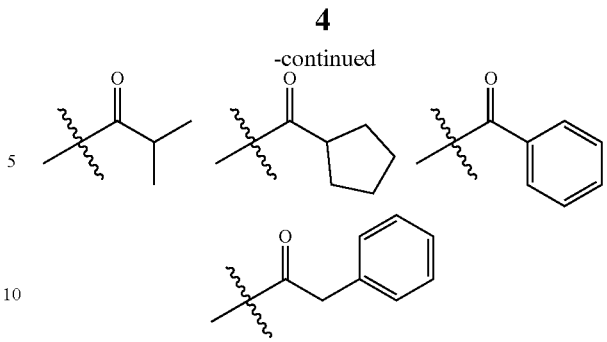

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

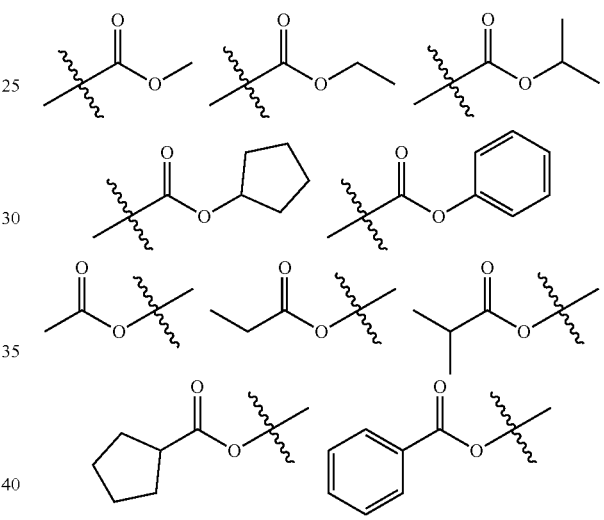

In the present disclosure, the carbon number of an imide group is not particularly limited, but is preferably 1 to 25. Specifically, the imide group may be a compound having the following structural formulas, but is not limited thereto.

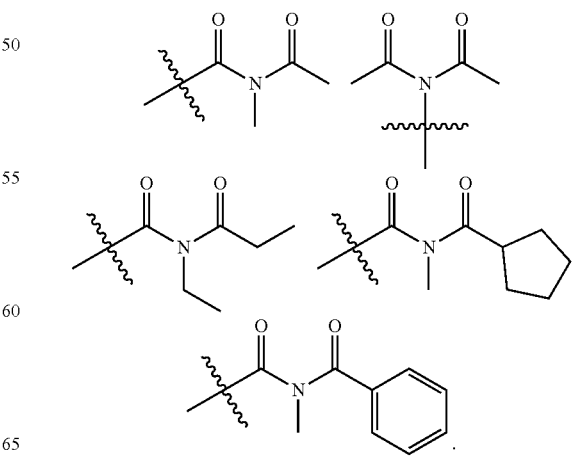

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, or the like, but is not limited thereto.

In the present disclosure, the fluorenyl group may be substituted, and two substituents may be linked with each other to form a Spiro structure. In the case where the fluorenyl group is substituted,

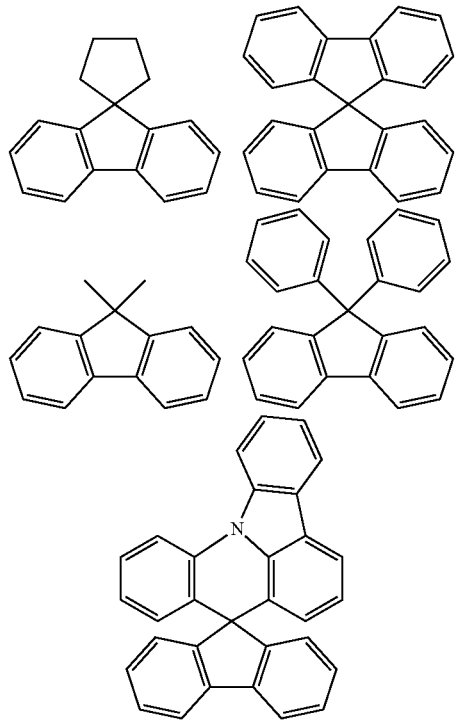

and the like can be formed. However, the structure is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heteroaryl group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

In Chemical Formula 1, preferably, $Q_1$ and $Q_2$ may be each independently a benzene or naphthalene ring, and more preferably, both $Q_1$ and $Q_2$ may be benzene rings.

Preferably, the Chemical Formula 1 may be one of the following Chemical Formulas 1-1 to 1-7.

[Chemical Formula 1-1]

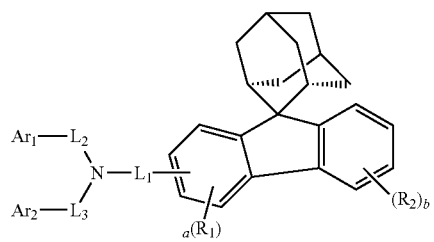

[Chemical Formula 1-2]

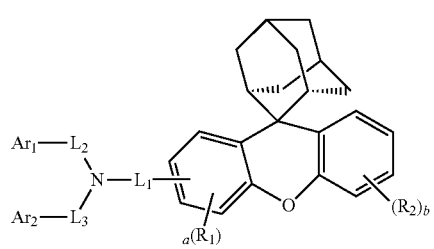

[Chemical Formula 1-3]

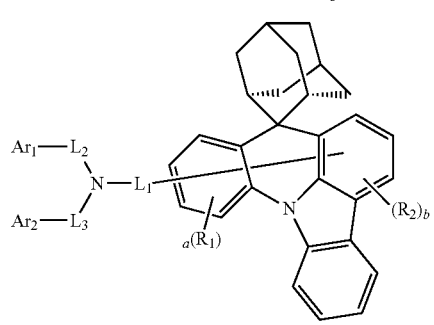

[Chemical Formula 1-4]

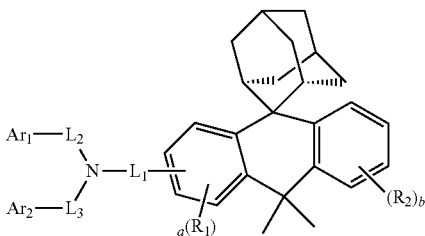

[Chemical Formula 1-5]

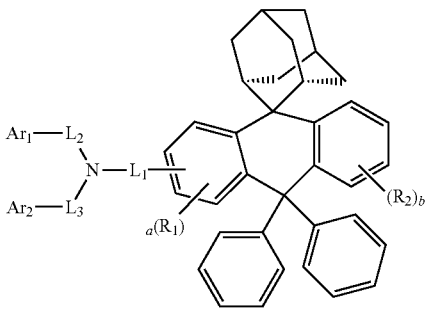

[Chemical Formula 1-6]

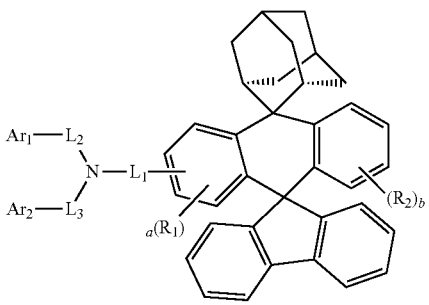

[Chemical Formula 1-7]

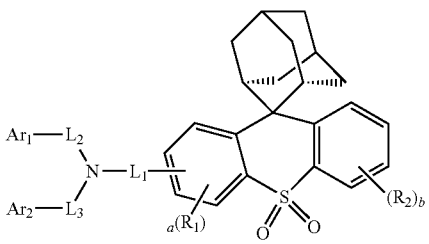

in the Chemical Formulas 1-1 to 1-7, a, b, $R_1$, $R_2$, $L_1$ to $L_3$, $Ar_1$ and $Ar_2$ are the same as defined above.

Preferably, both a and b may be 0.

Preferably, $L_1$ to $L_3$ may be each independently a single bond; biphenylene; or biphenylylene.

Preferably, $Ar_1$ and $Ar_2$ may be each independently phenyl, biphenylyl, terphenylyl, naphthyl, dimethylfluorenyl, dibenzofuranyl, dibenzothiophenyl, carbazolyl, or triphenylsilyl.

For example, the compound can be selected from the group consisting of:
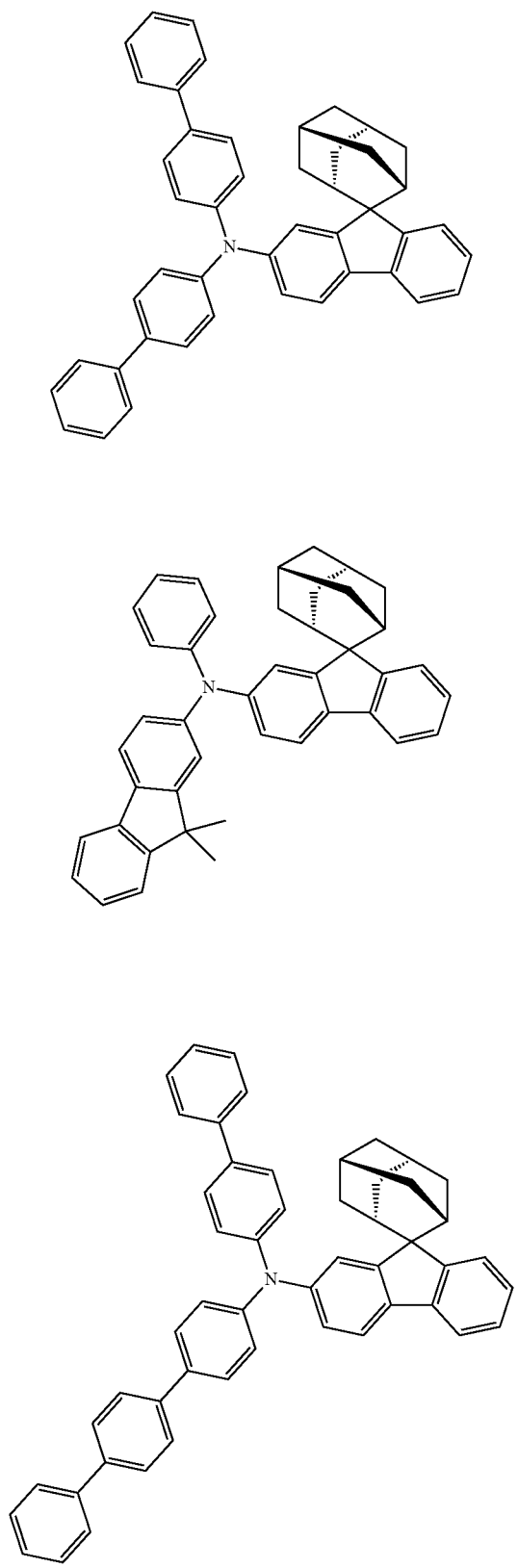
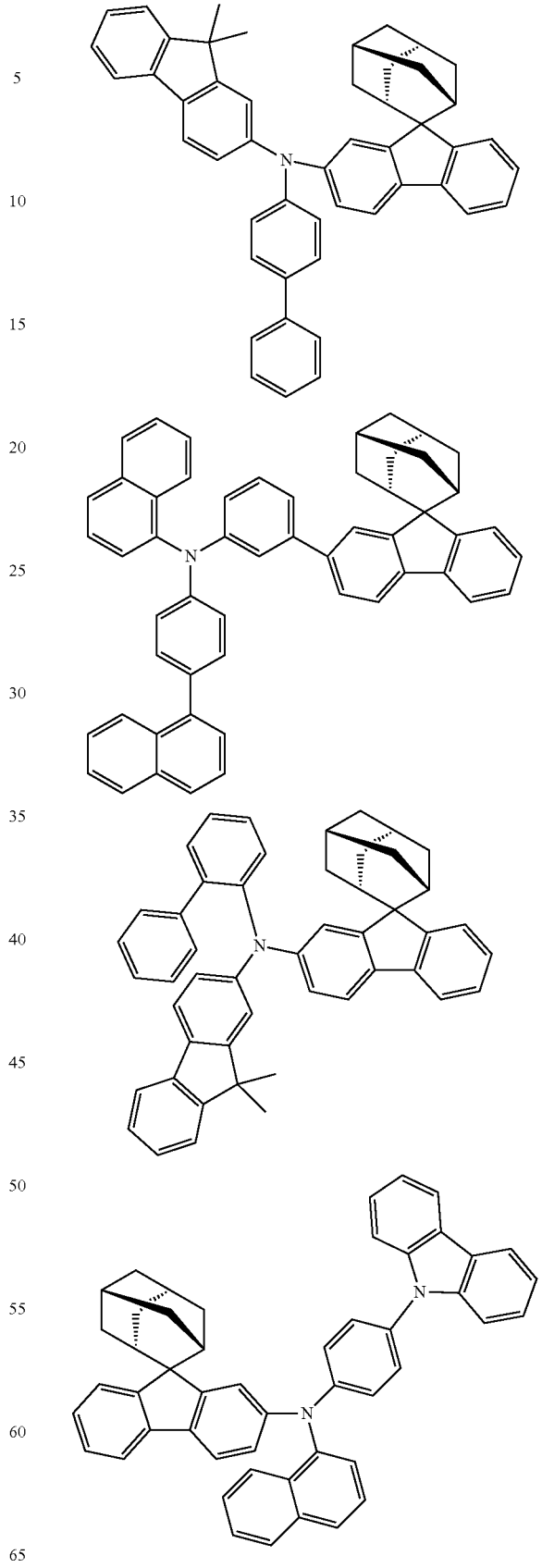

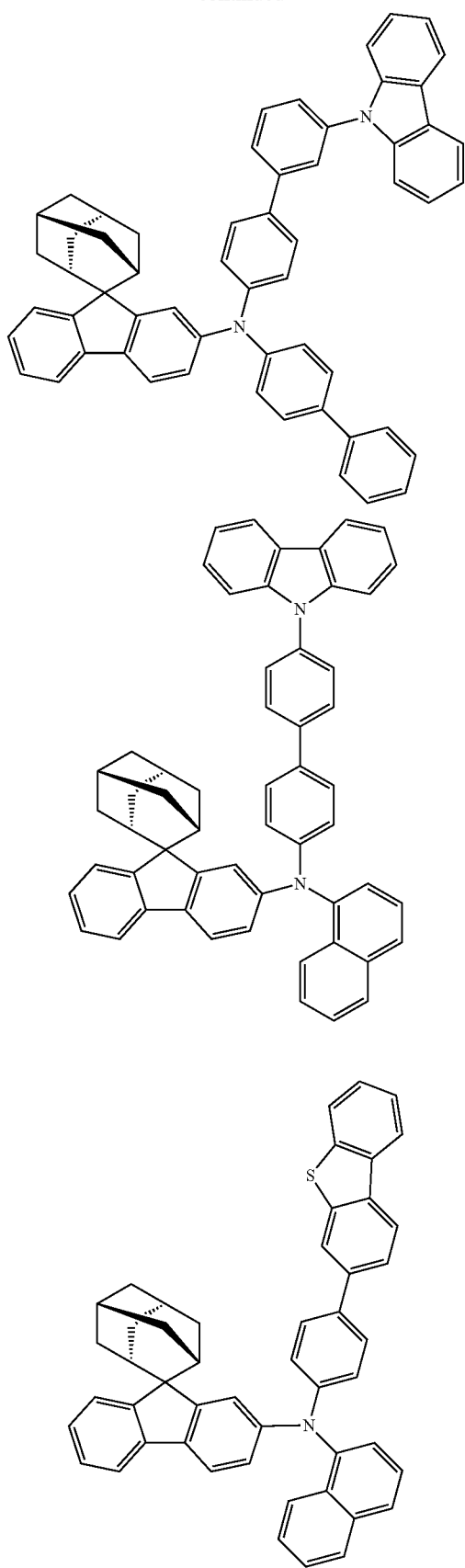
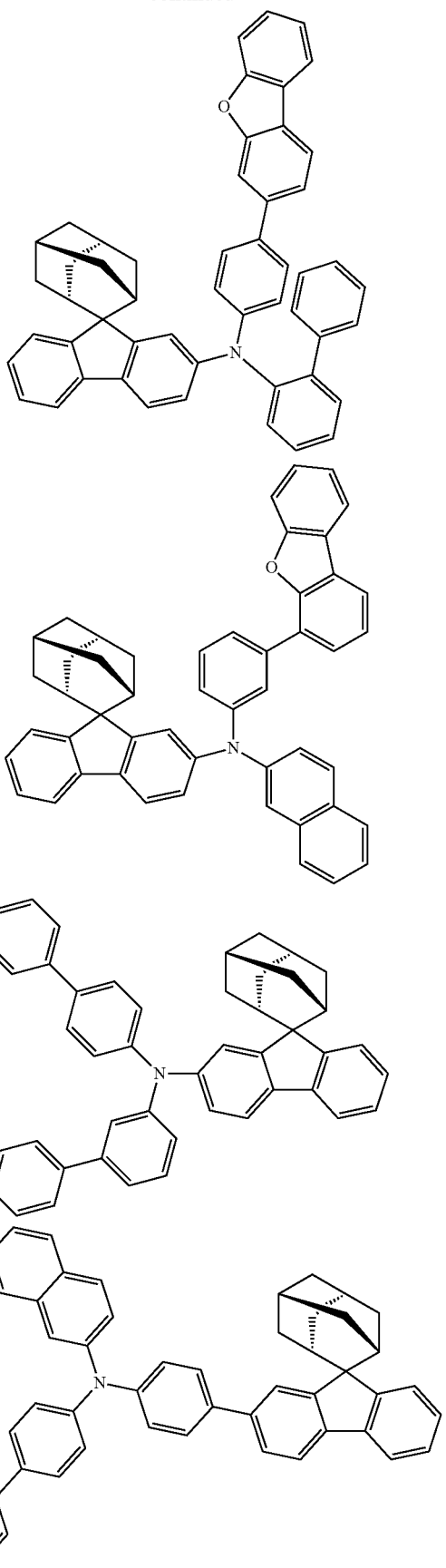

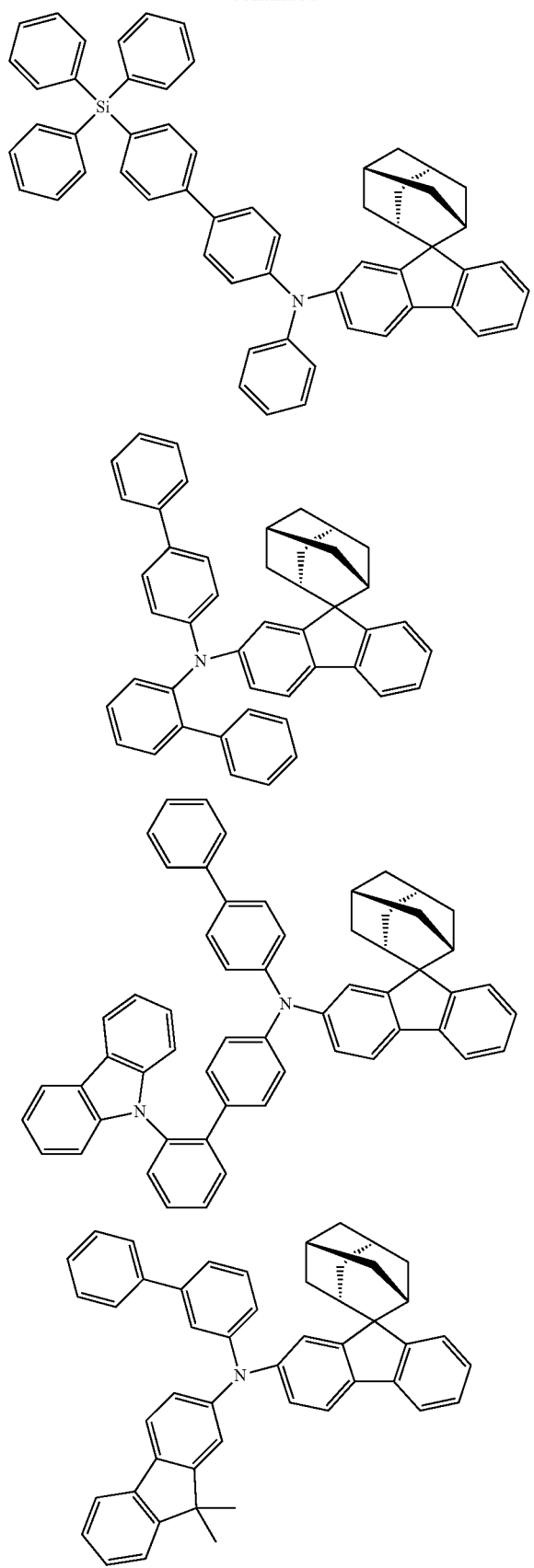
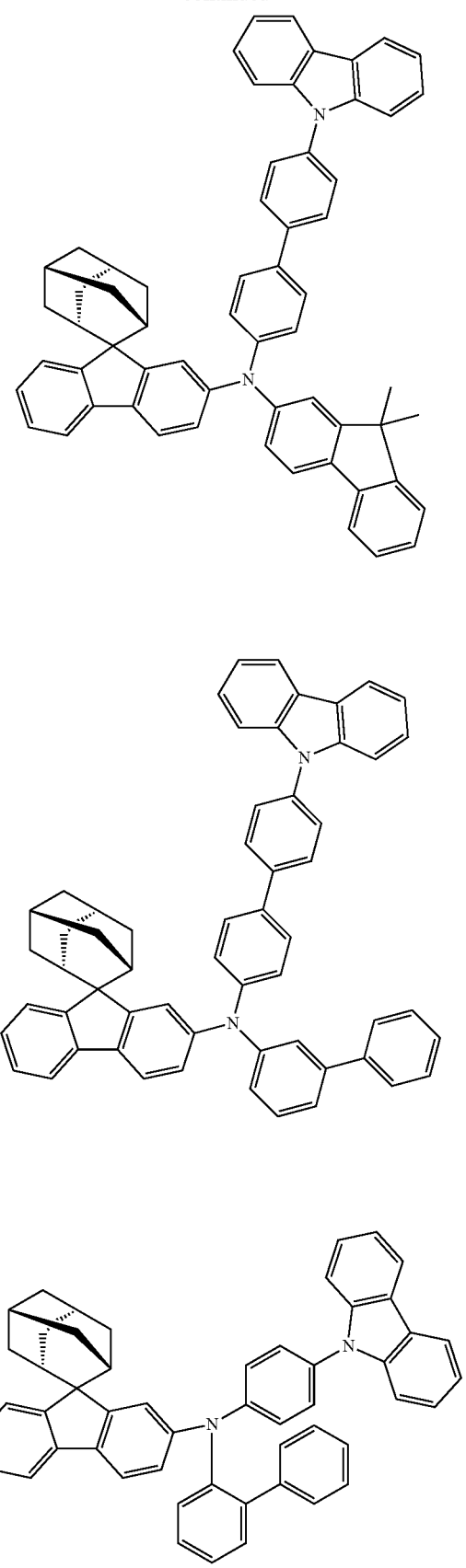

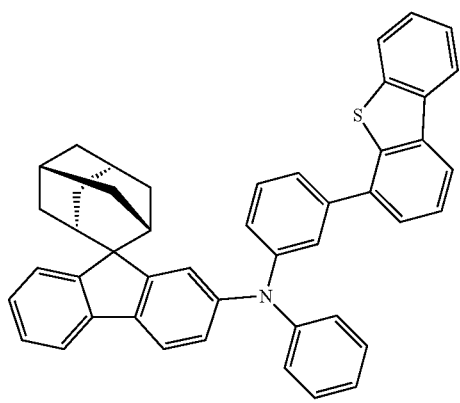
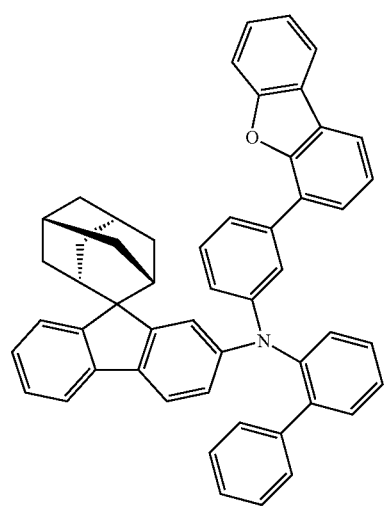
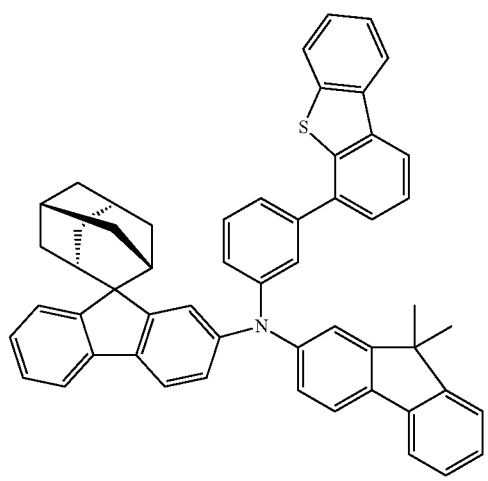
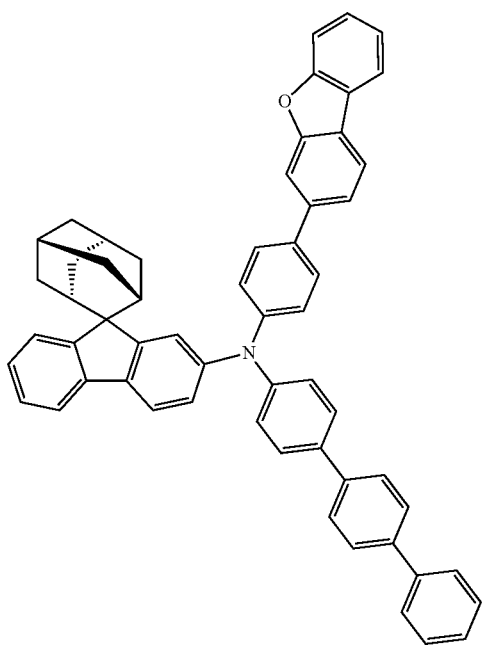
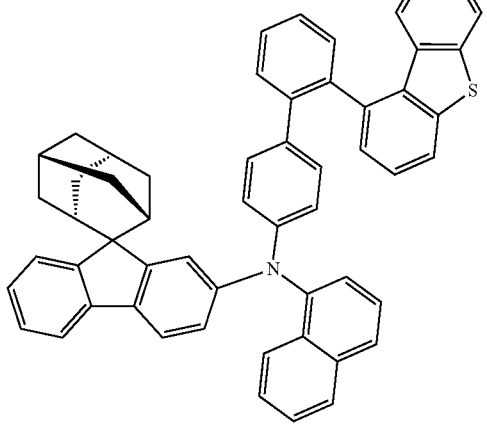
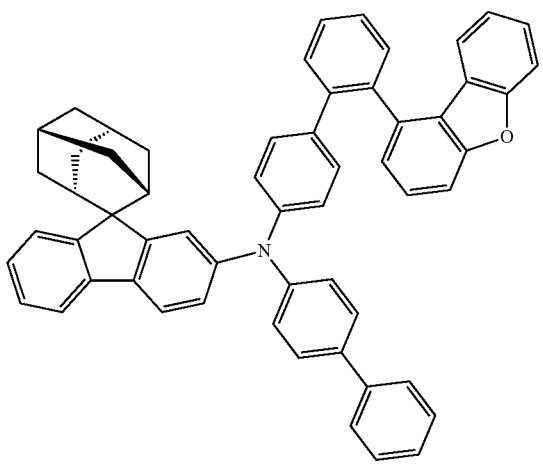

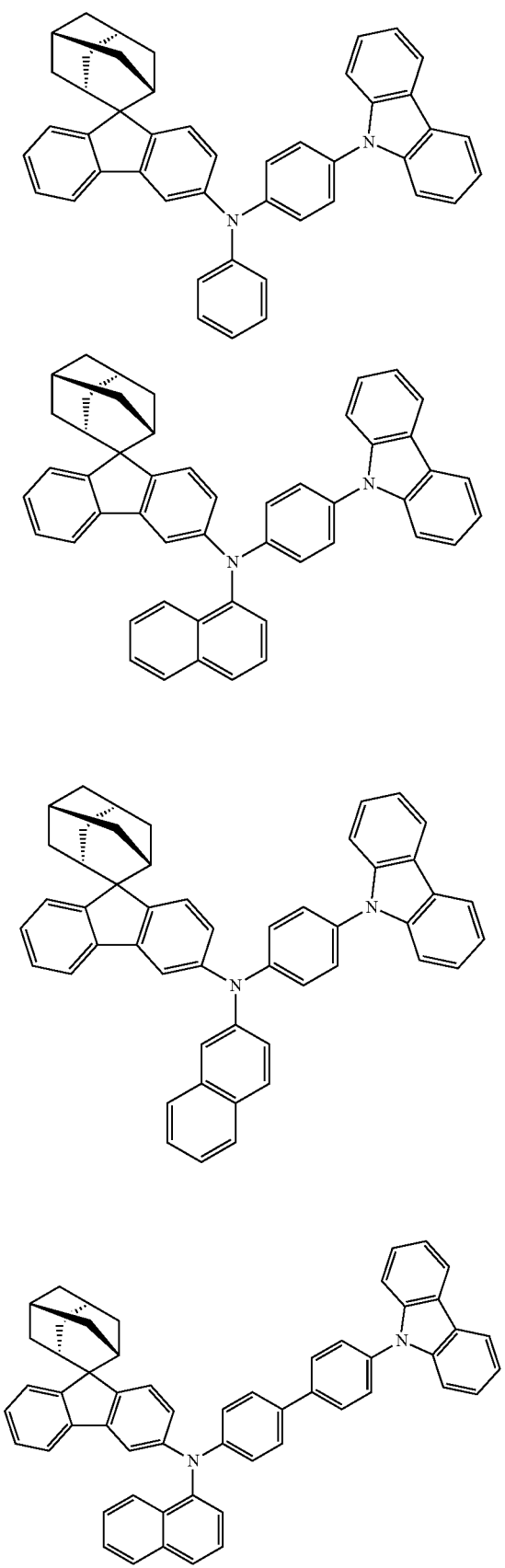
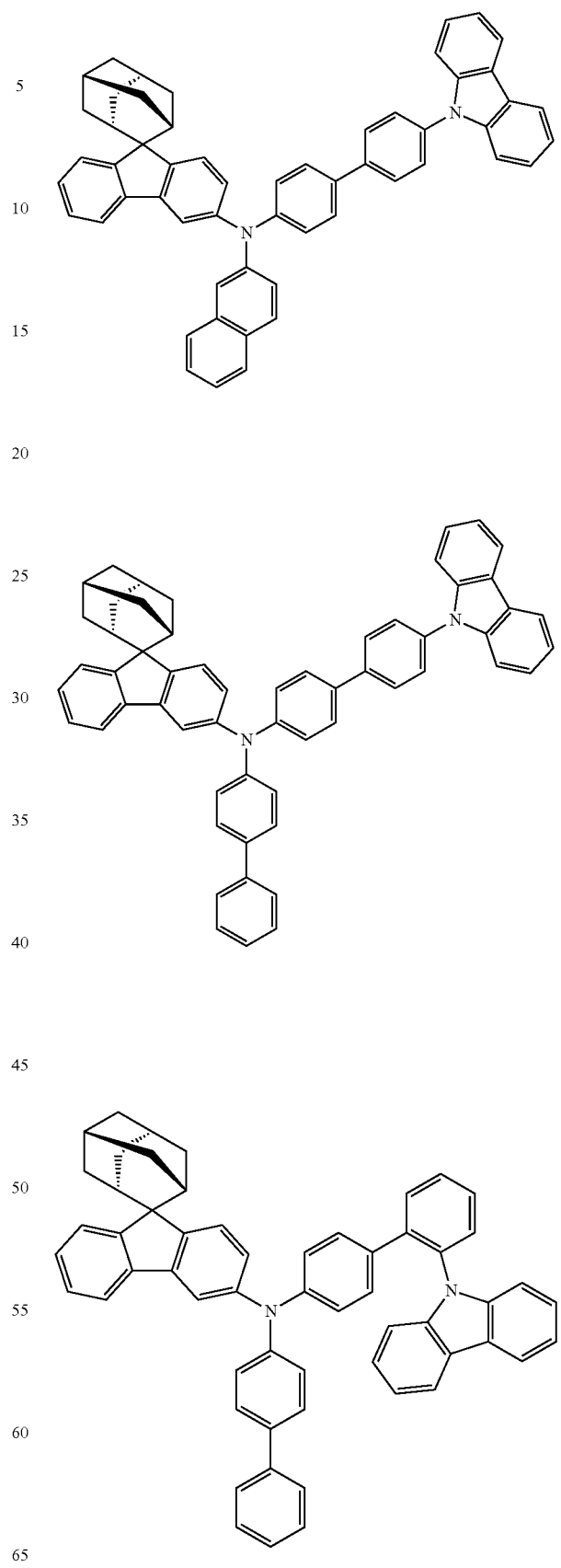

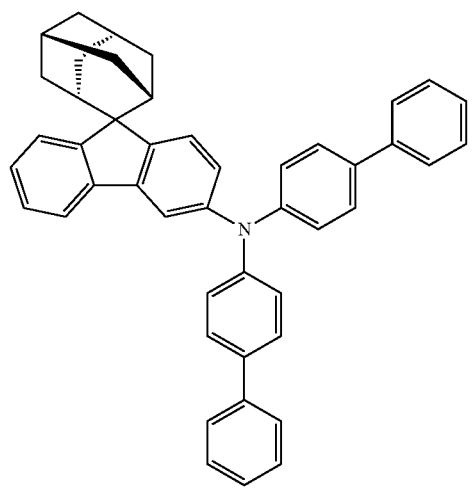
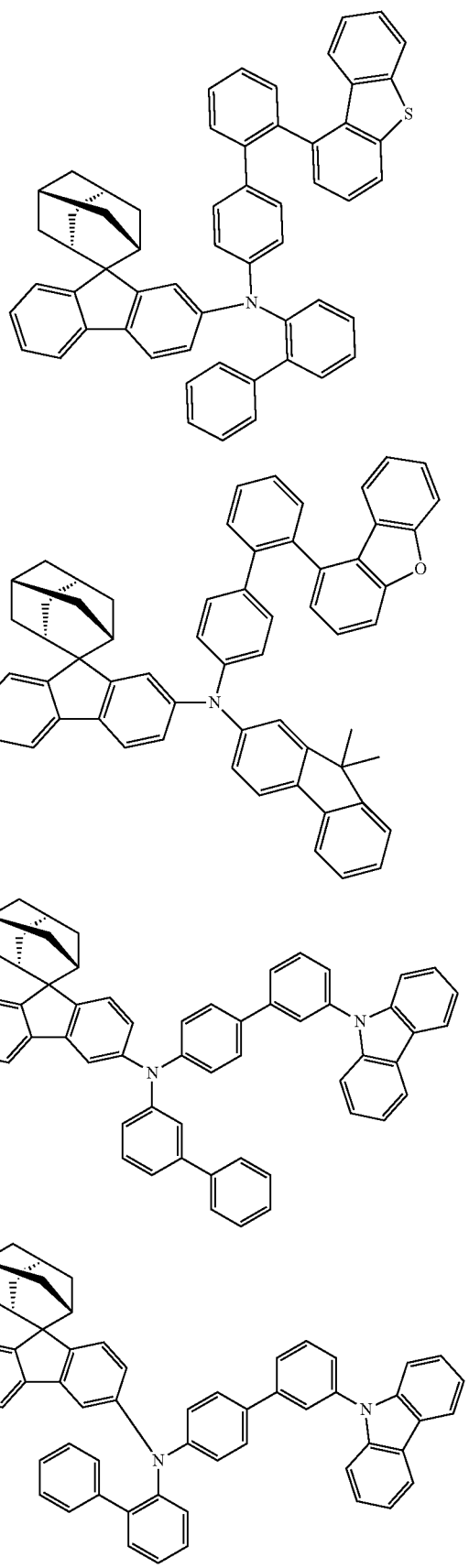

21
-continued
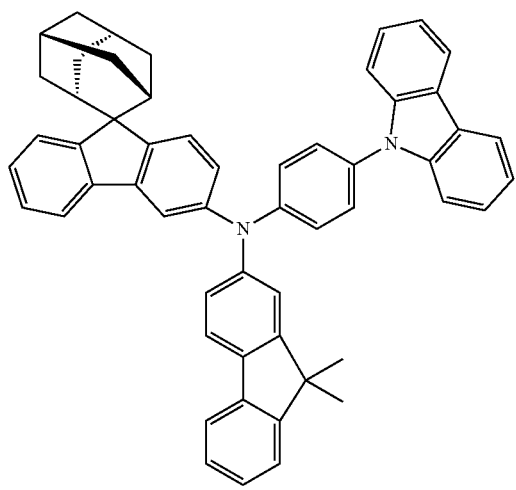
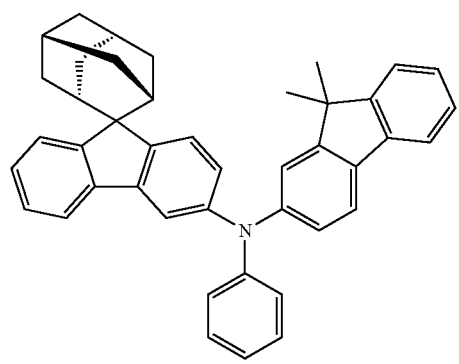
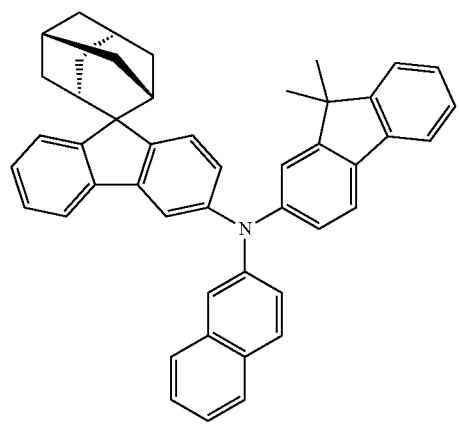
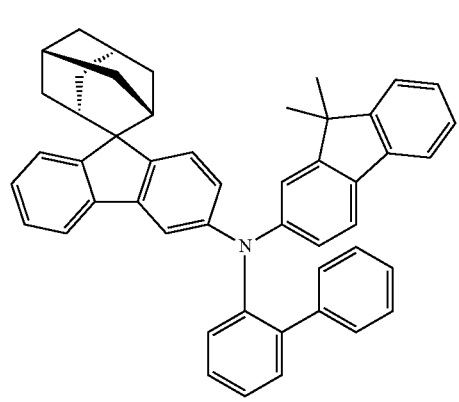
22
-continued
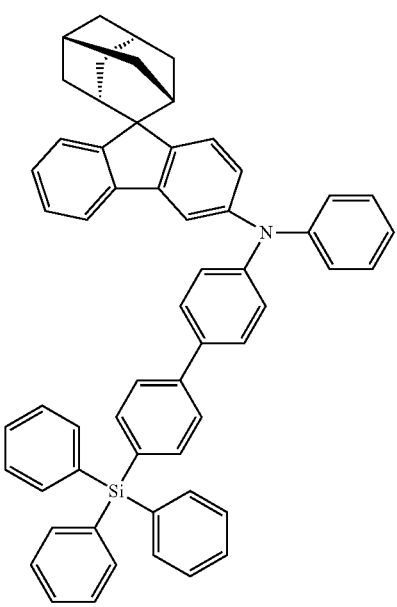
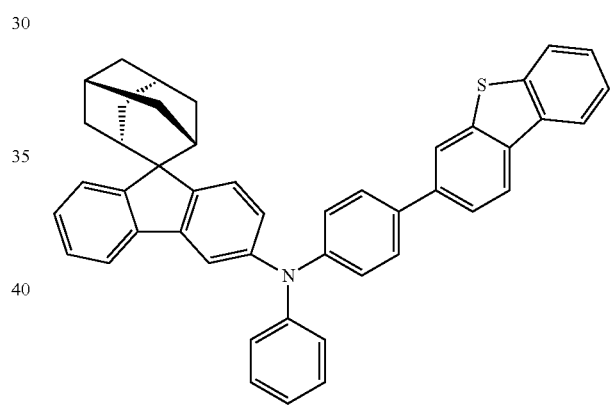
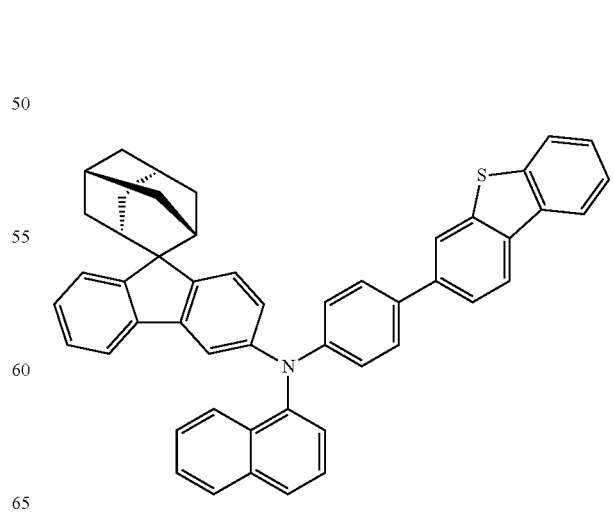

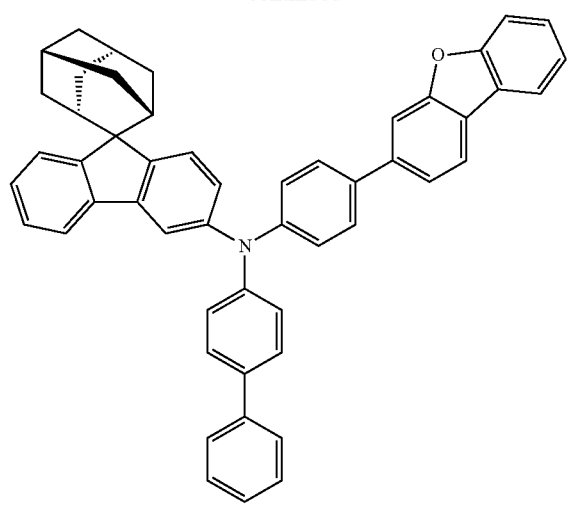
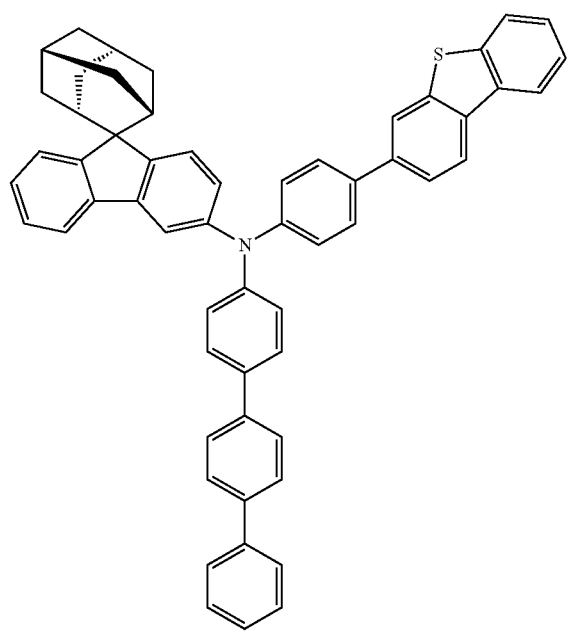
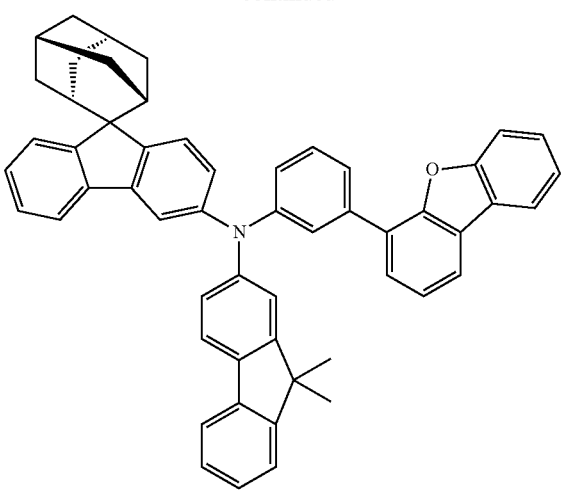
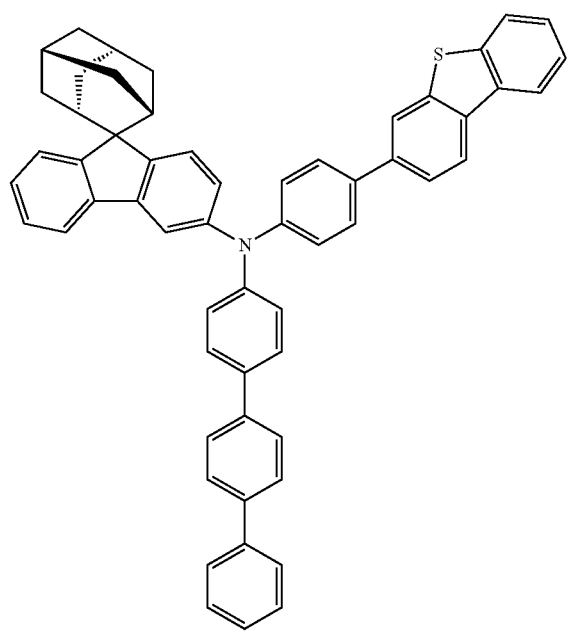
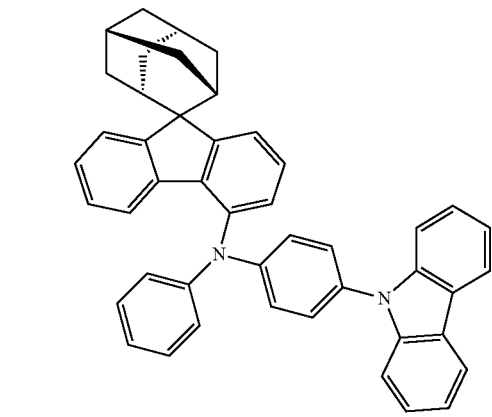

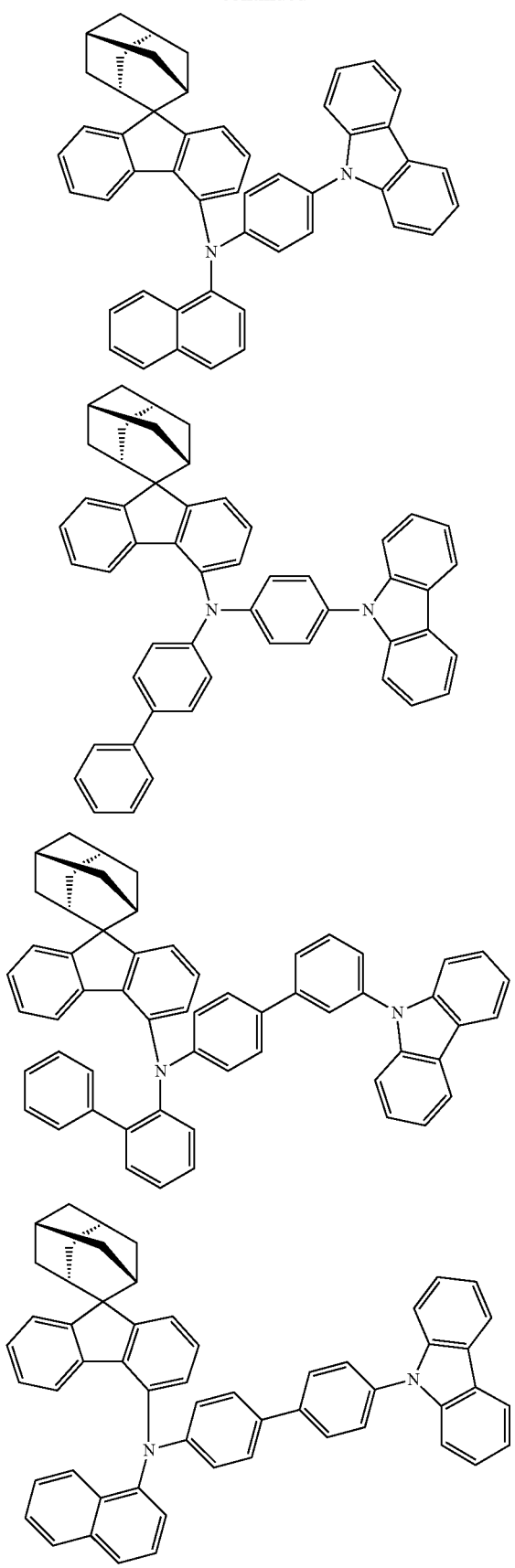
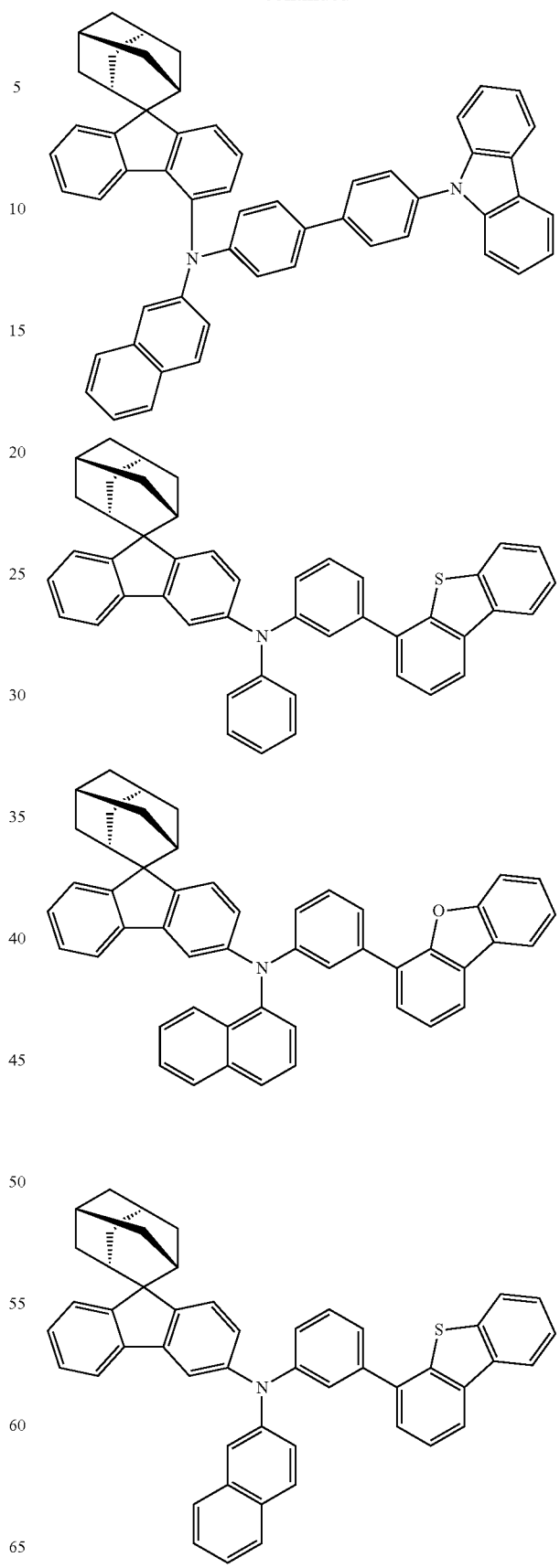

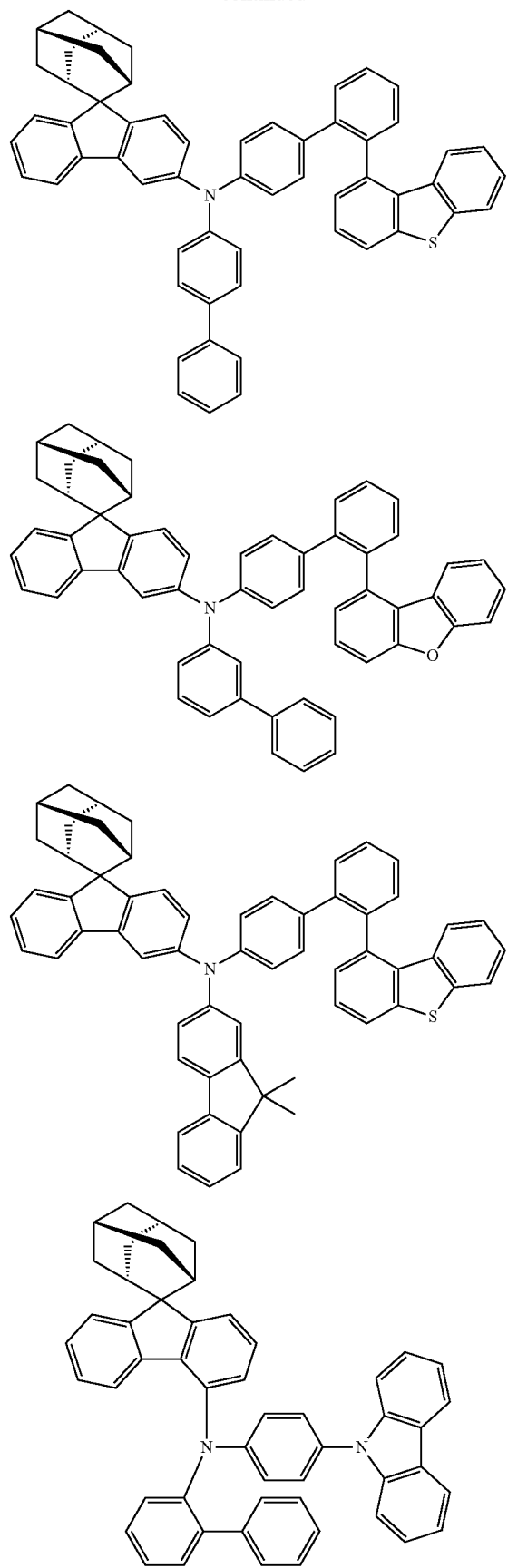
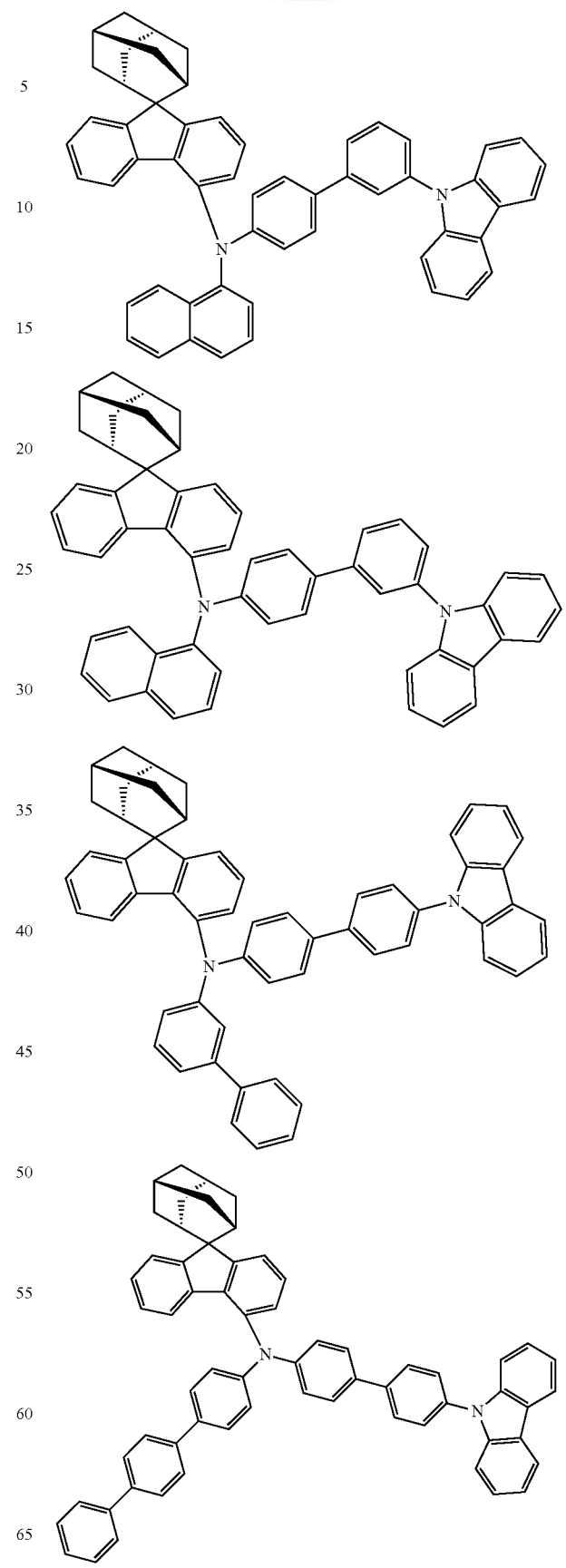

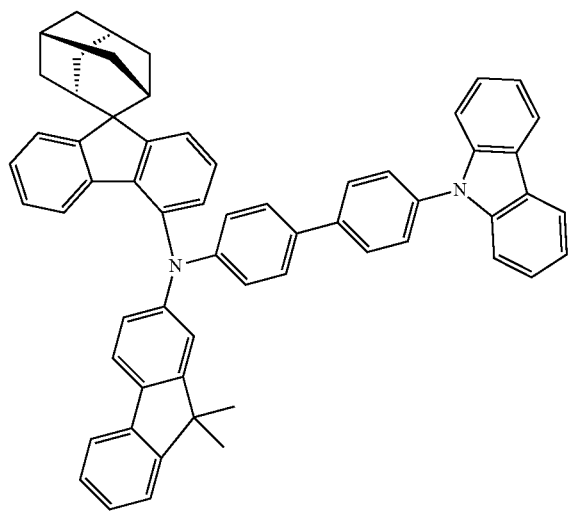
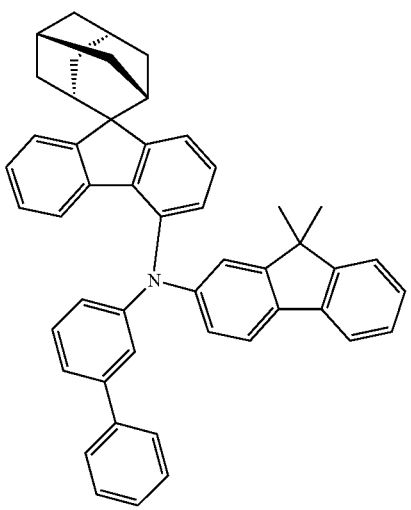
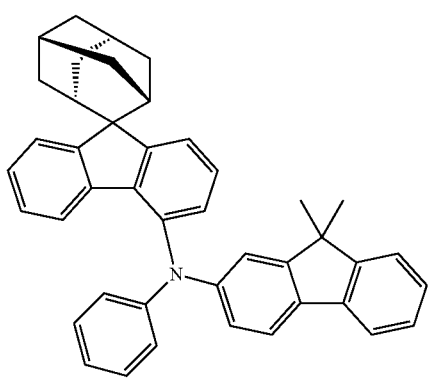
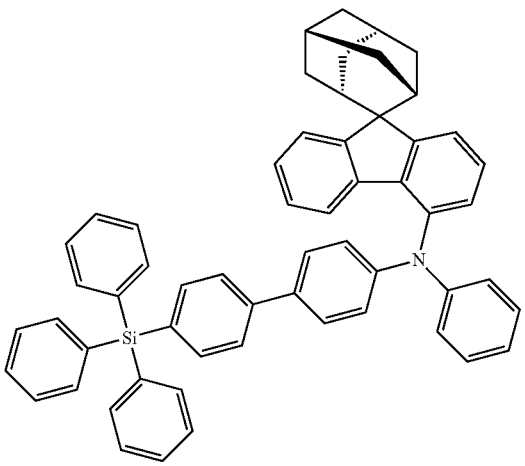
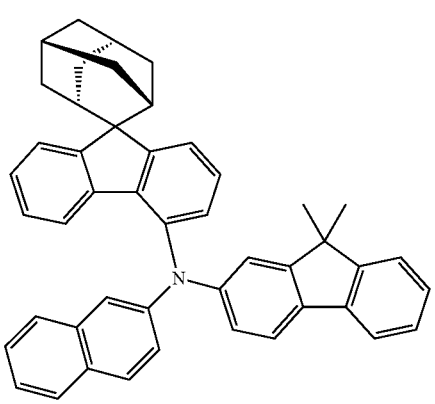
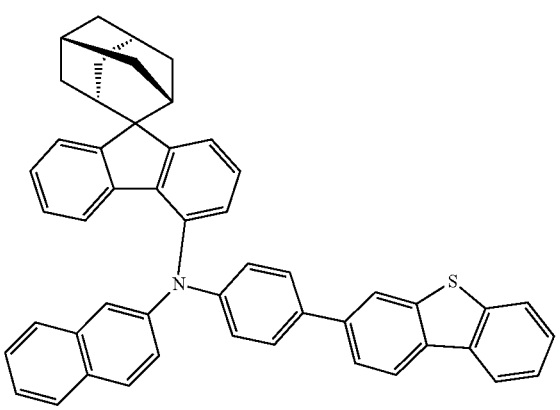

| 31 -continued | 32 -continued |
|---|---|
| 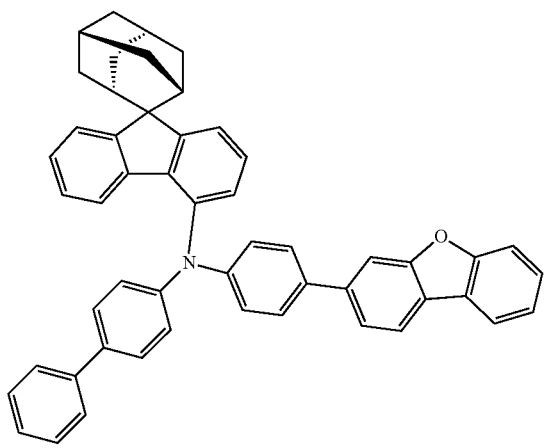 | 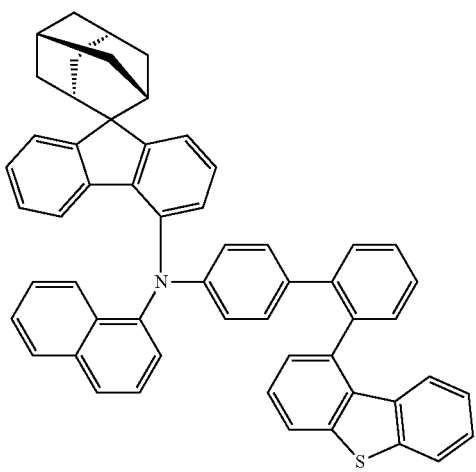 |
| 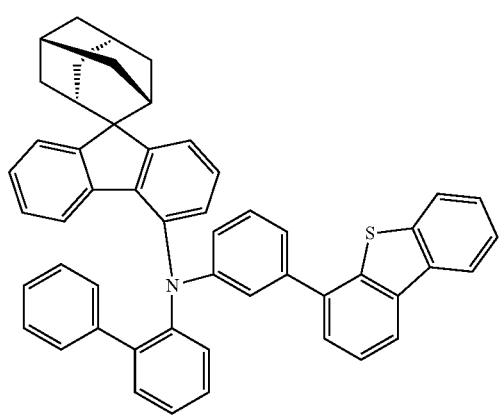 | 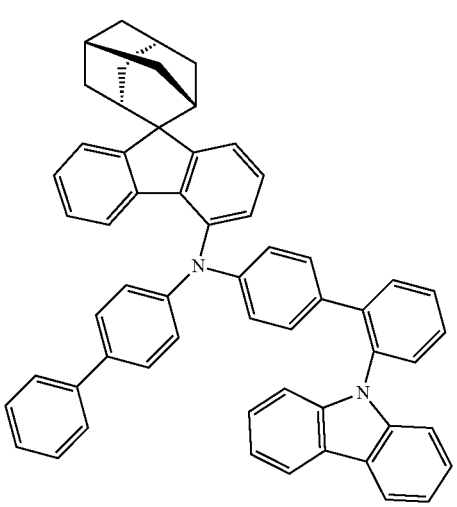 |
| 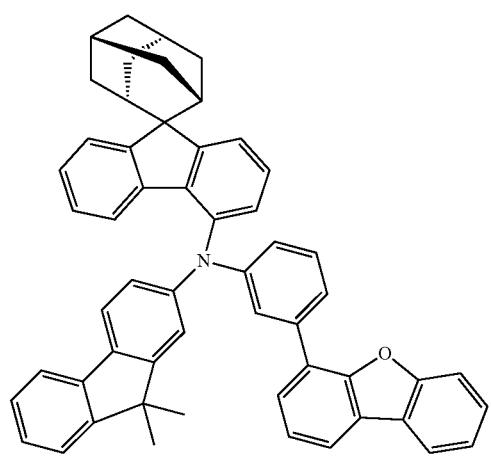 | 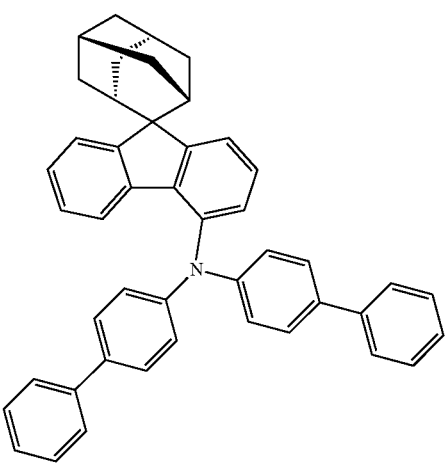 |

33
-continued
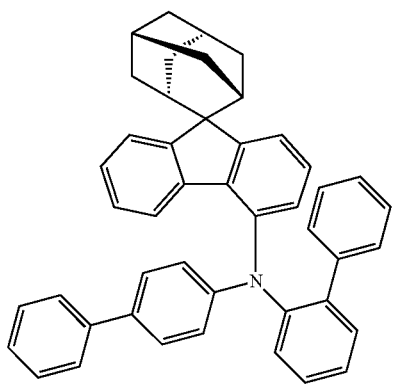
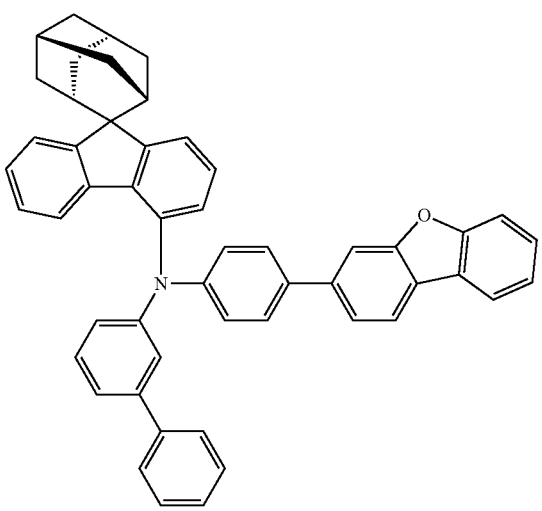
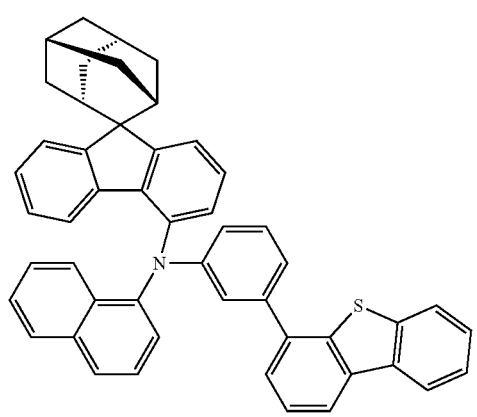
34
-continued
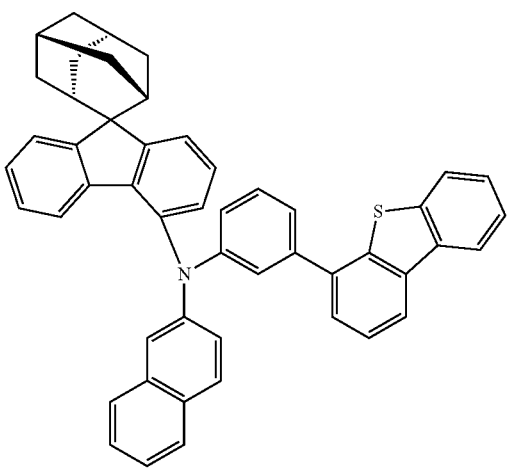
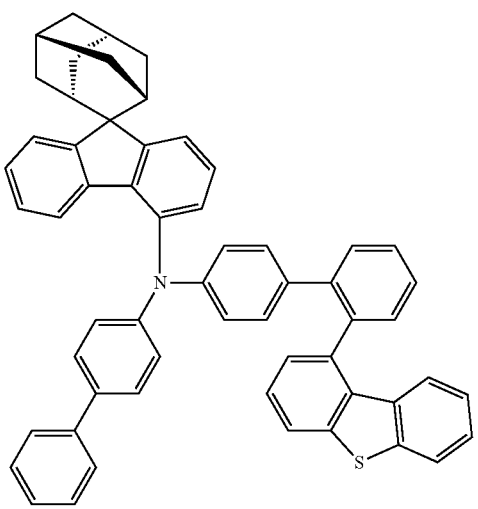
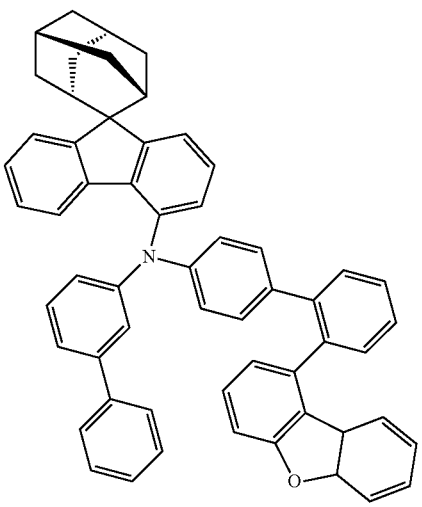

35
-continued
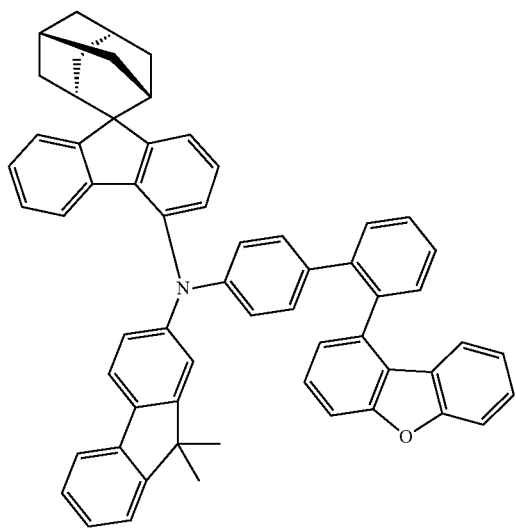
36
-continued
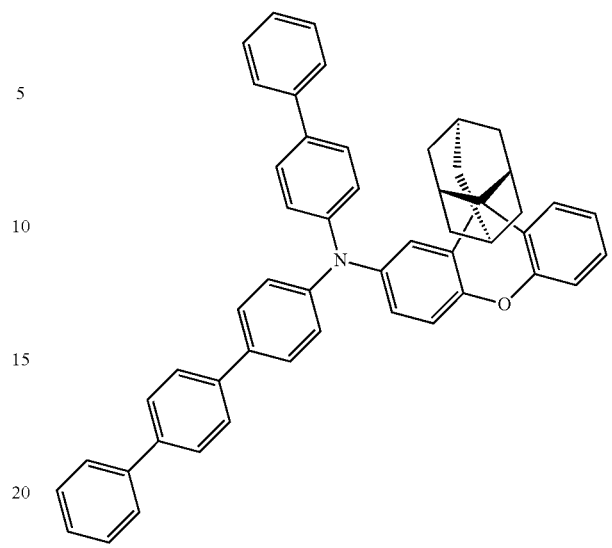
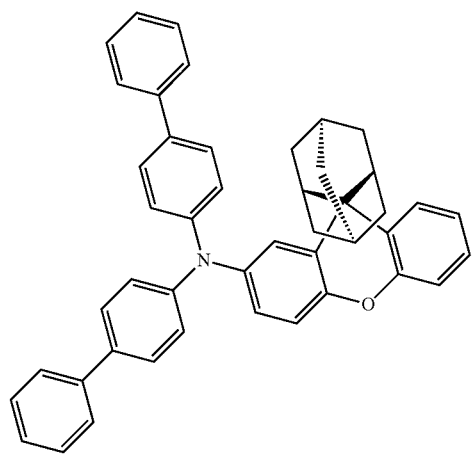
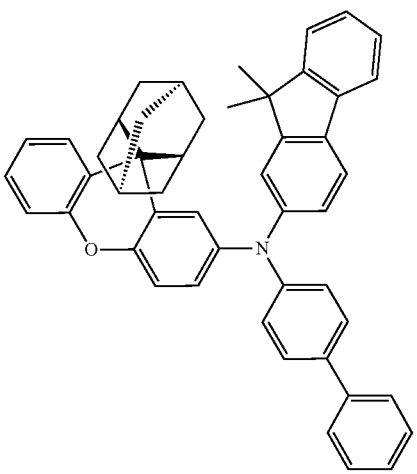
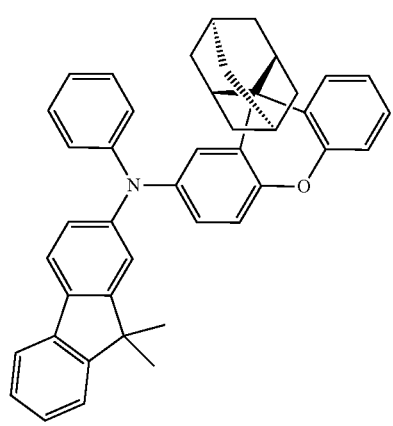
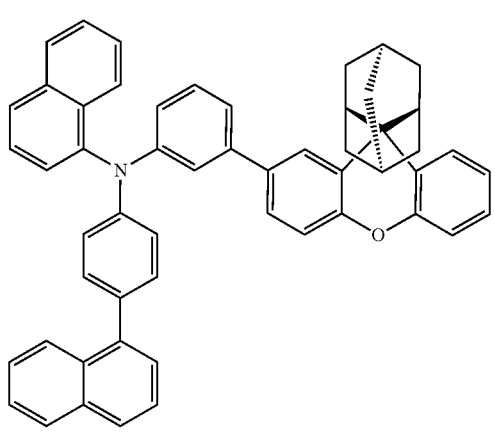

37
-continued
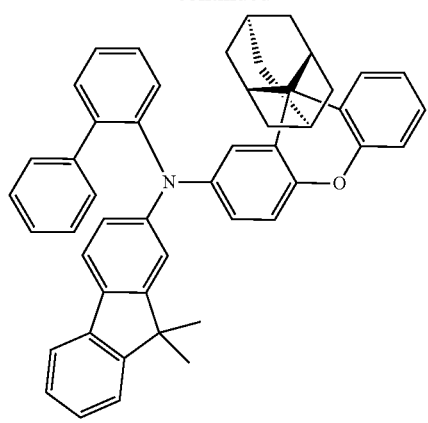
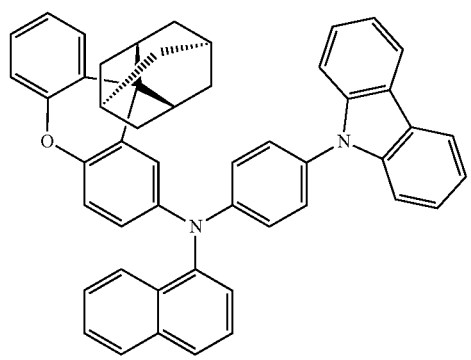
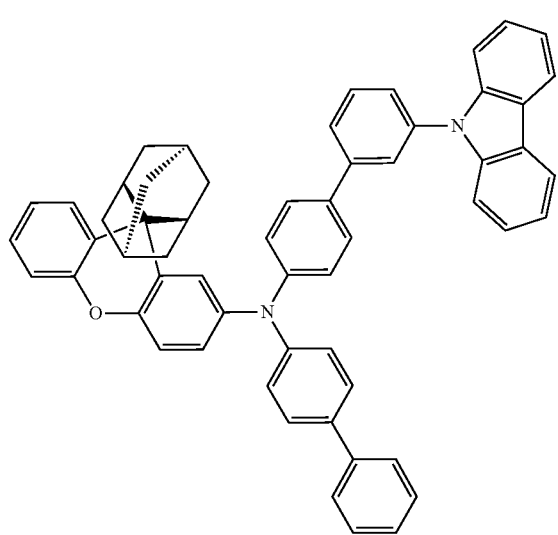
38
-continued
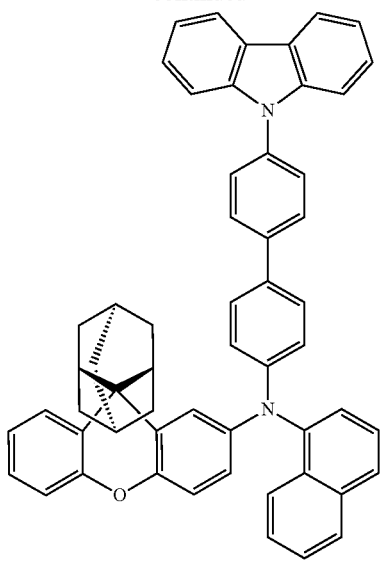
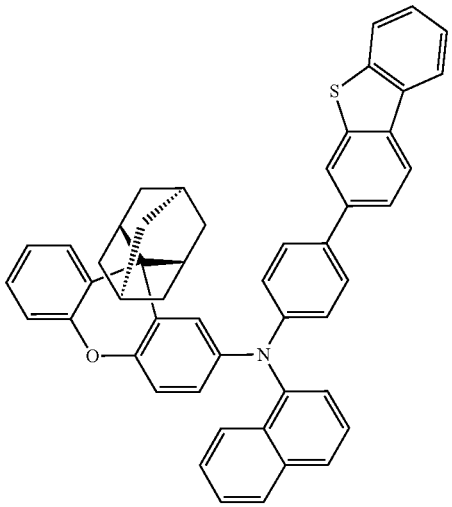
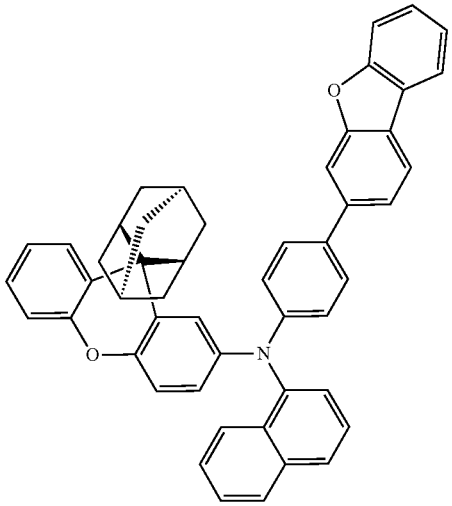

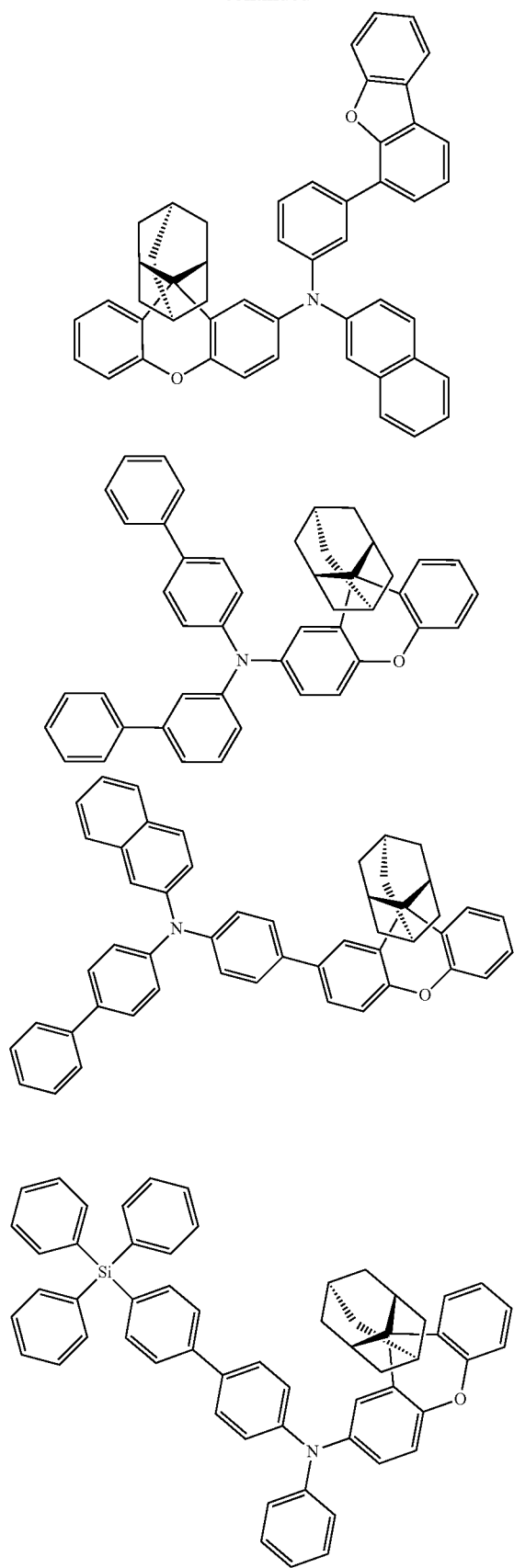
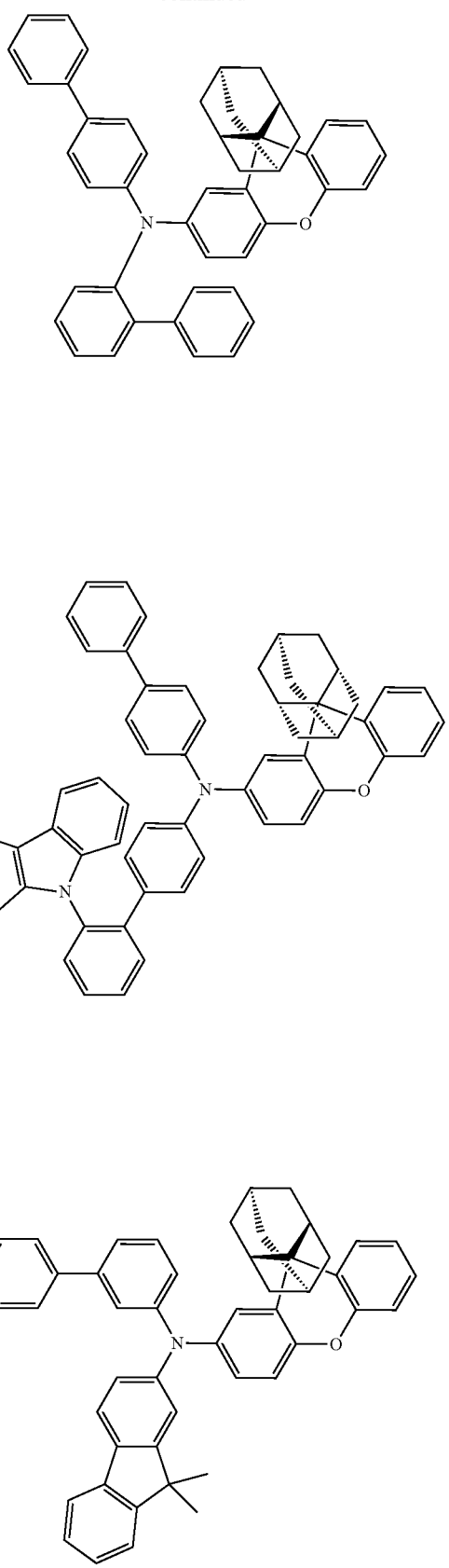

41
-continued
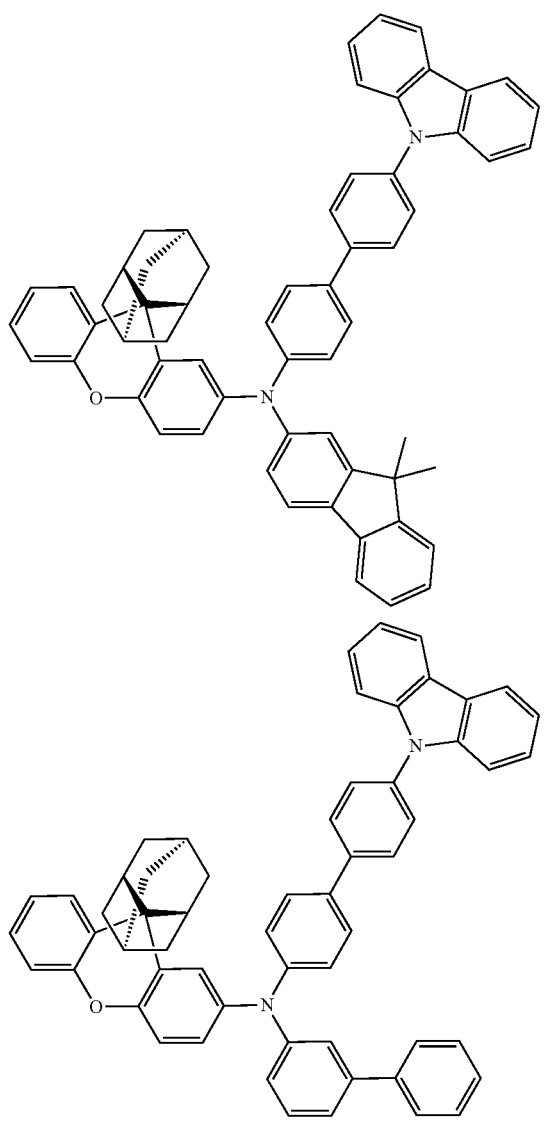
42
-continued
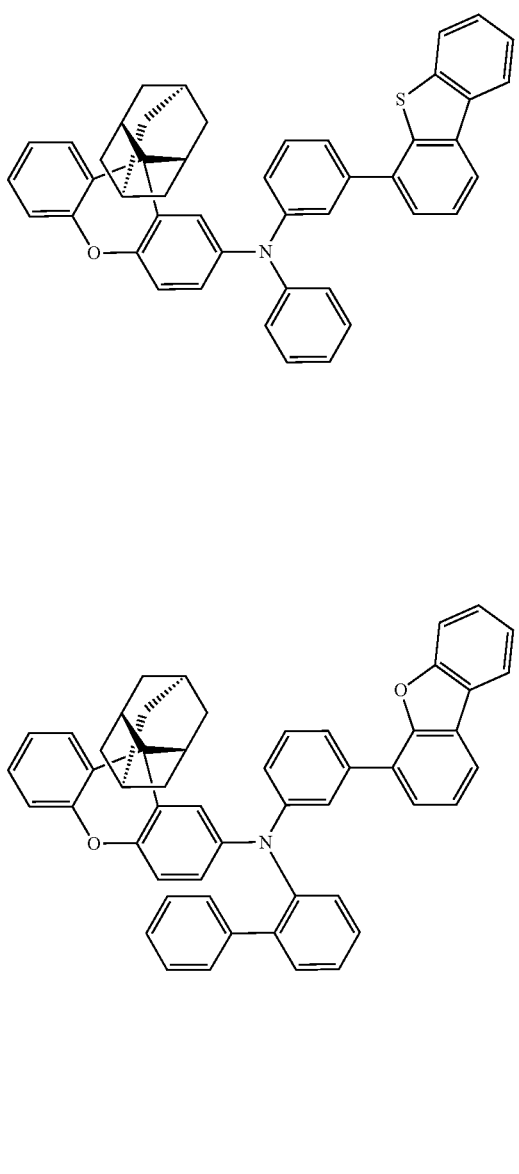
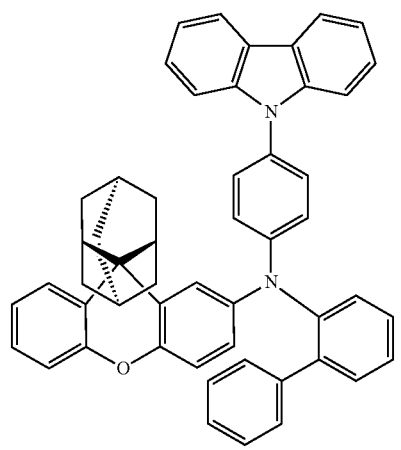
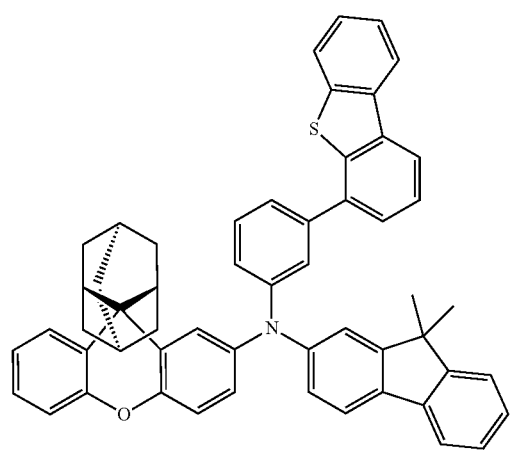

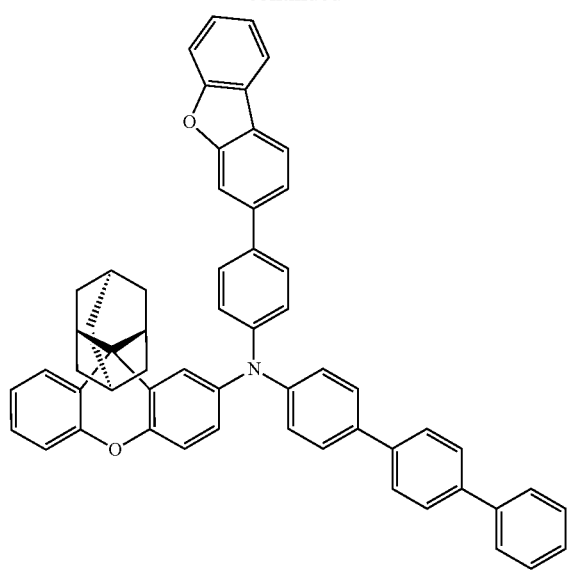
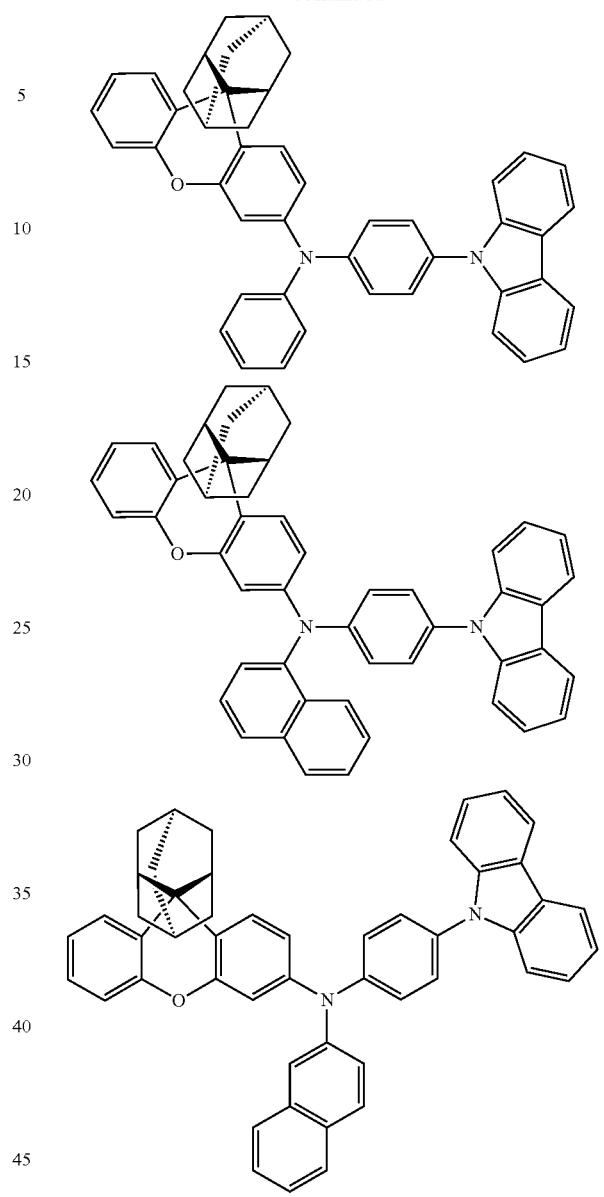
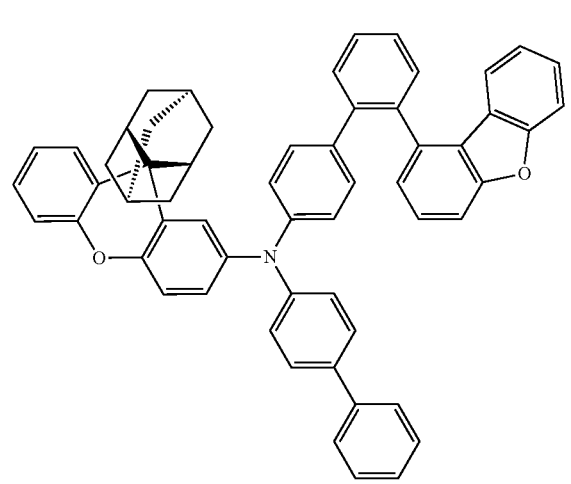
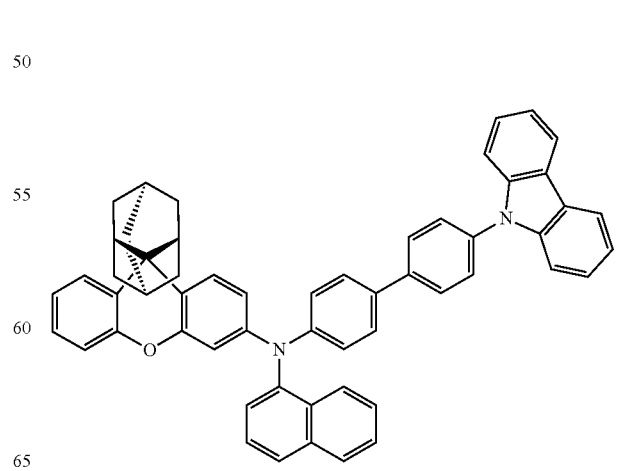

45
-continued
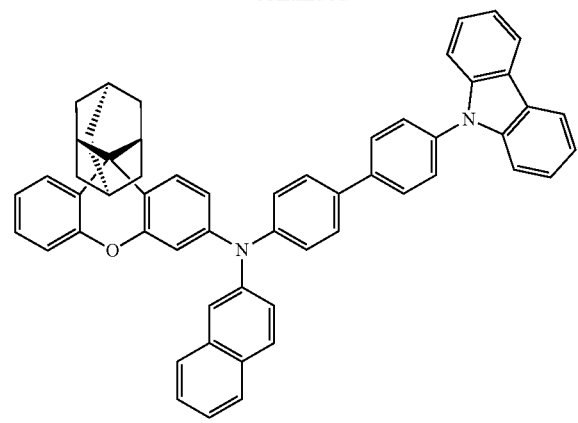
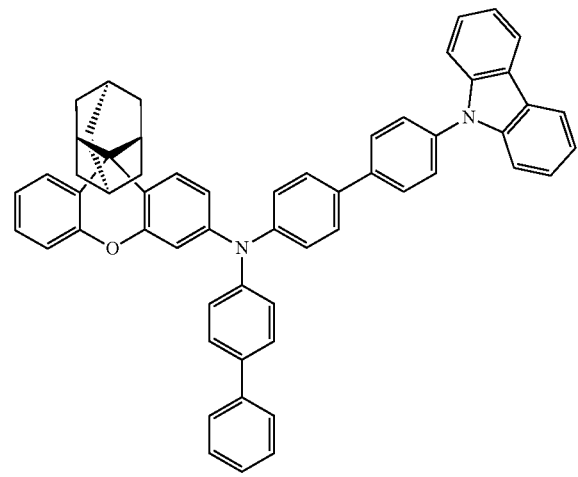
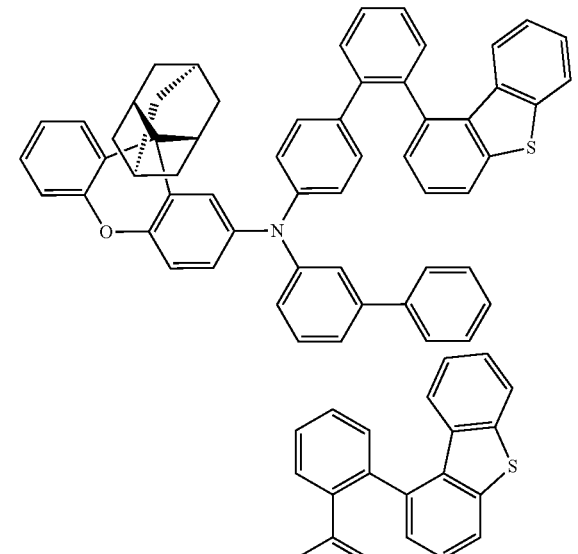
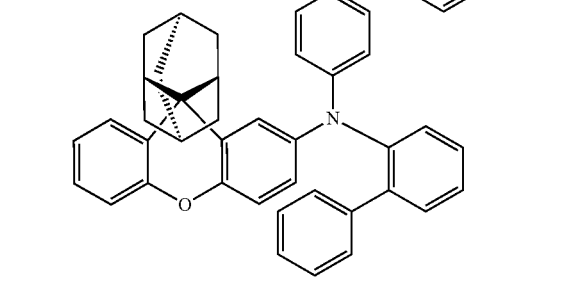
46
-continued
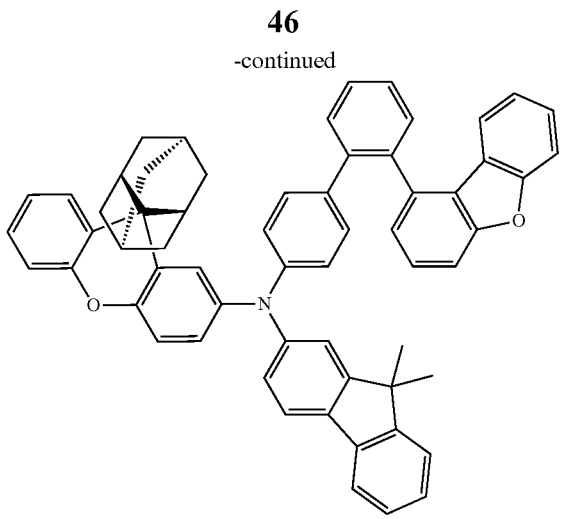
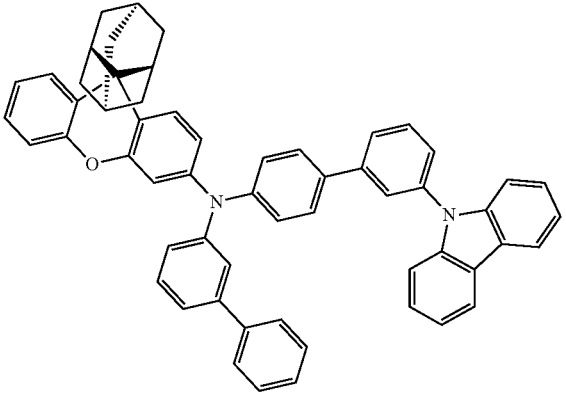
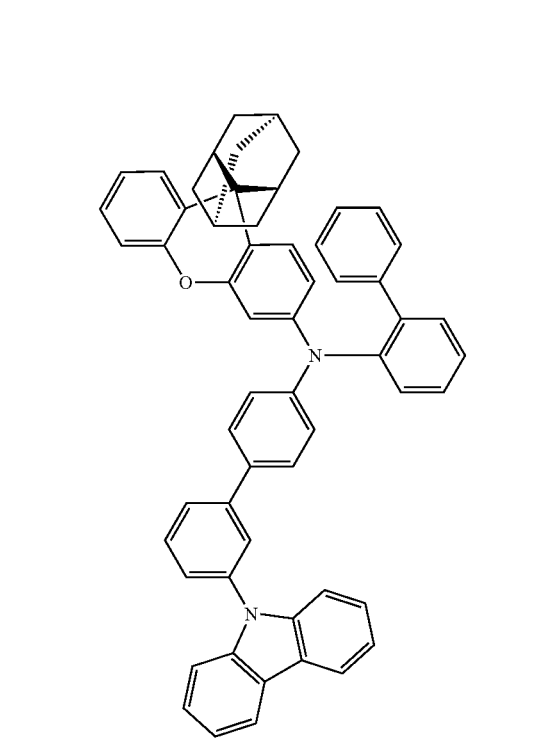

47
-continued
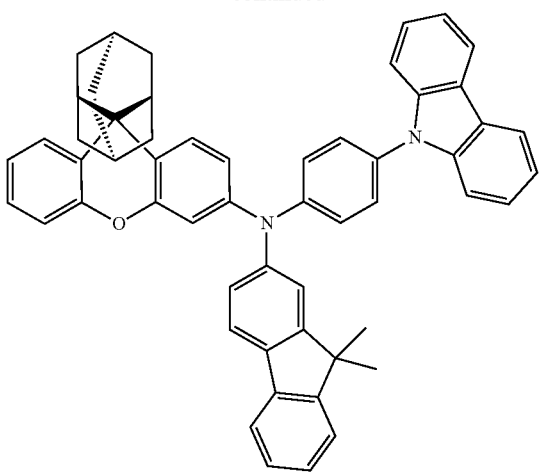
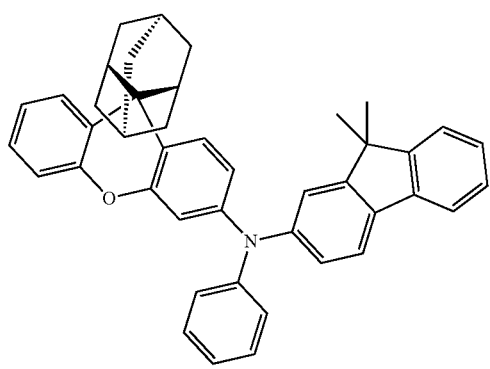
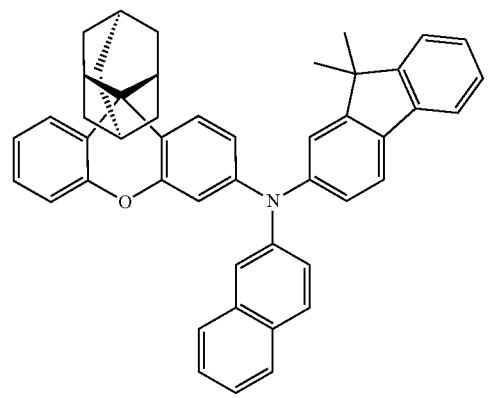
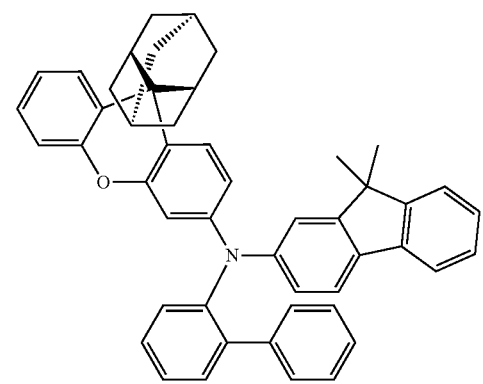
48
-continued
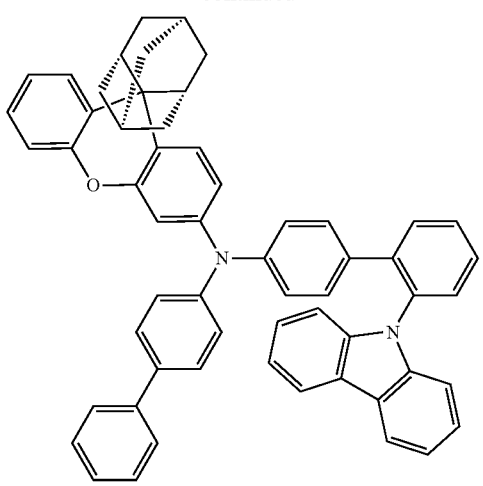
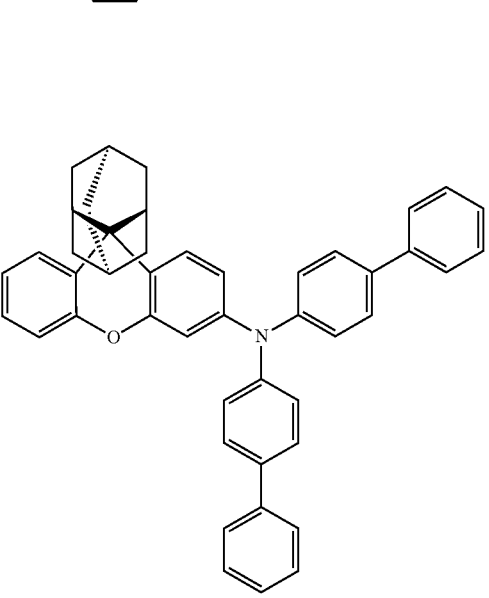
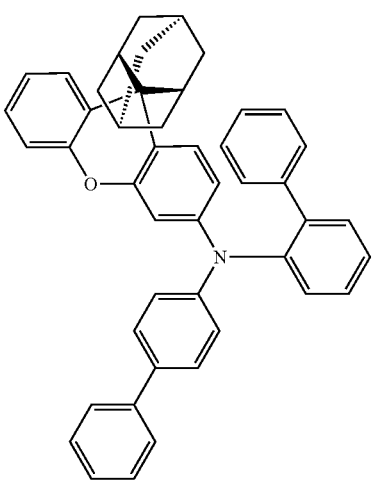

49
-continued
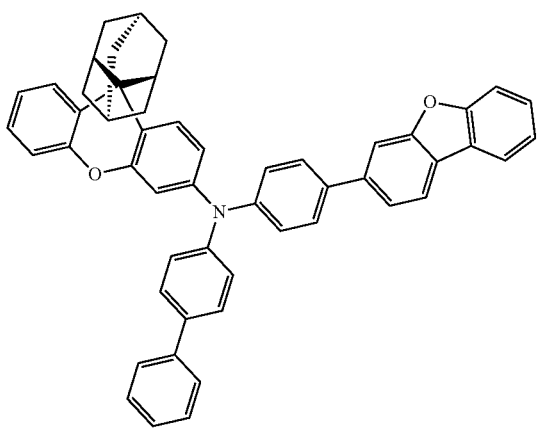
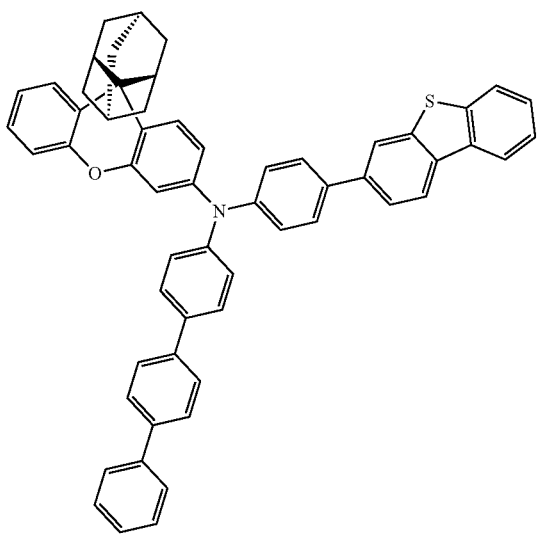
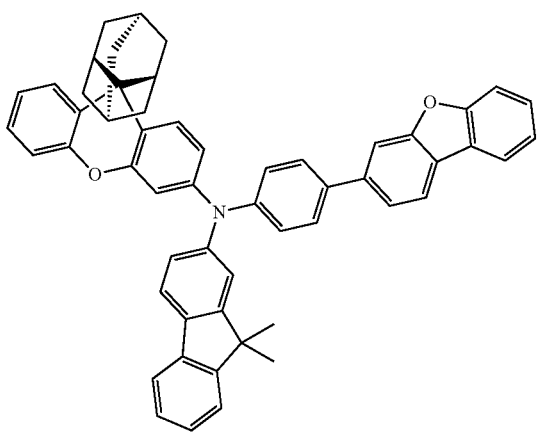
50
-continued
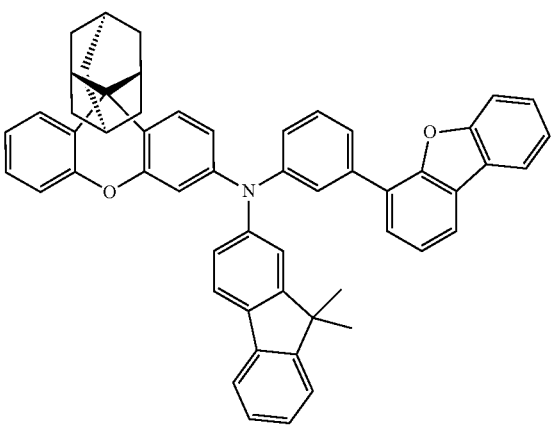
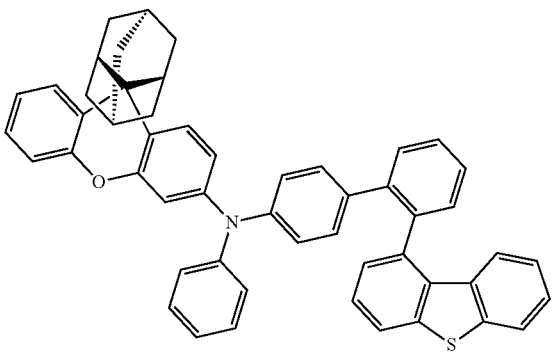
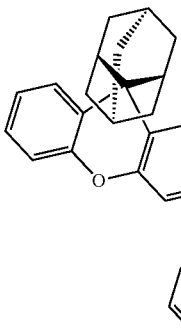

51
-continued
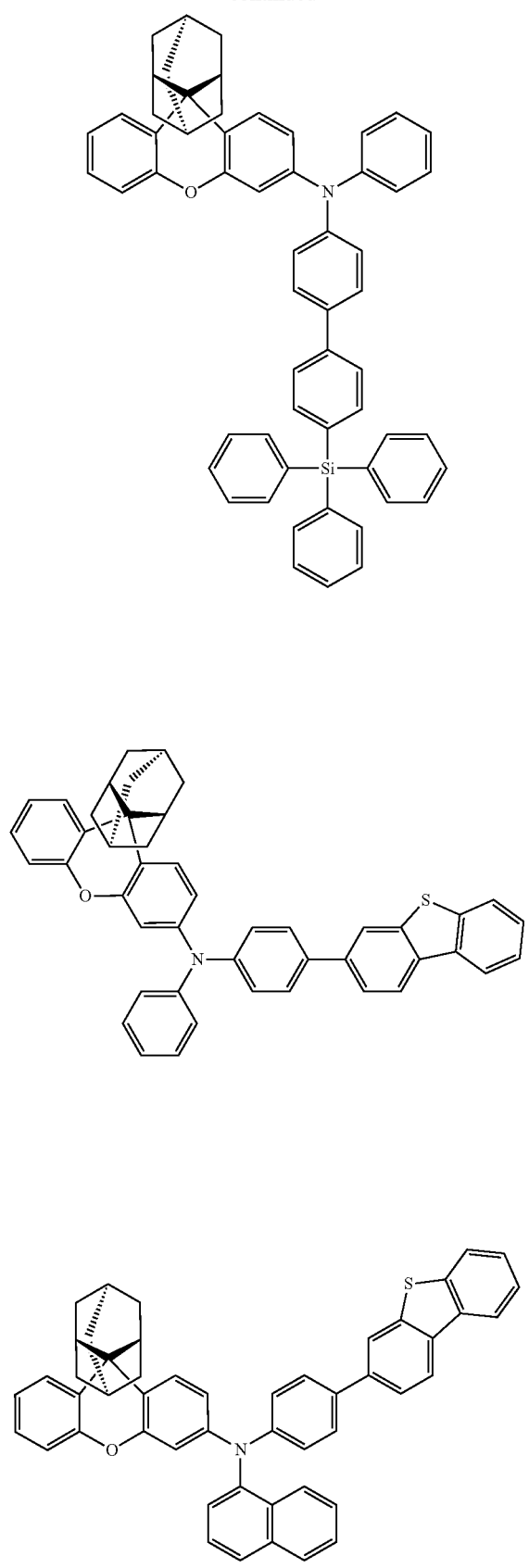
52
-continued
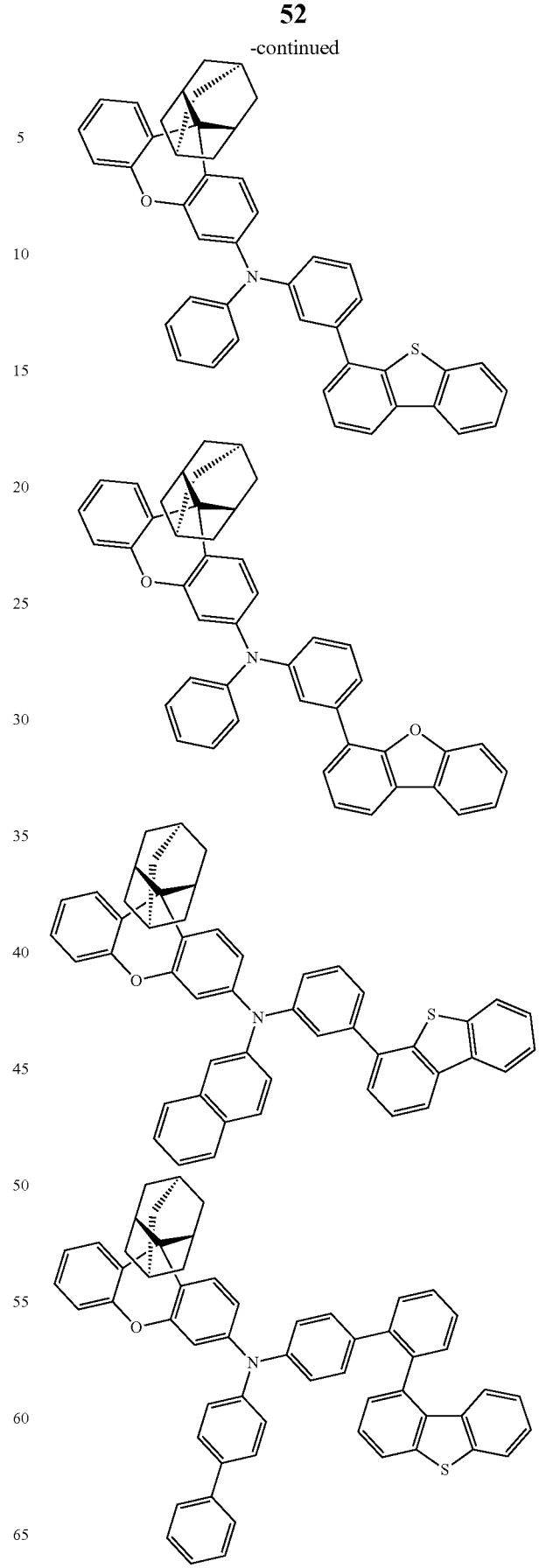

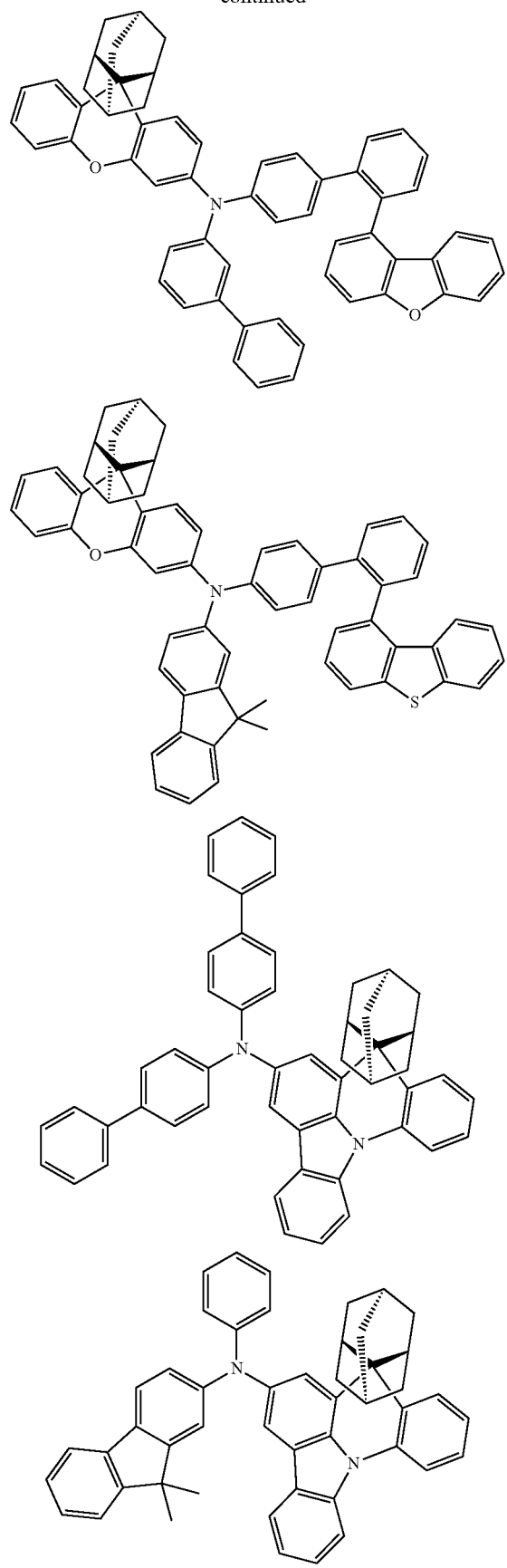
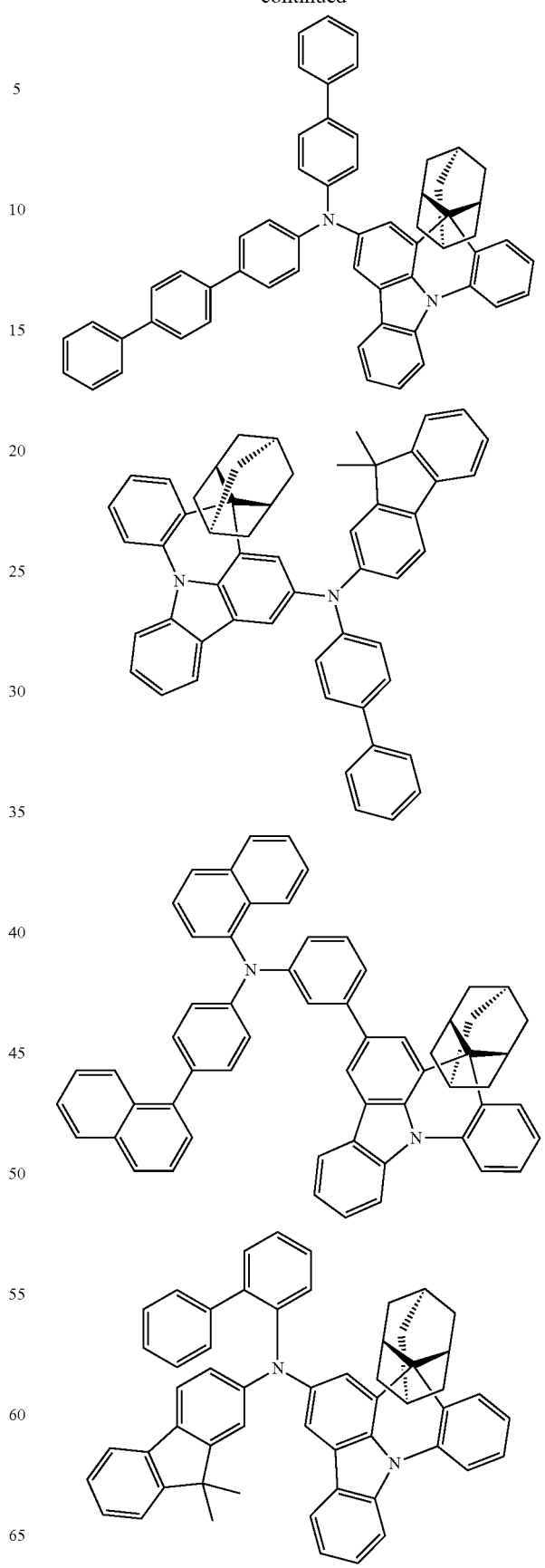

-continued
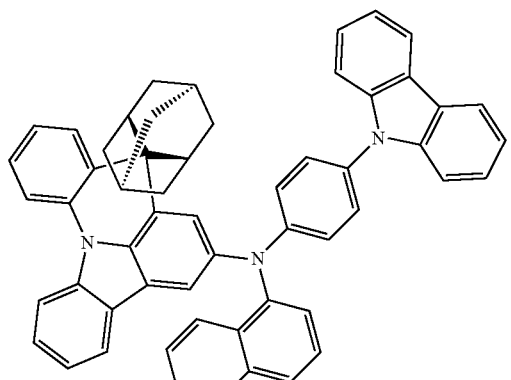
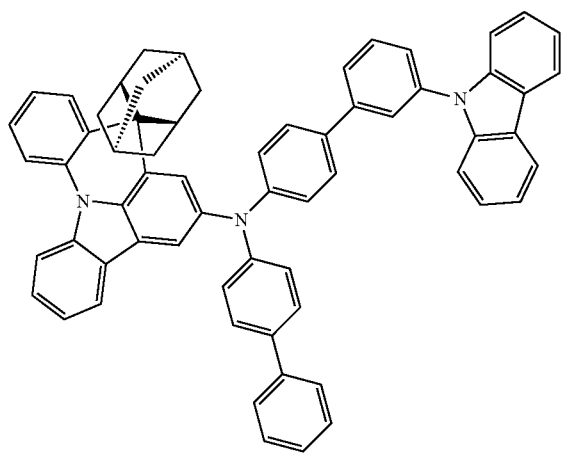
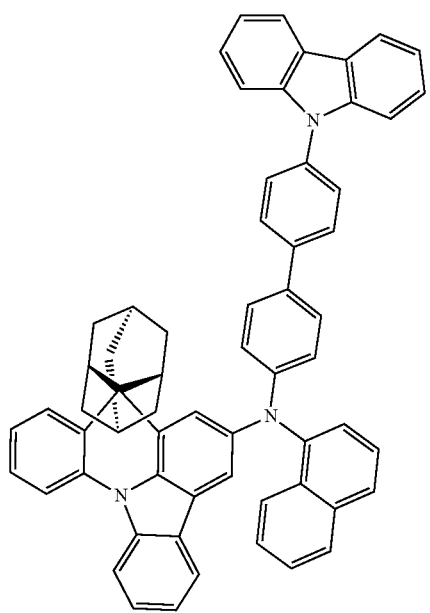
-continued
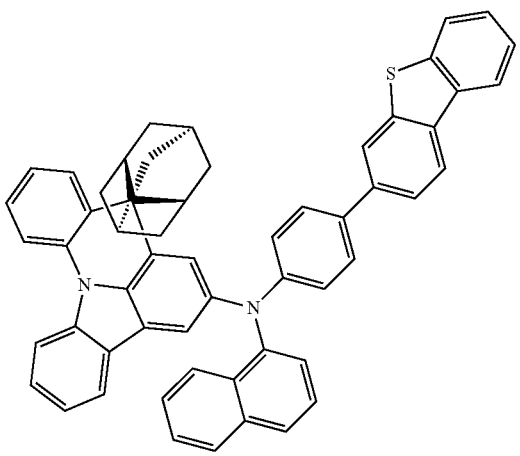
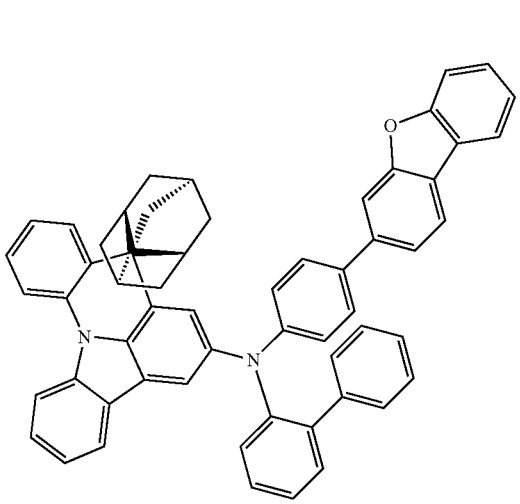
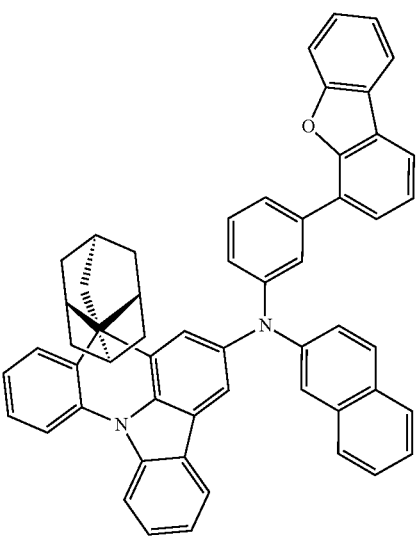

57
-continued
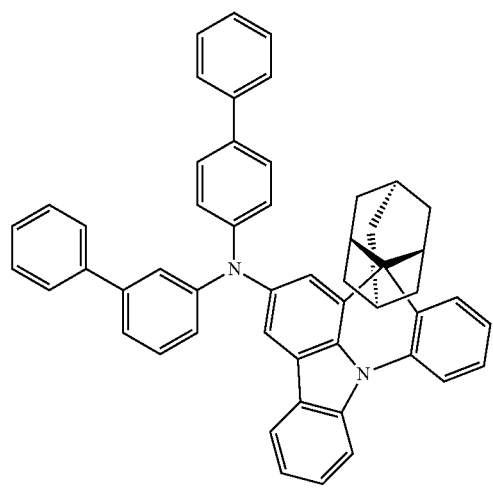
58
-continued
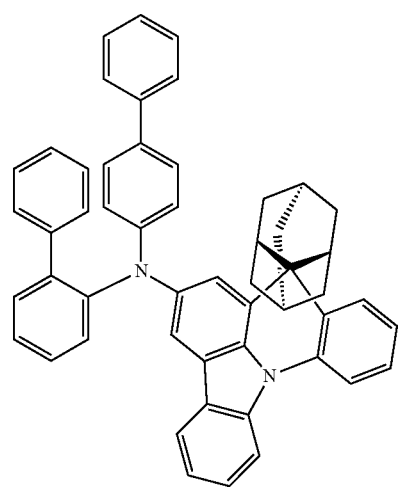
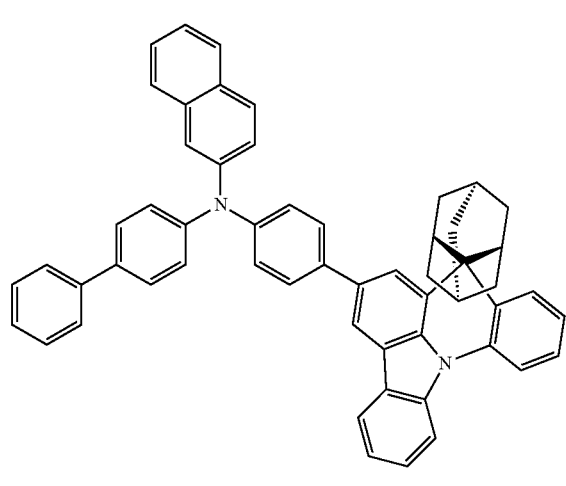
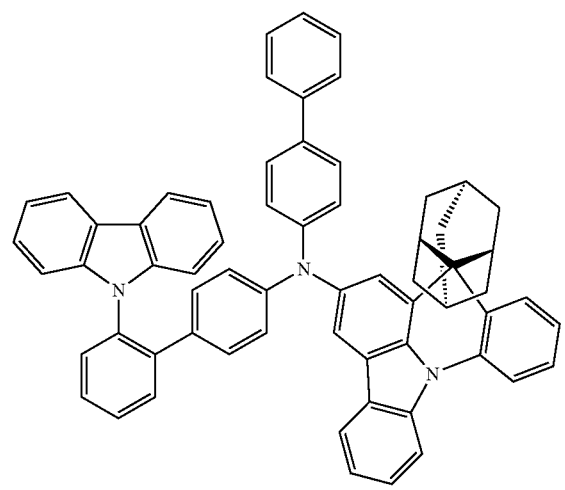
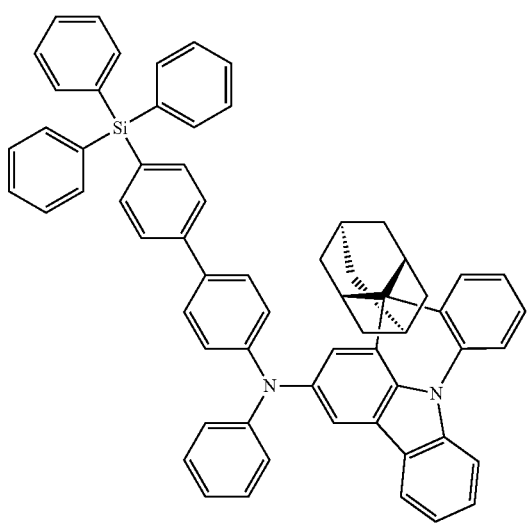
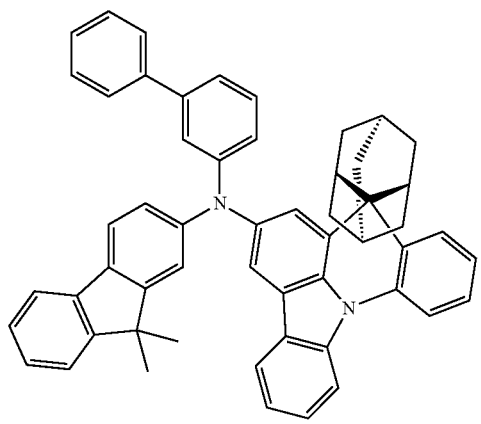

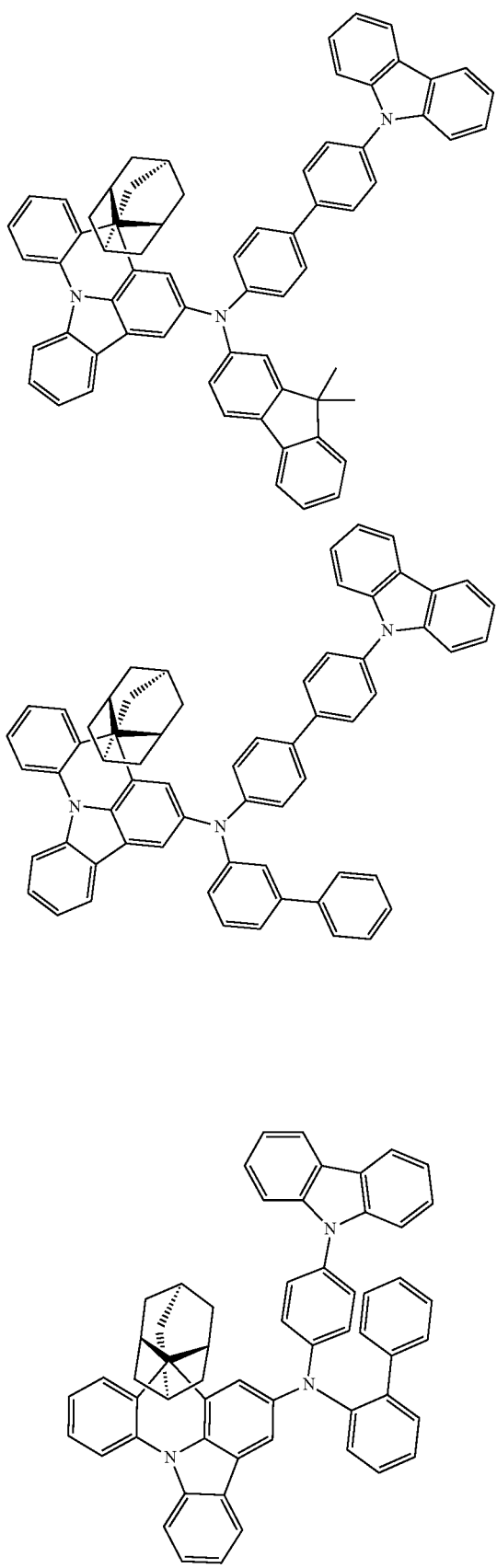
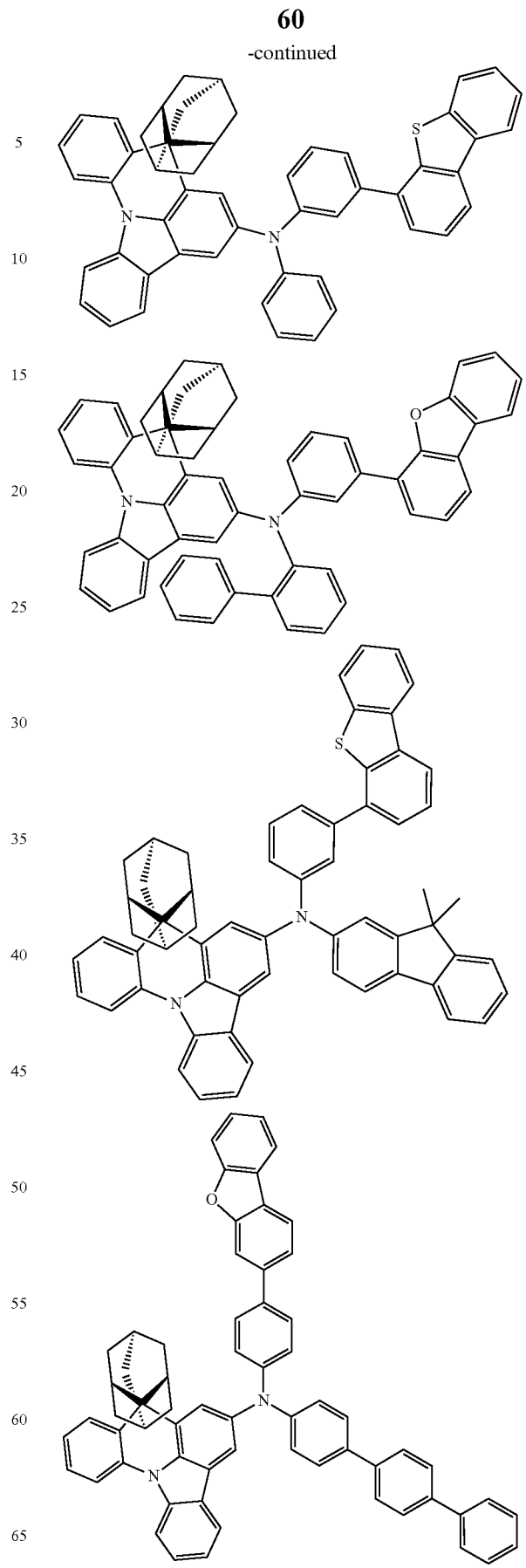

61
-continued
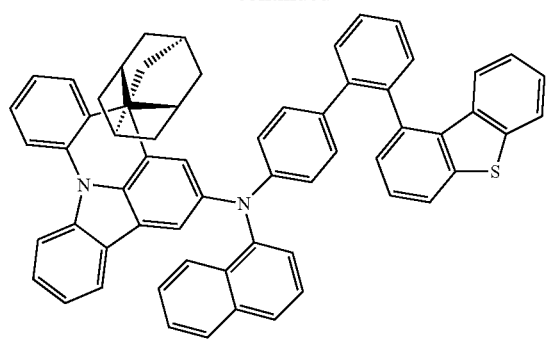
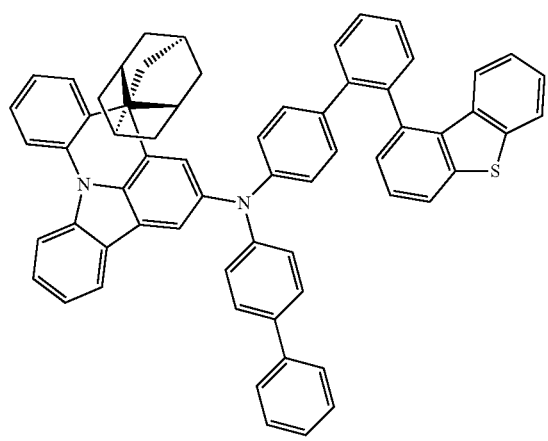
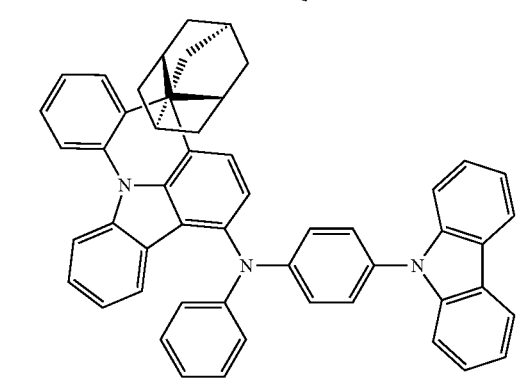
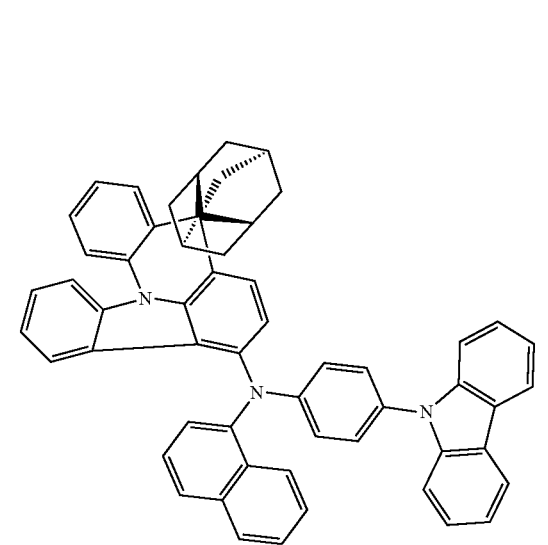
62
-continued
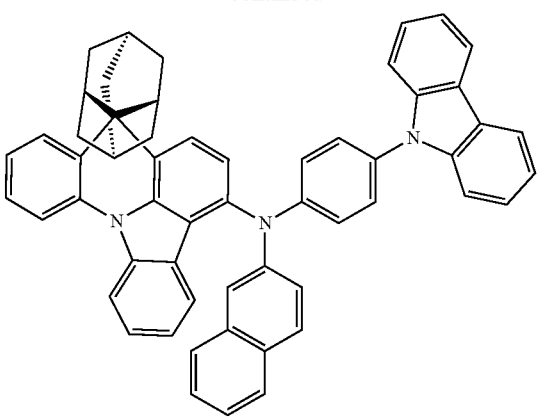
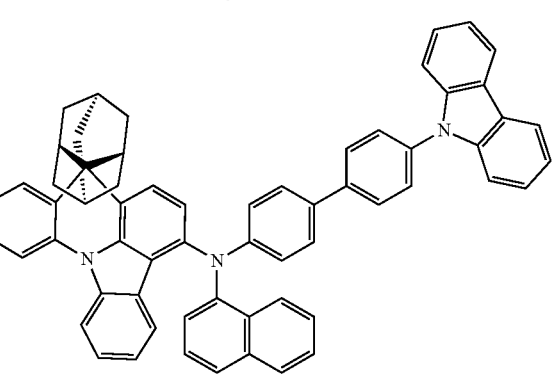
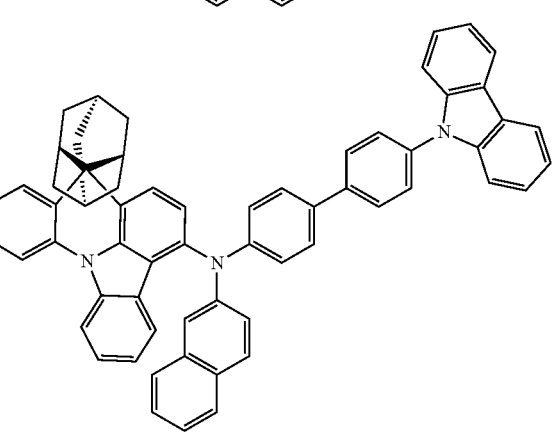

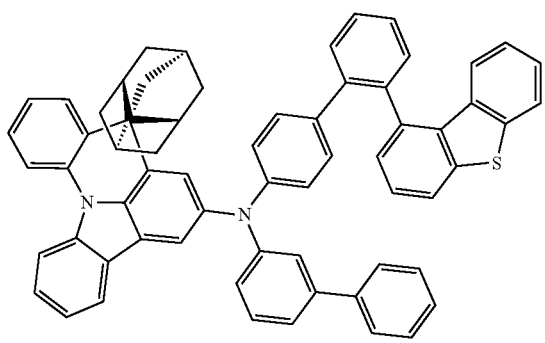
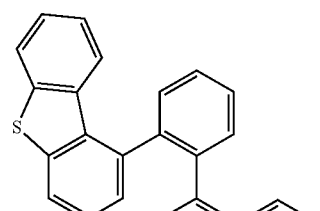
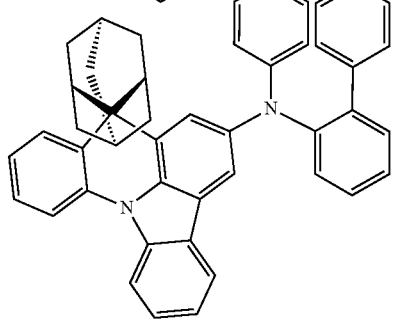
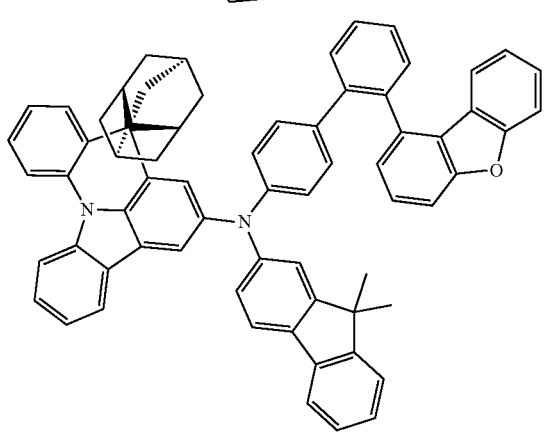
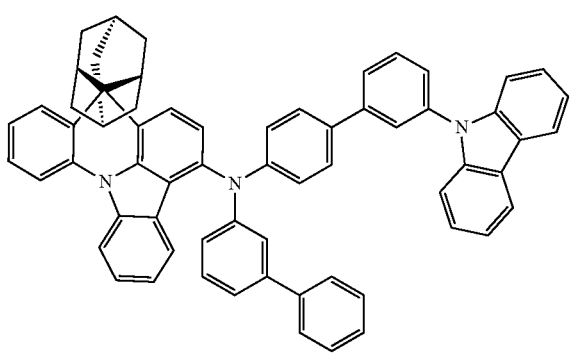
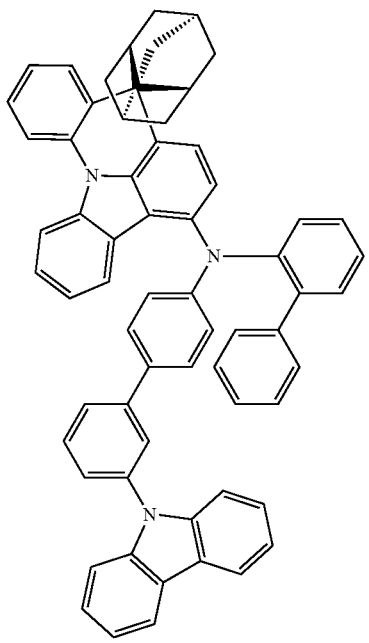
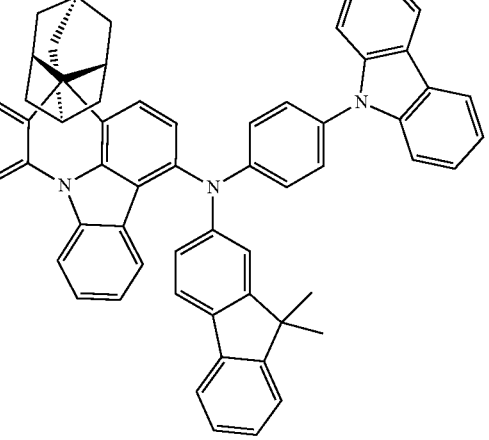
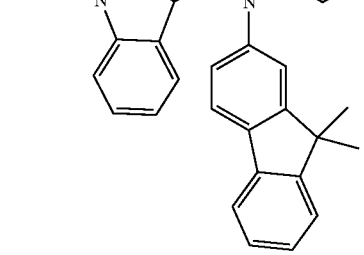
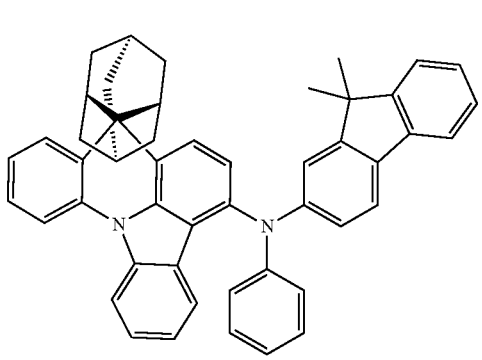

65
-continued
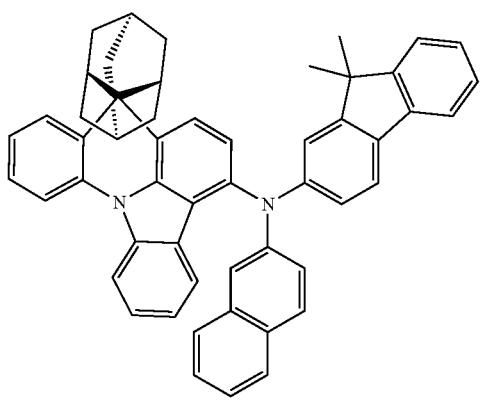
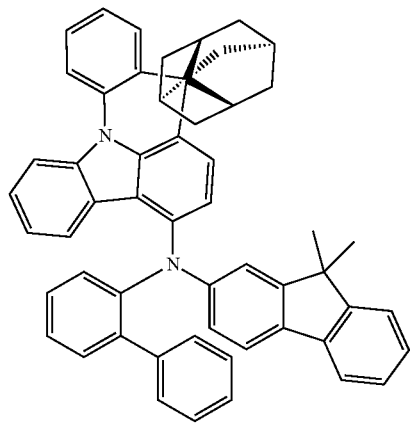
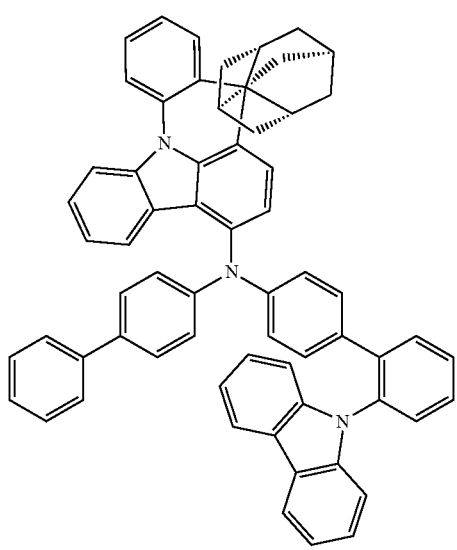
66
-continued
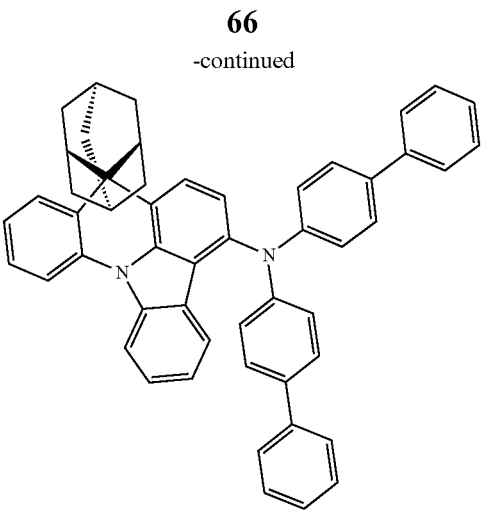
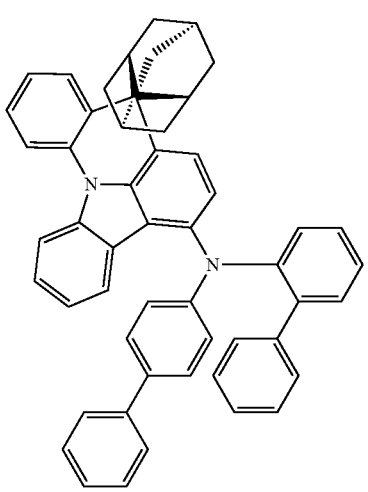
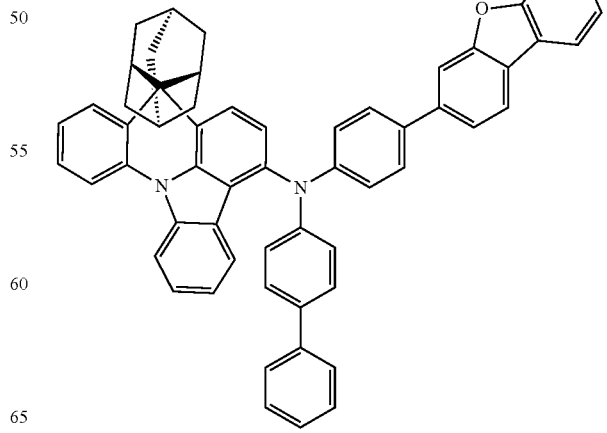

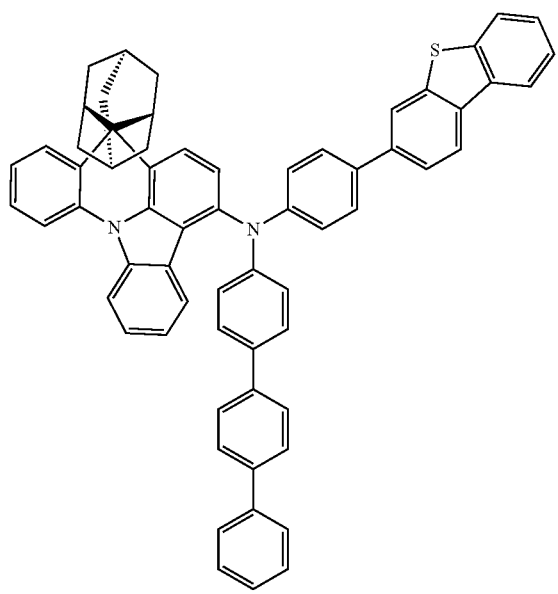
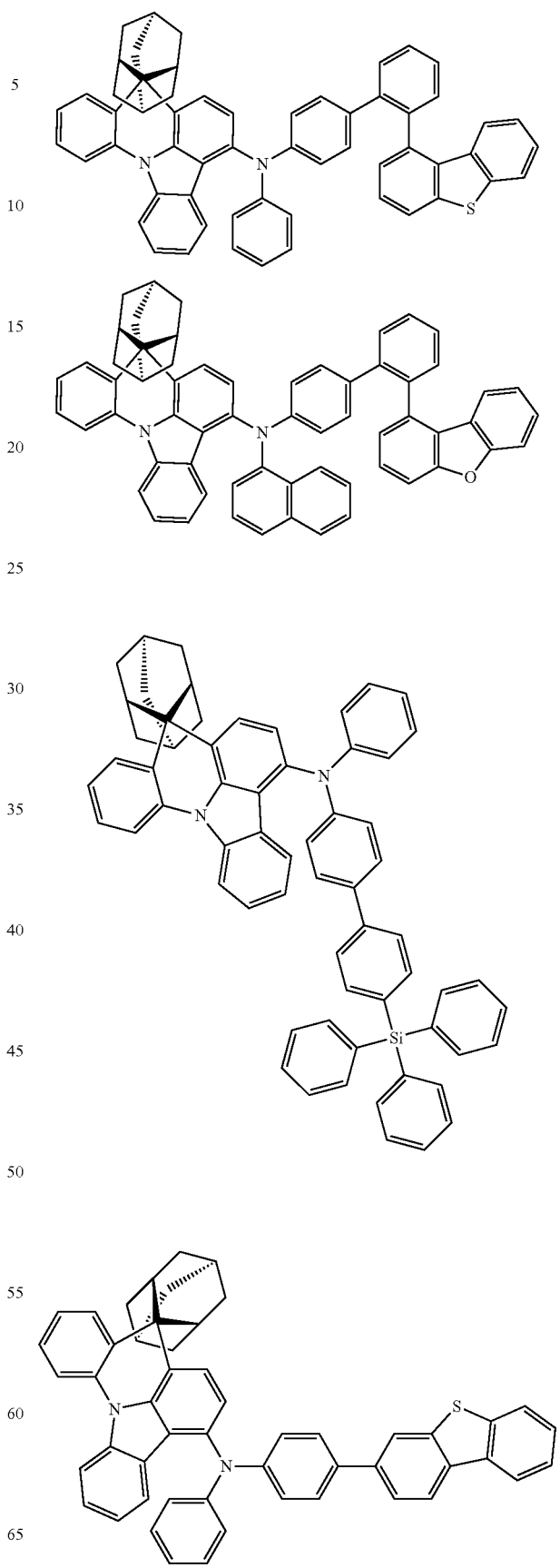

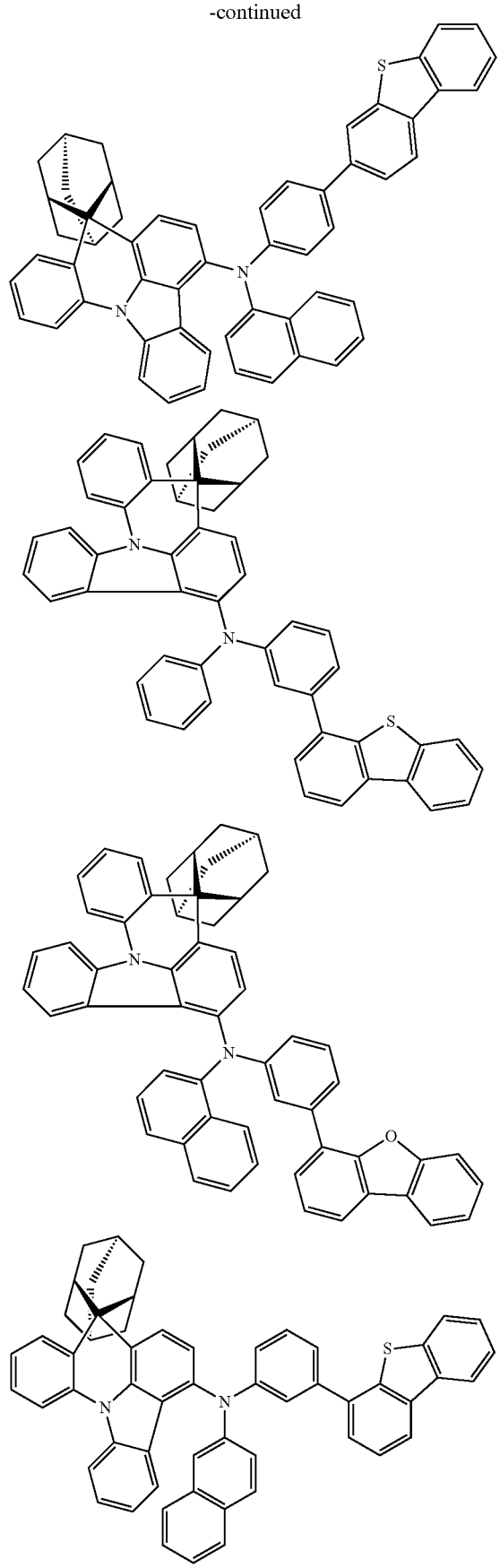
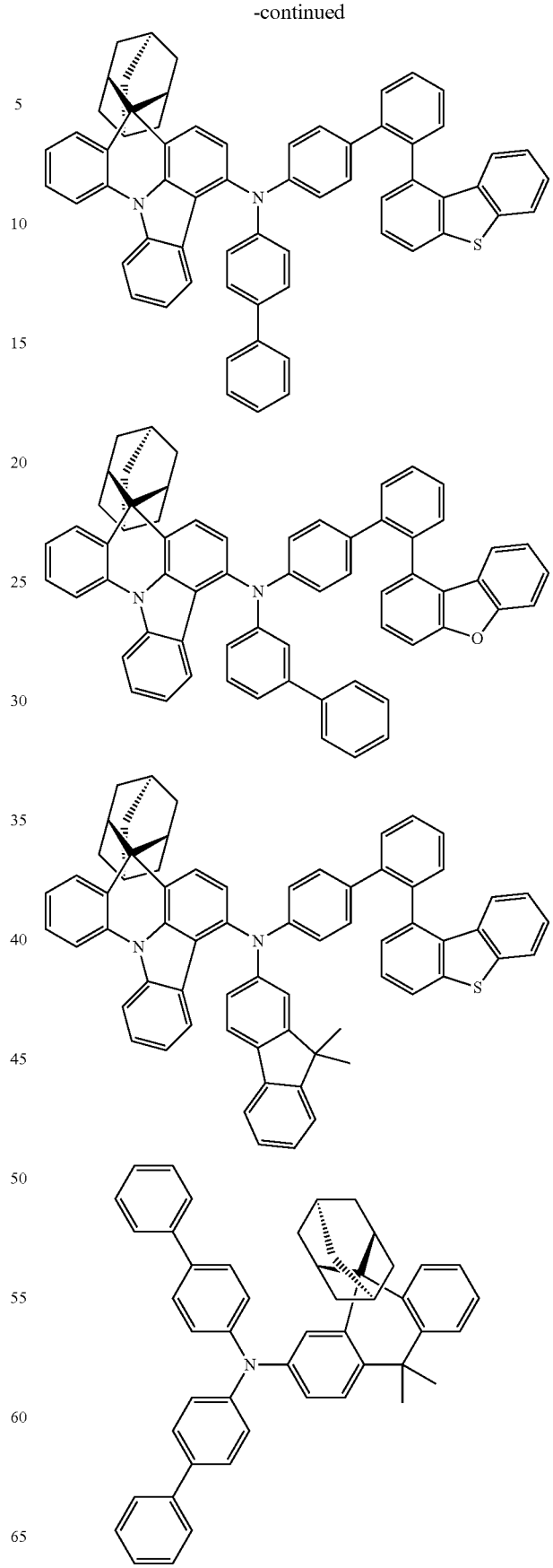

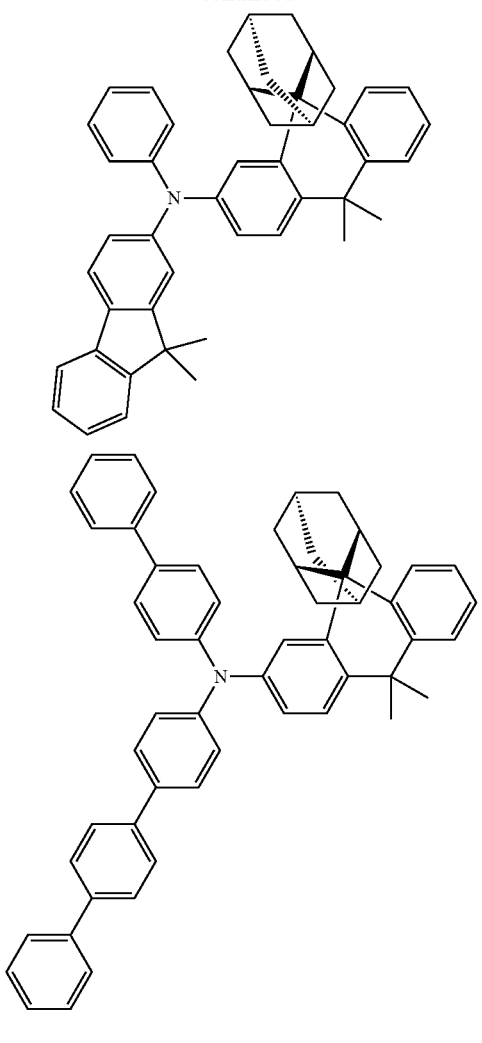
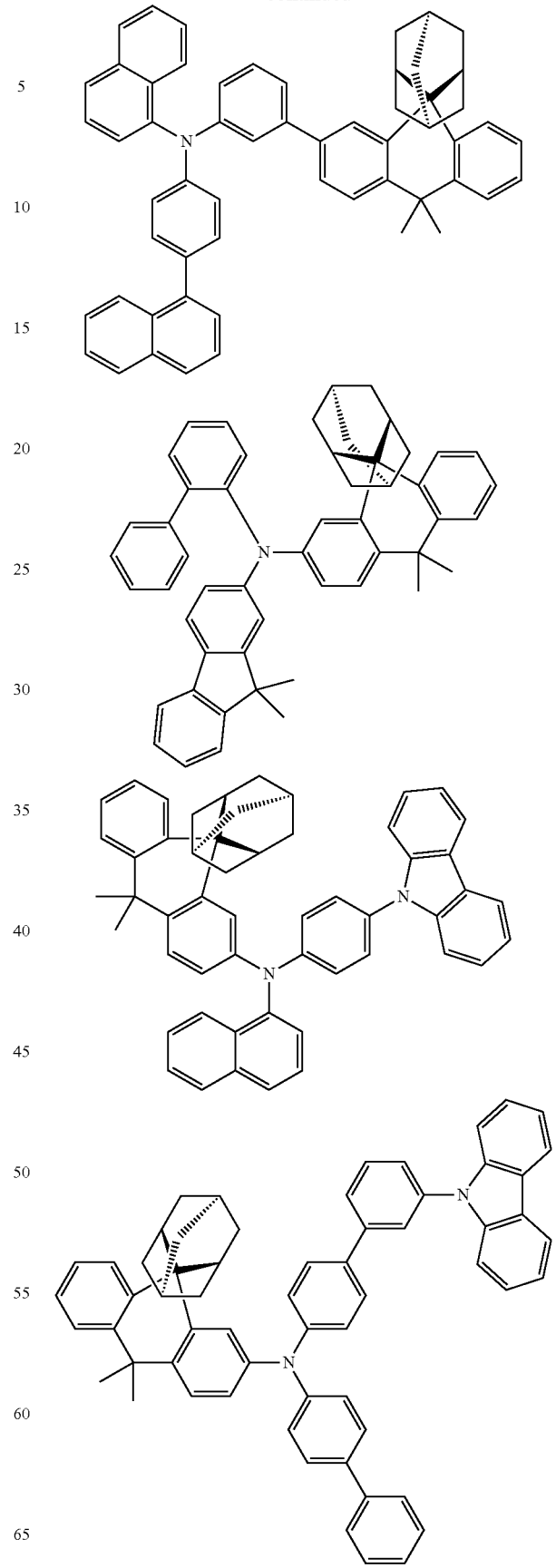

73
-continued
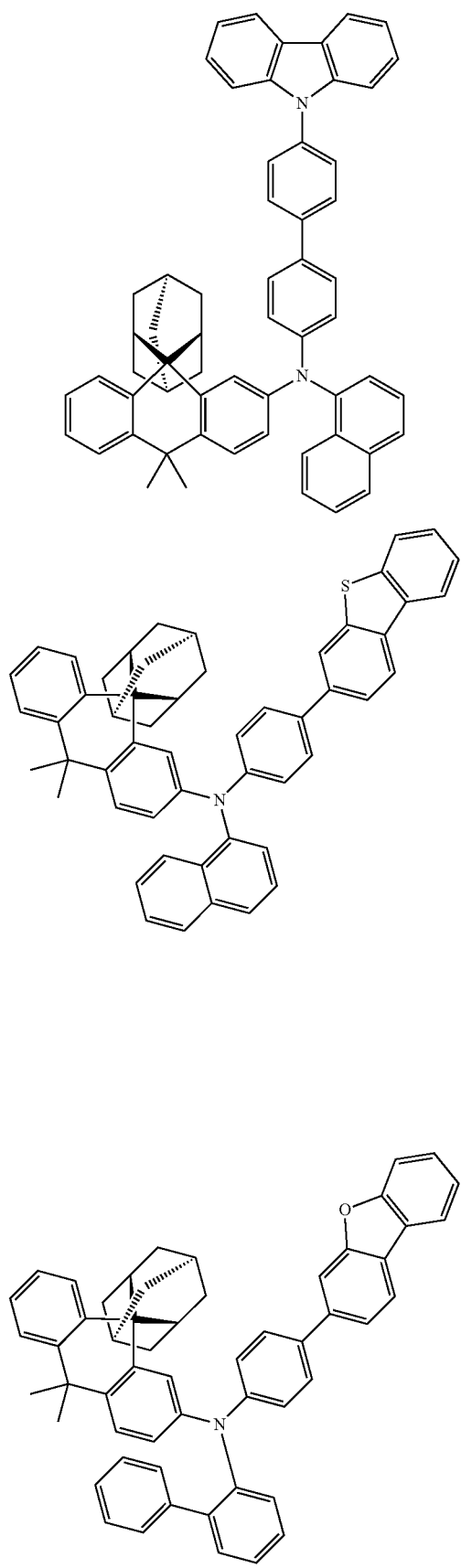
74
-continued
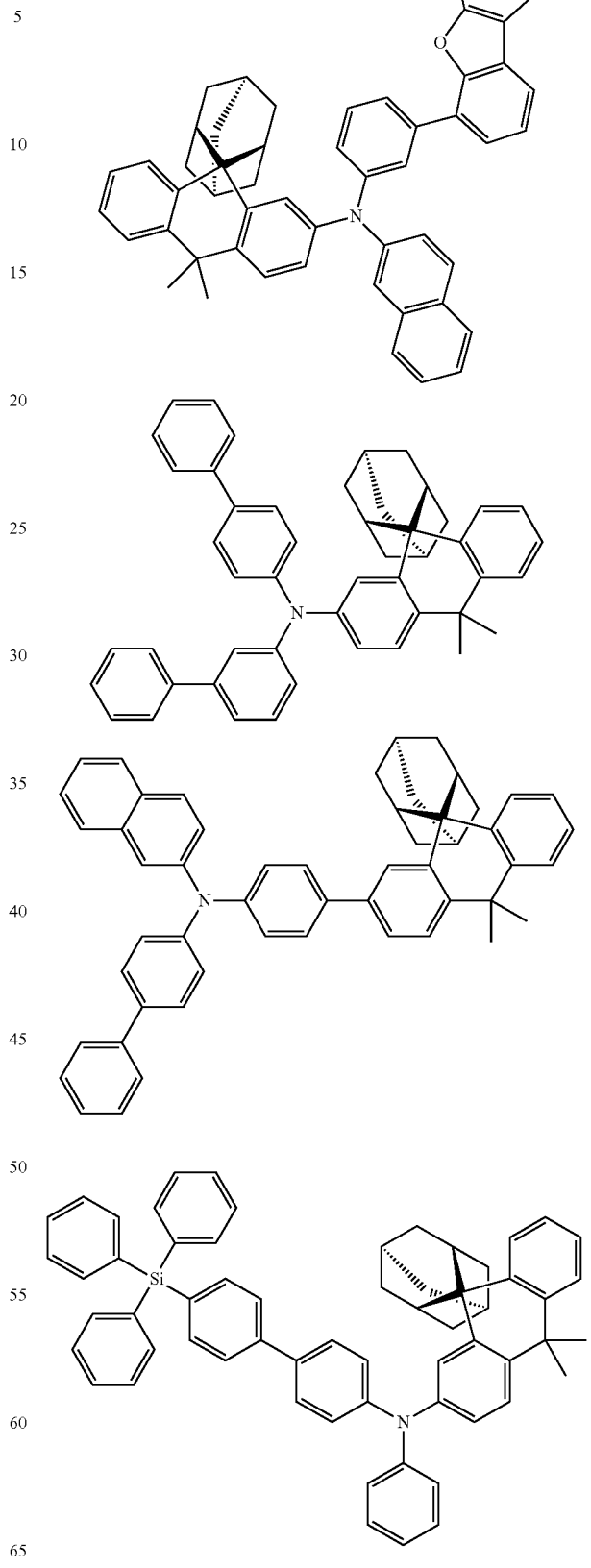

75
-continued
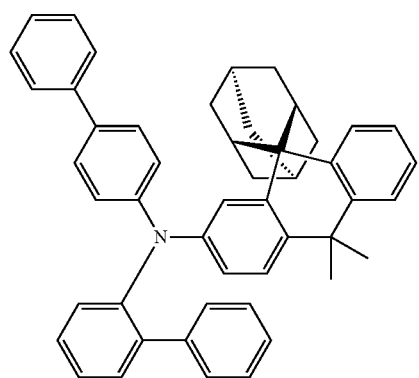
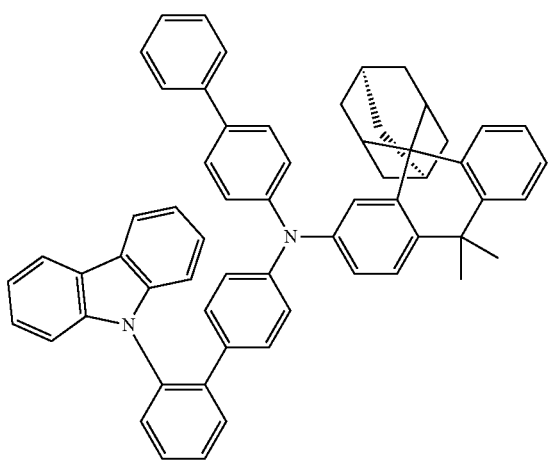
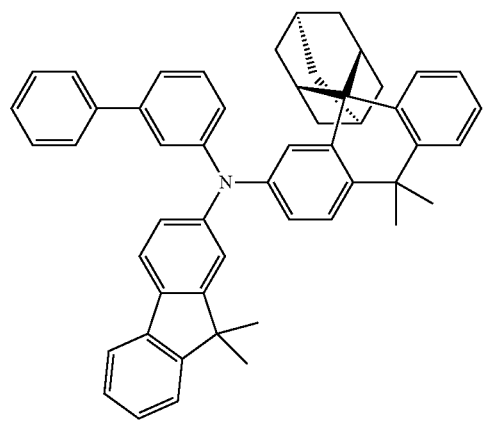
76
-continued
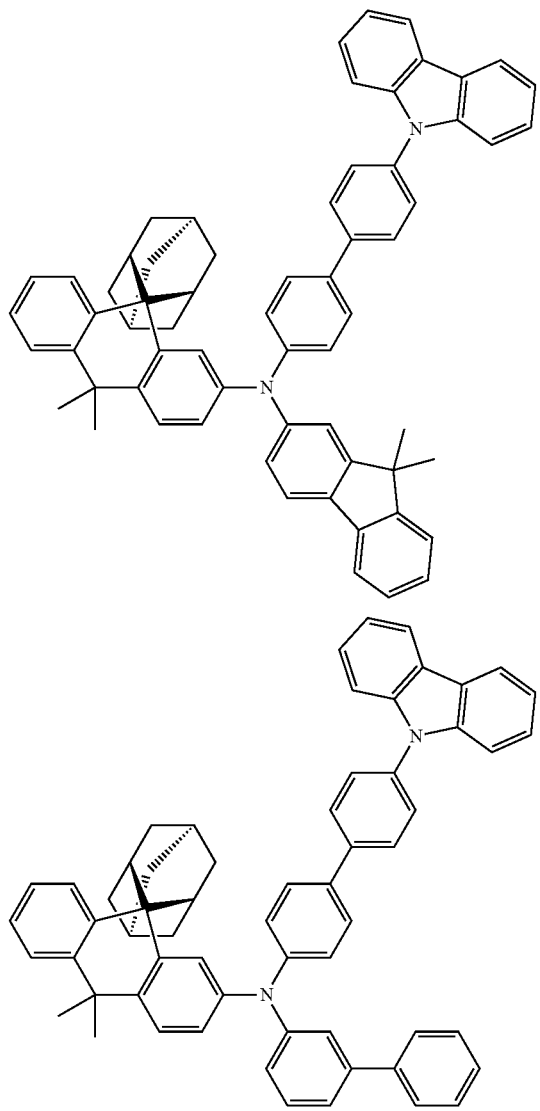
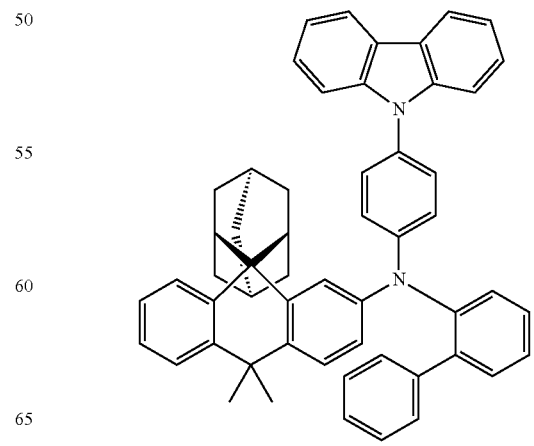

77
-continued
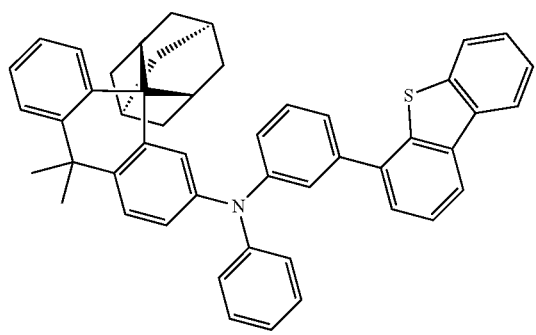
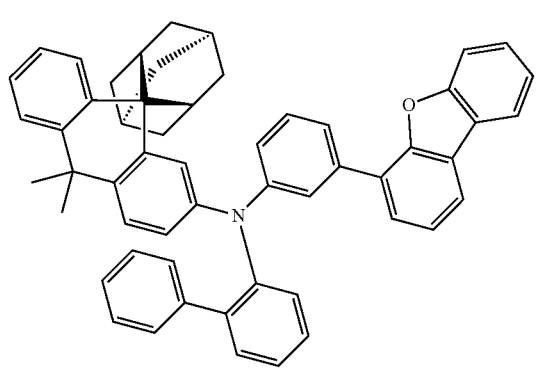
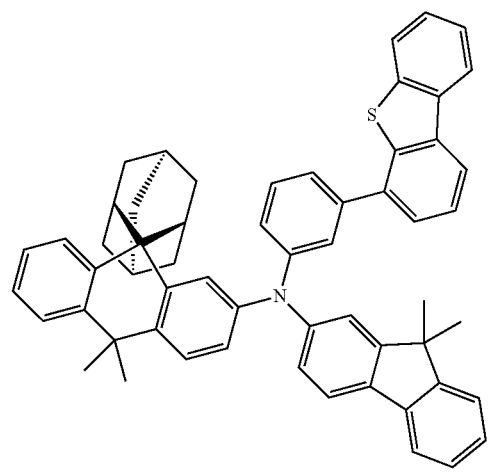
78
-continued
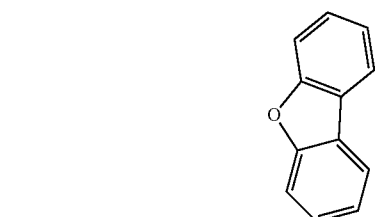
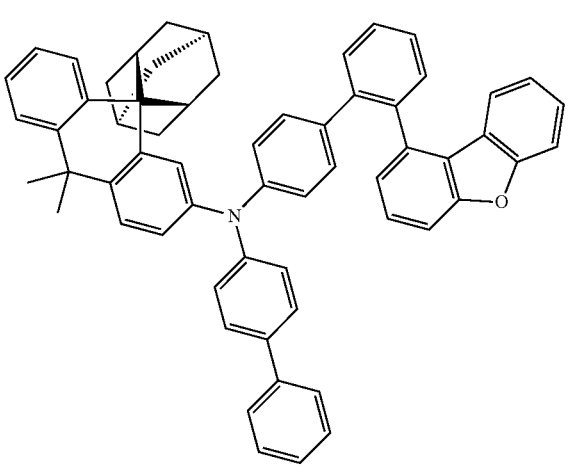

-continued
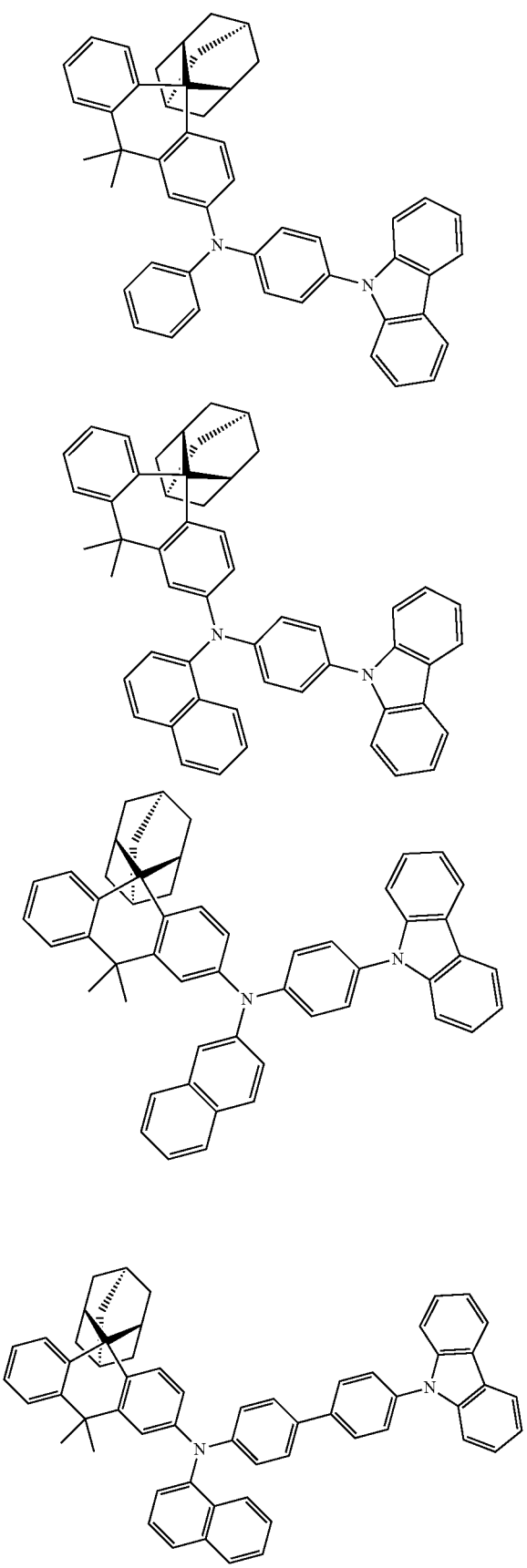
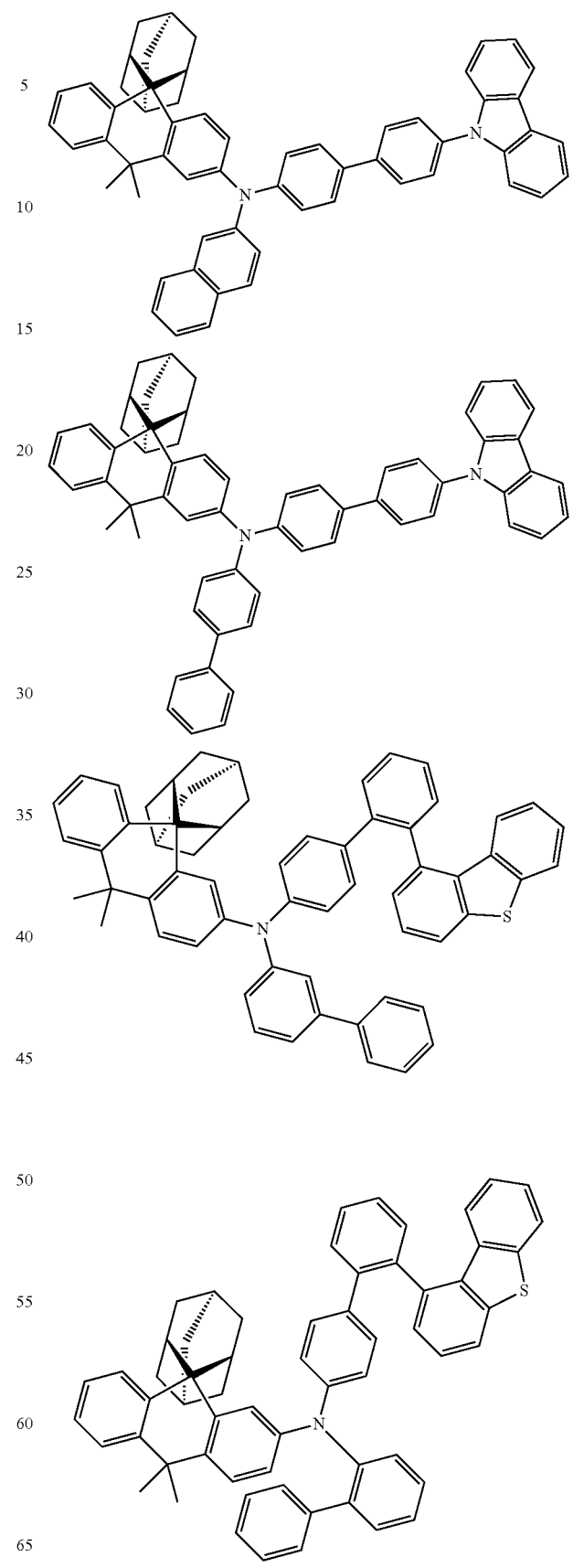

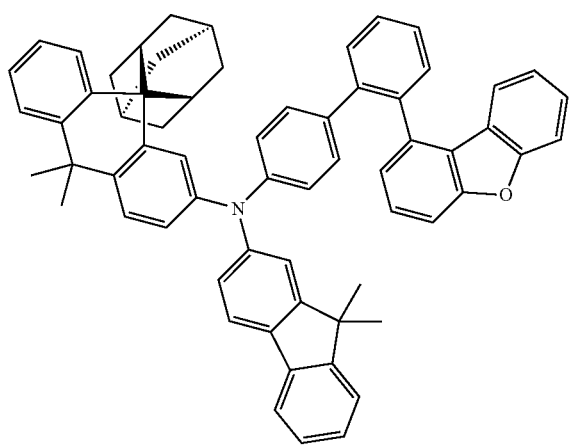
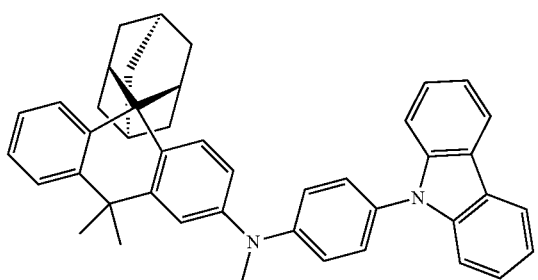
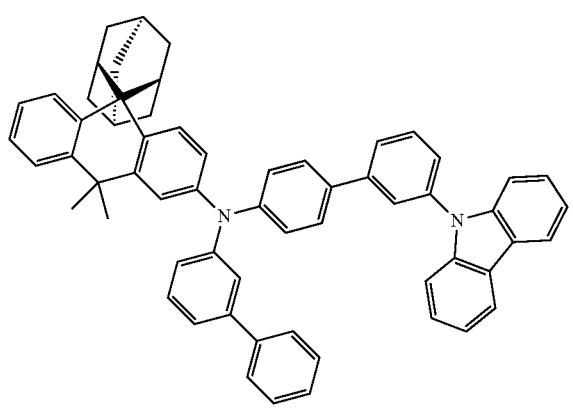
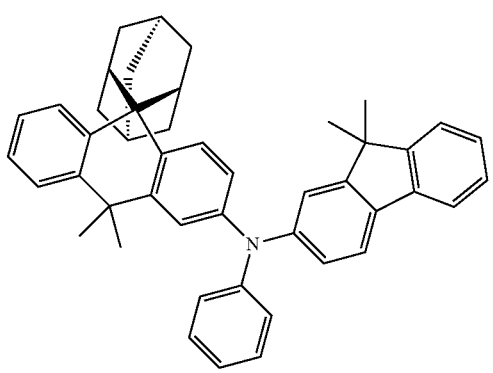
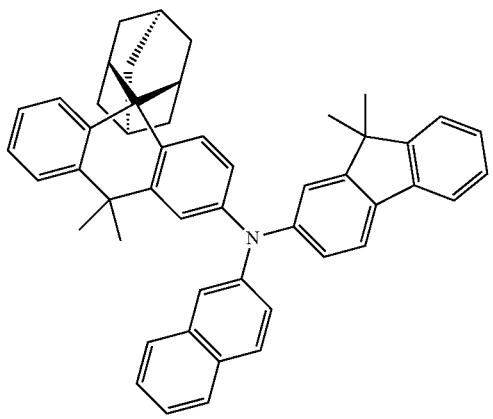
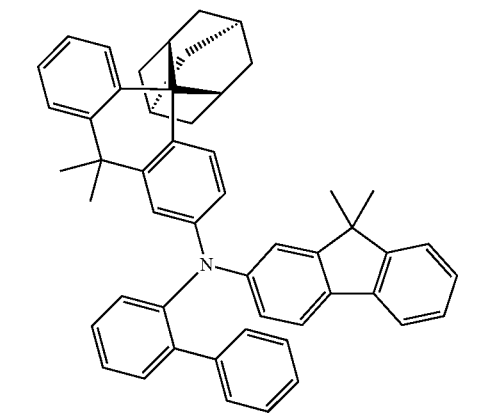

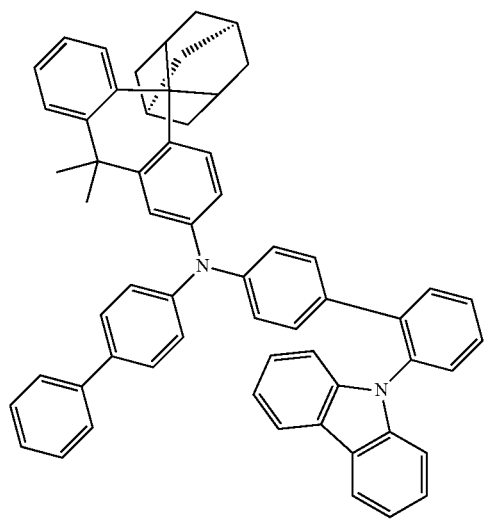
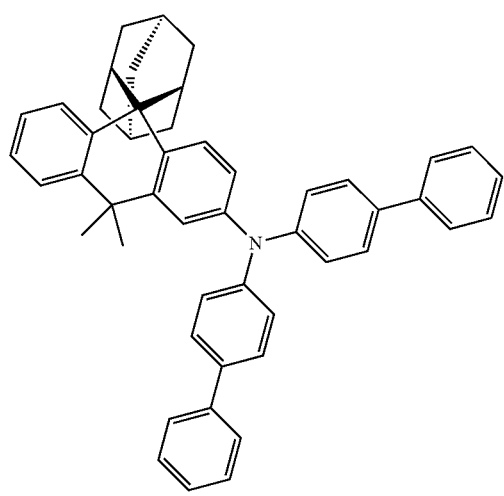
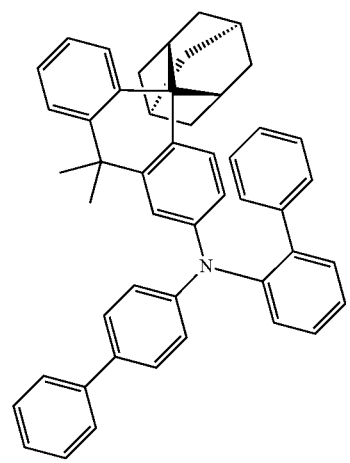
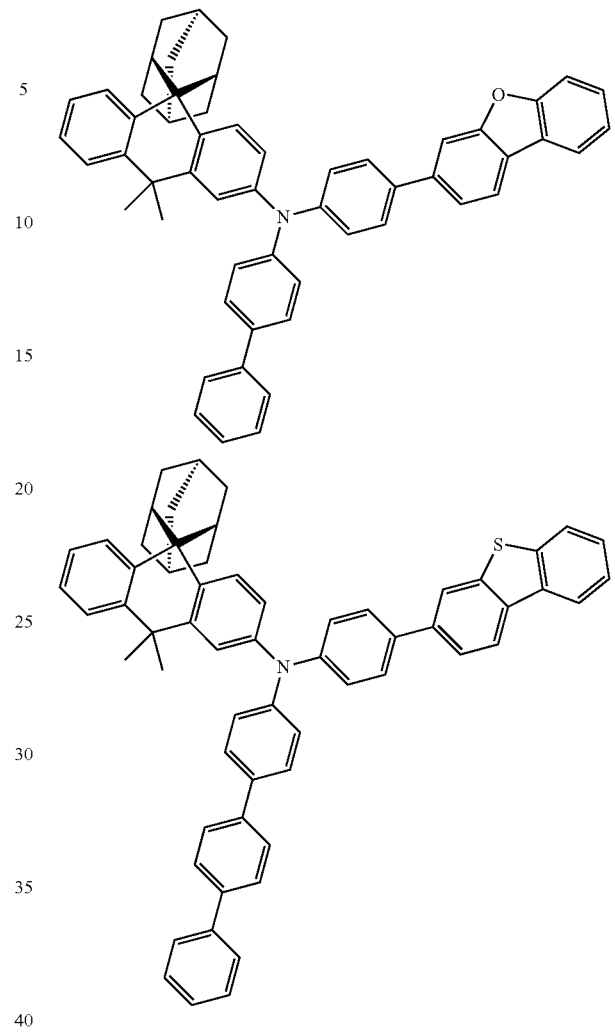
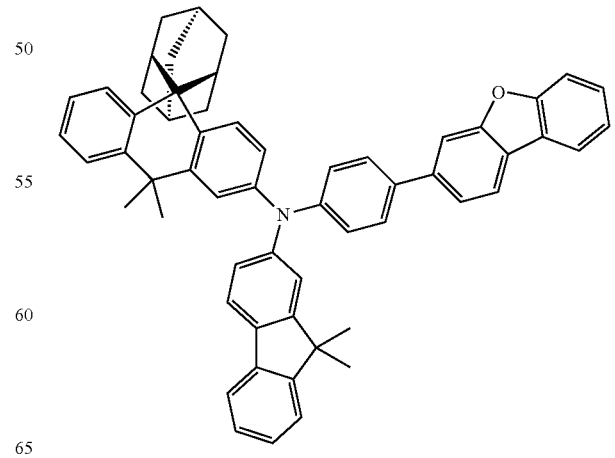

85
-continued
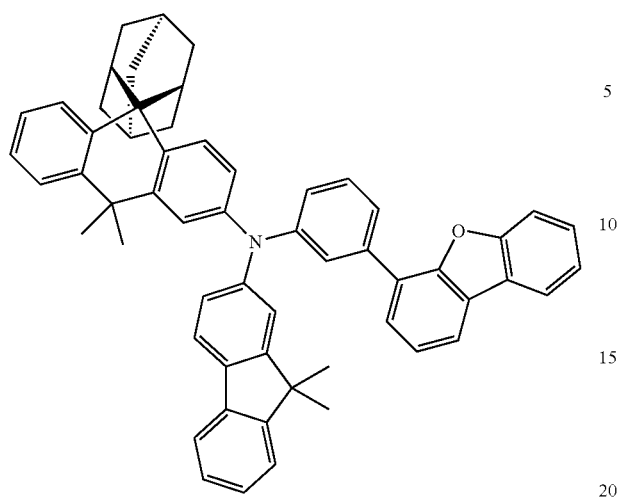
86
-continued
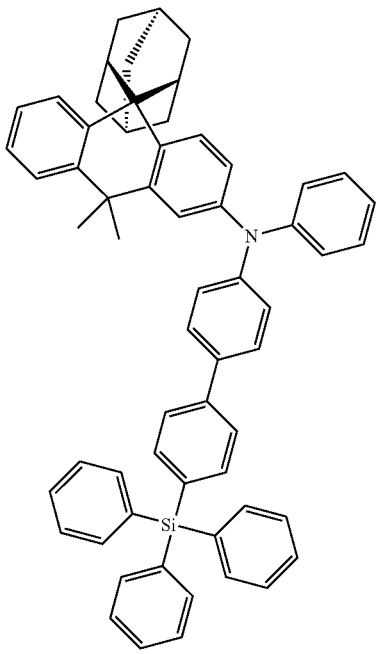
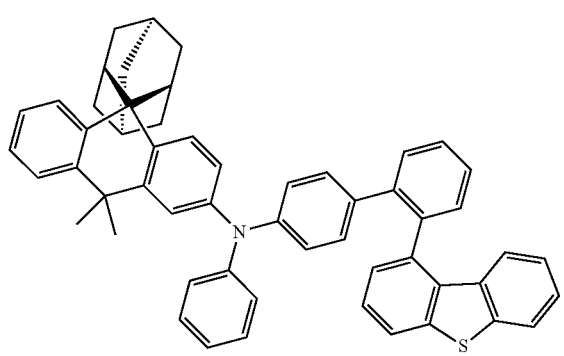
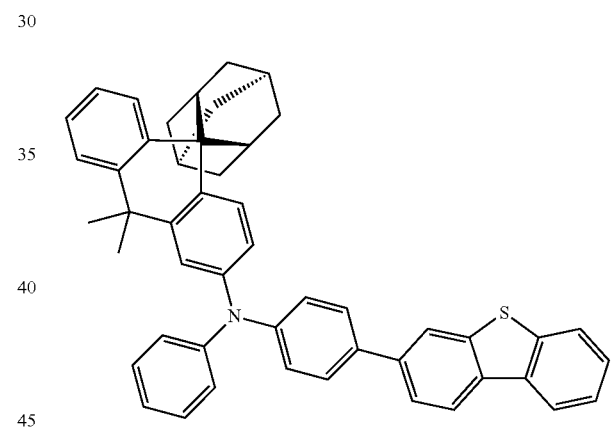
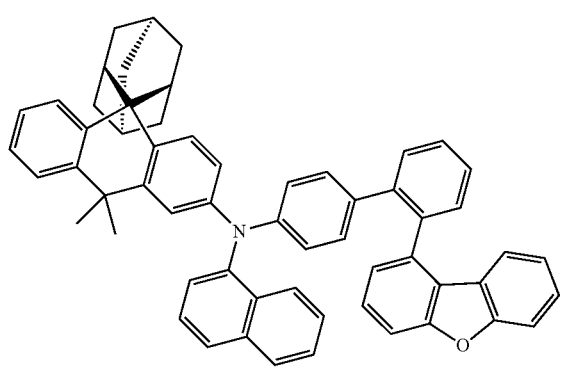
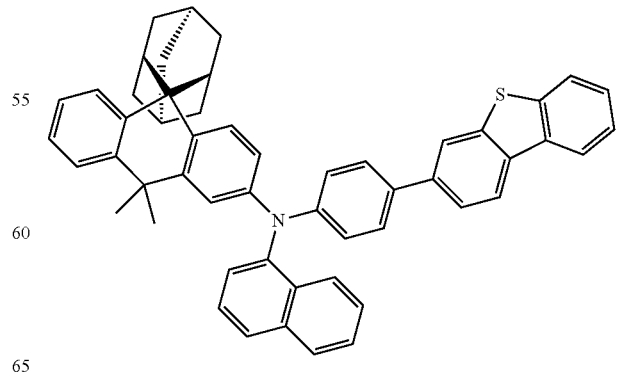

87
-continued
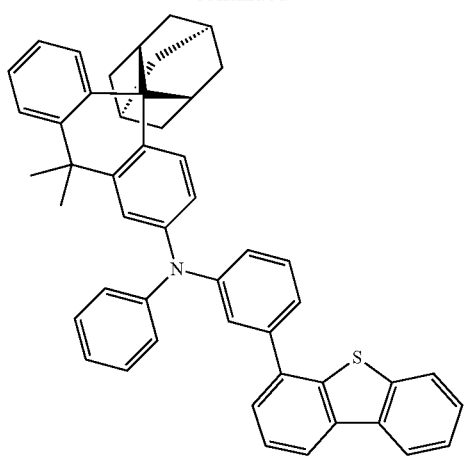
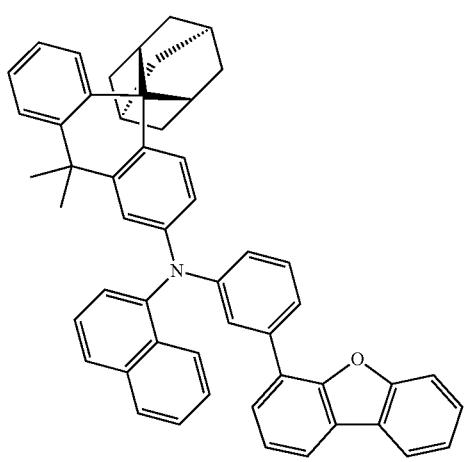
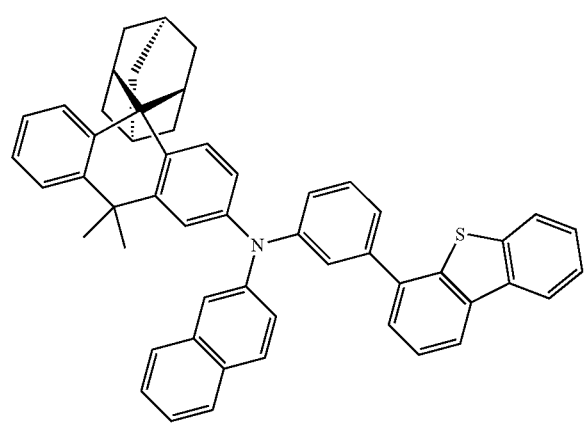
88
-continued
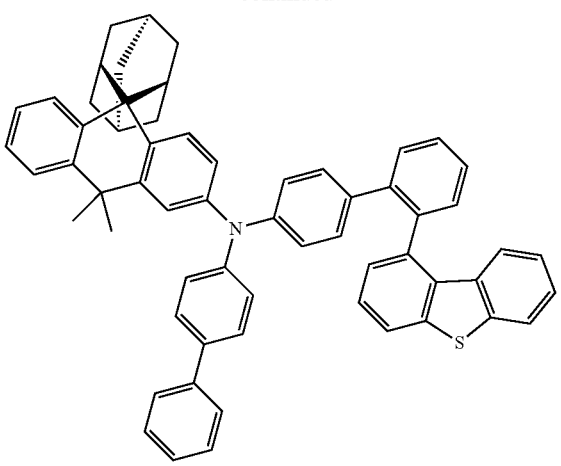
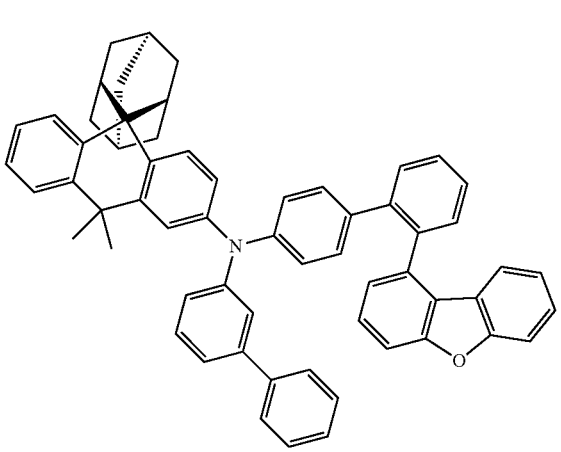

89
-continued
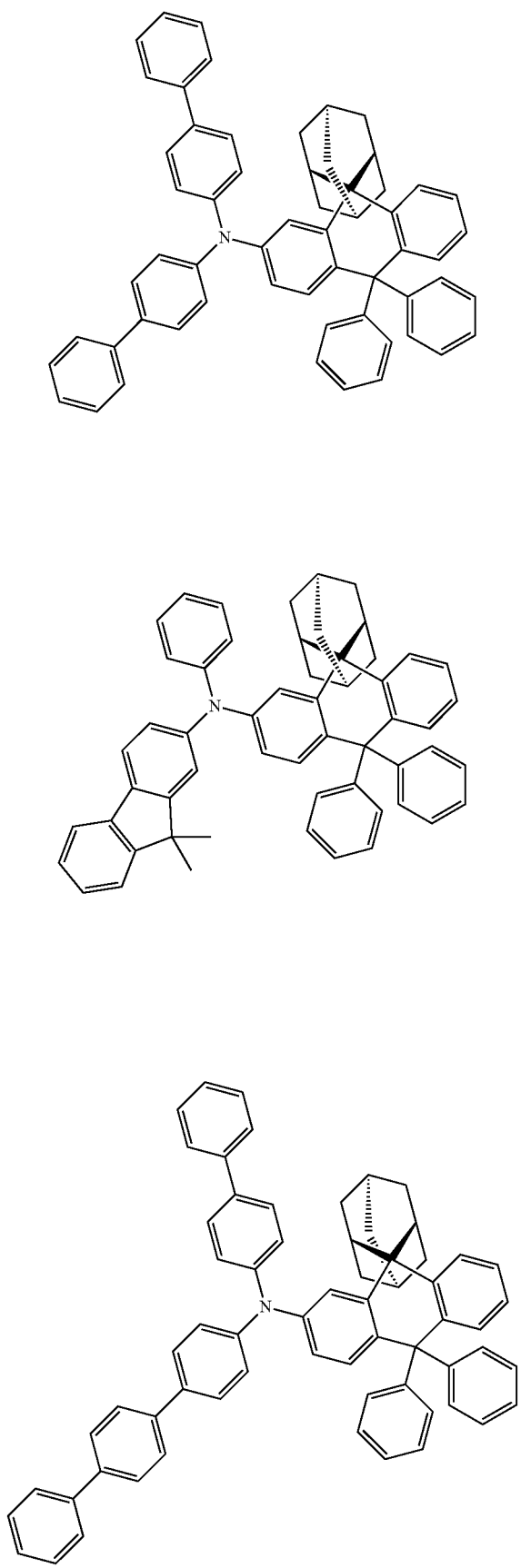
90
-continued
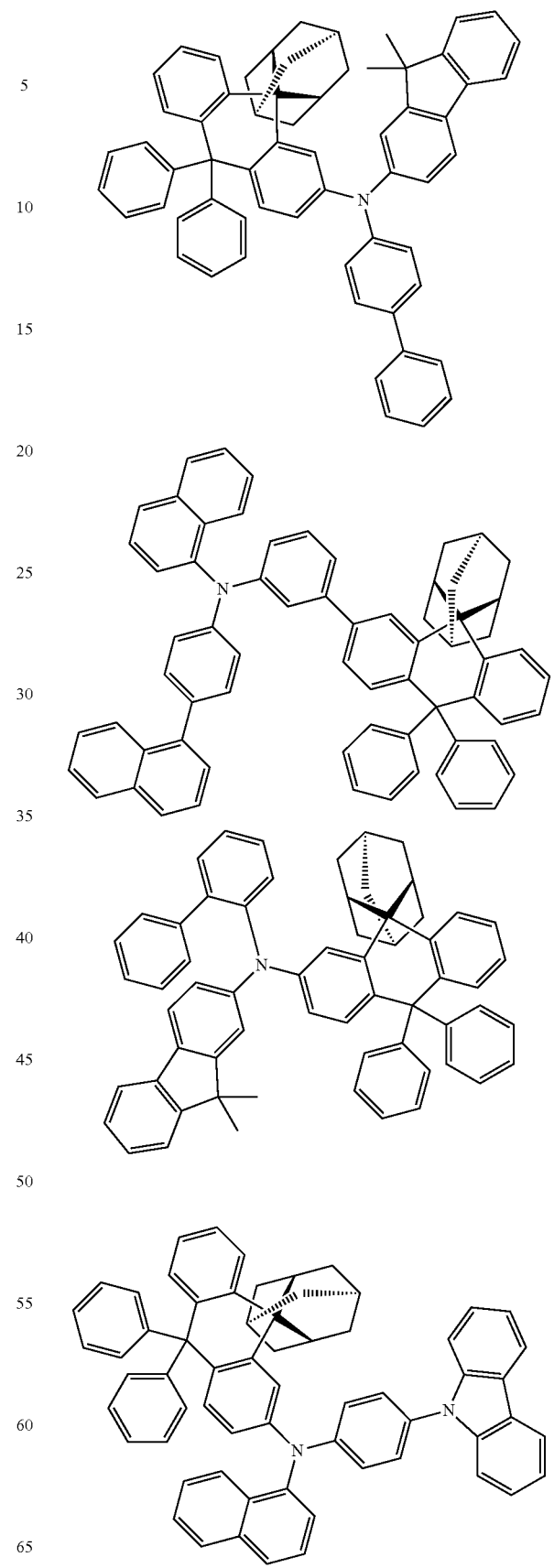

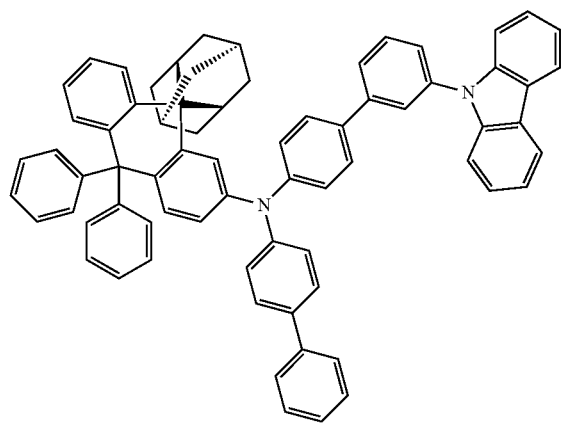
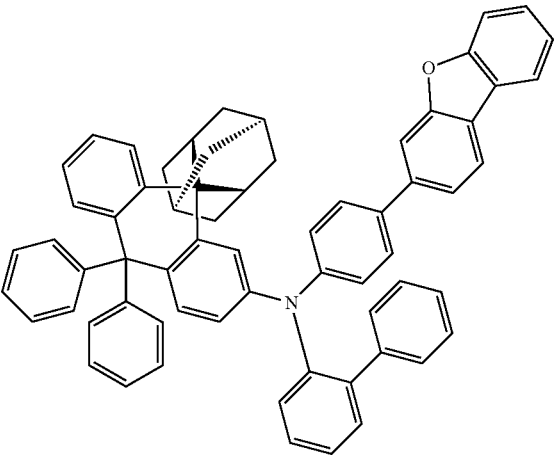
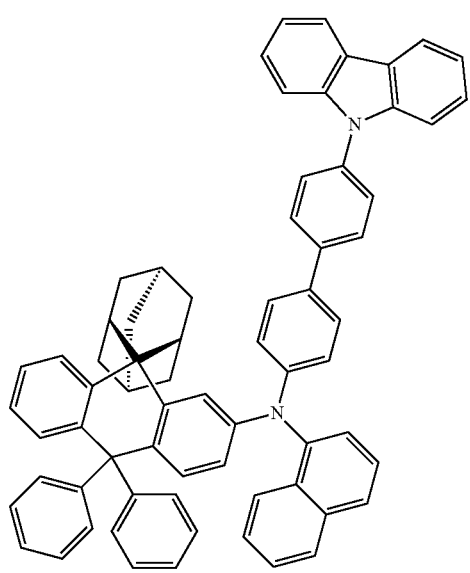
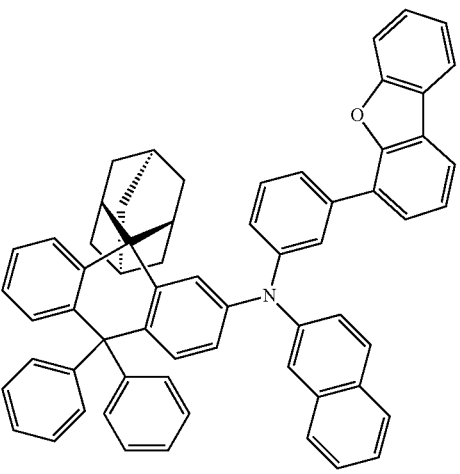
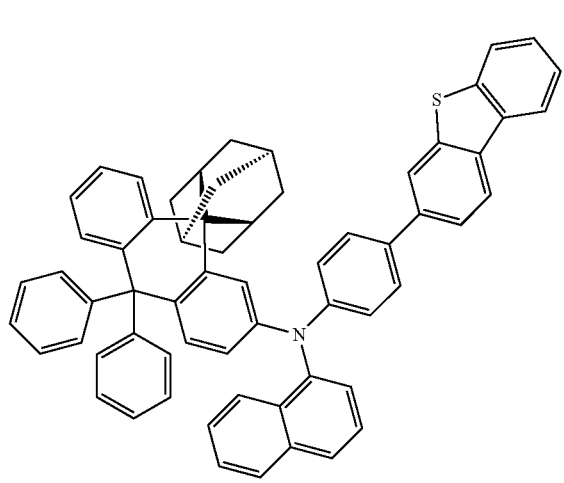
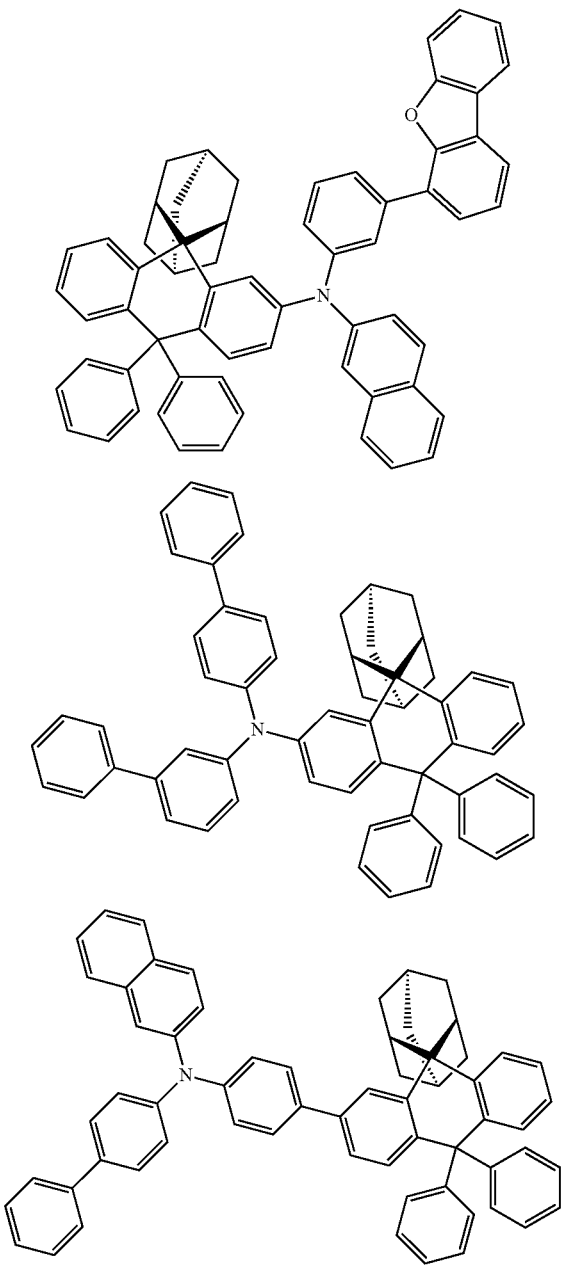

93
-continued
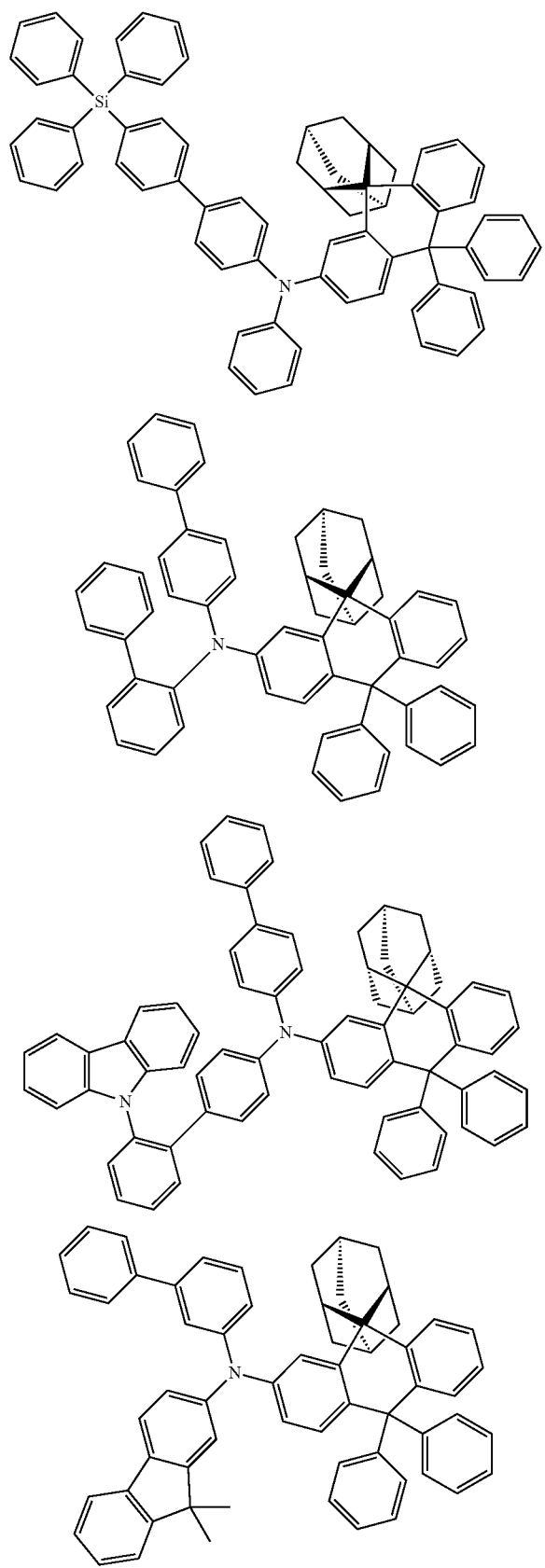
94
-continued
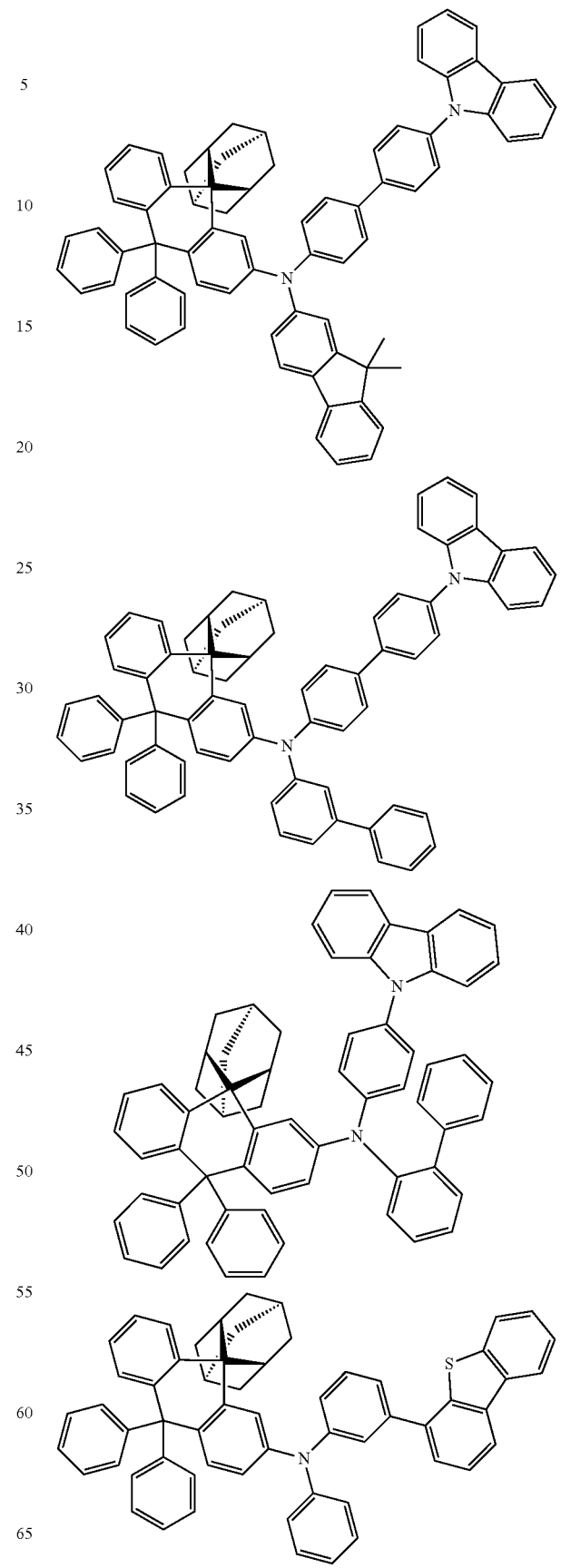

95
-continued
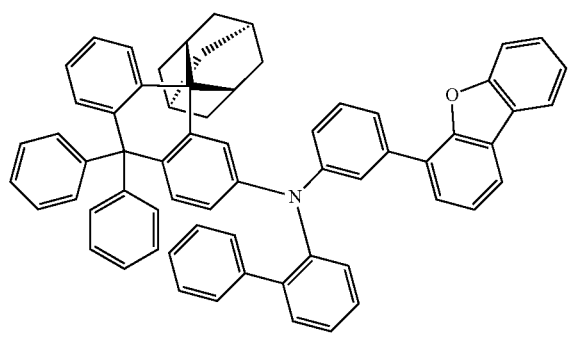
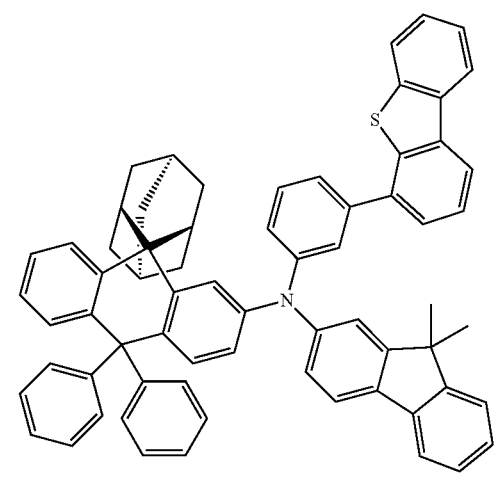
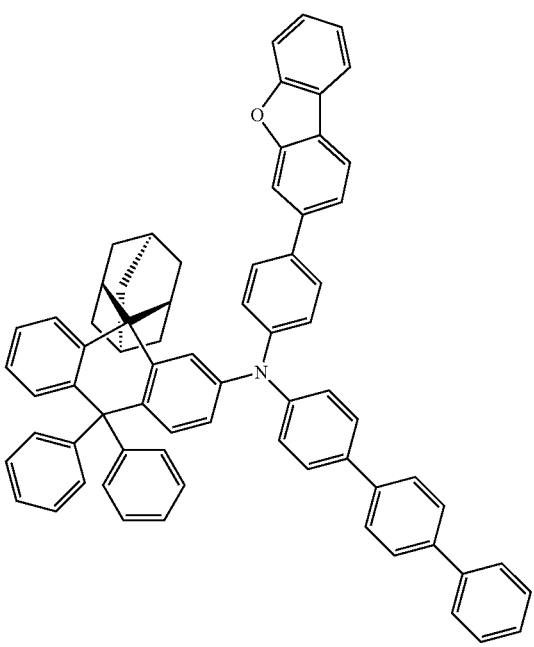
96
-continued
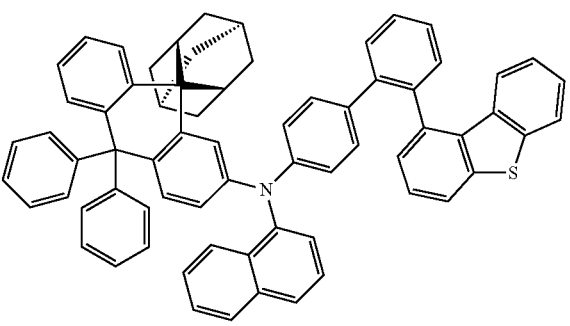
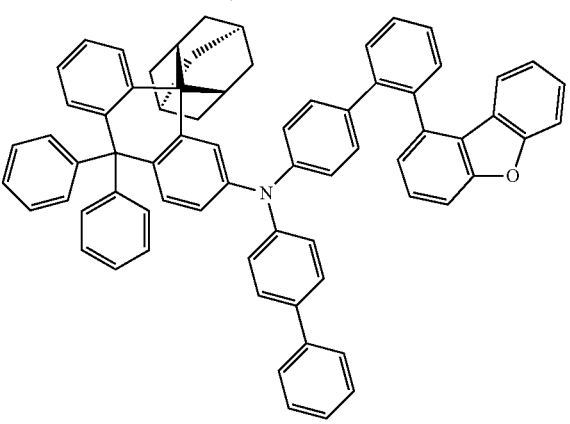
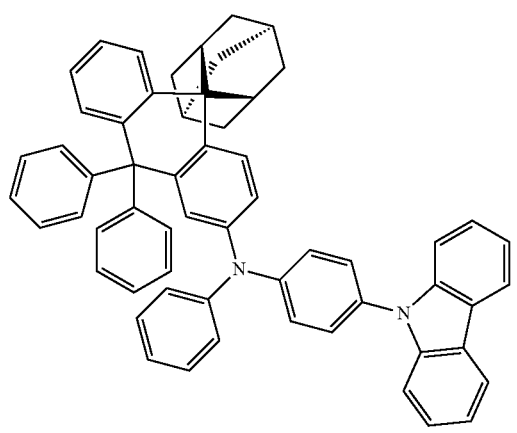
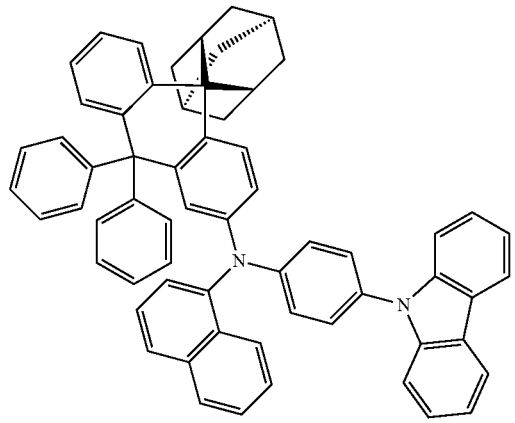

97
-continued
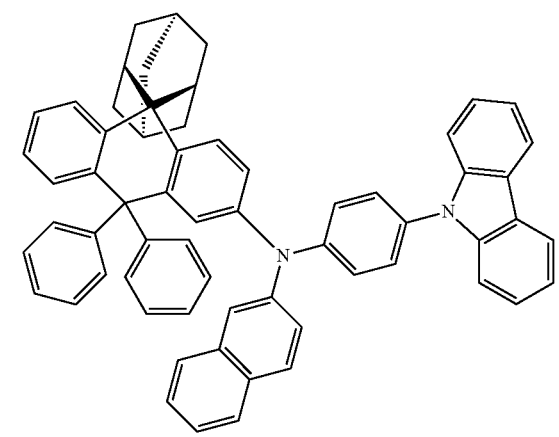
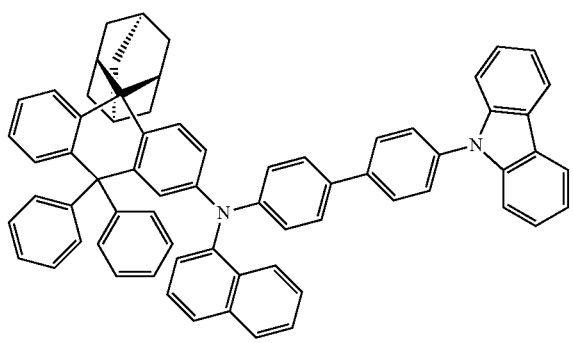
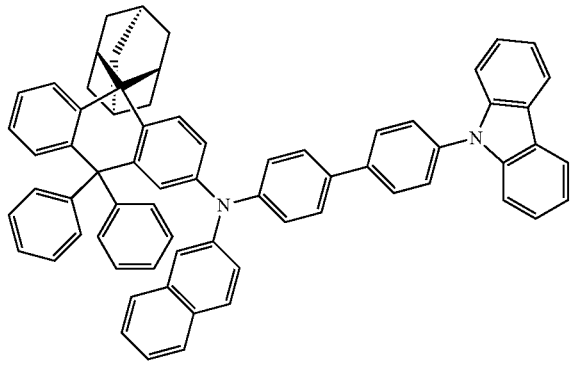
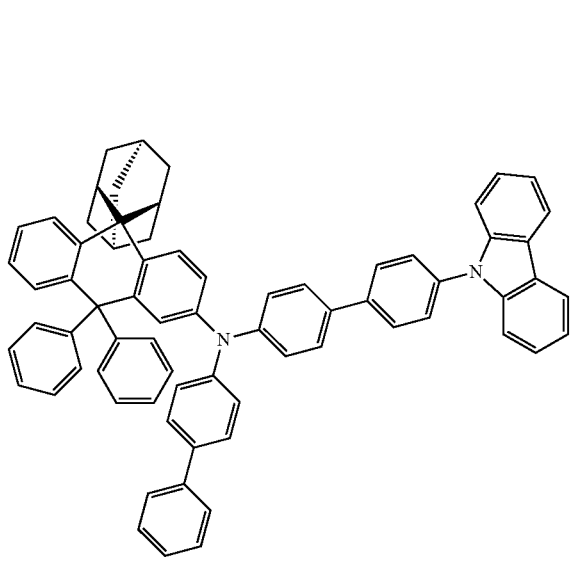
98
-continued
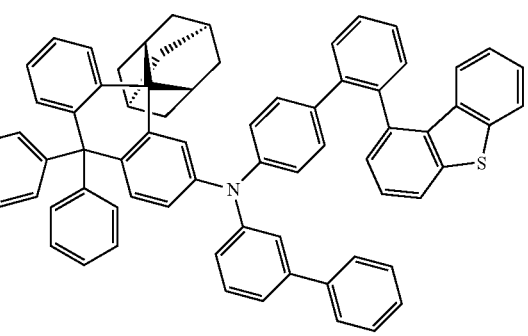
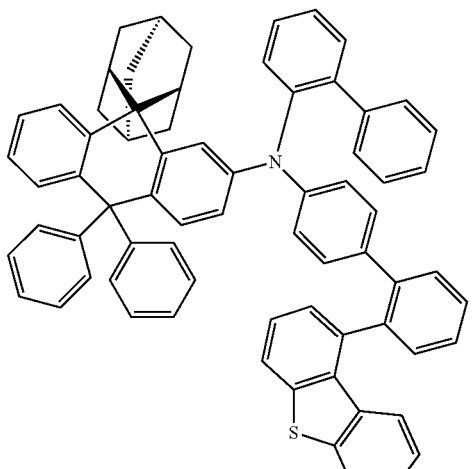
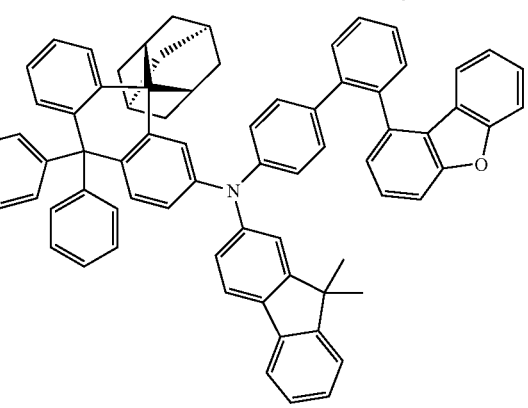
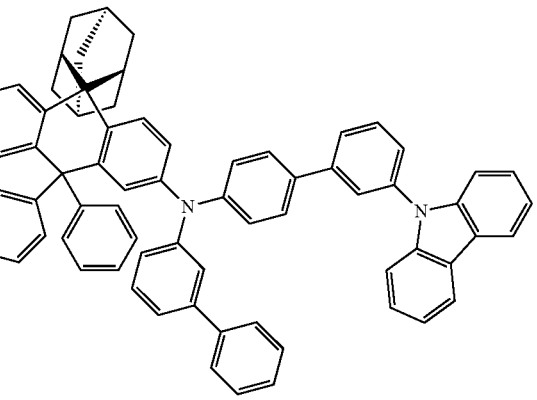

99
-continued
100
-continued
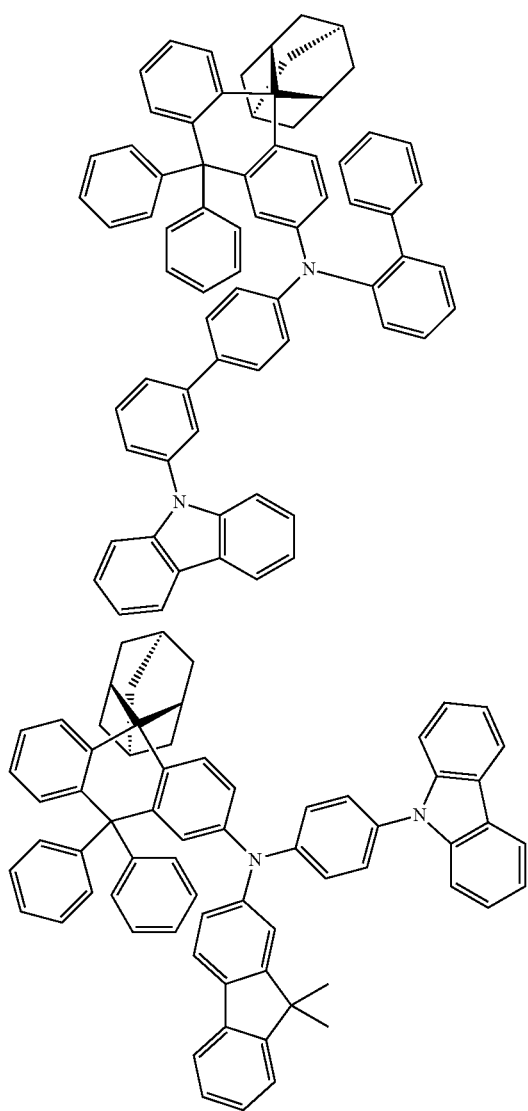
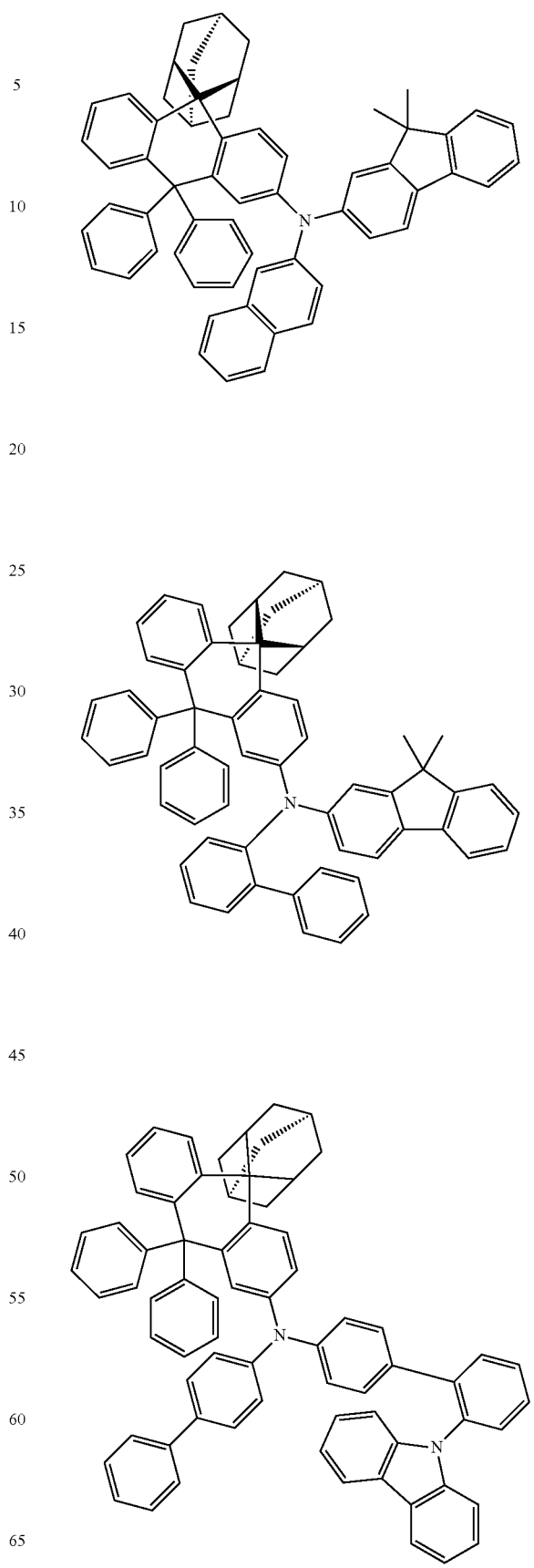

101
-continued
102
-continued
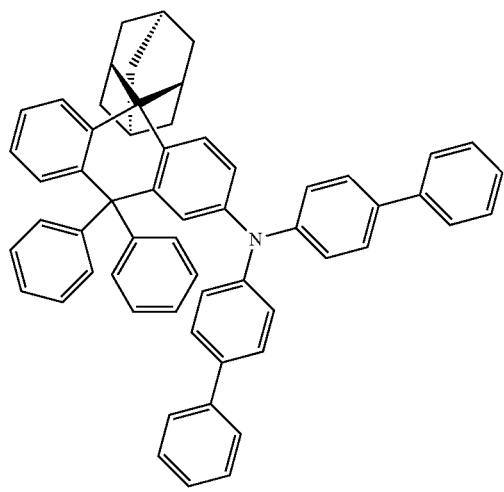
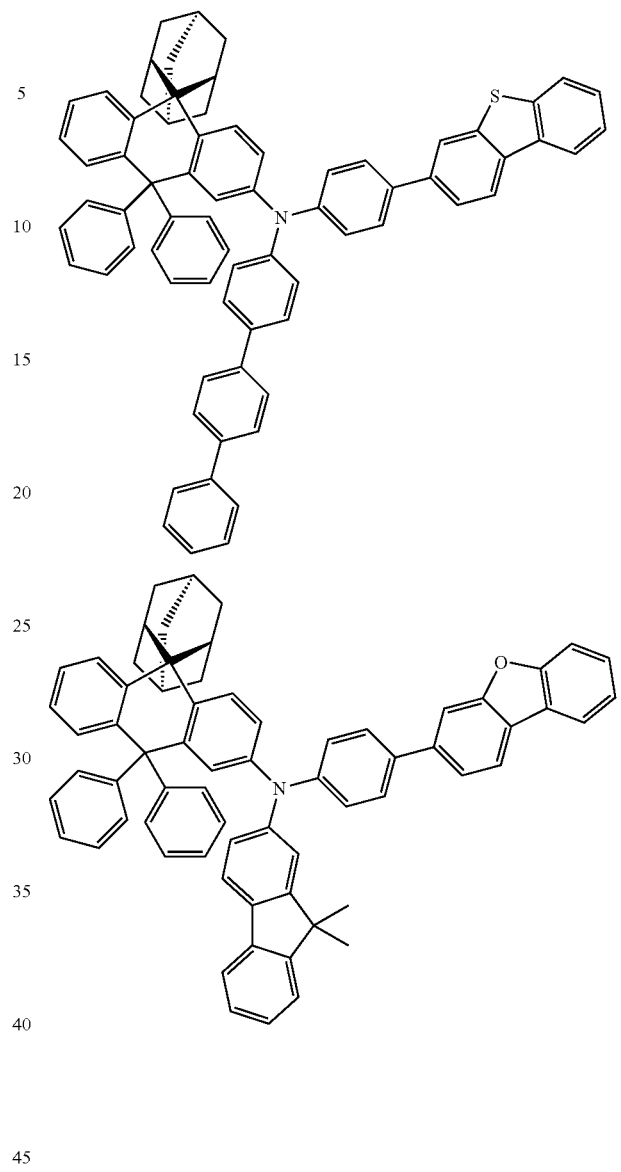
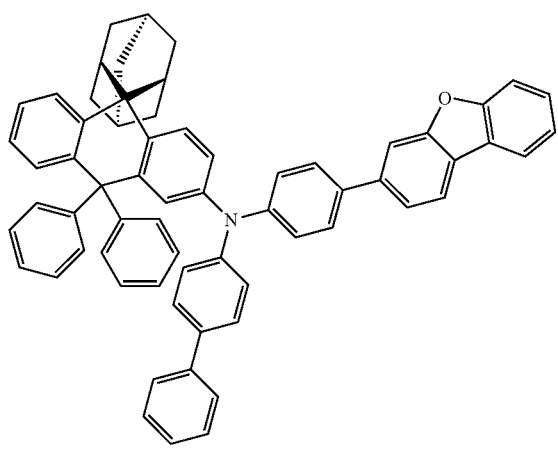

103
104
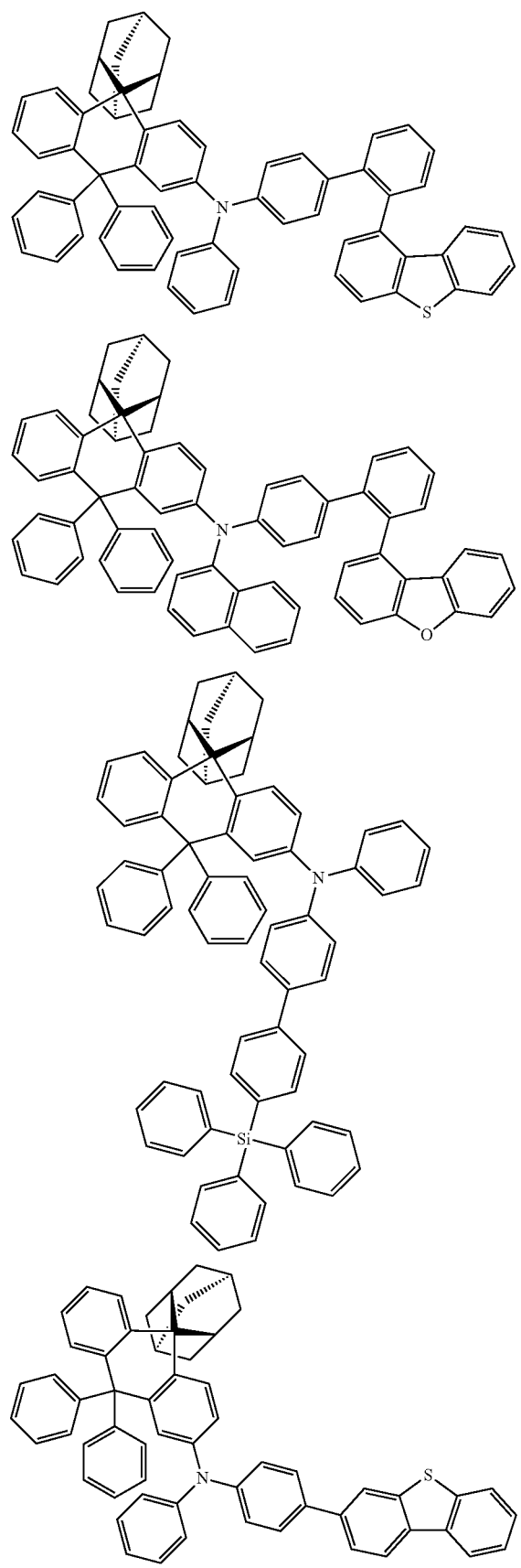
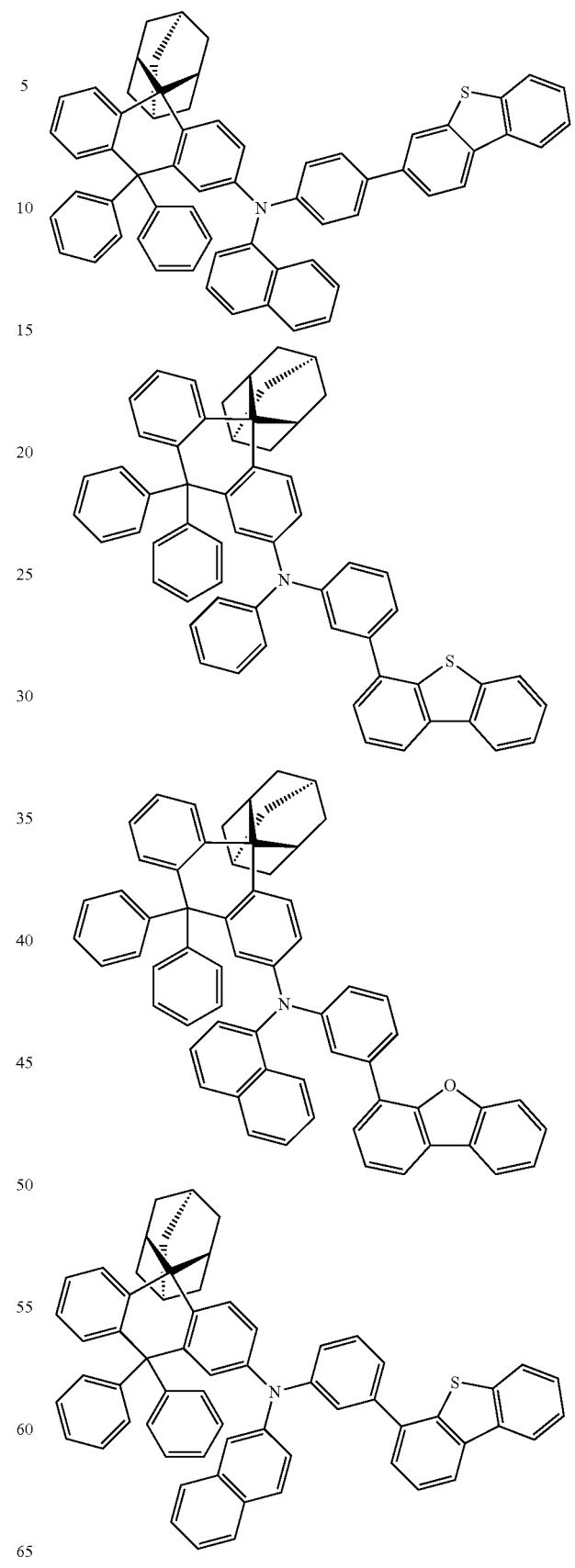

105
-continued
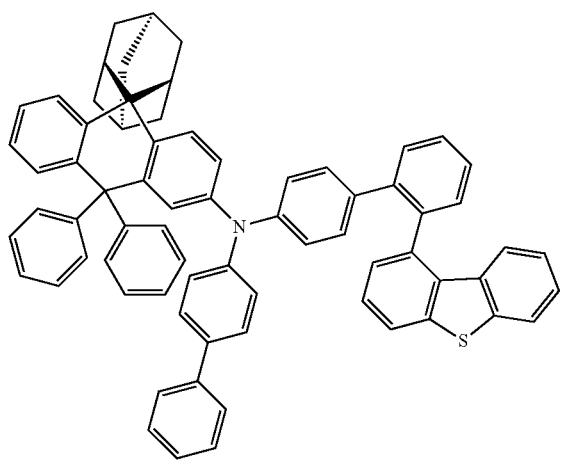
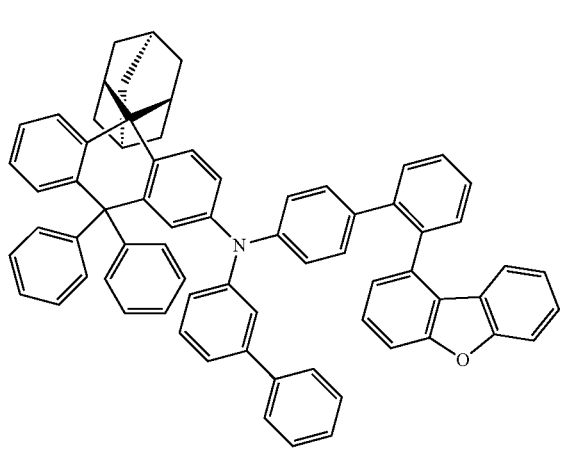
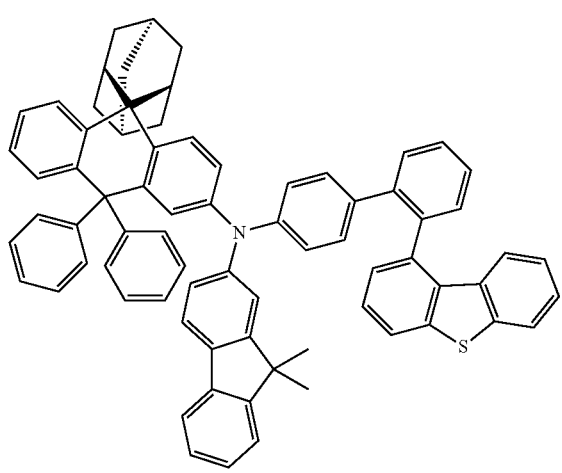
106
-continued
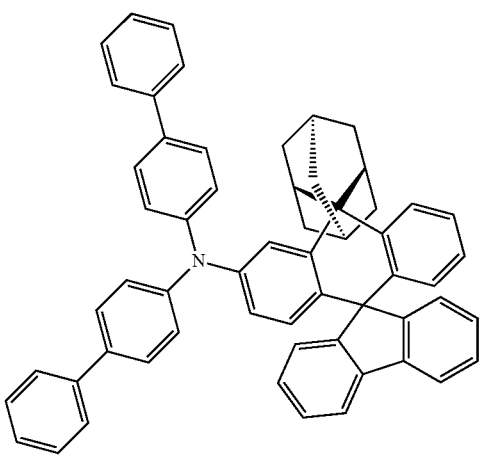
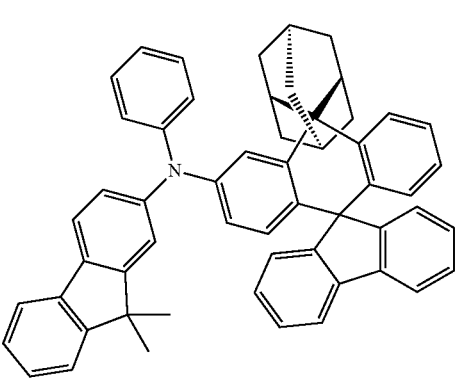
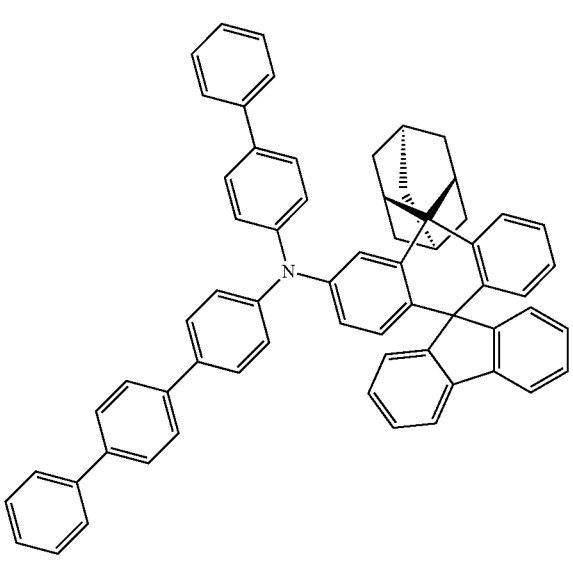

107
-continued
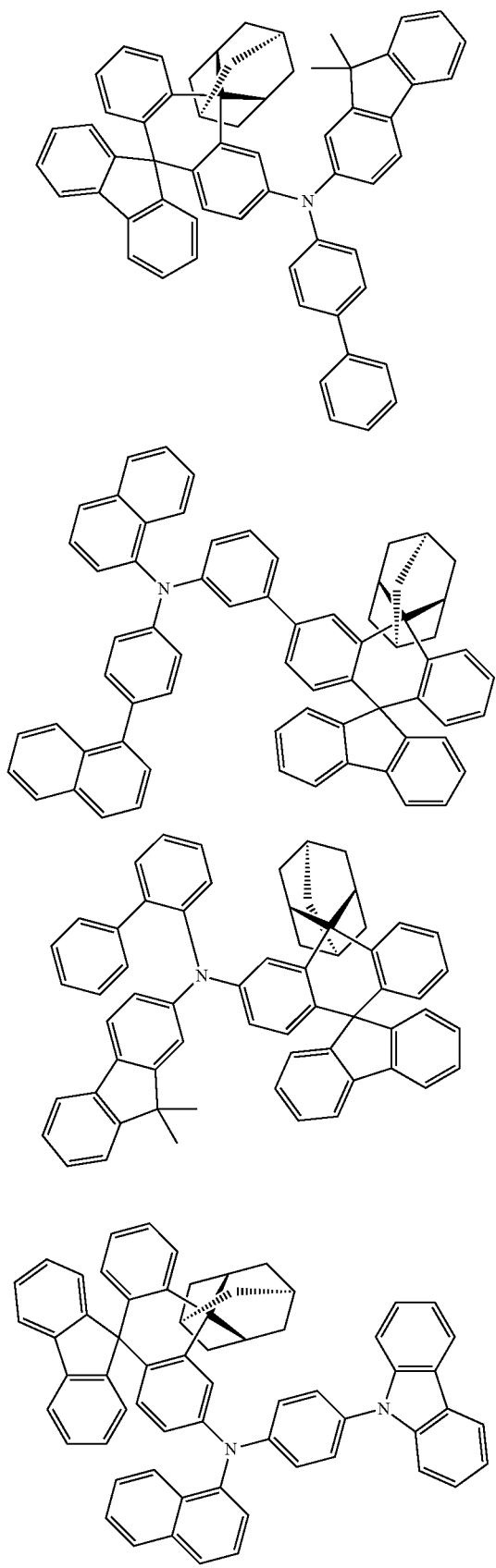
108
-continued
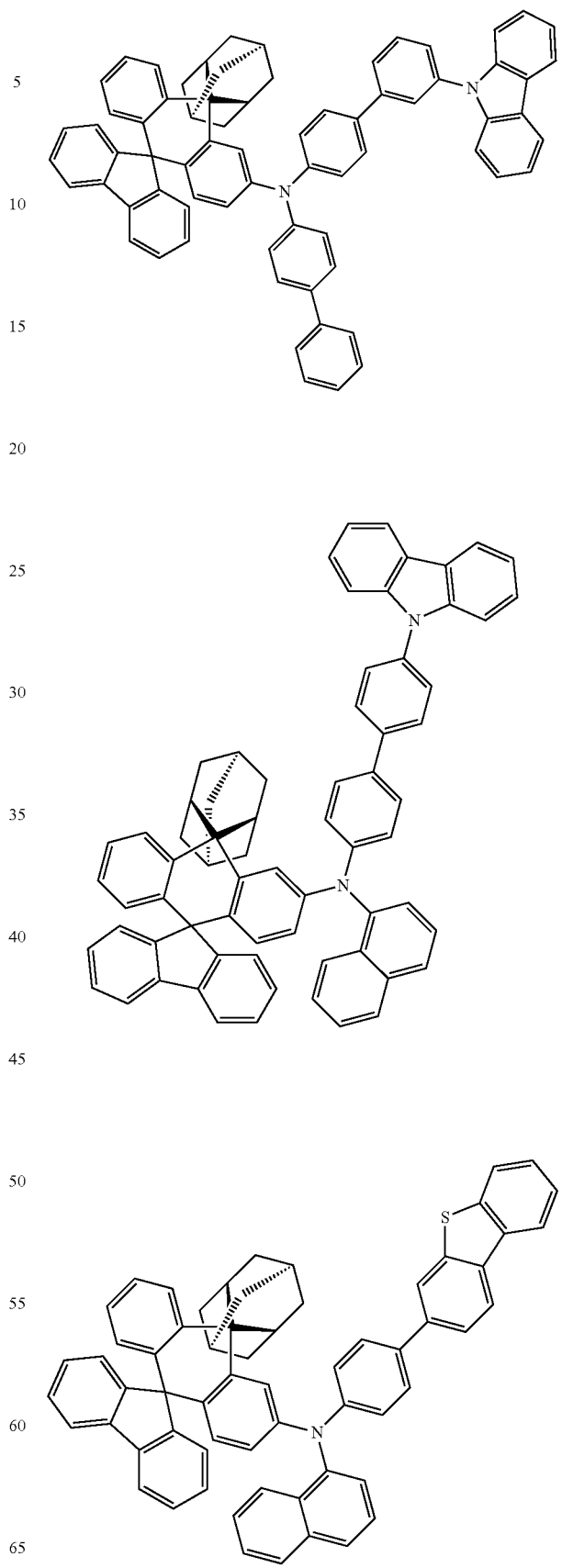

109
-continued
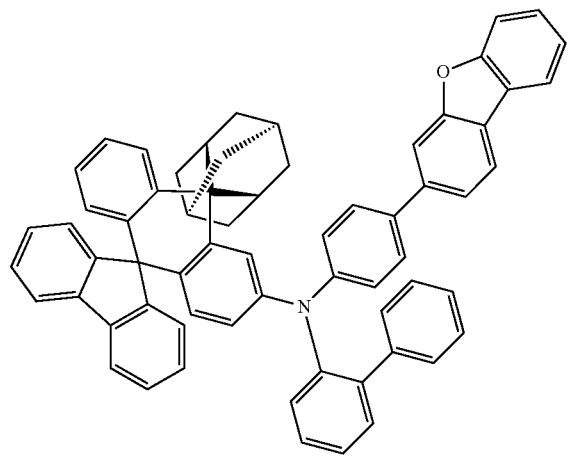
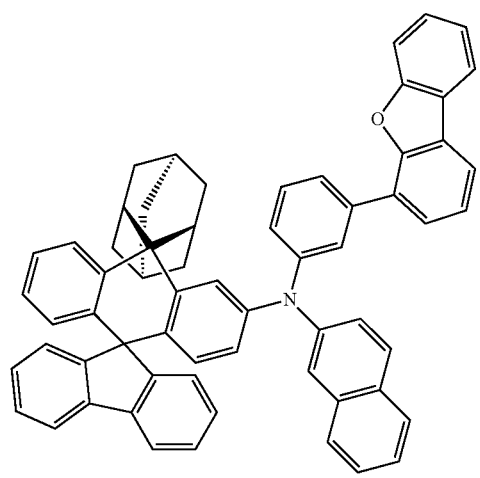
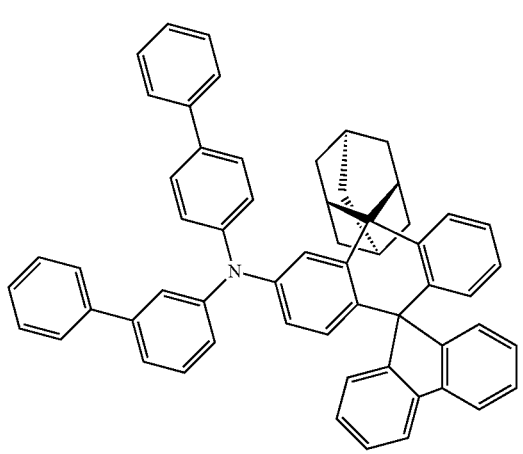
110
-continued
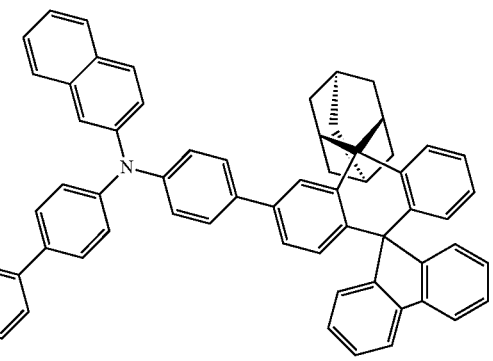
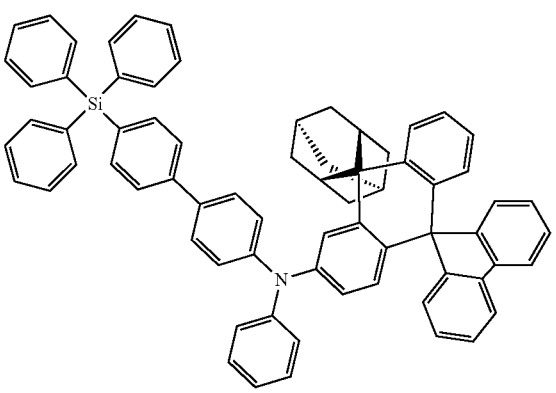
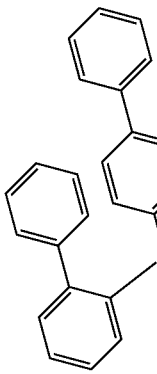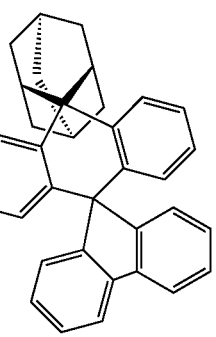
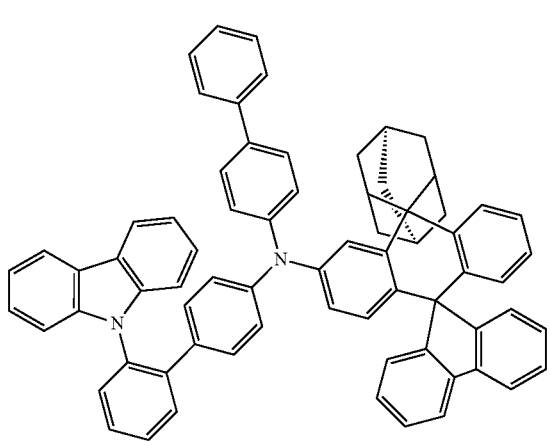

111
-continued
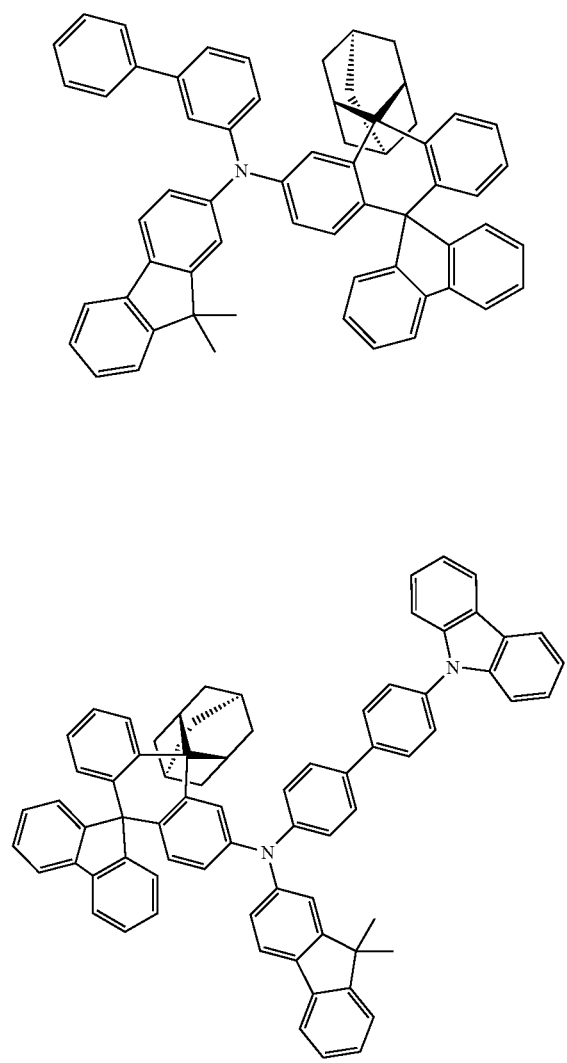
112
-continued
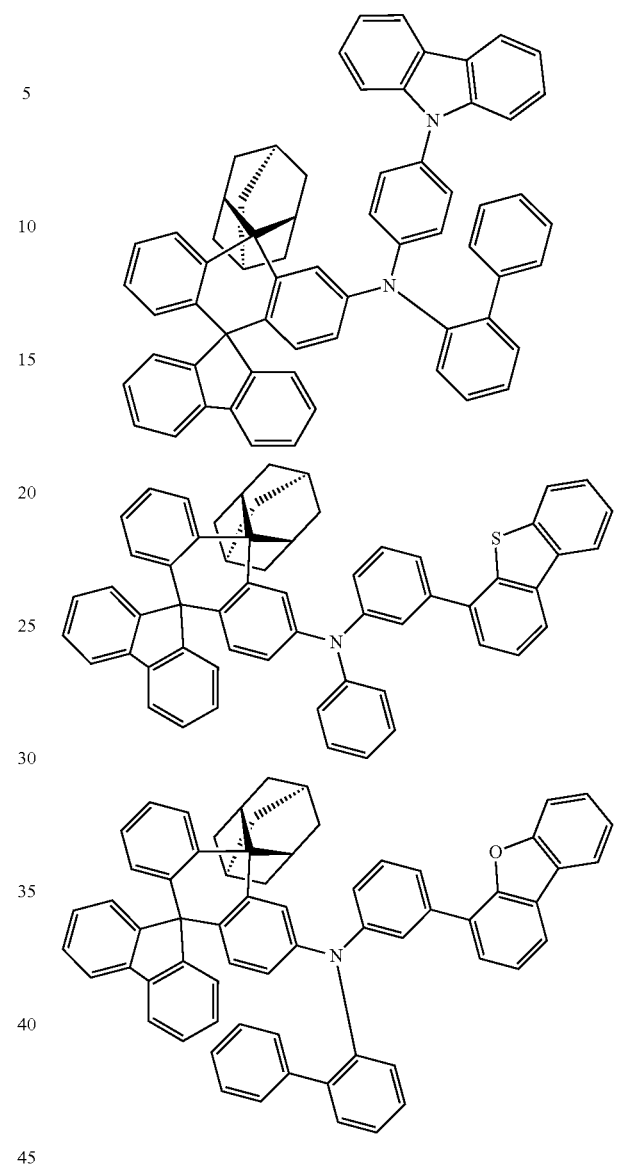
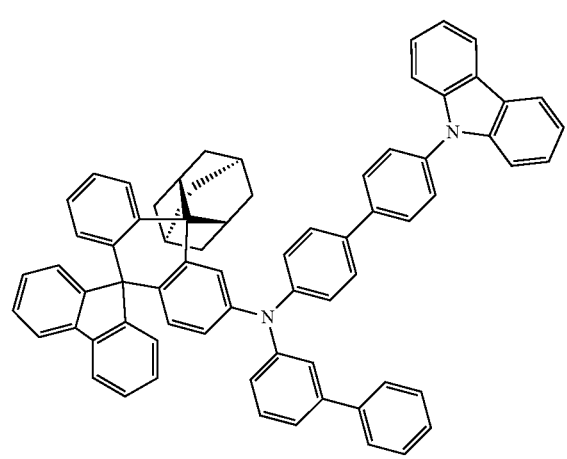
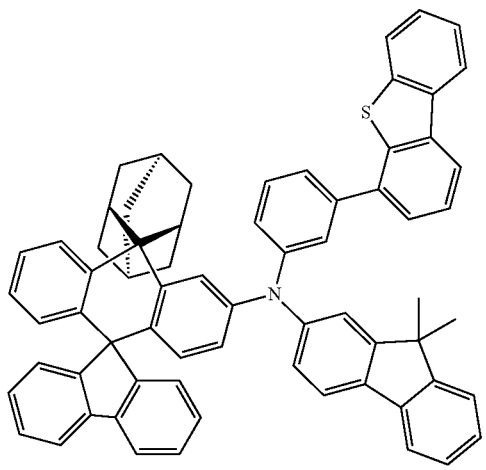

-continued
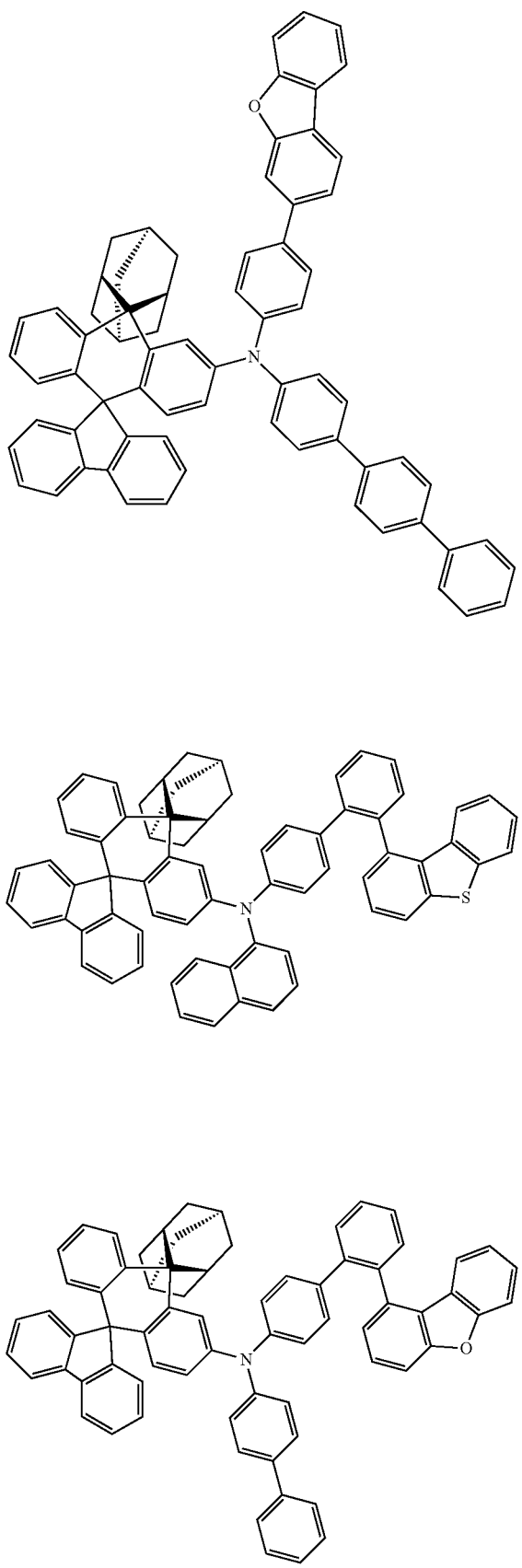
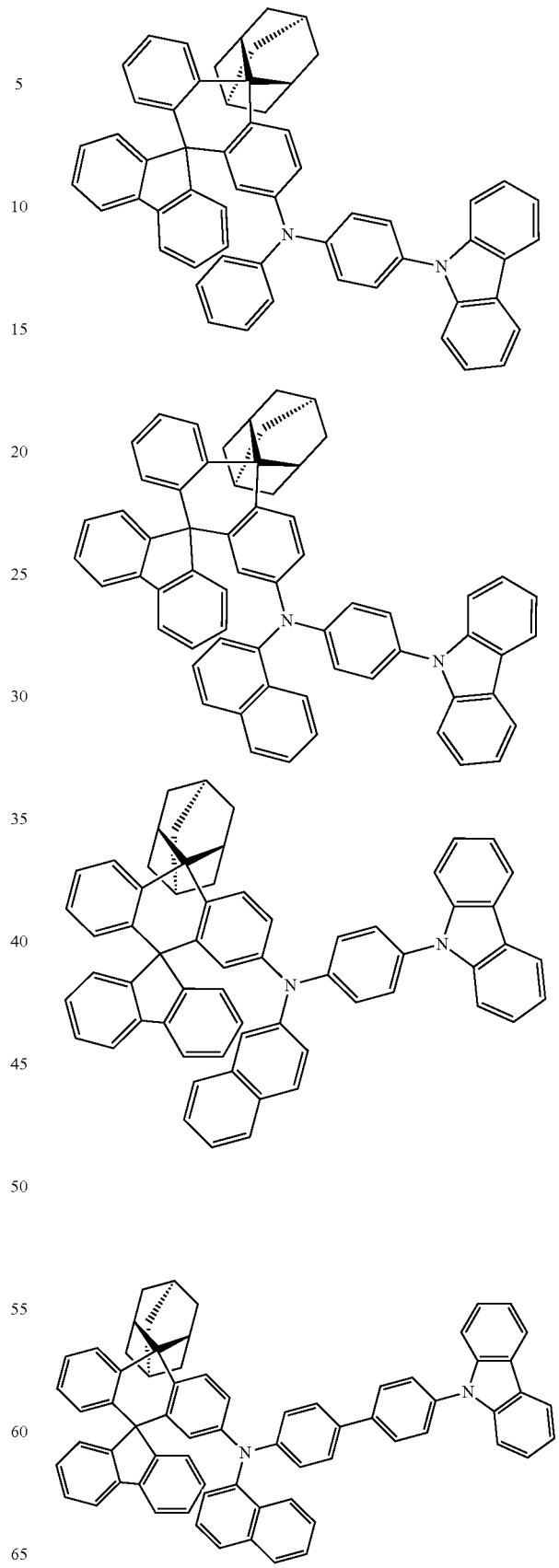

115
-continued
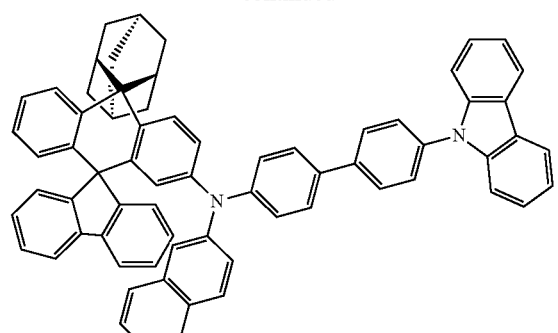
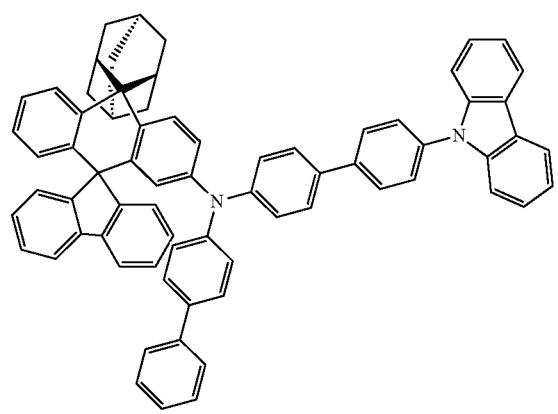
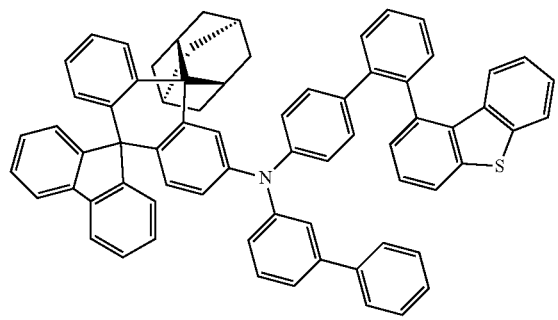
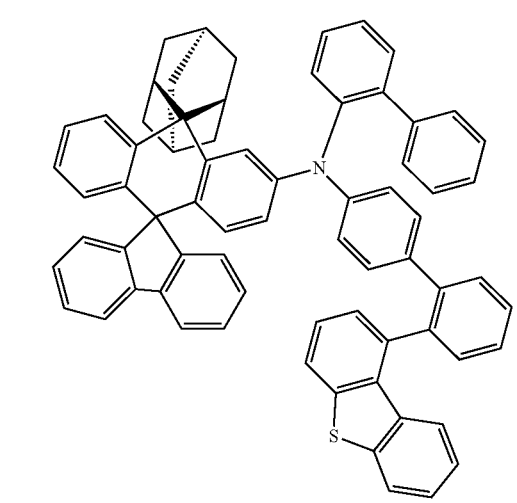
116
-continued
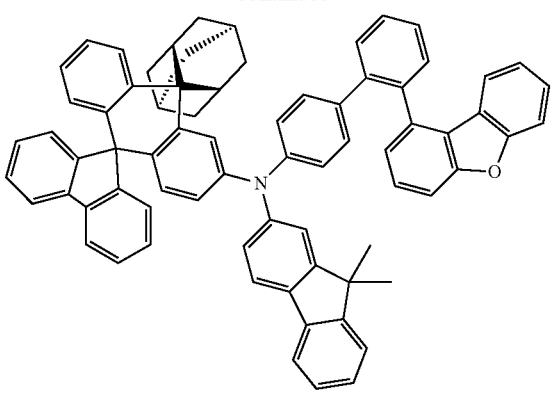
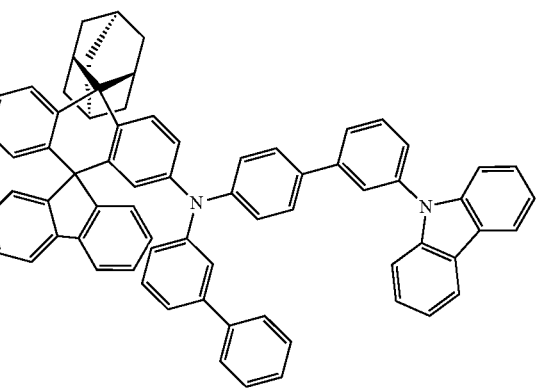
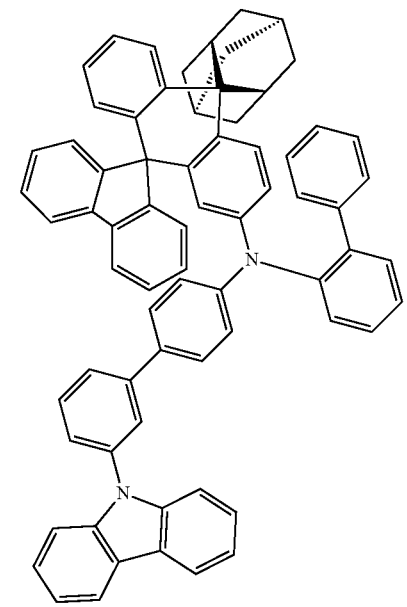

117
-continued
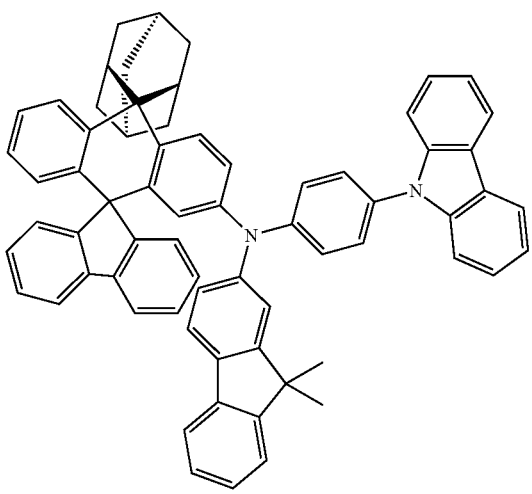
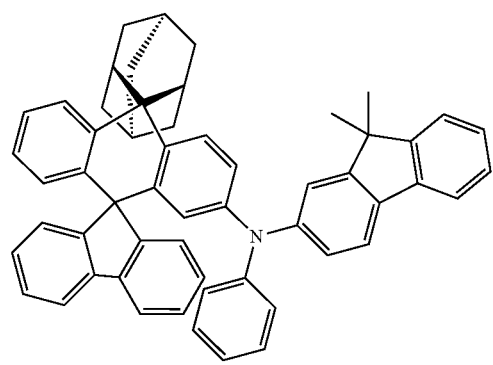
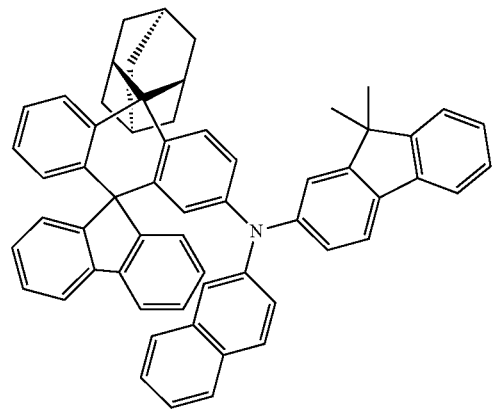
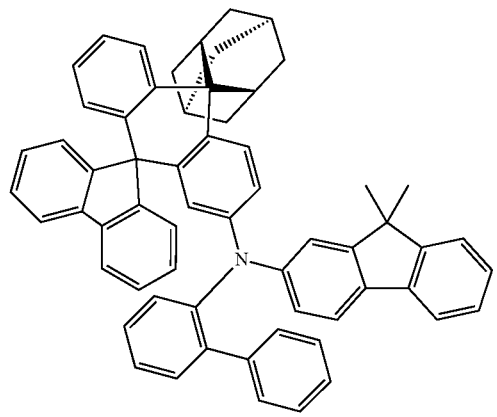
118
-continued
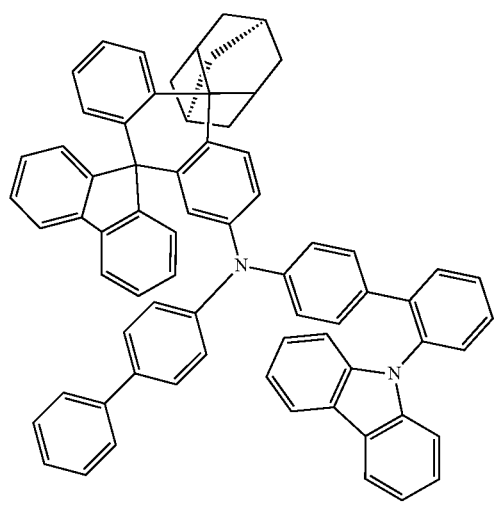
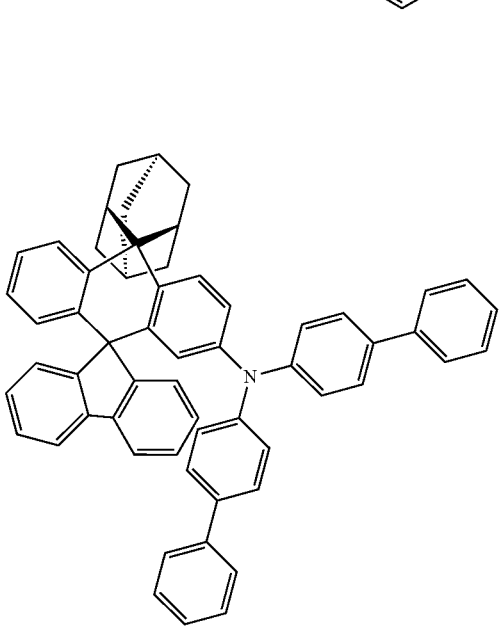
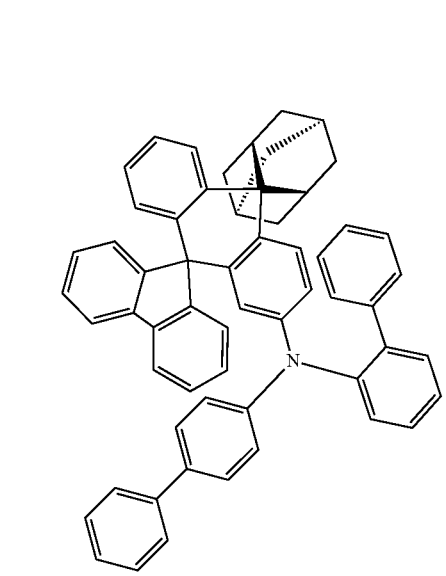

119
-continued
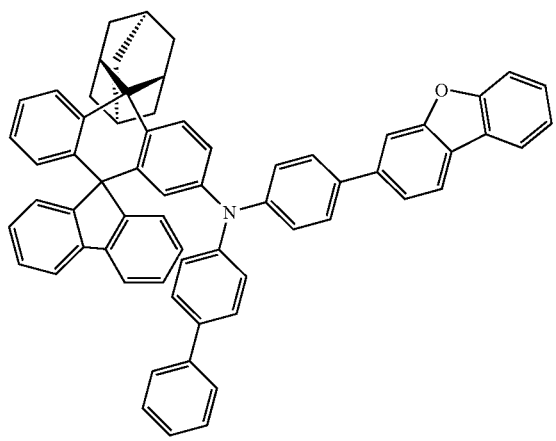
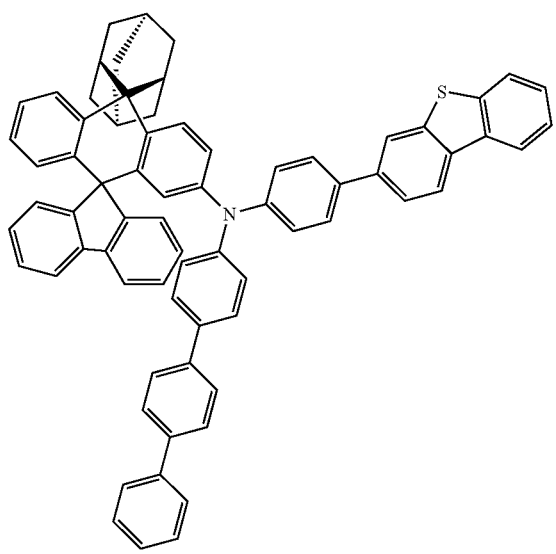
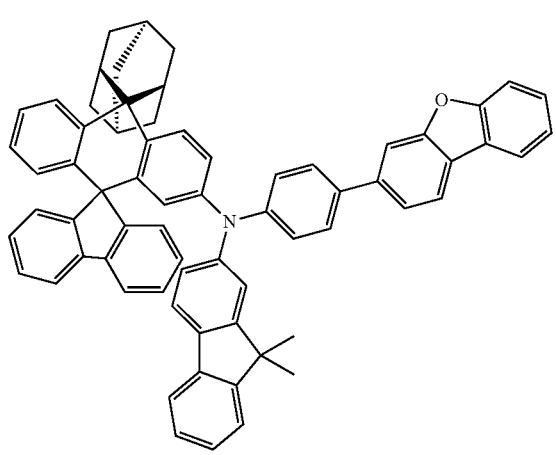
120
-continued
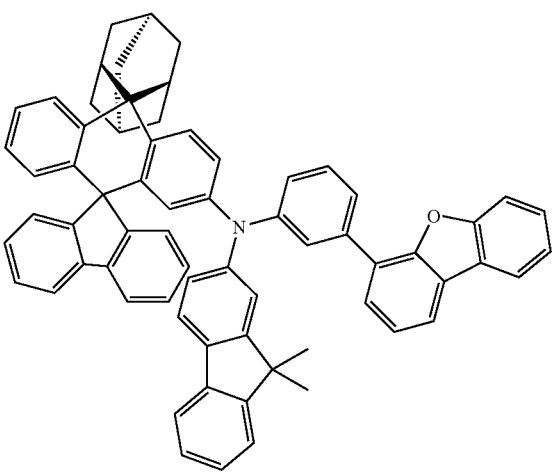
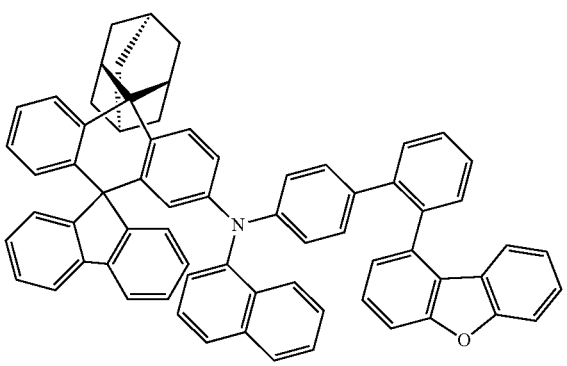

121
-continued
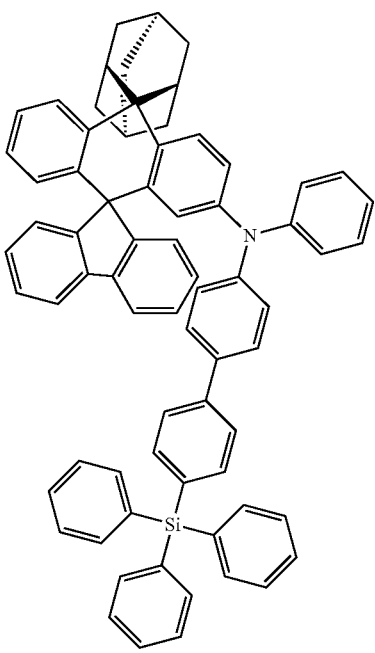
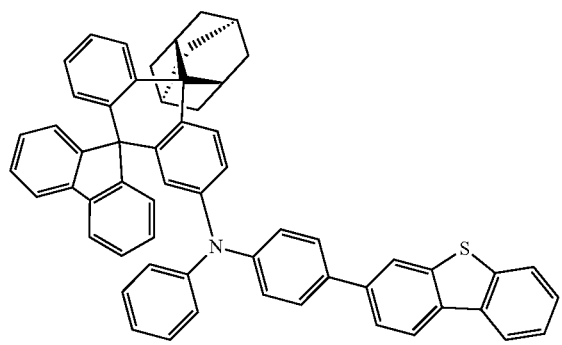
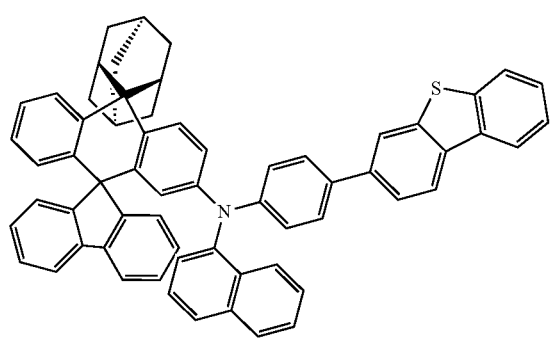
122
-continued
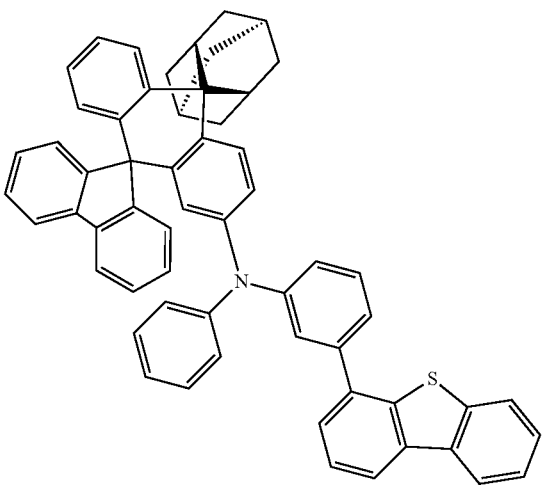
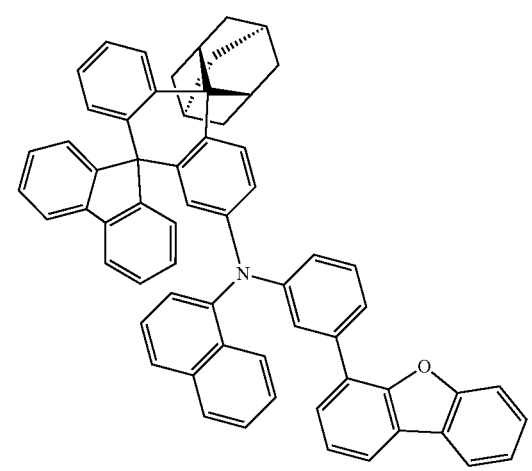
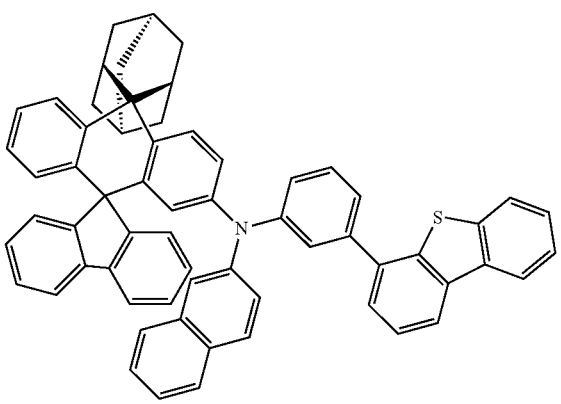

123
-continued
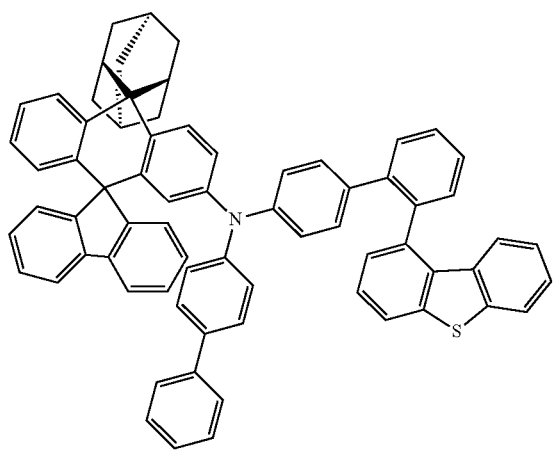
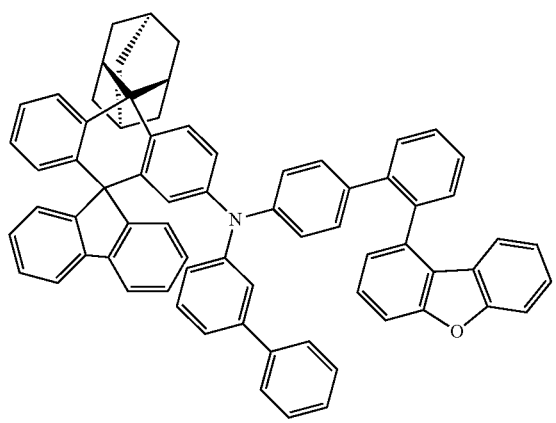
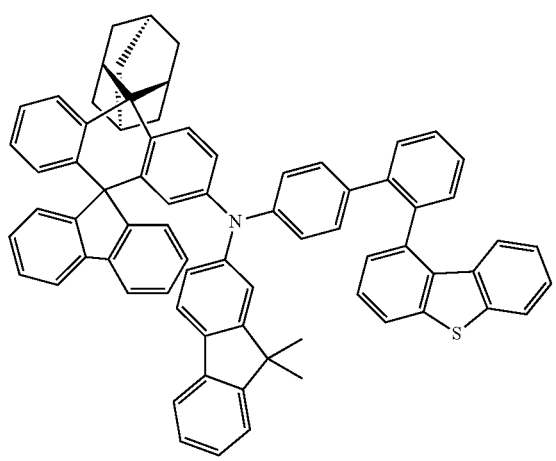
124
-continued
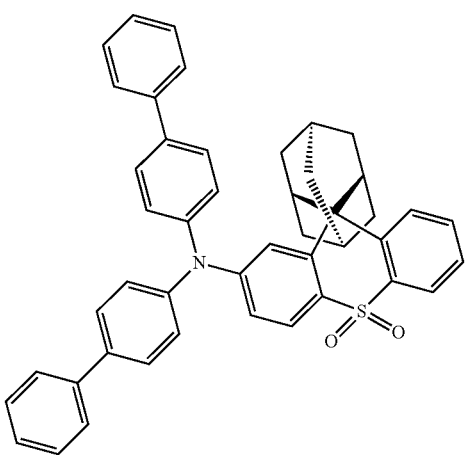
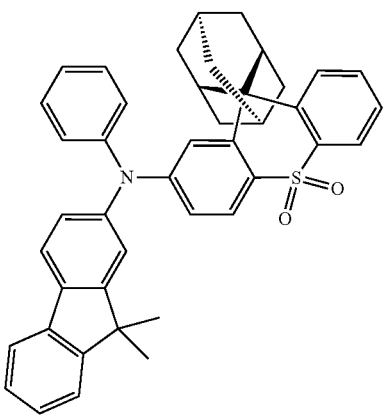
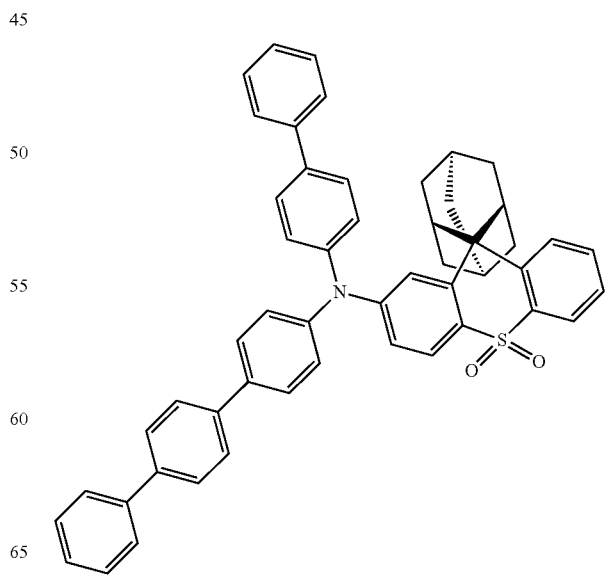

-continued
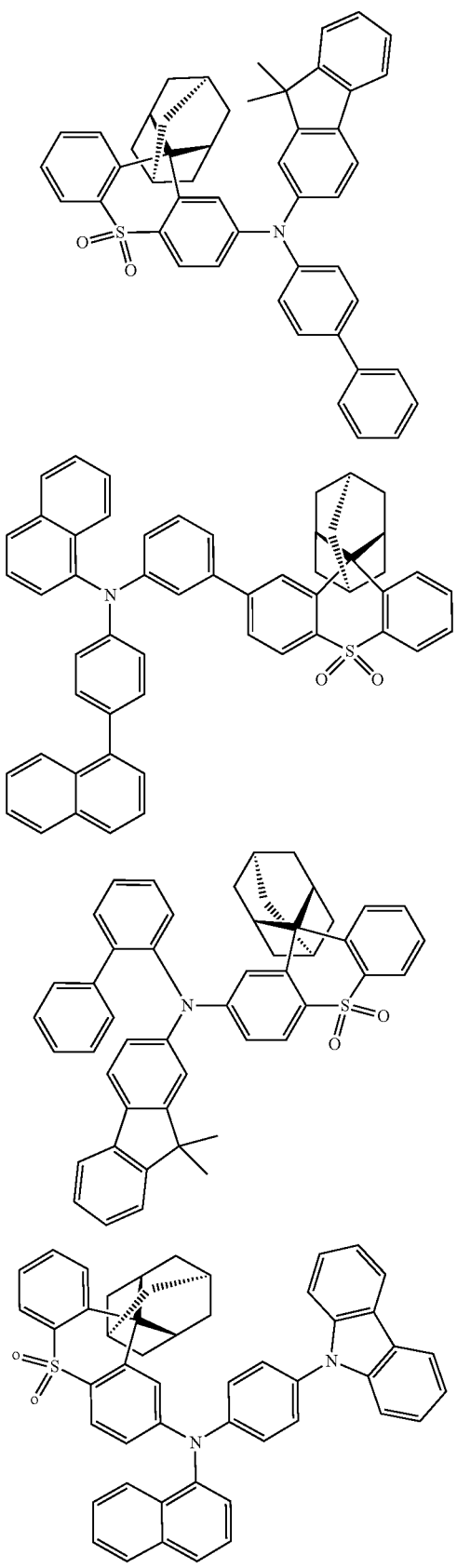
-continued
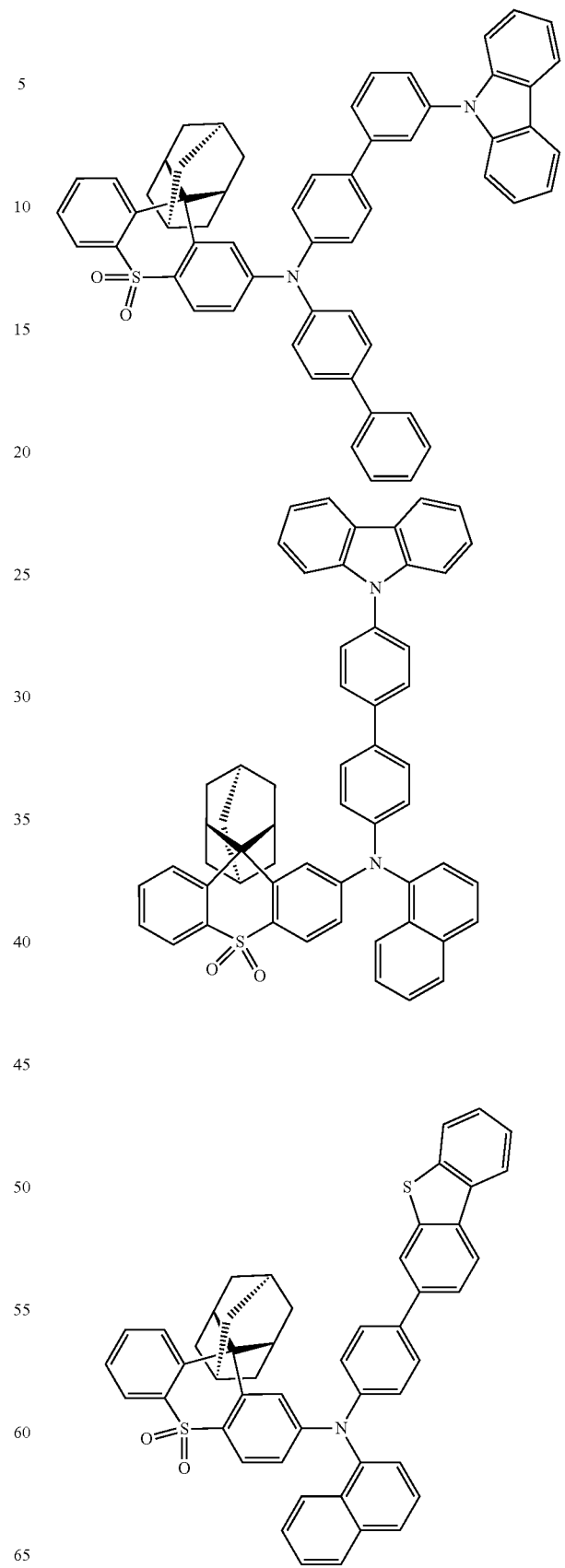

127
-continued
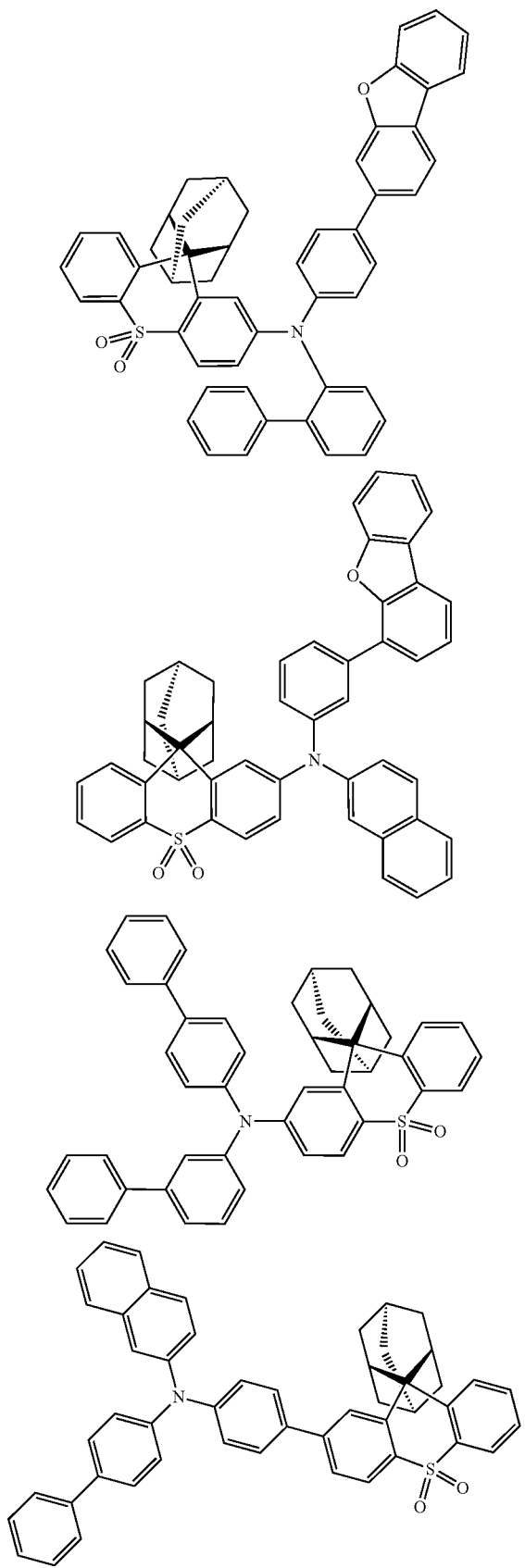
128
-continued
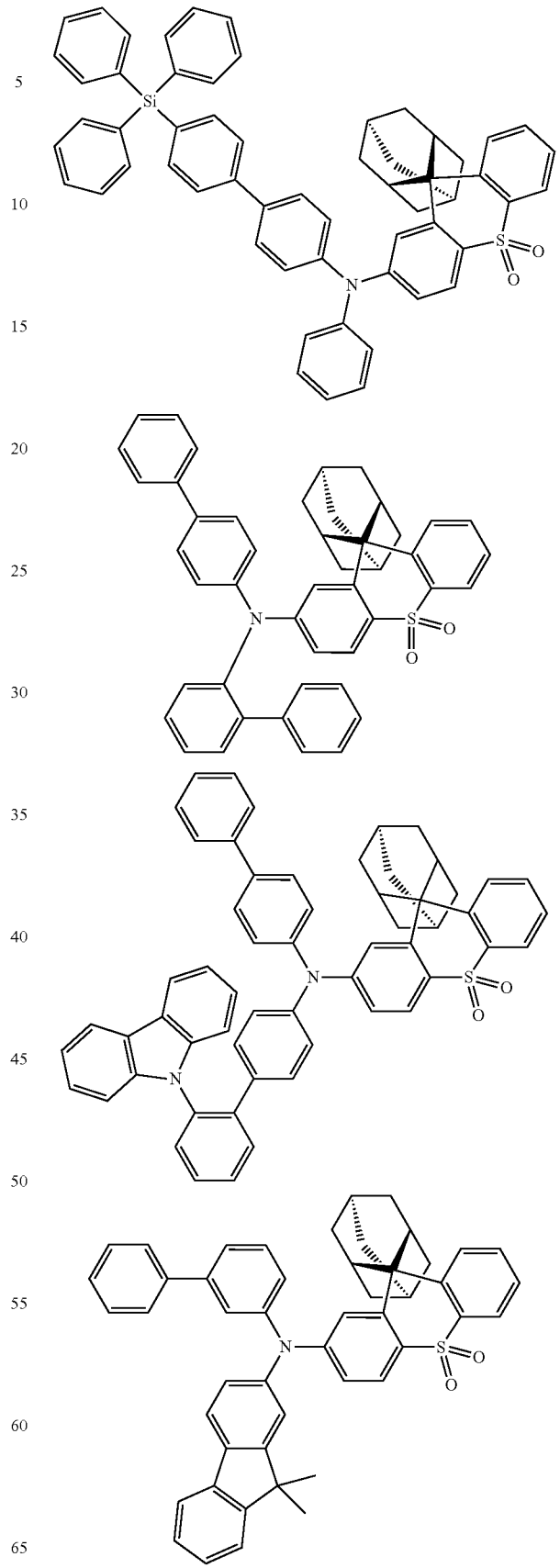

129
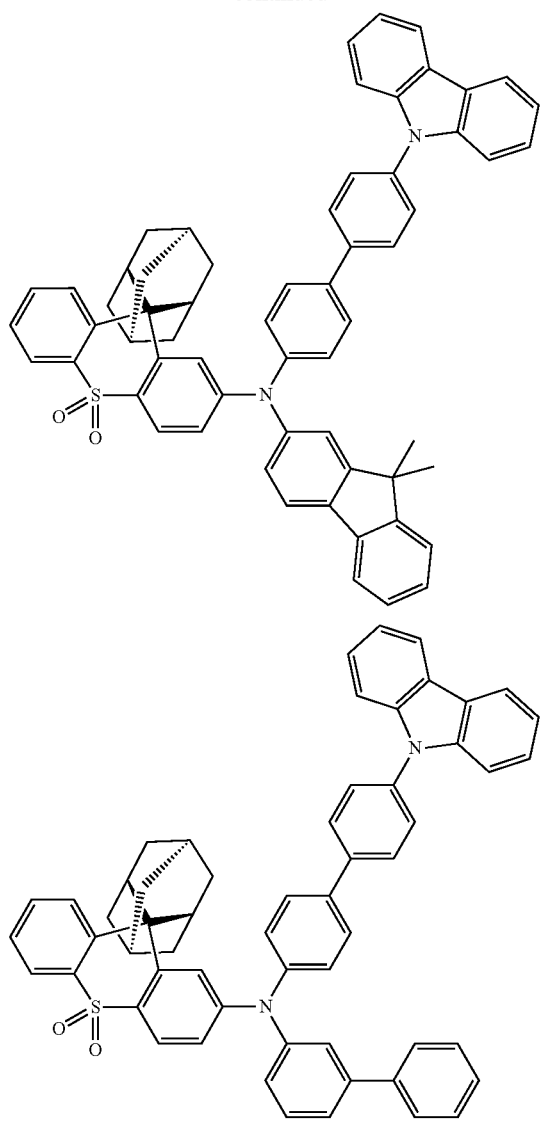
130
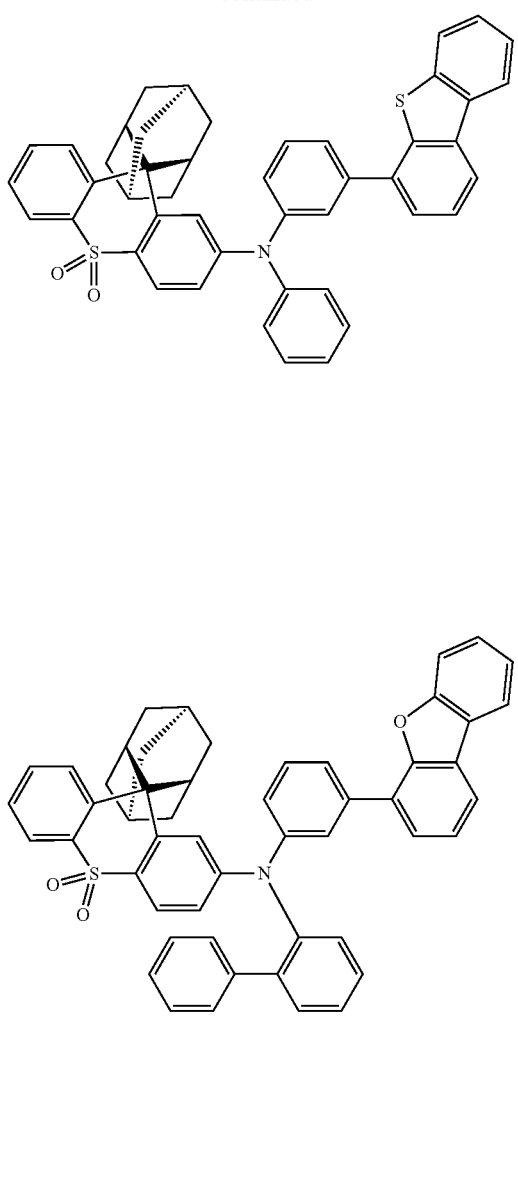
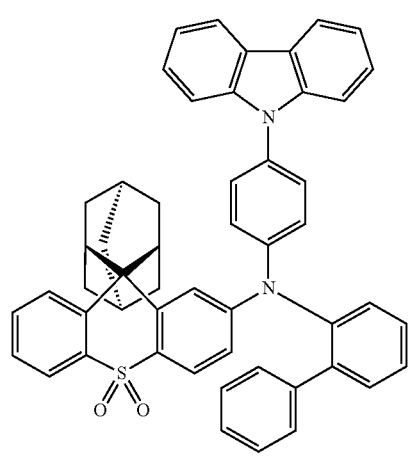
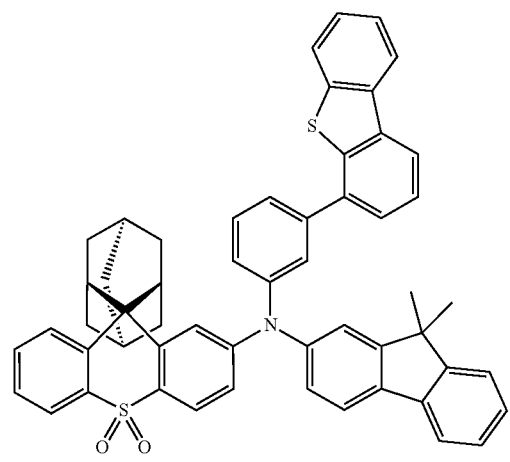

131
-continued
132
-continued
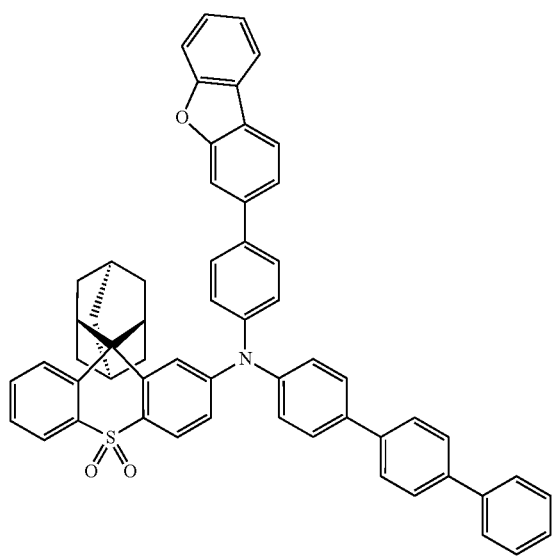
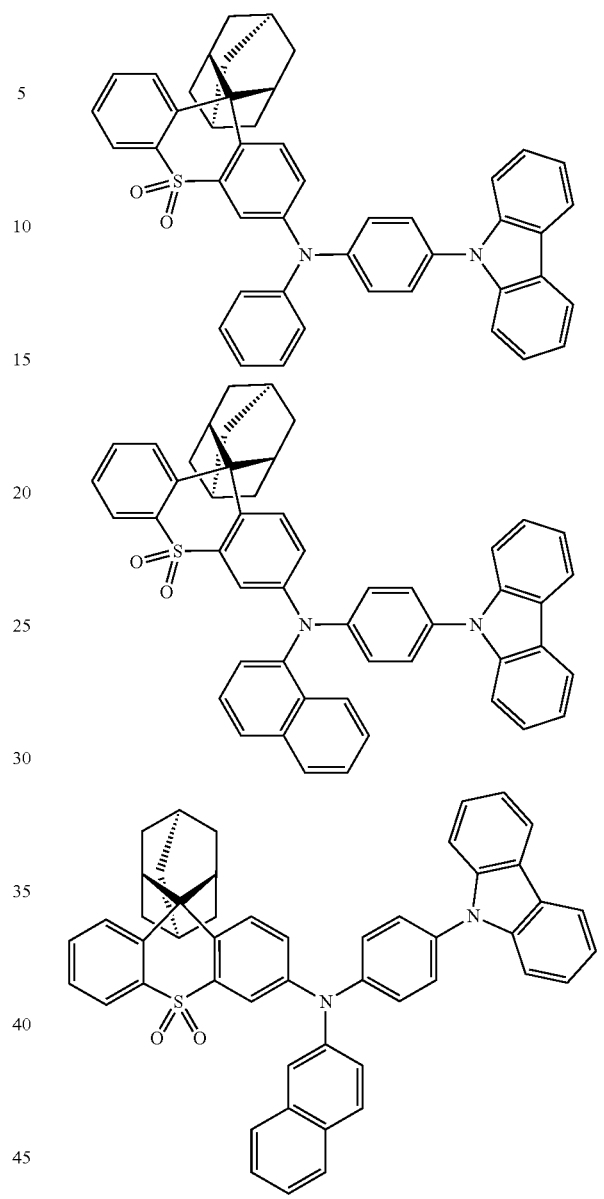
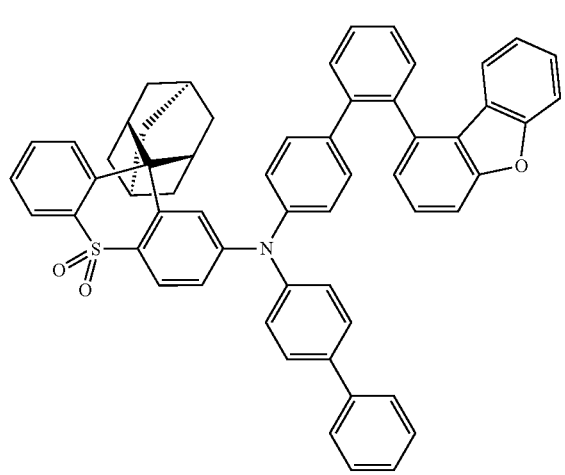
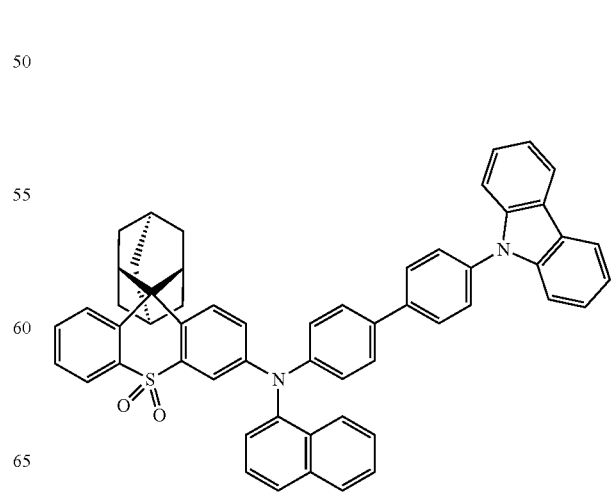

133
-continued
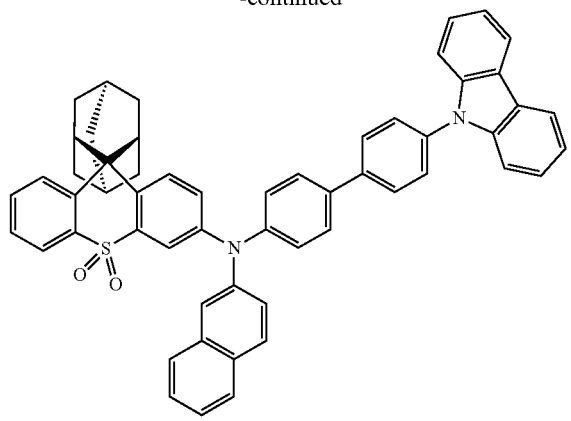
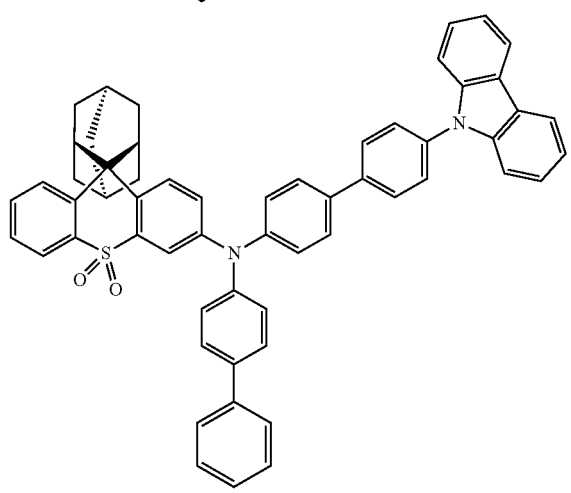
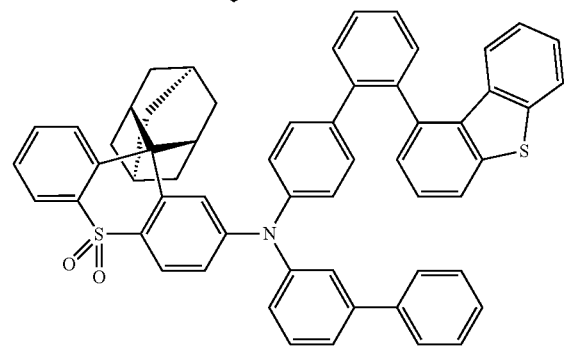
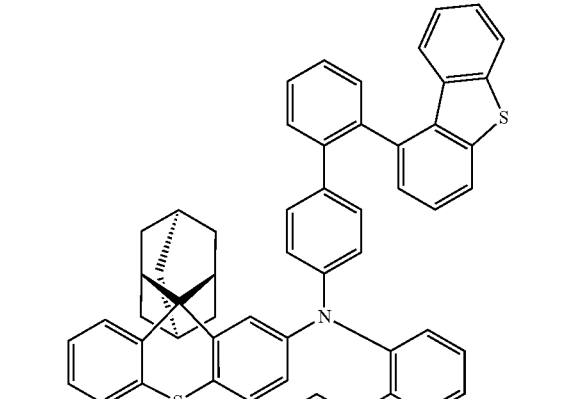
134
-continued
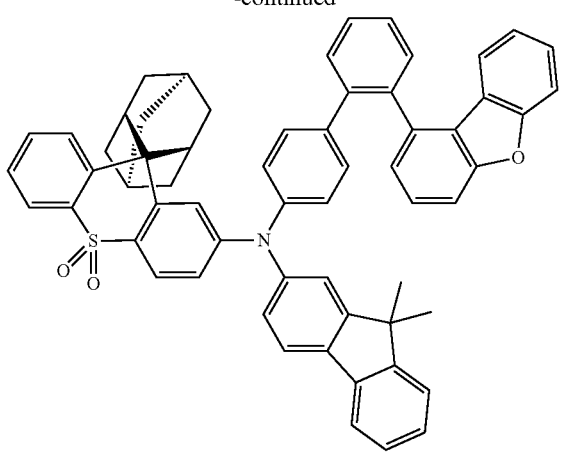
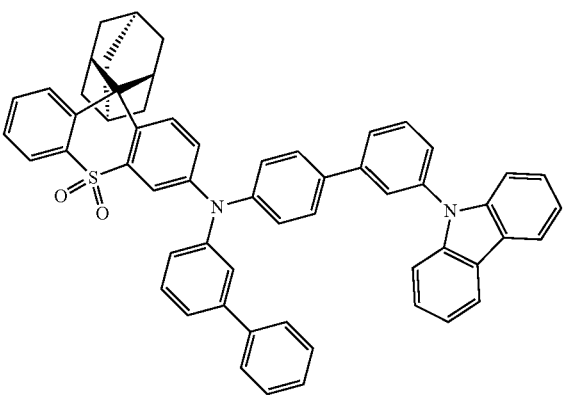
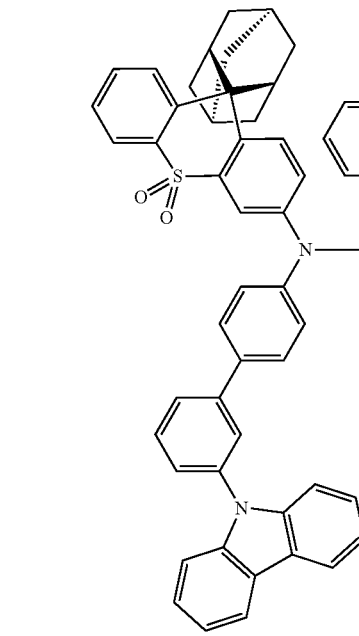

135
-continued
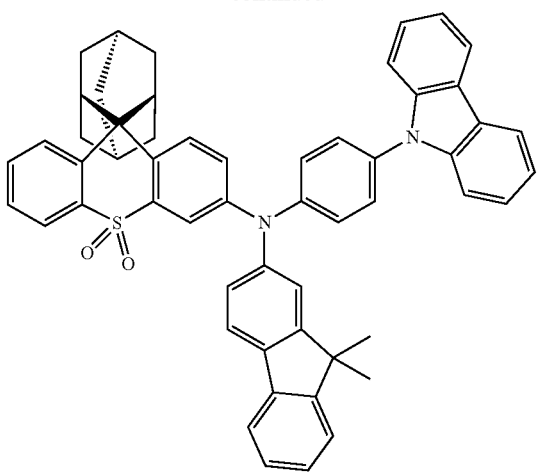
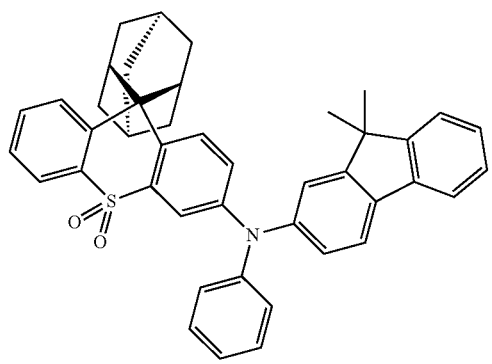
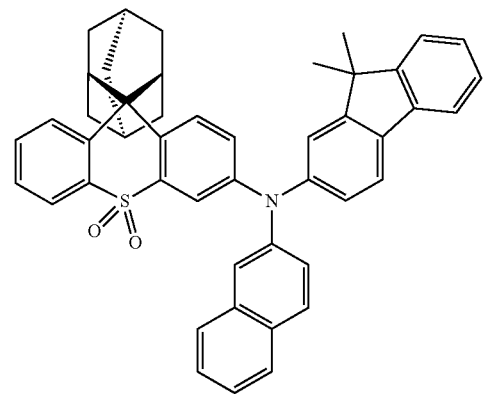
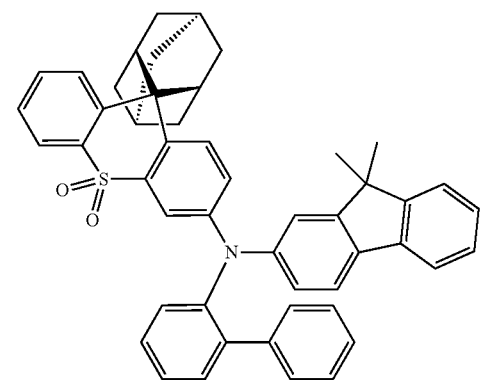
136
-continued
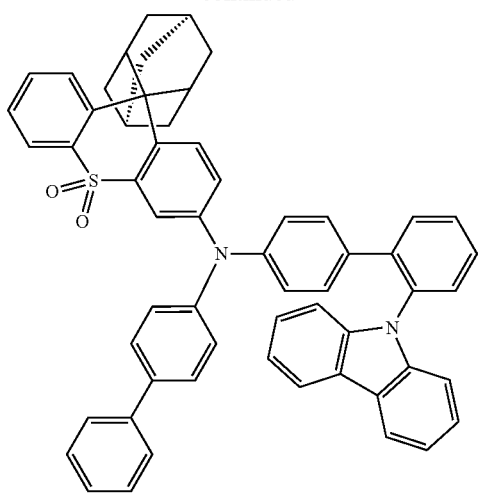
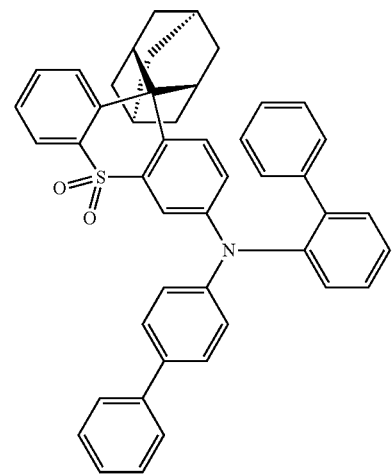

137
-continued
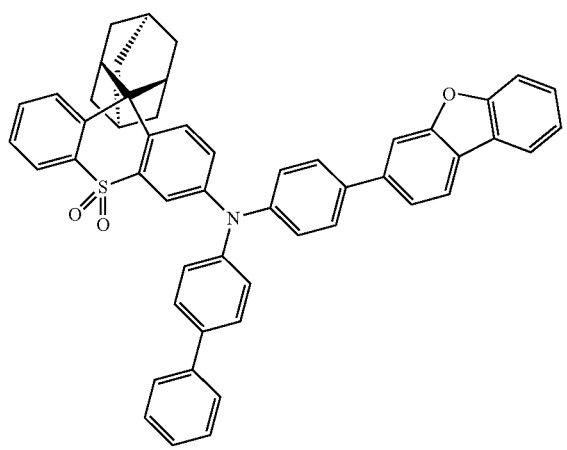
138
-continued
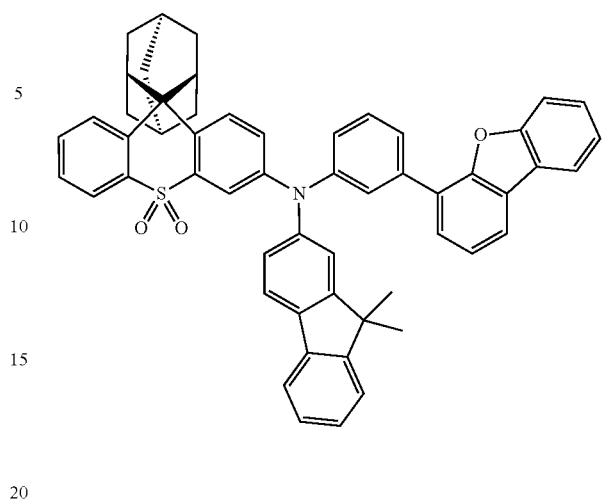
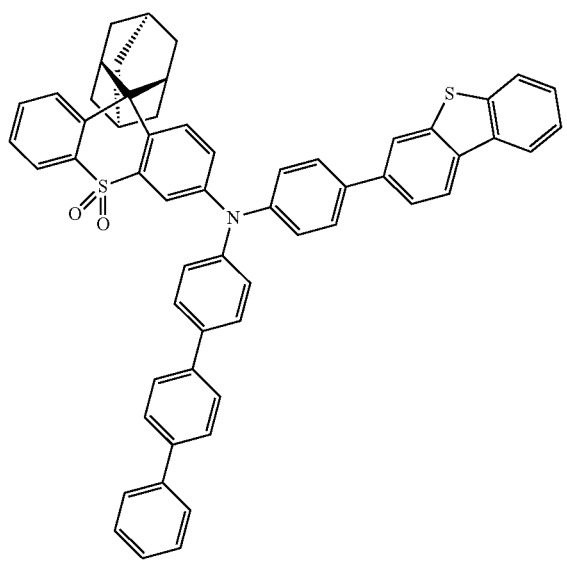
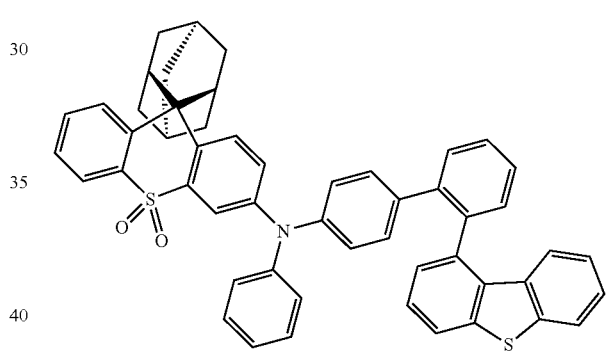
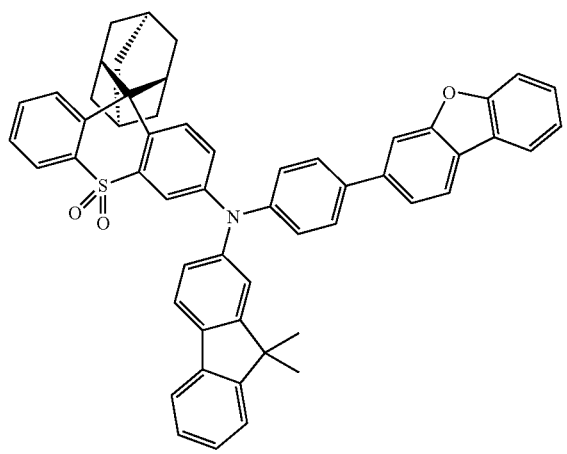
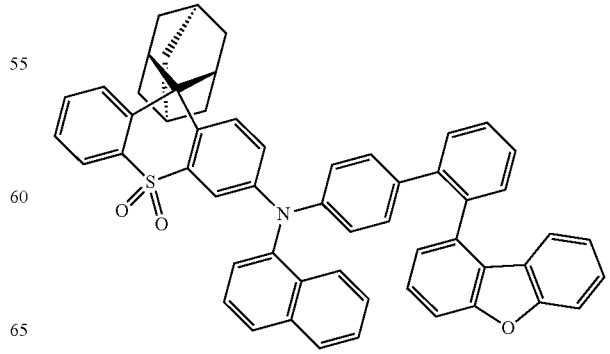

139
-continued
140
-continued
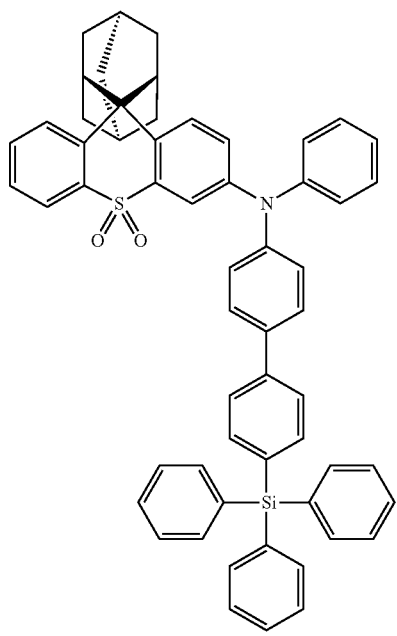
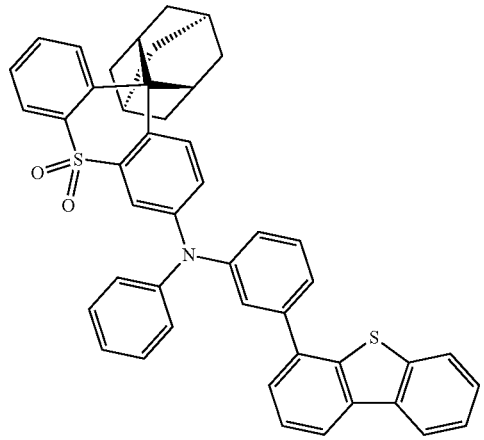
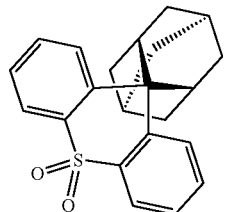
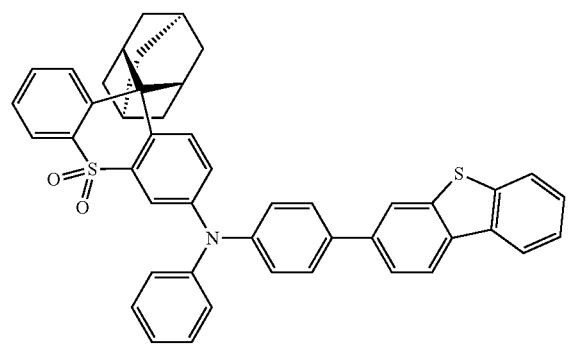
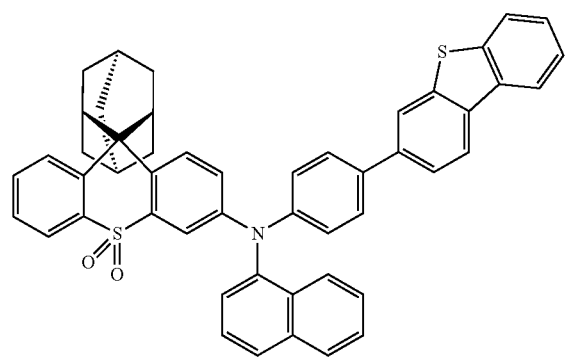

-continued

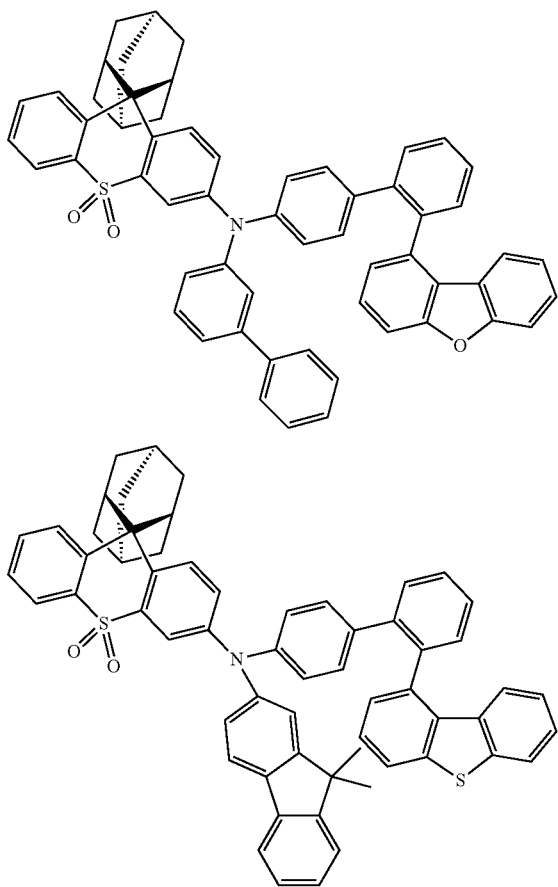

Meanwhile, the compound of Chemical Formula 1 can be prepared by the method shown in the following Chemical Scheme 1 or 2.

[Reaction Scheme 1]

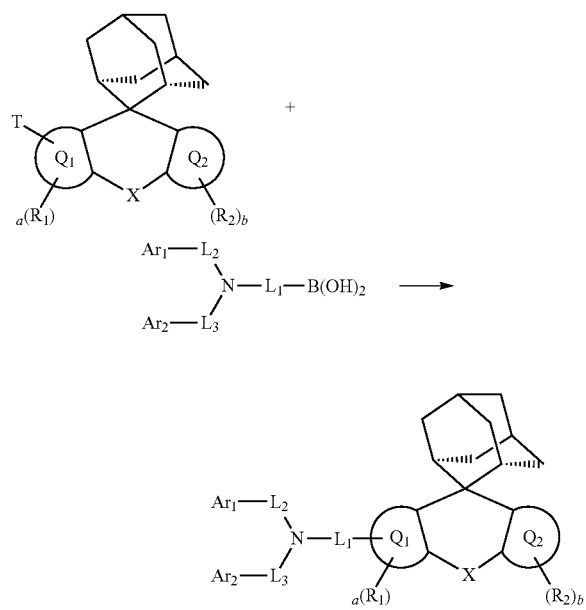

-continued
[Reaction Scheme 2]

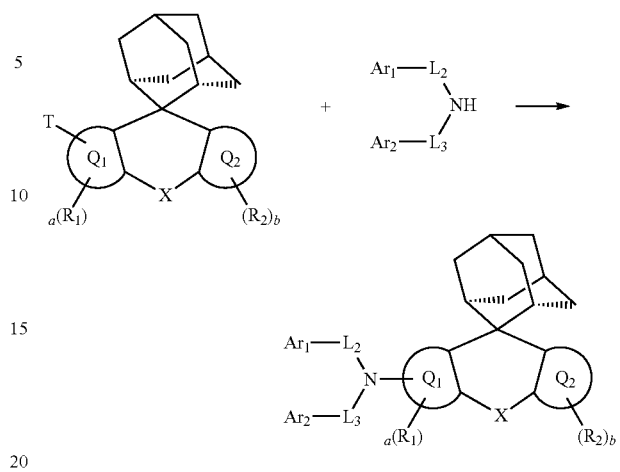

in the Chemical Scheme 1 to 2, T is a halogen, preferably bromo, or chloro, and the definitions of the other substituents are the same as described above Specifically, the compound of Chemical Formula 1 is prepared by coupling starting materials through a Suzuki coupling reaction. Such a Suzuki coupling reaction is preferably carried out in the presence of a palladium catalyst and a base, and a reactive group for the Suzuki coupling reaction can be modified as known in the art. The above preparation method may be further embodied in the Preparation Examples described hereinafter.

In another embodiment of the invention, there is provided an organic light emitting device including a compound of Chemical Formula 1 described above. As an example, there is provided an organic light emitting device including a first electrode; a second electrode that is provided opposite to the first electrode; and one or more organic material layers that are provided between the first electrode and the second electrode, wherein one or more layers of the organic material layers include the compound of Chemical Formula 1.

In general, in the case of adamantane, due to its three-dimensional size and rigidity, it has excellent sublimation properties and chemical structural stability, so it exhibits excellent thermal stability. Consequently, the compound of Chemical Formula 1 has excellent sublimation property and chemical structural stability through introduction of the bulky and rigid structure of adamantane, and thus has excellent thermal stability. Therefore, the efficiency and lifetime may be improved when an organic light emitting device including the compound of Chemical Formula 1 is produced.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic material layers.

Further, the organic material layer may include a hole injection layer, a hole transport layer, a layer for simultaneously performing hole injection and transport, wherein the hole injection layer, the hole transport layer, the layer for simultaneously performing hole injection and transport may include the compound of Chemical Formula 1.

Further, the organic material layer may include a light emitting layer, wherein the light emitting layer may include the compound of Chemical Formula 1.

Further, the organic material layer may include an electron transport layer, or an electron injection layer, wherein the electron transport layer, or the electron injection layer may include the compound of Chemical Formula 1.

Further, the electron transport layer, the electron injection layer, or the layer for simultaneously performing electron transport and electron injection may include the compound of Chemical Formula 1.

Further, the organic material layer may include a light emitting layer or an electron transport layer, wherein the electron transport layer may include the compound of Chemical Formula 1.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound of Chemical Formula 1 may be included in one or more layers of the hole injection layer, the hole transport layer, the light emitting layer and the electron transport layer.

The organic light emitting device according to the present disclosure may be manufactured by materials and methods known in the art, except that one or more layers of the organic material layers include the compound of Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound of Chemical Formula 1 may be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive compound, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive compound, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a Spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound of Chemical Formula 1 may be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present disclosure.

PREPARATION EXAMPLE

Preparation Example 1: Preparation of Compound 1

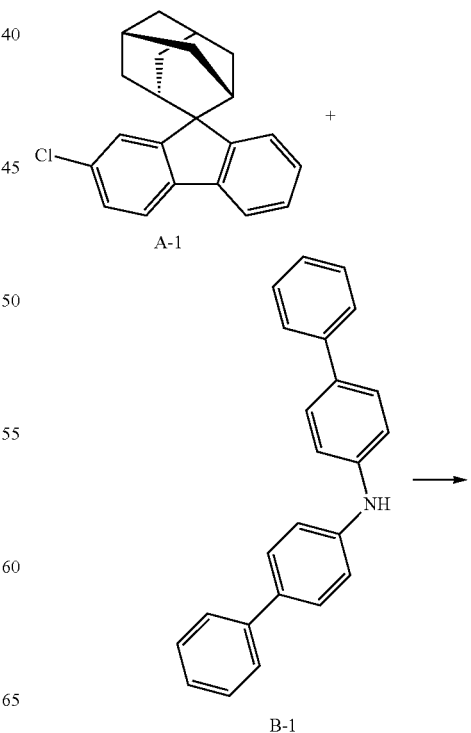

-continued

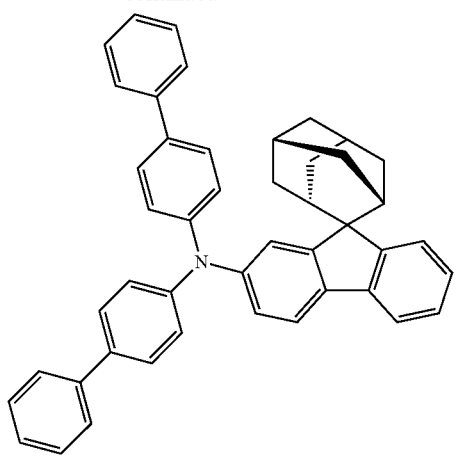

1

10 g (1 eq.) of Compound A-1 and 10.0 g (1 eq.) of Compound B-1 were added to toluene (150 mL). 6.0 g (2 eq.) of sodium tert-butoxide and 0.08 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 14.5 g of Compound 1 (yield: 77%).

MS:[M+H]$^+$=606

Preparation Example 2: Preparation of Compound 2

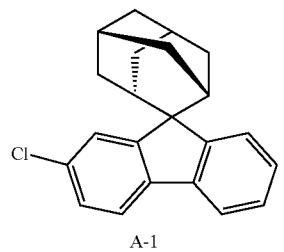

A-1

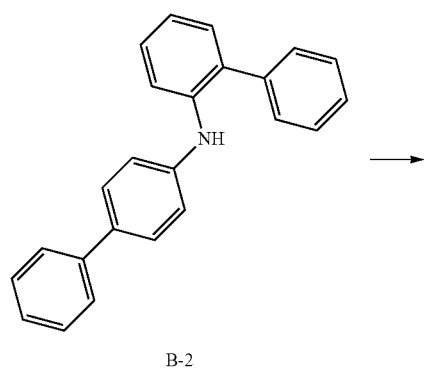

B-2

-continued

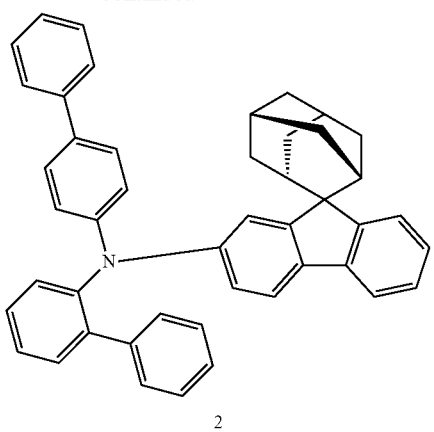

2

10 g (1 eq.) of Compound A-1 and 10.0 g (1 eq.) of Compound B-2 were added to toluene (150 mL). 6.0 g (2 eq.) of sodium tert-butoxide and 0.08 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 12.3 g of Compound 2 (yield: 65%).

MS:[M+H]$^+$=606

Preparation Example 3: Preparation of Compound 3

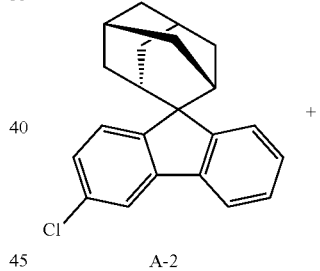

A-2

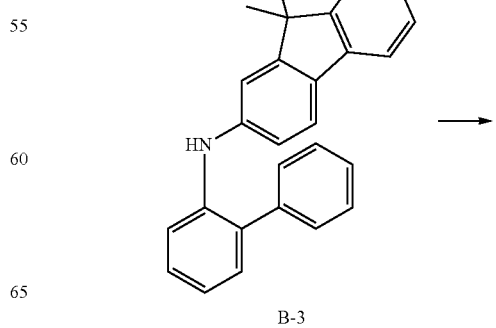

B-3

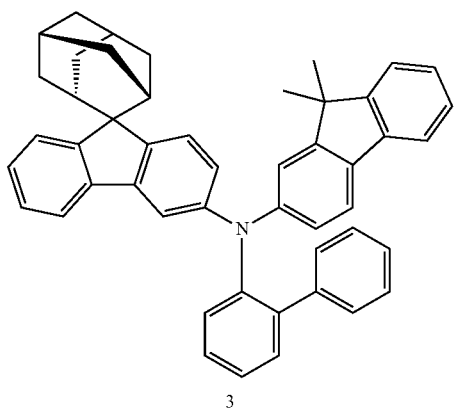

3

10 g (1 eq.) of Compound A-2 and 11.3 g (1 eq.) of Compound B-3 were added to toluene (150 mL). 6.0 g (2 eq.) of sodium tert-butoxide and 0.08 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 14.3 g of Compound 3 (yield: 71%).

MS:[M+H]$^+$=646

Preparation Example 4: Preparation of Compound 4

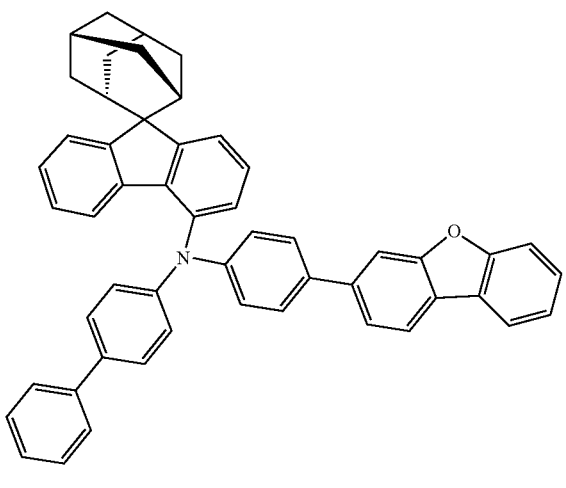

4

10 g (1 eq.) of Compound A-3 and 12.8 g (1 eq.) of Compound B-4 were added to toluene (150 mL). 6.0 g (2 eq.) of sodium tert-butoxide and 0.08 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 16.8 g of Compound 4 (yield: 78%).

MS:[M+H]$^+$=692

Preparation Example 5: Preparation of Compound 5

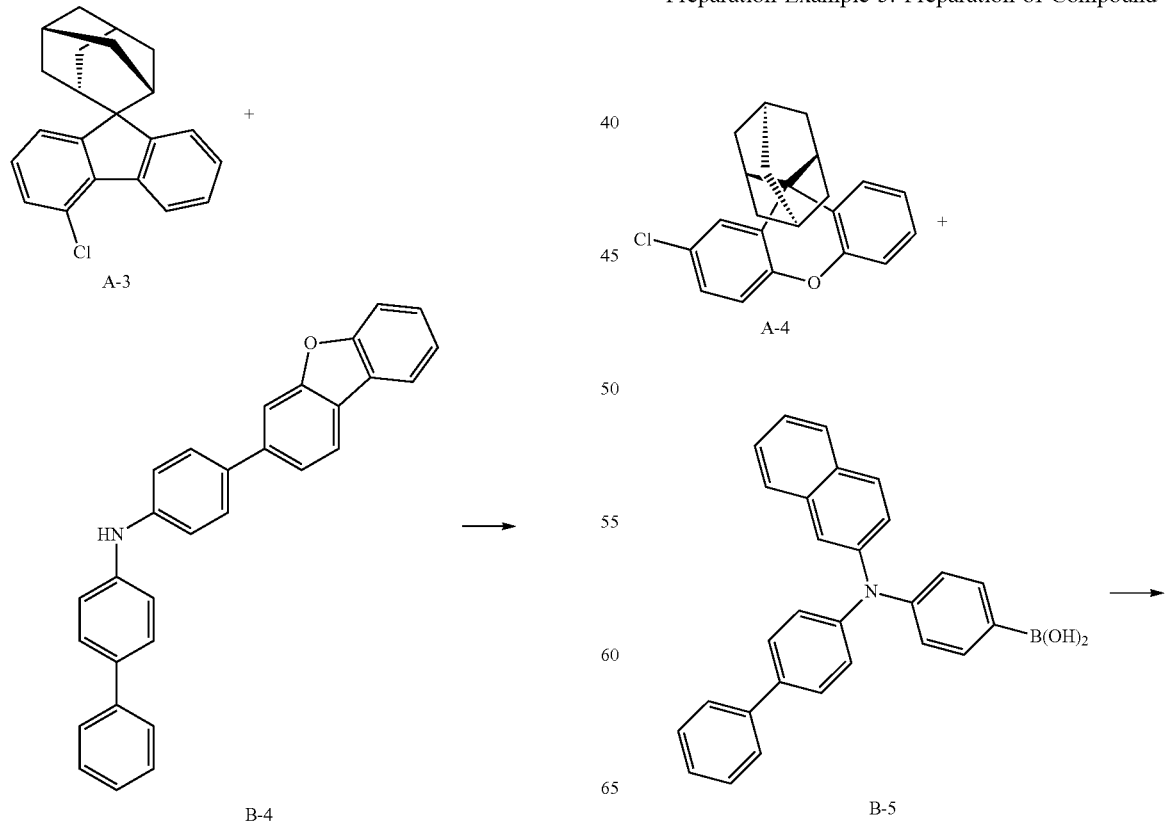

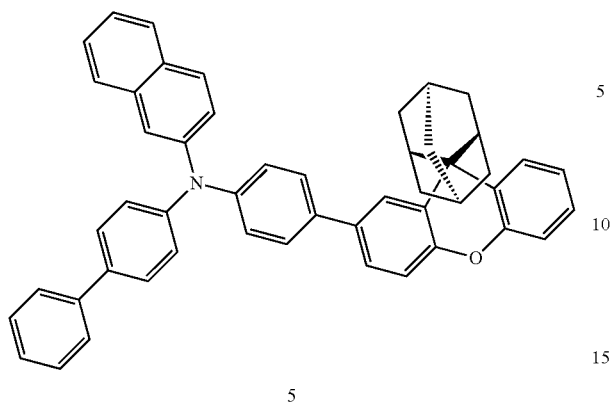

5

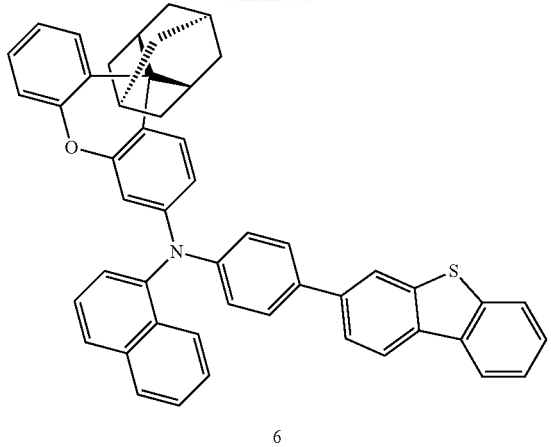

6

10 g (1 eq.) of Compound A-4 and 8.3 g (1 eq.) of Compound B-5 were added to tetrahydrofuran (150 mL). 2M aqueous potassium carbonate solution (100 mL) and 0.08 g (0.005 eq.) of bis(tri-tert-butylphosphine)palladium(0) were added thereto, and then stirred and refluxed for 5 hours. After the reaction temperature was lowered to room temperature and the reaction was completed, the potassium carbonate solution was removed to filter a white solid. The filtered solid was washed with tetrahydrofuran twice and washed with ethyl acetate twice to give 14.0 g of Compound 5 (yield: 70%).

MS:[M+H]$^+$=672

Preparation Example 6: Preparation of Compound 6

10 g (1 eq.) of Compound A-5 and 11.9 g (1 eq.) of Compound B-6 were added to toluene (150 mL). 5.7 g (2 eq.) of sodium tert-butoxide and 0.08 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 16.5 g of Compound 6 (yield: 79%).

MS:[M+H]$^+$=702

Preparation Example 7: Preparation of Compound 7

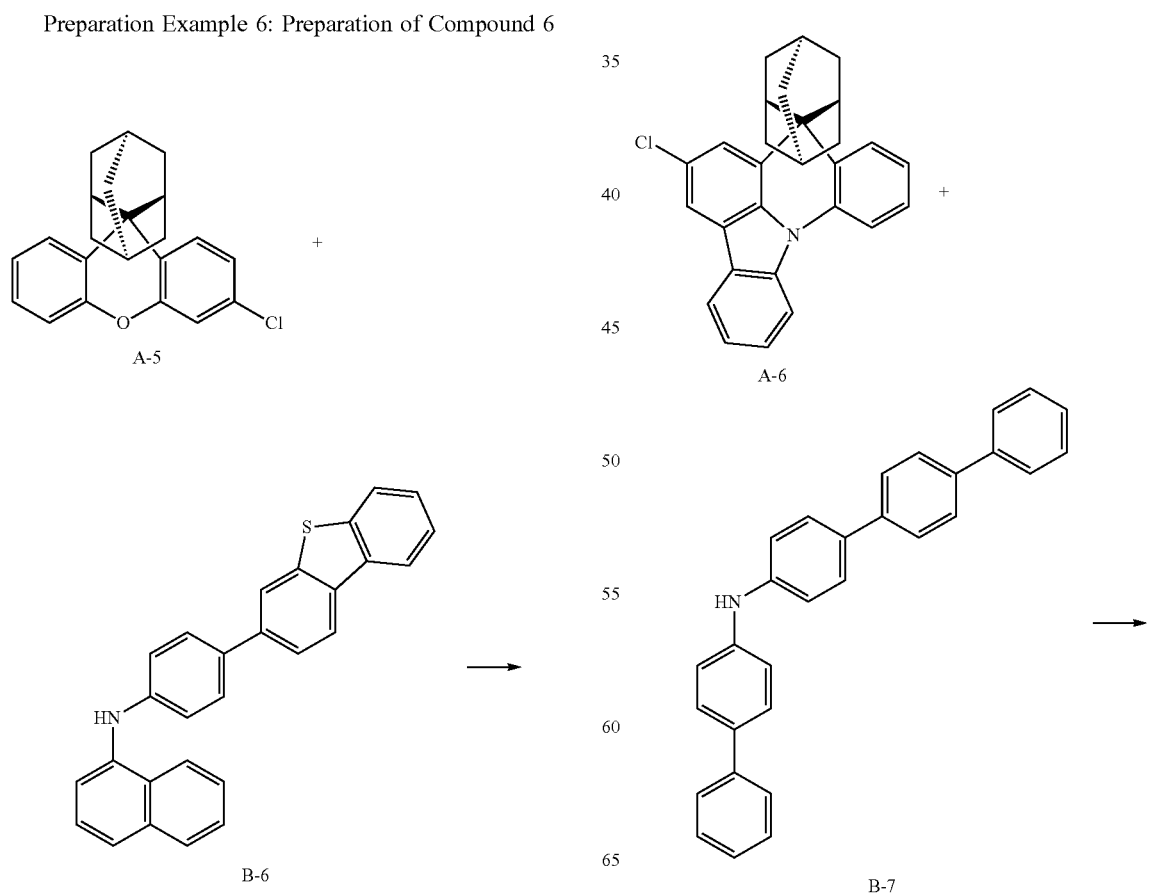

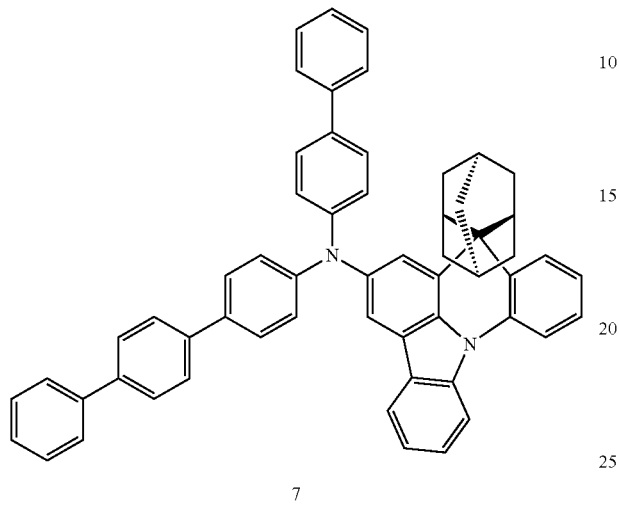

7

10 g (1 eq.) of Compound A-6 and 11.9 g (1 eq.) of Compound B-7 were added to toluene (150 mL). 4.7 g (2 eq.) of sodium tert-butoxide and 0.06 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 12.8 g of Compound 7 (yield: 68%).

MS:[M+H]⁺=772

Preparation Example 8: Preparation of Compound 8

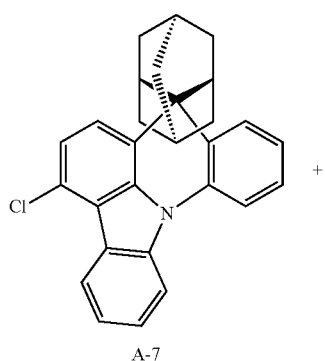

A-7

+

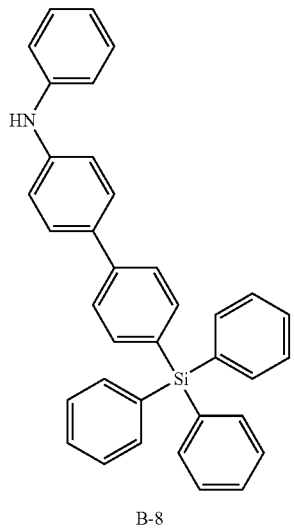

B-8

⟶

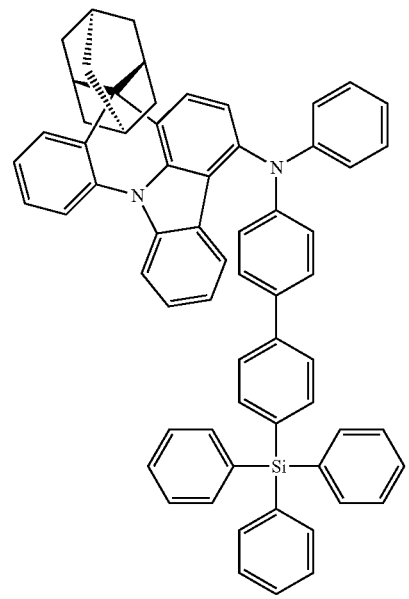

8

10 g (1 eq.) of Compound A-7 and 12.3 g (1 eq.) of Compound B-8 were added to toluene (150 mL). 4.7 g (2 eq.) of sodium tert-butoxide and 0.06 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 16.0 g of Compound 8 (yield: 75%).

MS:[M+H]⁺=878

Preparation Example 9: Preparation of Compound 9

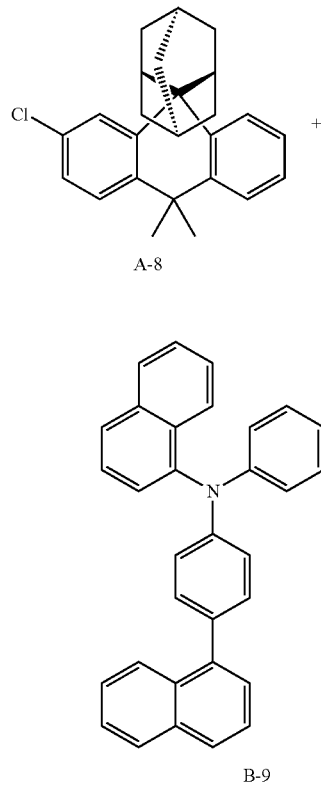

10 g (1 eq.) of Compound A-8 and 12.8 g (1 eq.) of Compound B-9 were added to tetrahydrofuran (150 mL). 2M aqueous potassium carbonate solution (100 mL) and 0.07 g (0.005 eq.) of bis(tri-tert-butylphosphine)palladium (0) were added thereto, and then stirred and refluxed for 5 hours. After the reaction temperature was lowered to room temperature and the reaction was completed, the potassium carbonate solution was removed to filter a white solid. The filtered solid was washed with tetrahydrofuran twice and washed with ethyl acetate twice to give 14.2 g of Compound 9 (yield: 69%).

MS:[M+H]$^+$=749

Preparation Example 10: Preparation of Compound 10

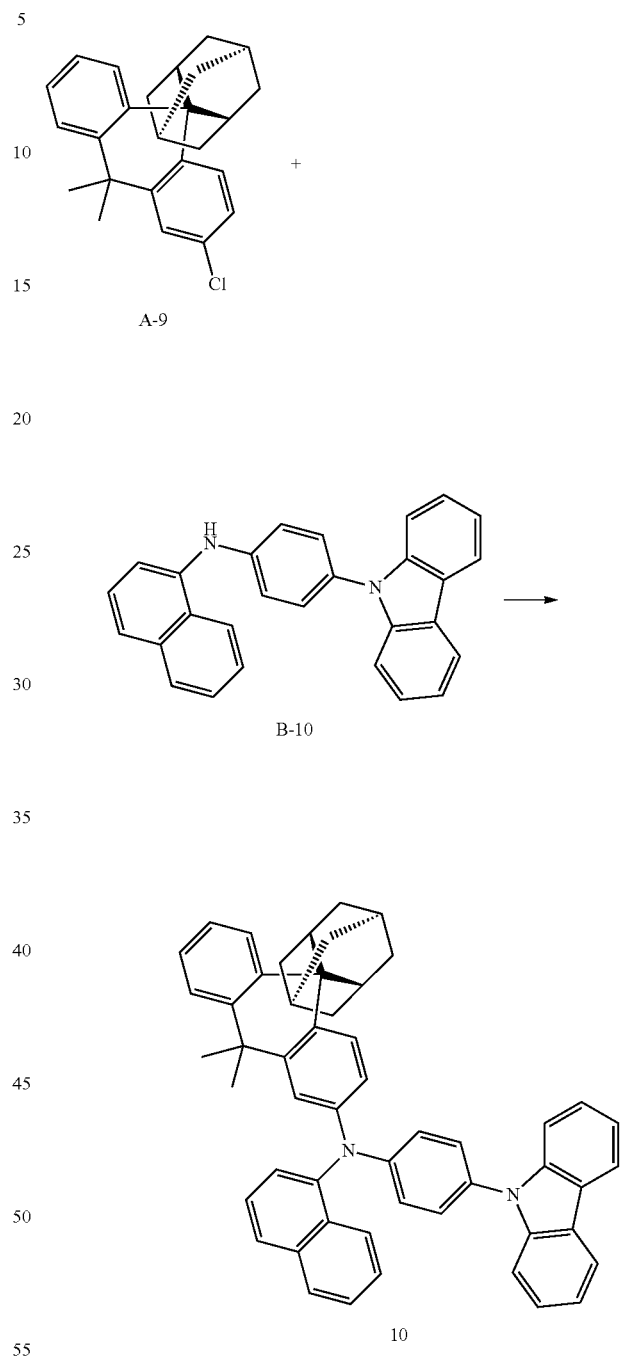

10 g (1 eq.) of Compound A-9 and 10.6 g (1 eq.) of Compound B-10 were added to toluene (150 mL). 5.3 g (2 eq.) of sodium tert-butoxide and 0.07 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 15.1 g of Compound 10 (yield: 77%).

MS:[M+H]$^+$=711

Preparation Example 11: Preparation of Compound 11

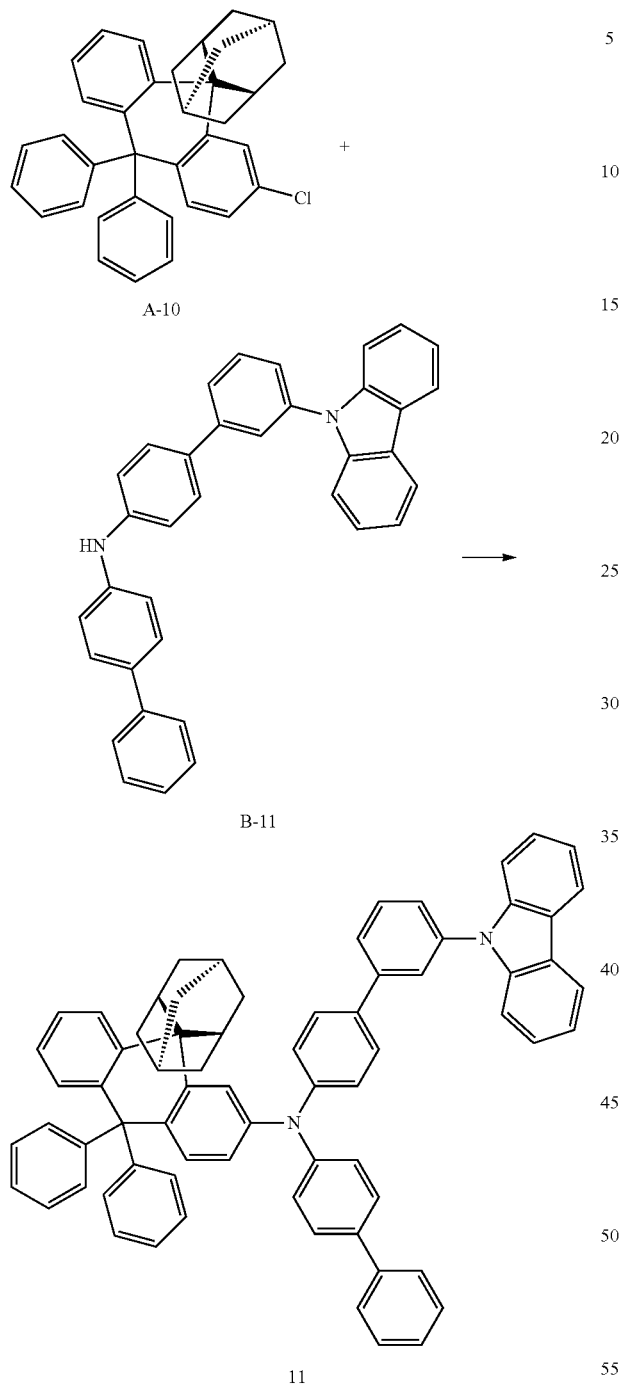

10 g (1 eq.) of Compound A-10 and 10.0 g (1 eq.) of Compound B-11 were added to toluene (150 mL). 3.9 g (2 eq.) of sodium tert-butoxide and 0.05 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 11.7 g of Compound 11 (yield: 61%).

MS:[M+H]$^+$=938

Preparation Example 12: Preparation of Compound 12

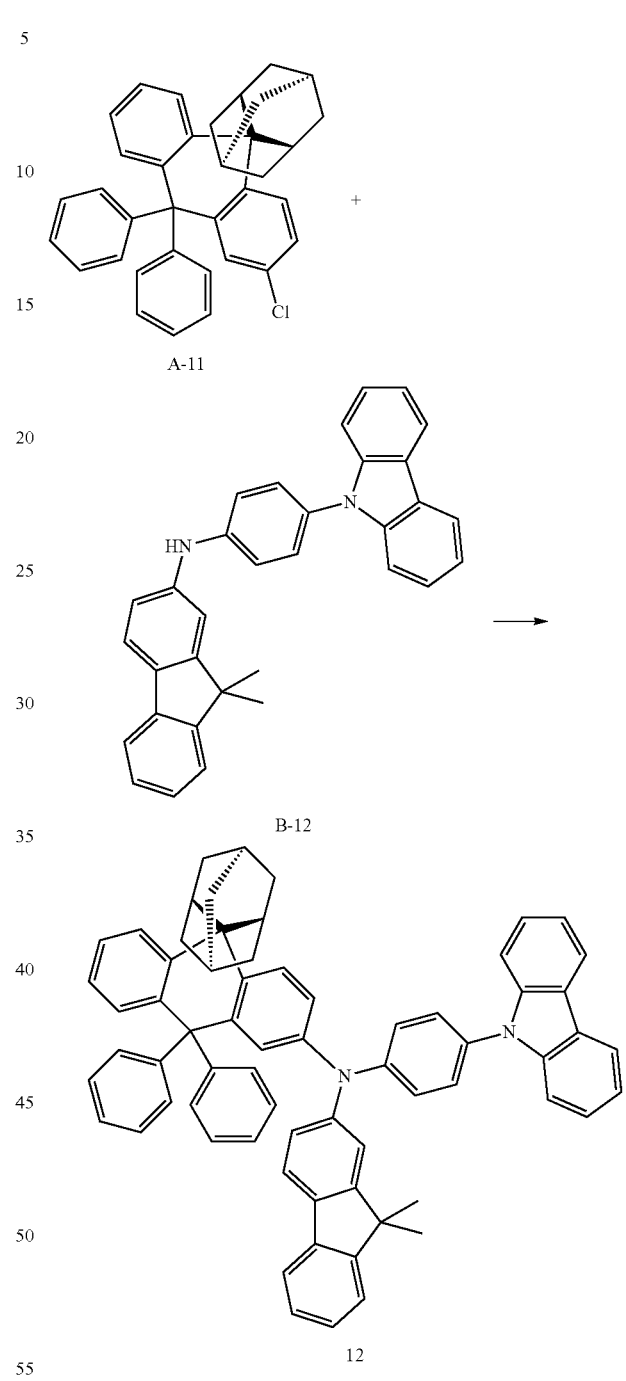

10 g (1 eq.) of Compound A-11 and 9.3 g (1 eq.) of Compound B-12 were added to toluene (150 mL). 3.9 g (2 eq.) of sodium tert-butoxide and 0.05 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 12.6 g of Compound 12 (yield: 68%).

MS:[M+H]$^+$=902

Preparation Example 13: Preparation of Compound 13

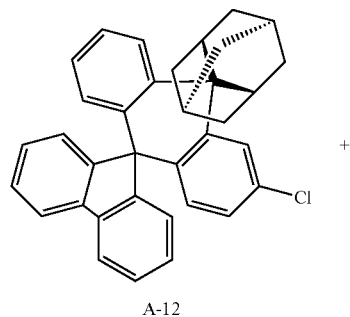

A-12

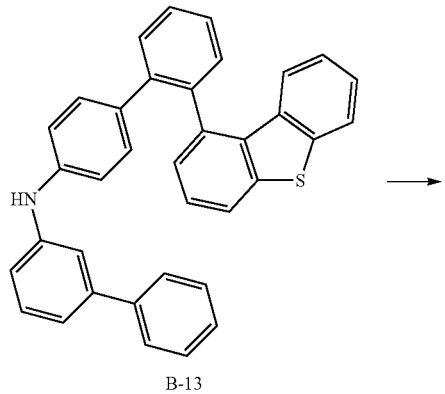

B-13

→

13

10 g (1 eq.) of Compound A-12 and 10.4 g (1 eq.) of Compound B-13 were added to toluene (150 mL). 4.0 g (2 eq.) of sodium tert-butoxide and 0.05 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 15.9 g of Compound 13 (yield: 81%).

MS:[M+H]$^+$=953

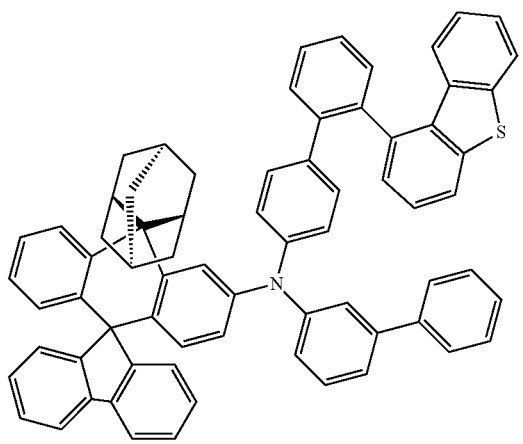

Preparation Example 14: Preparation of Compound 14

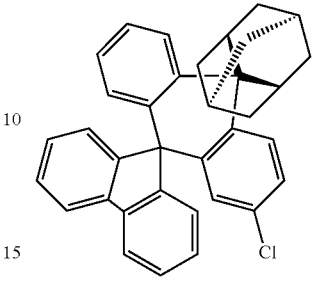

A-13

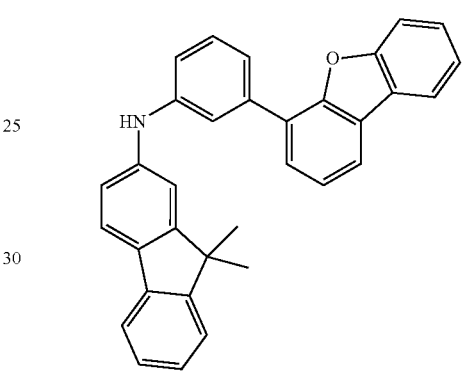

B-14

→

14

10 g (1 eq.) of Compound A-13 and 9.3 g (1 eq.) of Compound B-14 were added to toluene (150 mL). 4.0 g (2 eq.) of sodium tert-butoxide and 0.05 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 14.3 g of Compound 14 (yield: 77%).

MS:[M+H]$^+$=901

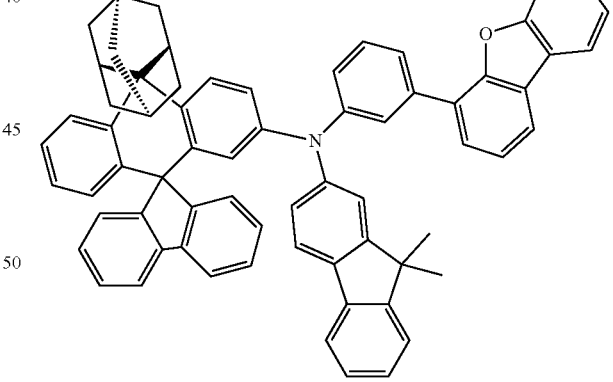

Preparation Example 15: Preparation of Compound 15

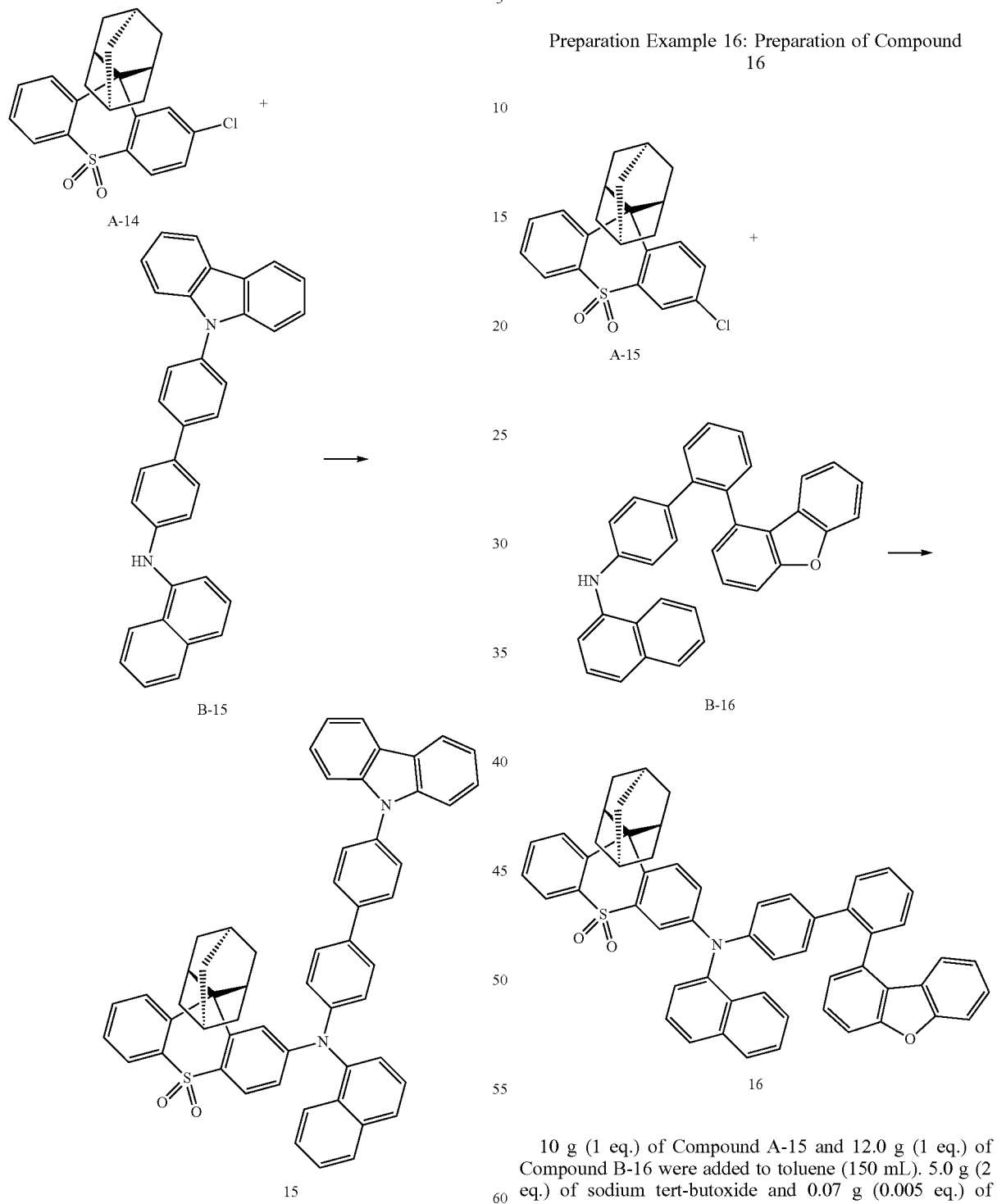

10 g (1 eq.) of Compound A-14 and 12.0 g (1 eq.) of Compound B-15 were added to toluene (150 mL). 5.0 g (2 eq.) of sodium tert-butoxide and 0.07 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 15.1 g of Compound 15 (yield: 72%).

MS:[M+H]$^+$=810

Preparation Example 16: Preparation of Compound 16

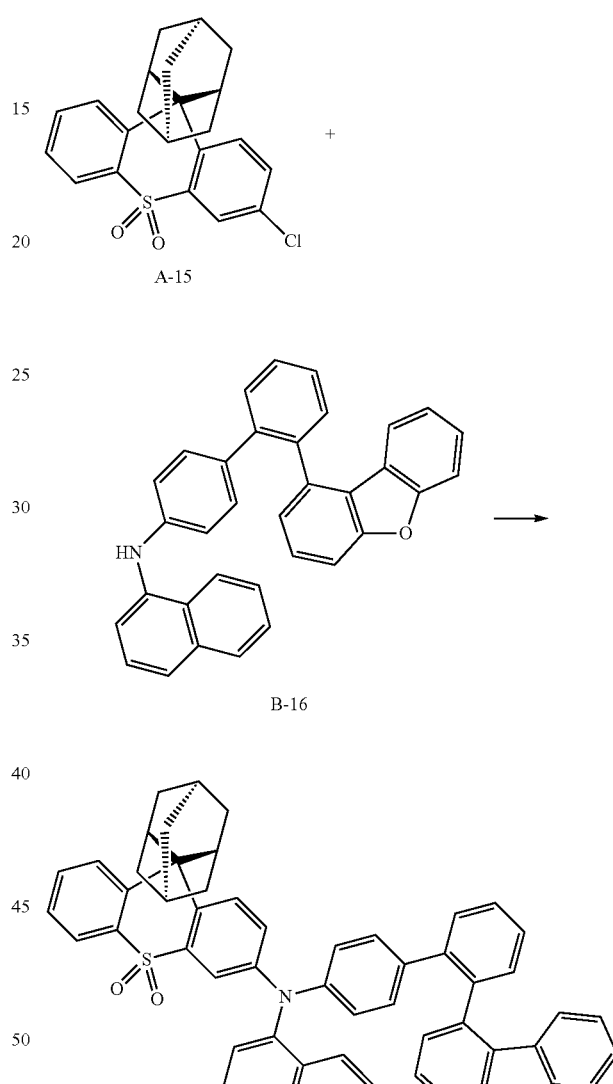

10 g (1 eq.) of Compound A-15 and 12.0 g (1 eq.) of Compound B-16 were added to toluene (150 mL). 5.0 g (2 eq.) of sodium tert-butoxide and 0.07 g (0.005 eq.) of bis(tri-tert-butylphosphine)palladium(0) were added thereto, and then stirred and refluxed for 2 hours. The mixture was cooled to room temperature and then filtered to give a solid. The resulting solid was recrystallized from chloroform and ethanol to give 15.3 g of Compound 16 (yield: 68%).

MS:[M+H]$^+$=811

EXPERIMENTAL EXAMPLE

Experimental Example 1

A glass substrate on which ITO (indium tin oxide) was coated as a thin film to a thickness of 1,000 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, a compound [H1-A] below was thermally vacuum-deposited to a thickness of 600 Å to form a hole injection layer. The compound 1 prepared in Preparation Example 1 was vacuum-deposited on the hole injection layer to form a hole transport layer.

Then, a compound [BH] below and a compound [BD] below were vacuum-deposited at a ratio of 25:1 to a thickness of 200 Å on the hole transport layer to form a light emitting layer.

A compound [ET] below and a compound [LiQ] (lithiumquinolate) below were vacuum-deposited at a ratio of 1:1 to form an electron injection and transport layer with a thickness of 150 Å. Lithium fluoride (LiF) and aluminum were sequentially deposited to have a thickness of 10 Å and 1,000 Å, respectively, on the electron injection and transport layer, thereby forming a cathode.

In the above-mentioned process, the vapor deposition rate of the organic material was maintained at 0.4 to 0.9 Å/sec, the deposition rates of lithium fluoride and aluminum of the cathode were maintained at 0.3 Å/sec and at 2 Å/sec, respectively, and the degree of vacuum during the deposition was maintained at $1 \times 10^{-7}$ to $5 \times 10^{-8}$ torr, thereby manufacturing an organic light emitting device.

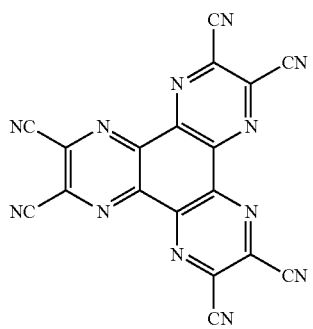
[HAT]

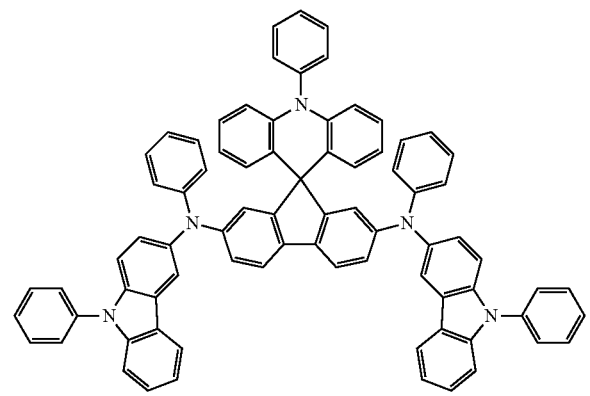
[H1-A]

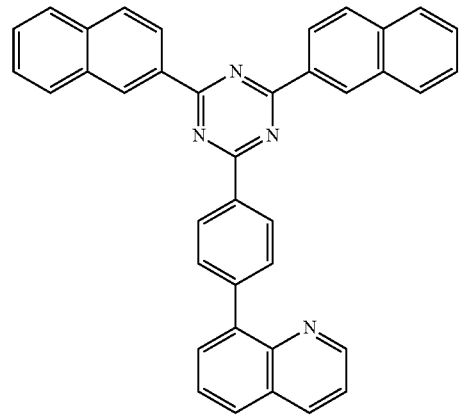
[ET]

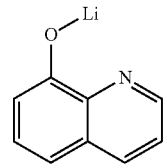
[LiQ]

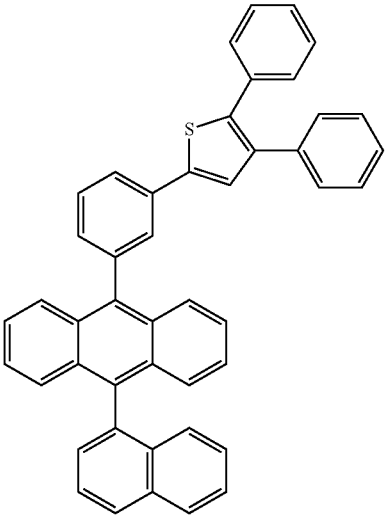
[BH]

[BD]

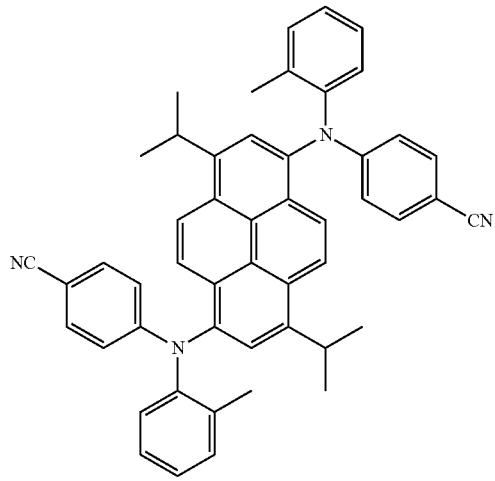

Experimental Examples 2 to 16

The organic light emitting devices were manufactured in the same manner as in Experimental Example 1, except that the compounds shown in Table 1 below were used instead of the compound in Experimental Example 1.

Comparative Examples 1 to 6

The organic light emitting devices were manufactured in the same manner as in Experimental Example 1, except that the compounds shown in Table 1 below were used instead of the compound in Experimental Example 1. The compounds of HT-01 to HT-06 used in Table 1 below are as follows.

[HT-01]

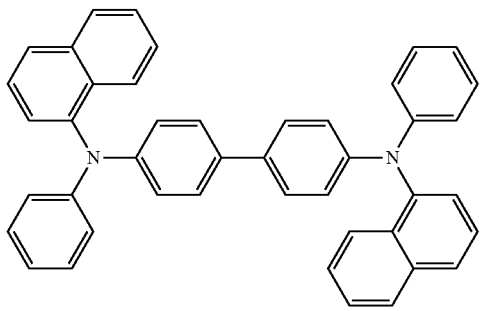

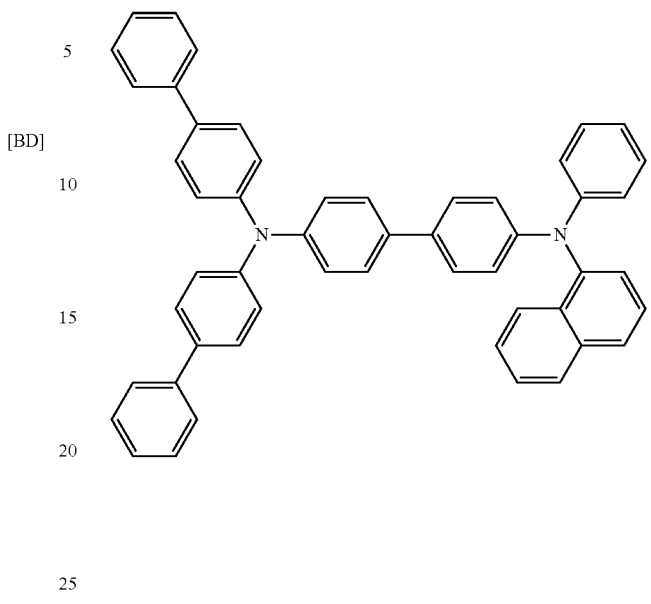

[HT-02]

[HT-03]

[HT-04]

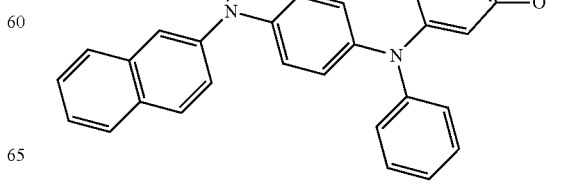

-continued

[HT-05]

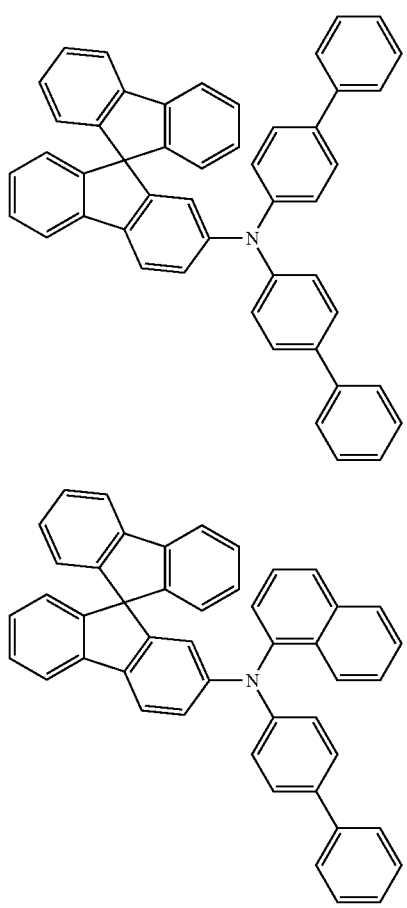

[HT-06]

For the organic light emitting devices manufactured using the respective compounds as the hole transport layer in the Experimental Examples and Comparative Experimental Examples, the driving voltage and emission efficiency were measure at a current density of 10 mA/cm², and the time ($LT_{98}$) required for the luminance to be reduced to 98% of the initial luminance was measured at a current density of 20 mA/cm², and the results are shown in Table 1 below.

TABLE 1

| Category | Hole transport layer | Voltage (V) | Current efficiency (cd/A) | Life Time(hr) $LT_{98}$ at 20 mA/cm² |
|---|---|---|---|---|
| Experimental Example 1 | Compound 1 | 3.71 | 5.64 | 70 |
| Experimental Example 2 | Compound 2 | 3.72 | 5.50 | 72 |
| Experimental Example 3 | Compound 3 | 3.77 | 5.55 | 75 |
| Experimental Example 4 | Compound 4 | 3.61 | 5.51 | 76 |
| Experimental Example 5 | Compound 5 | 3.68 | 5.62 | 71 |
| Experimental Example 6 | Compound 6 | 3.76 | 5.60 | 70 |
| Experimental Example 7 | Compound 7 | 3.80 | 5.66 | 69 |
| Experimental Example 8 | Compound 8 | 3.74 | 5.69 | 77 |
| Experimental Example 9 | Compound 9 | 3.69 | 5.61 | 80 |

TABLE 1-continued

| Category | Hole transport layer | Voltage (V) | Current efficiency (cd/A) | Life Time(hr) $LT_{98}$ at 20 mA/cm² |
|---|---|---|---|---|
| Experimental Example 10 | Compound 10 | 3.66 | 5.59 | 71 |
| Experimental Example 11 | Compound 11 | 3.70 | 5.70 | 76 |
| Experimental Example 12 | Compound 12 | 3.60 | 5.67 | 75 |
| Experimental Example 13 | Compound 13 | 3.82 | 5.66 | 68 |
| Experimental Example 14 | Compound 14 | 3.83 | 5.79 | 66 |
| Experimental Example 15 | Compound 15 | 3.75 | 5.71 | 74 |
| Experimental Example 16 | Compound 16 | 3.73 | 5.66 | 73 |
| Comparative Example 1 | HT-01 | 4.71 | 4.42 | 30 |
| Comparative Example 2 | HT-02 | 4.80 | 4.40 | 31 |
| Comparative Example 3 | HT-03 | 4.81 | 4.44 | 35 |
| Comparative Example 4 | HT-04 | 4.88 | 4.45 | 30 |
| Comparative Example 5 | HT-05 | 4.90 | 4.50 | 28 |
| Comparative Example 6 | HT-06 | 4.86 | 4.52 | 25 |

As shown in Table 1, it was confirmed that when the compound of the present disclosure was used as a hole transport layer material, it exhibited excellent efficiency and lifetime compared to Comparative Examples. This is considered to be because the chemical structural stability of the compound of Chemical Formula 1 was increased by introducing the adamantane structure in the core.

EXPLANATION OF SIGN

1: substrate
2: anode
3: light emitting layer
4: cathode
5: hole injection layer
6: hole transport layer
7: light emitting layer
8. electron transport layer

What is claimed is:
1. A compound of the following Chemical Formula 1:

[Chemical Formula 1]

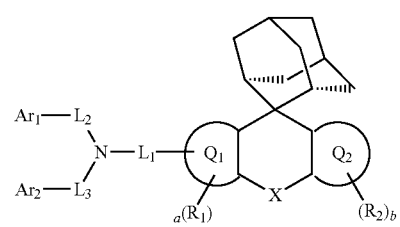

in the Chemical Formula 1,
$Q_1$ and $Q_2$ are each independently a $C_{6-30}$ aromatic ring;
a and b are each independently an integer of 0 to 3;
X is a single bond; $CR_3R_4$; $SiR_5R_6$; $NR_7$; O; S; or $SO_2$, $R_1$ to $R_7$ are each independently hydrogen; deuterium; a substituted or unsubstituted $C_{1-60}$ alkyl; a substituted or unsubstituted $C_{1-60}$ alkoxy; a substituted or unsubstituted $C_{6-60}$ aryl; a substituted or unsubstituted $C_{5-60}$ heteroaryl containing one or more heteroatoms selected from the group consisting of N, O and S; or may be bonded to adjacent groups to form a ring, $L_1$ to $L_3$ are each independently a single bond; a substituted or unsubstituted $C_{6-60}$ arylene; or a substituted or unsubstituted $C_{2-60}$ heteroarylene containing any one or more heteroatoms selected from the group consisting of N, O and S, and $Ar_1$ and $Ar_2$ are each independently a substituted or unsubstituted $C_{6-60}$ aryl excluding a diphenylfluorene; a substituted or unsubstituted $C_{2-60}$ heteroaryl containing one or more heteroatoms selected from the group consisting of N, O and S; a substituted or unsubstituted $C_{1-30}$ alkyl silyl; or a substituted or unsubstituted $C_{6-30}$ aryl silyl.

2. The compound of claim 1, wherein $Q_1$ and $Q_2$ are each independently a benzene or naphthalene ring.

3. The compound of claim 1, wherein the Chemical Formula 1 is one of the following Chemical Formulas 1-1 to 1-7,

[Chemical Formula 1-1]

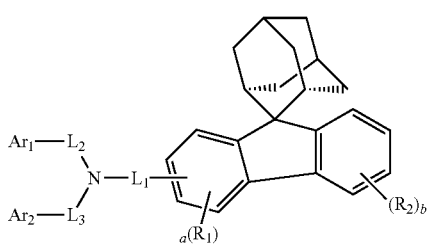

[Chemical Formula 1-2]

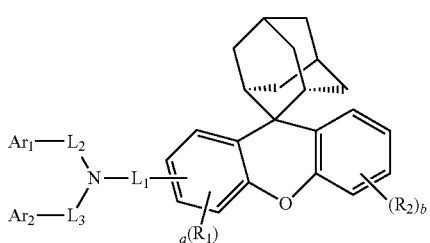

[Chemical Formula 1-3]

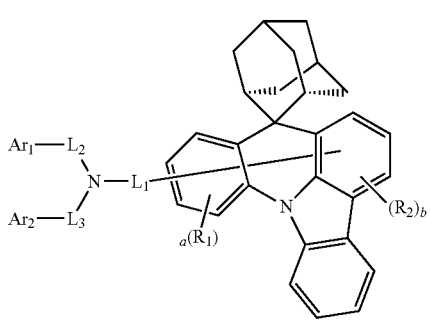

[Chemical Formula 1-4]

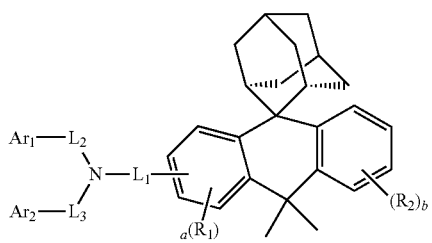

[Chemical Formula 1-5]

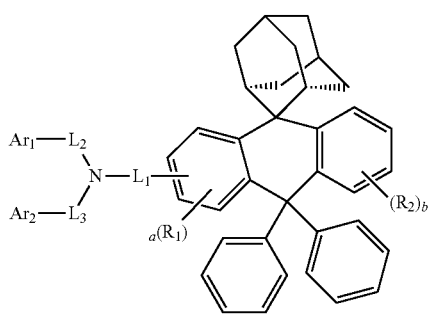

[Chemical Formula 1-6]

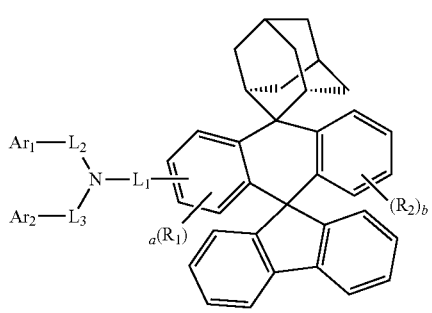

[Chemical Formula 1-7]

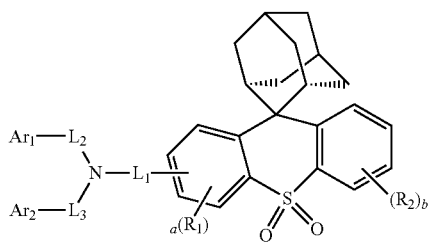

in the Chemical Formulas 1-1 to 1-7, a, b, $R_1$, $R_2$, $L_1$ to $L_3$, $Ar_1$ and $Ar_2$ are the same as defined in claim 1.

4. The compound of claim 1, wherein both a and b are 0.

5. The compound of claim 1, wherein $L_1$ to $L_3$ are independently a single bond; phenylene; or biphenylylene.

6. The compound of claim 1, wherein $Ar_1$ and $Ar_2$ are each independently phenyl, biphenylyl, terphenylyl, naphthyl, dimethylfluorenyl, dibenzofuranyl, dibenzothiophenyl, carbazolyl, or triphenylsilyl.

7. The compound of claim 1,
wherein the compound of Chemical Formula 1 is selected from the group consisting of:
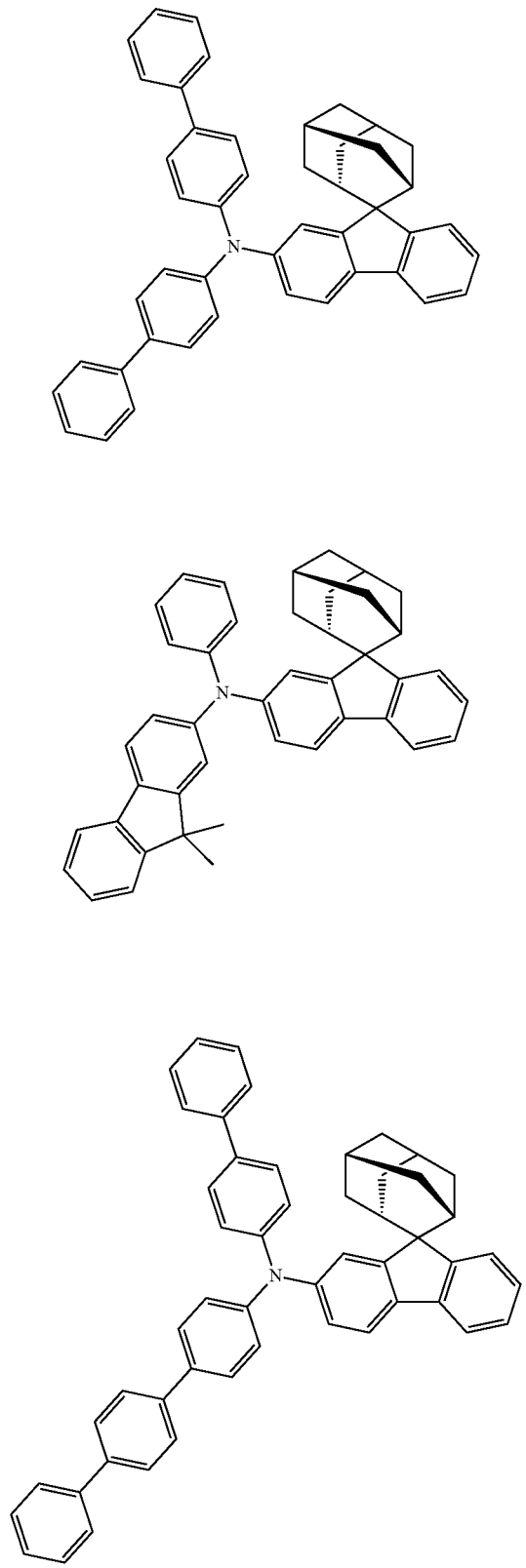
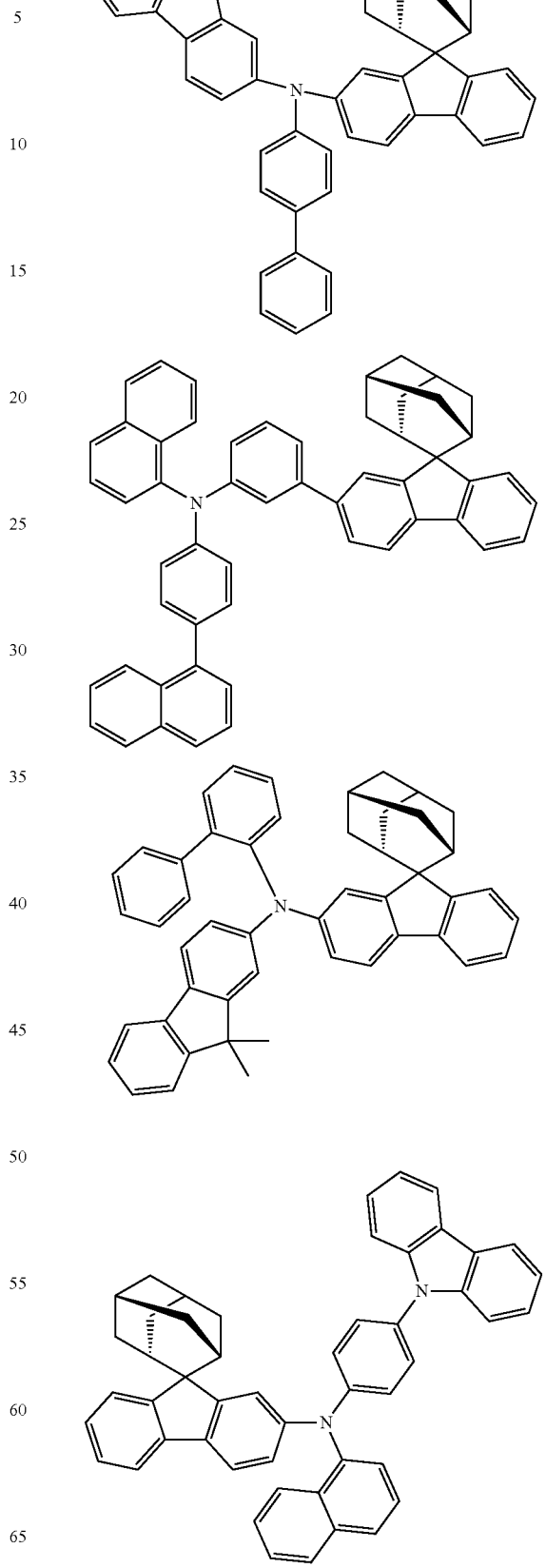

173
-continued
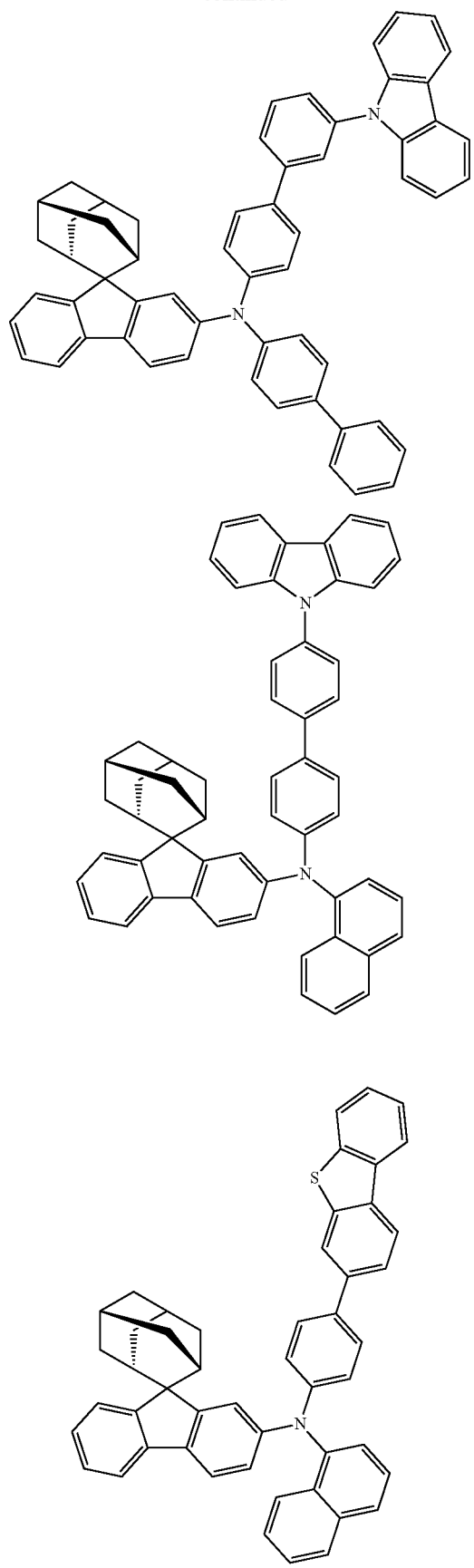
174
-continued
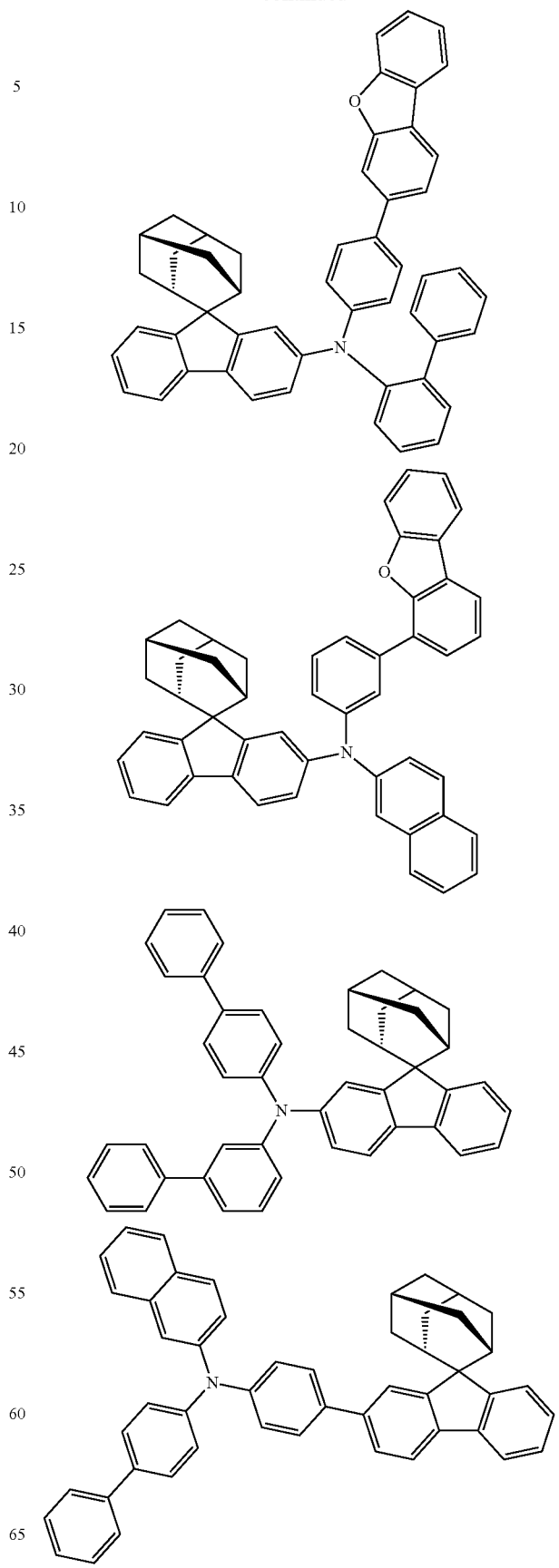

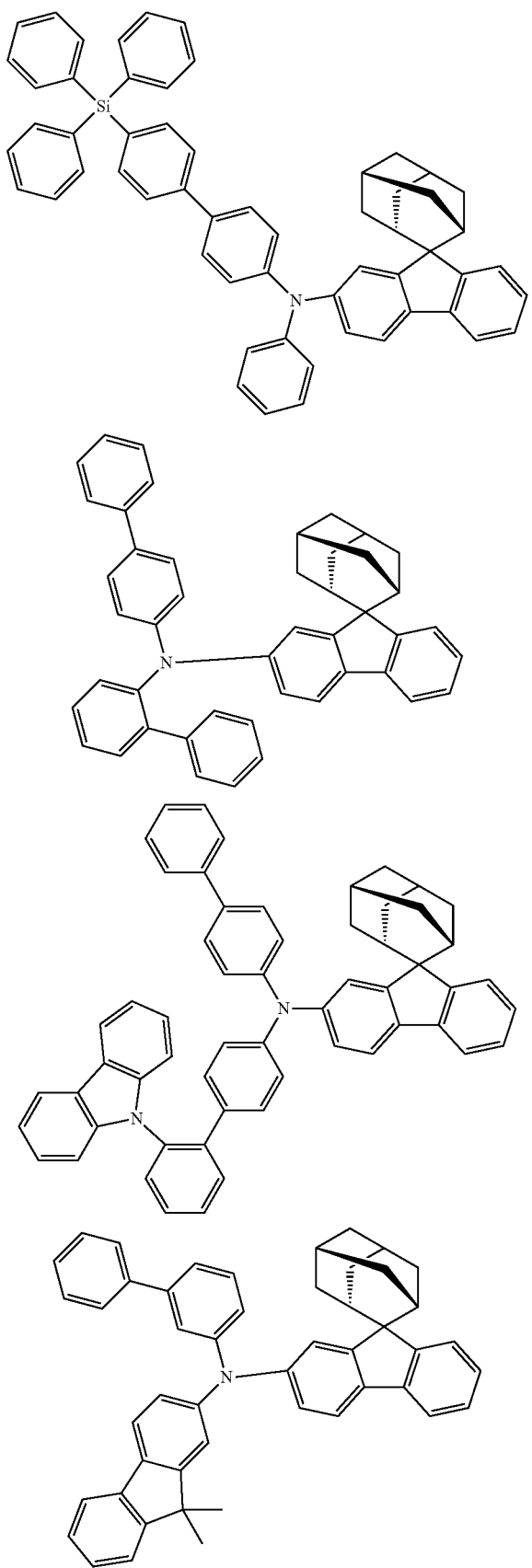
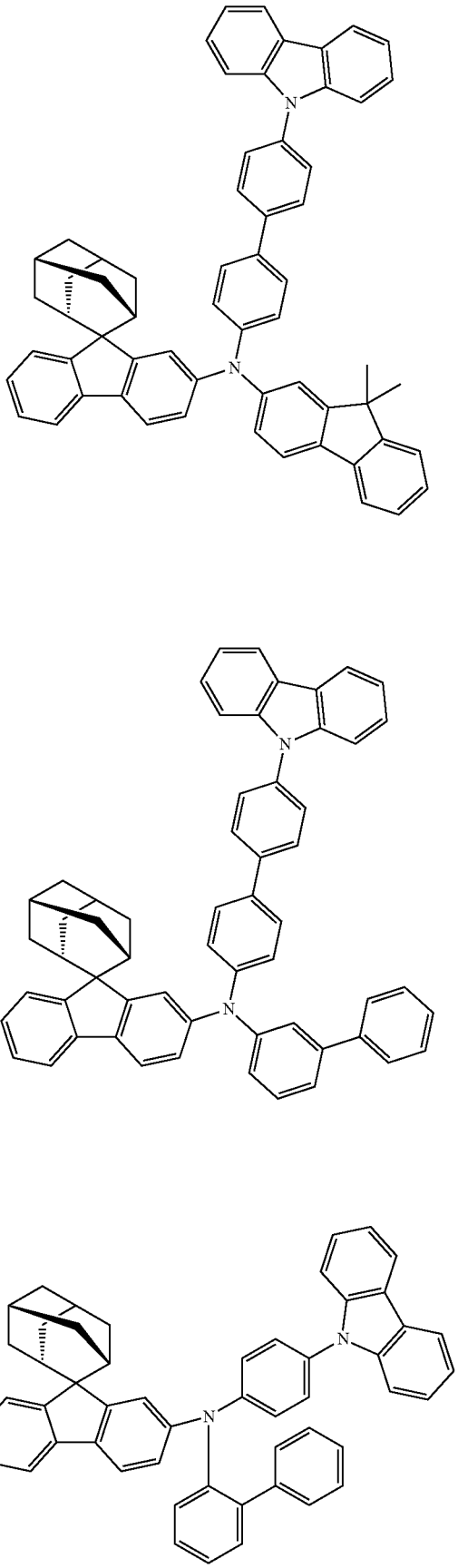

177
-continued
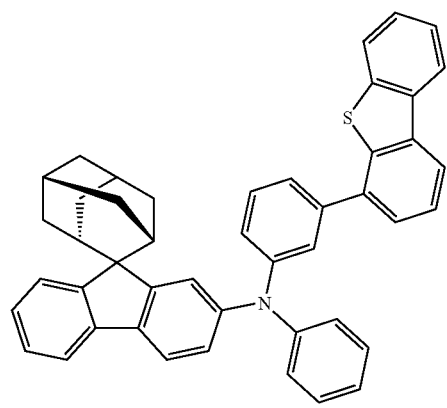
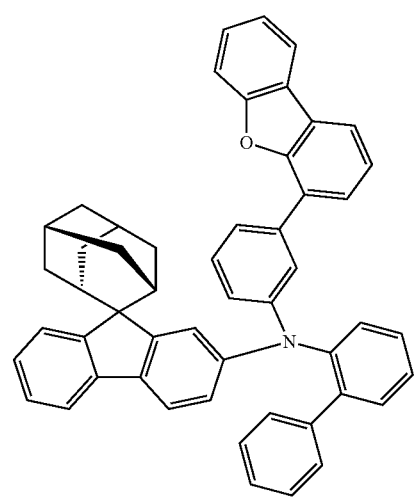
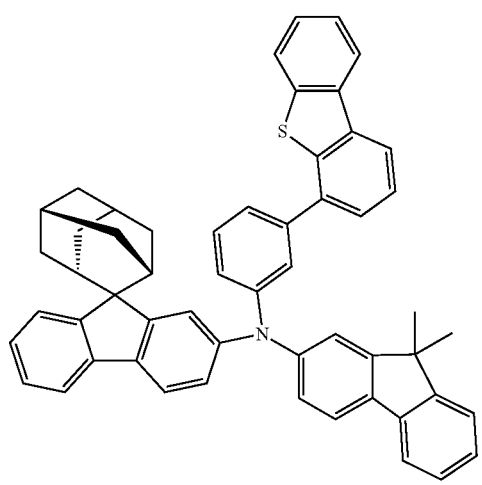
178
-continued
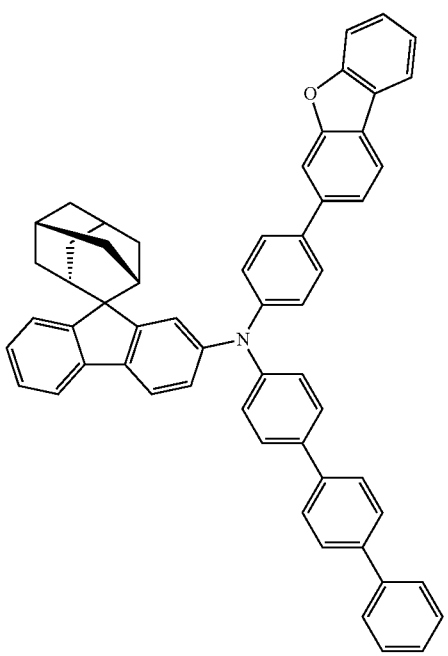
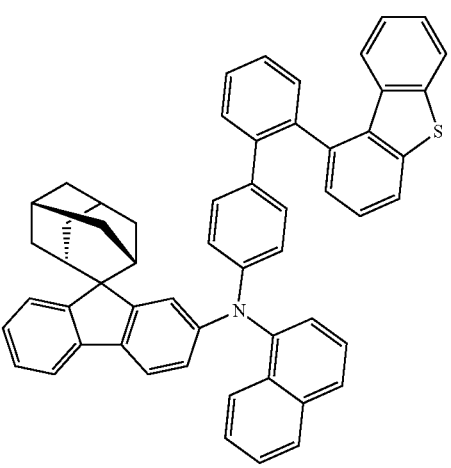
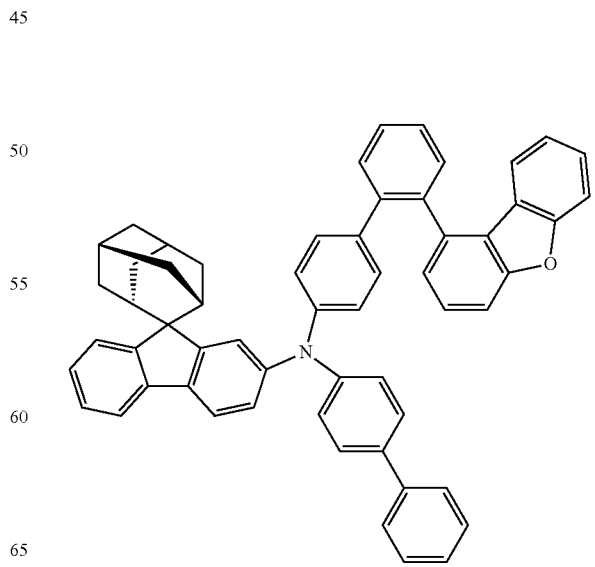

179
-continued
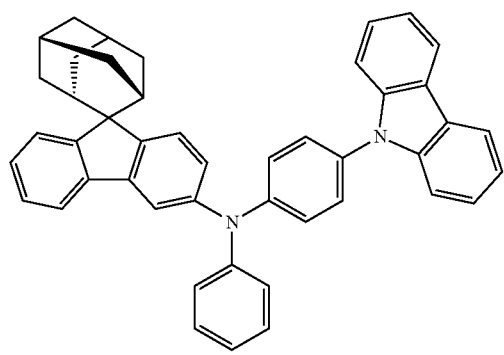
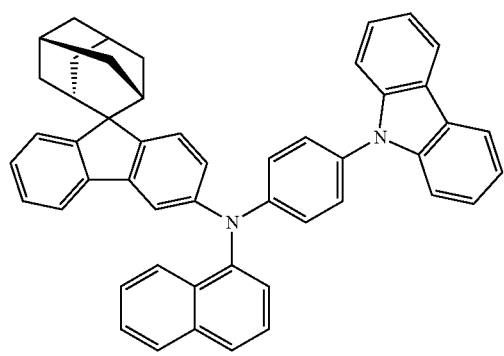
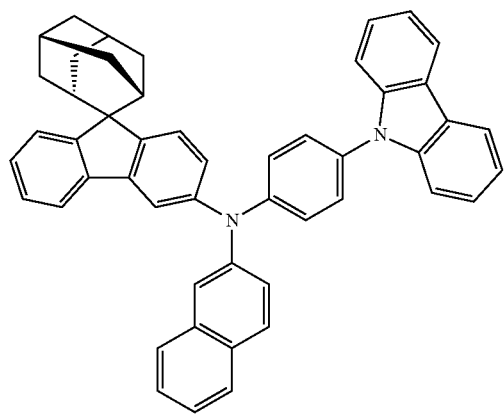
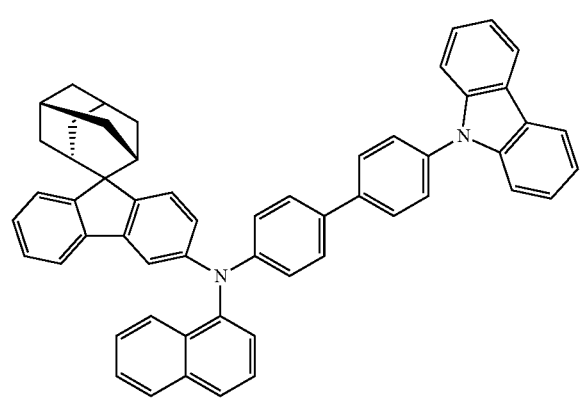
180
-continued
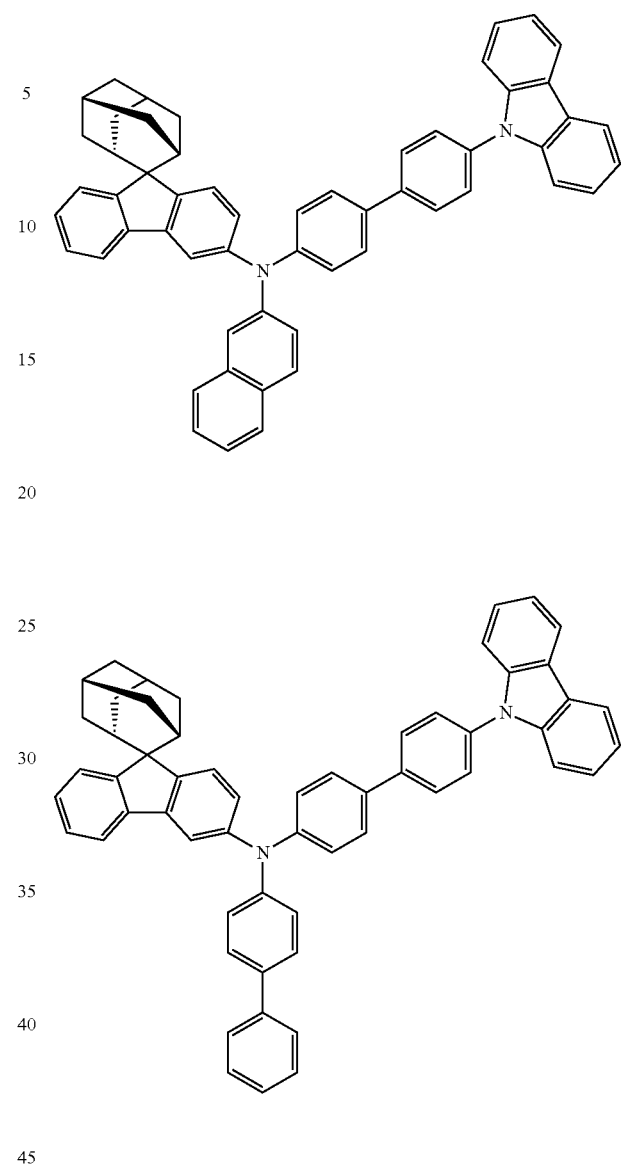
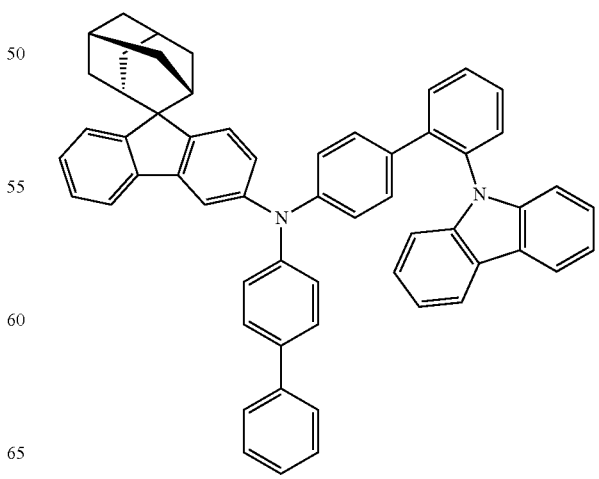

181
-continued
182
-continued
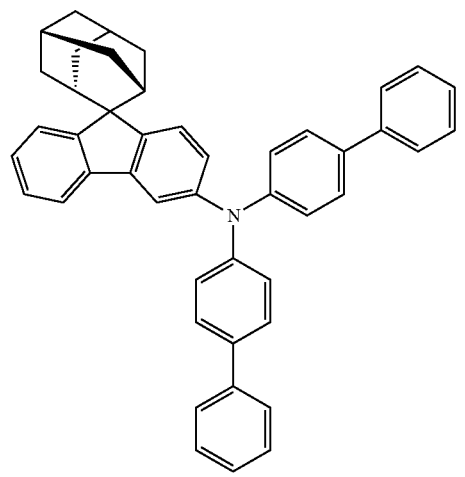
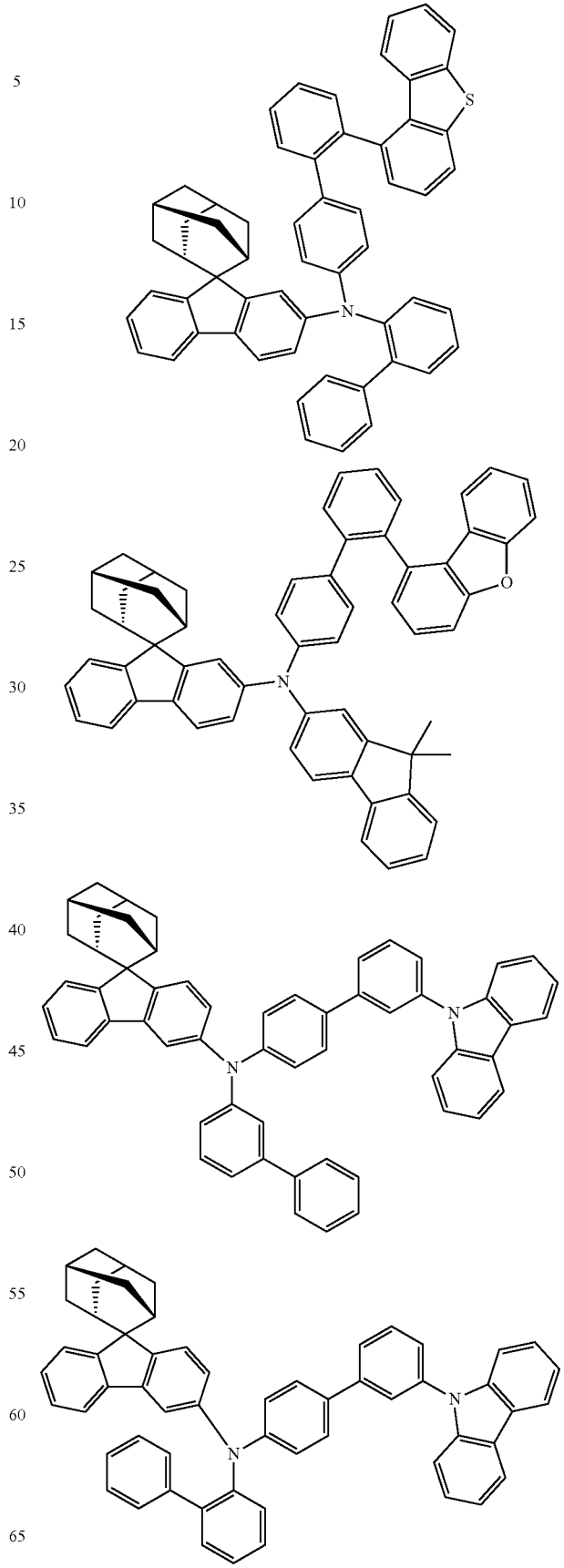

183
-continued
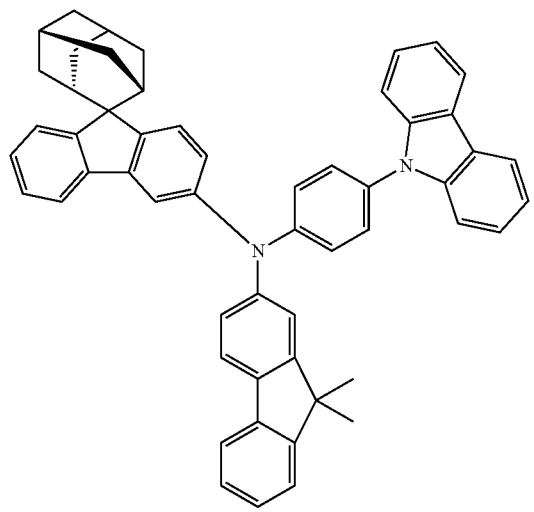
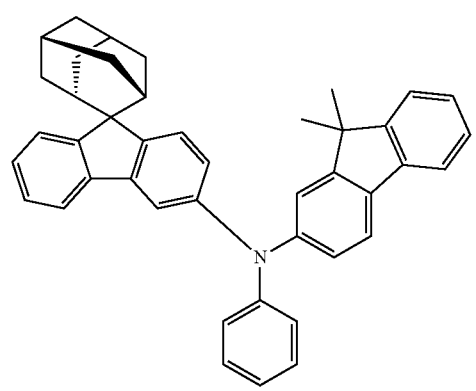
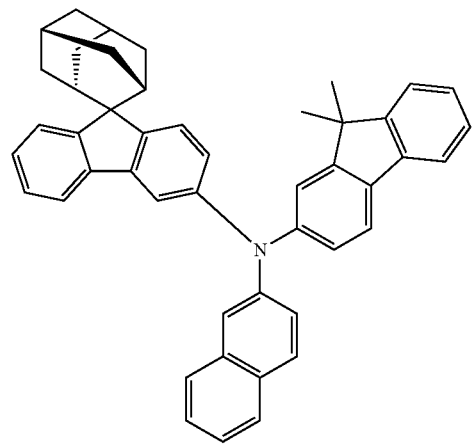
184
-continued
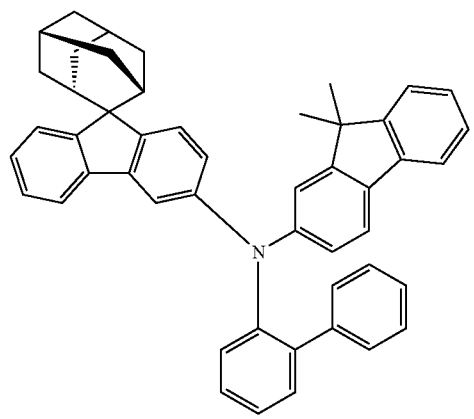
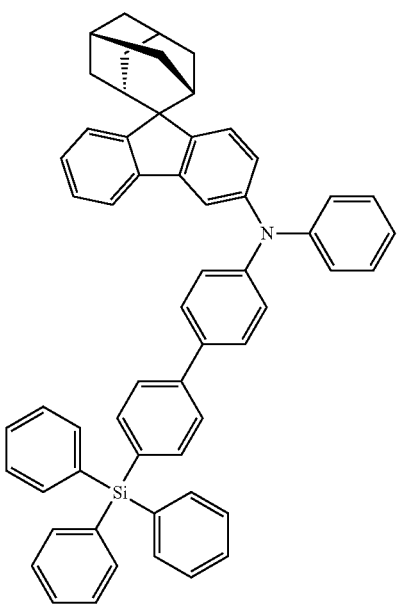
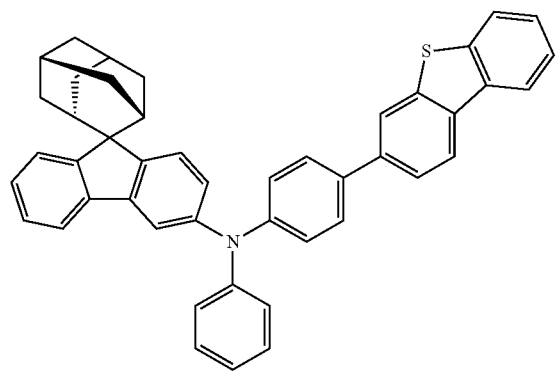

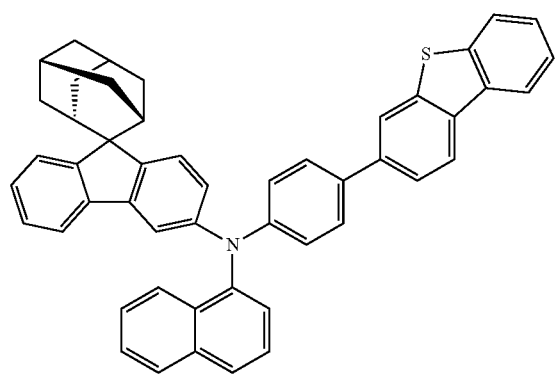
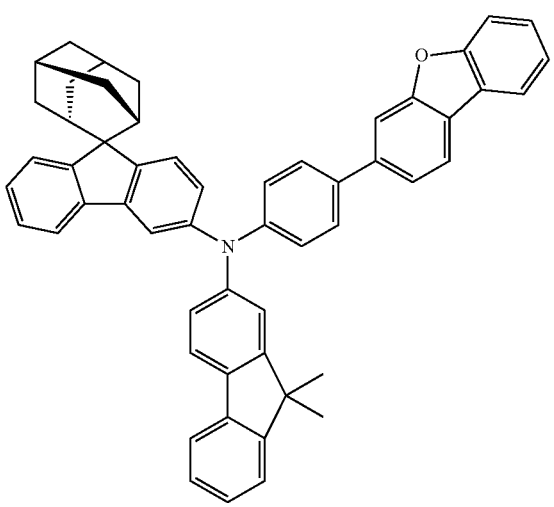
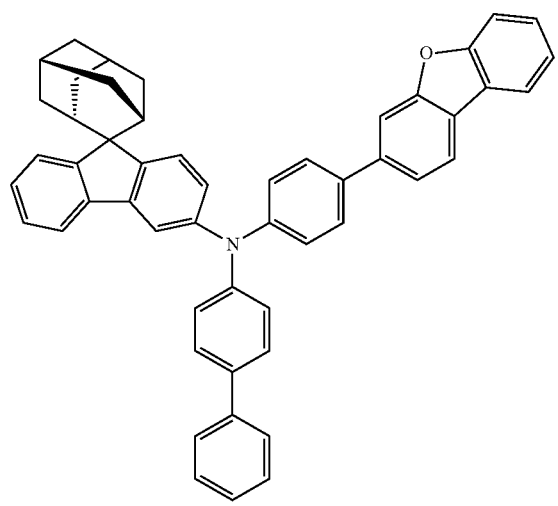
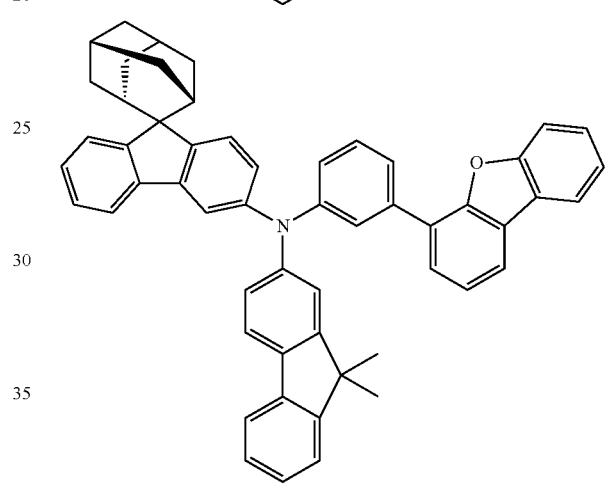
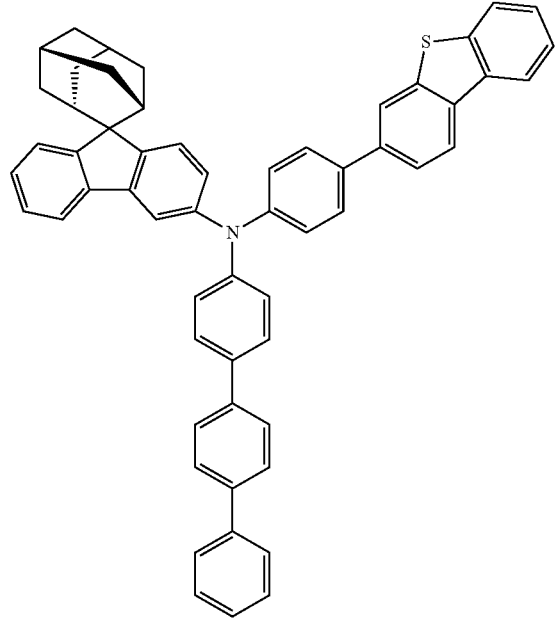
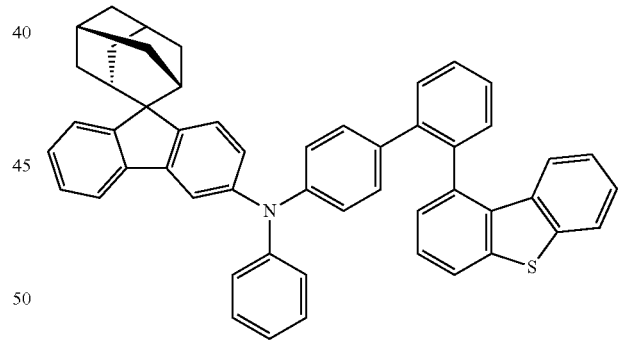
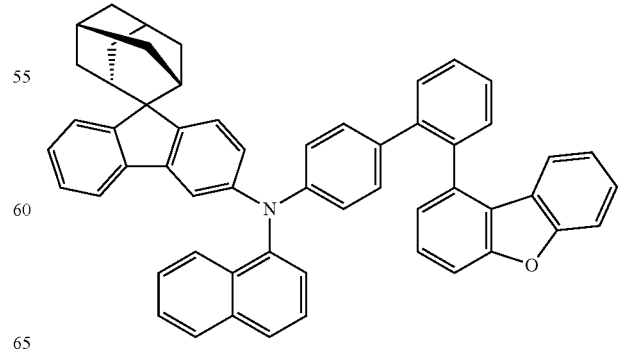

187
-continued
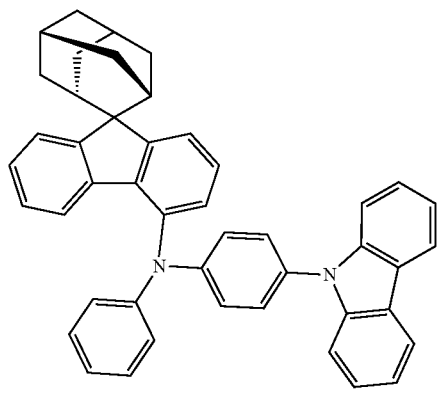
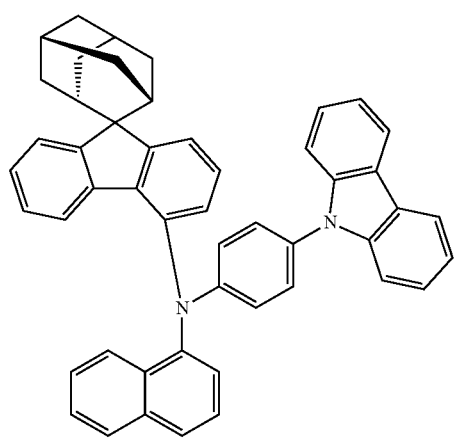
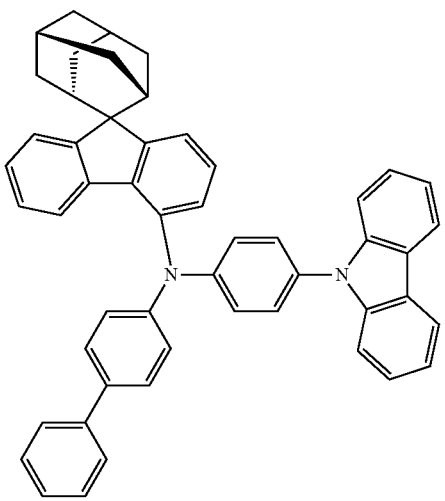
188
-continued
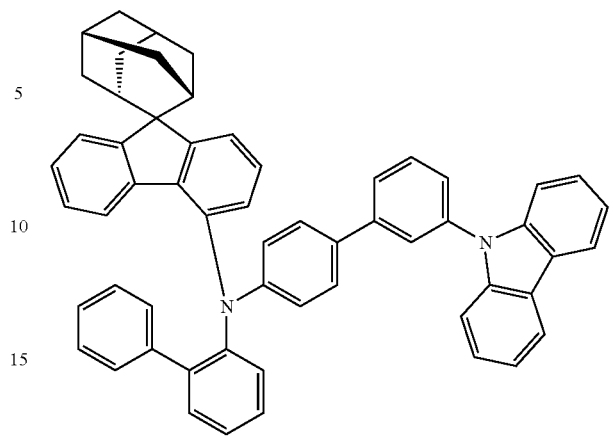
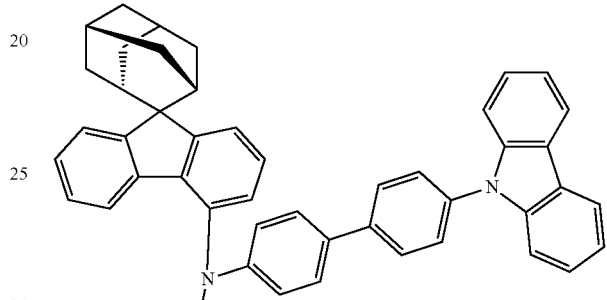
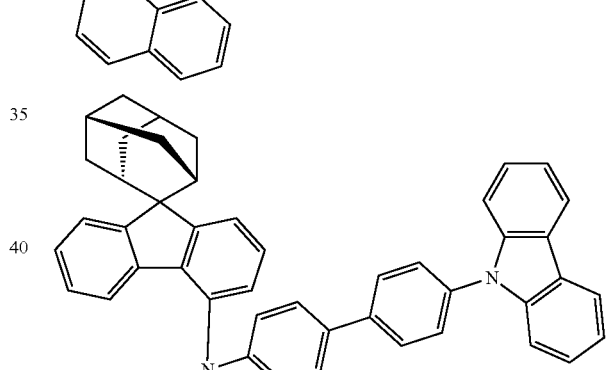
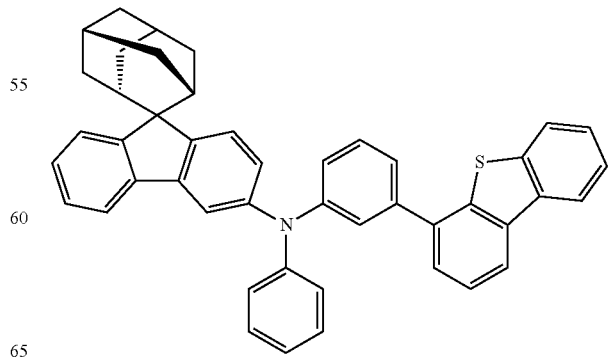

189
-continued
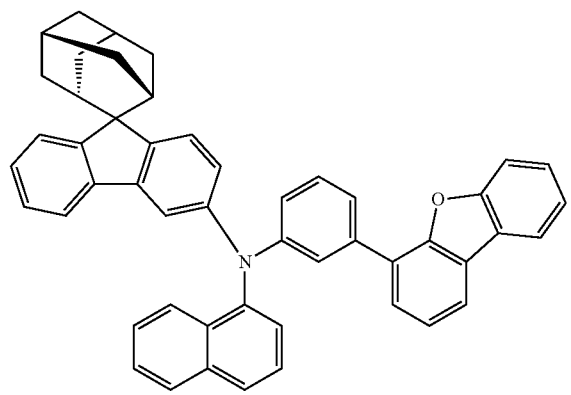
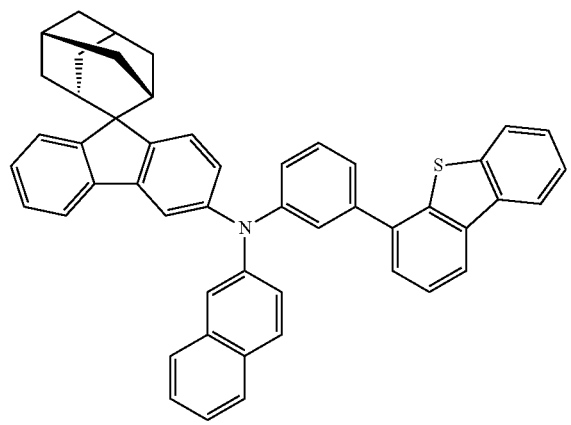
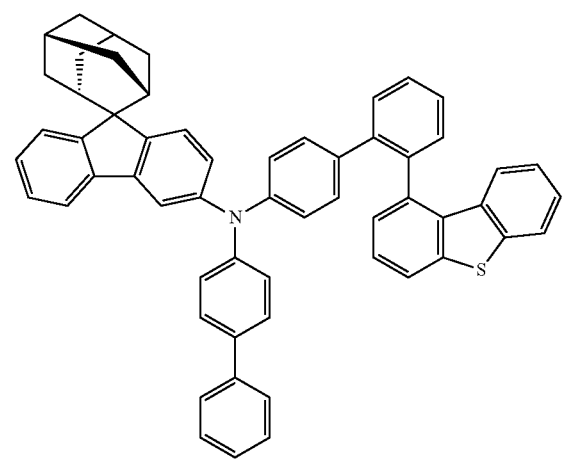
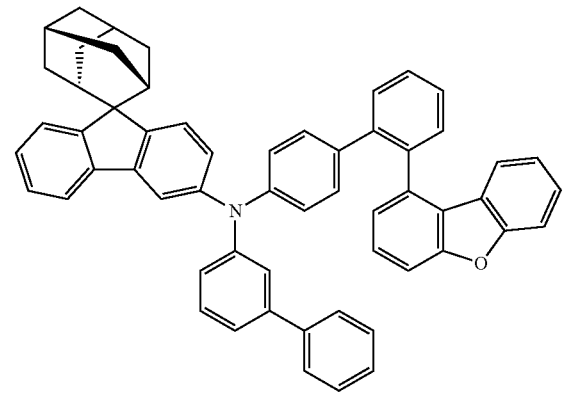
190
-continued
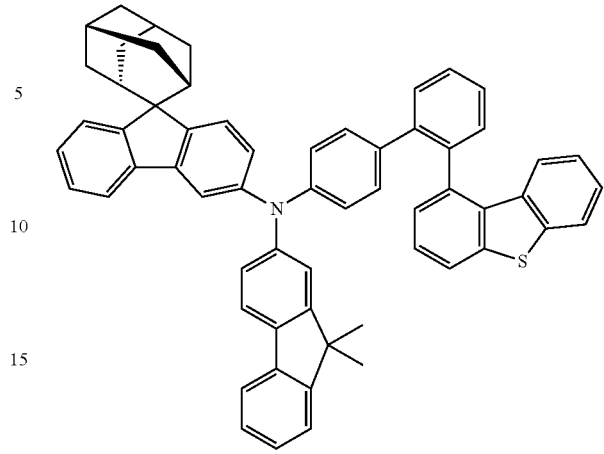
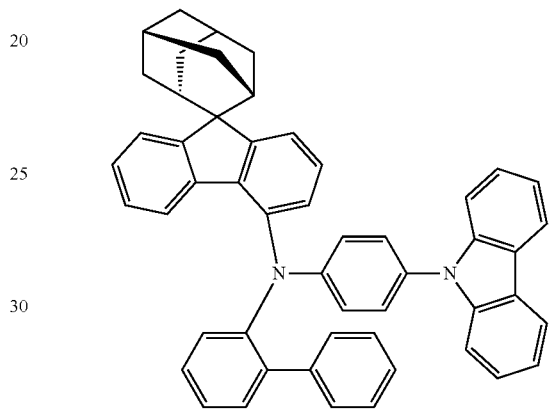
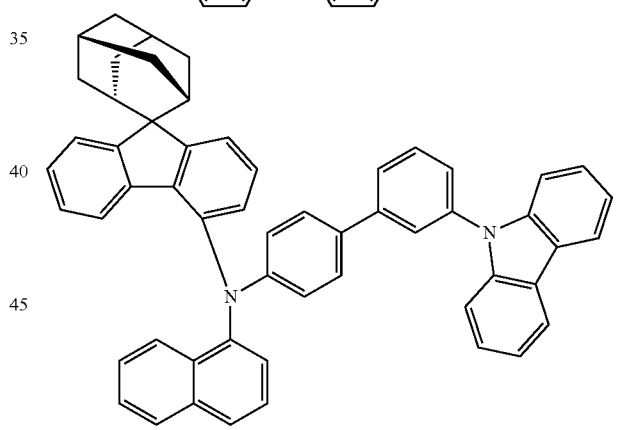
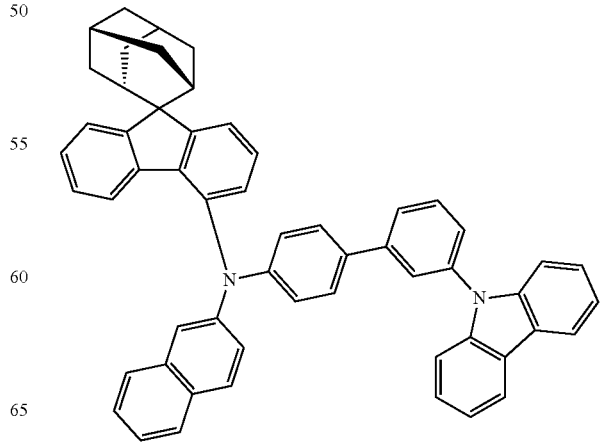

191
-continued
192
-continued
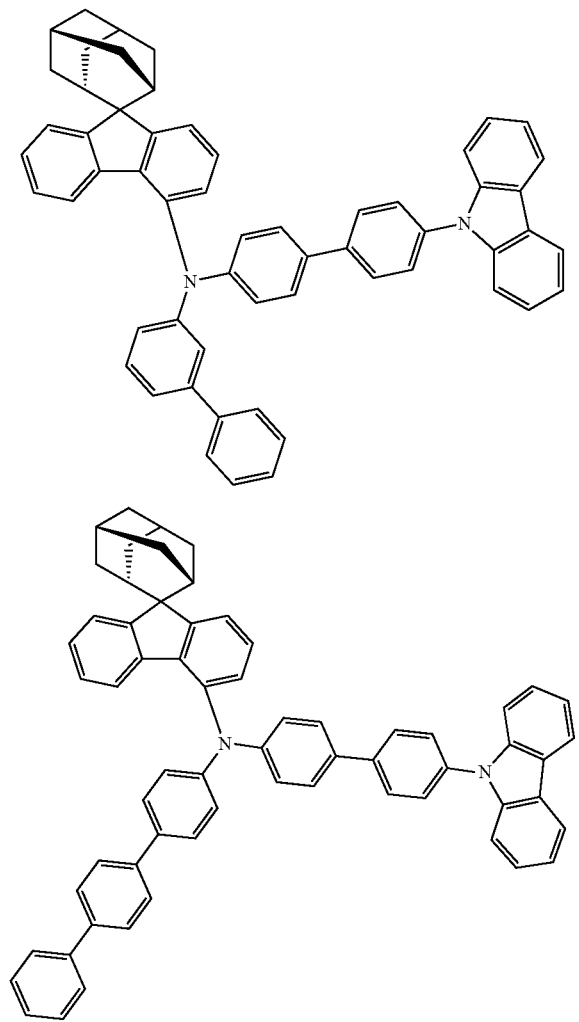
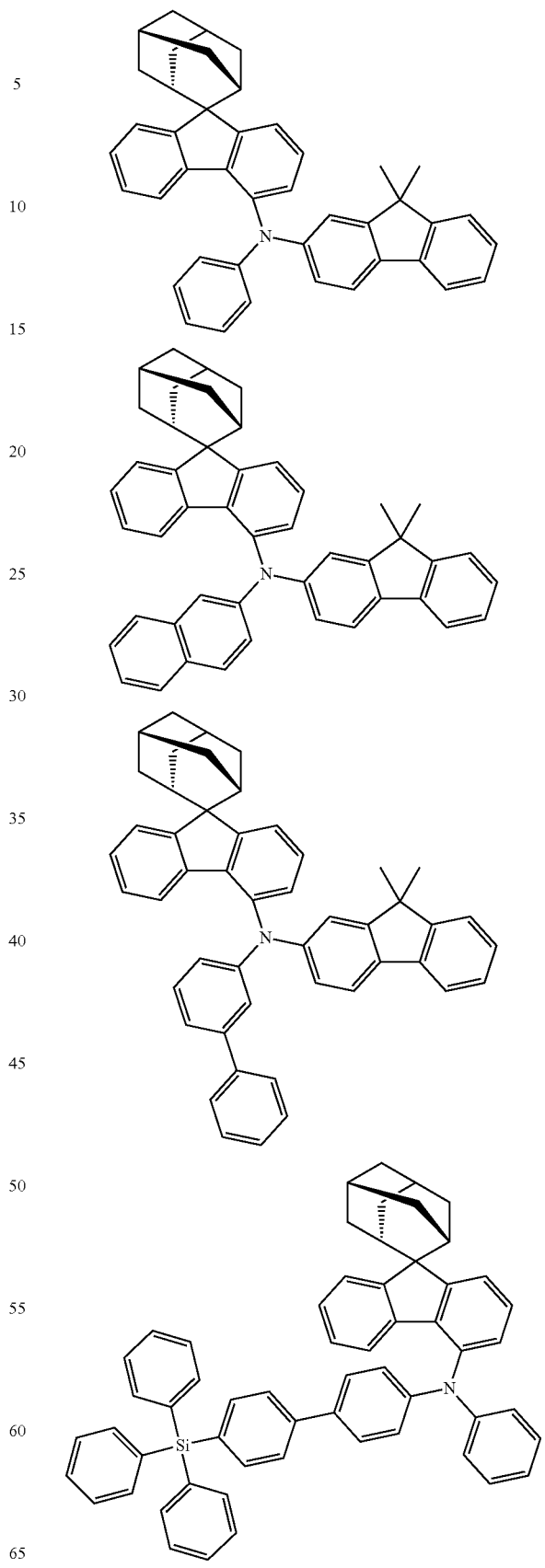

193
-continued
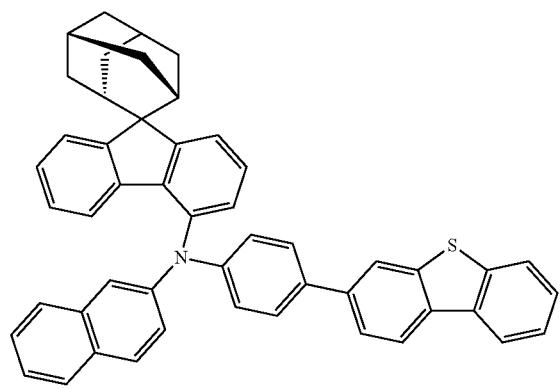
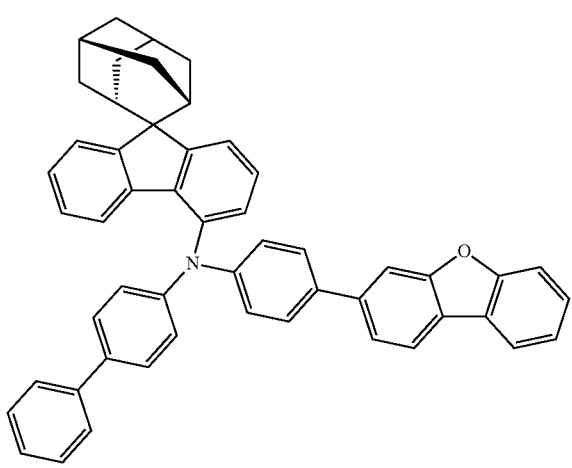
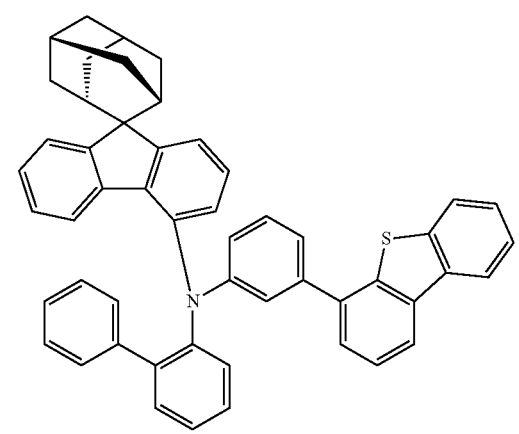
194
-continued
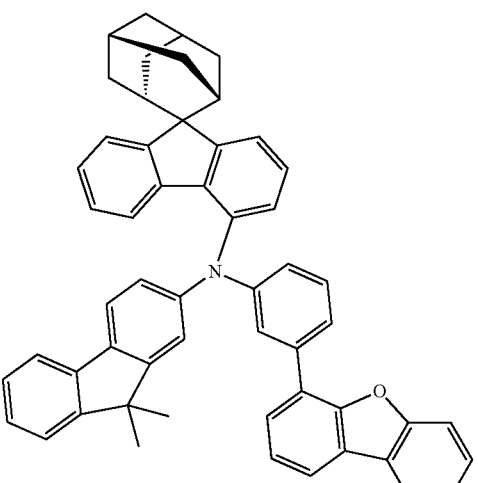
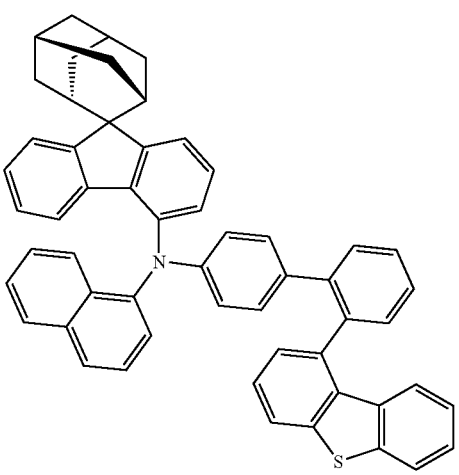
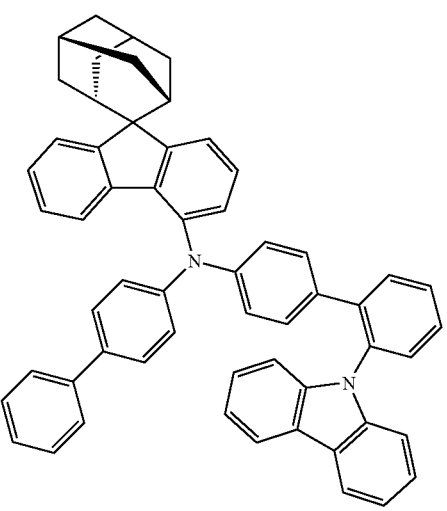

195
-continued
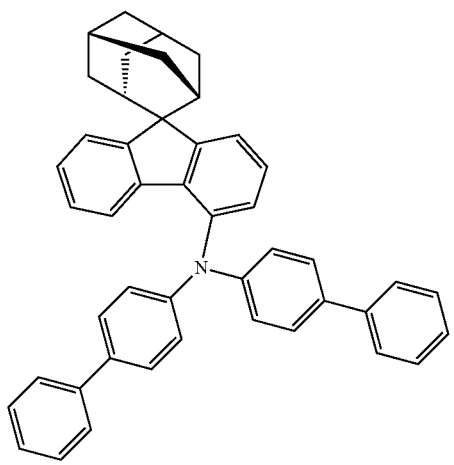
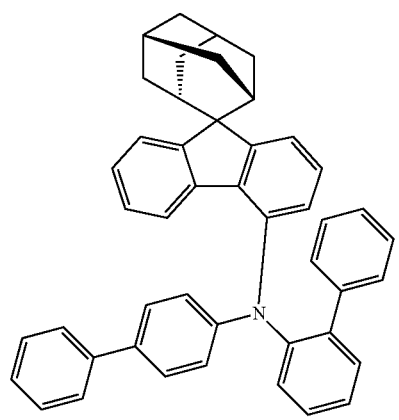
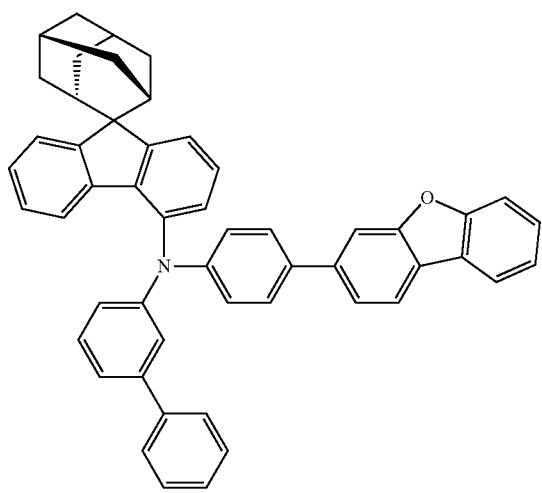
196
-continued
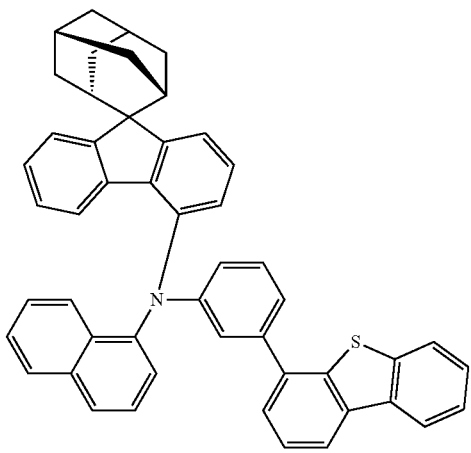
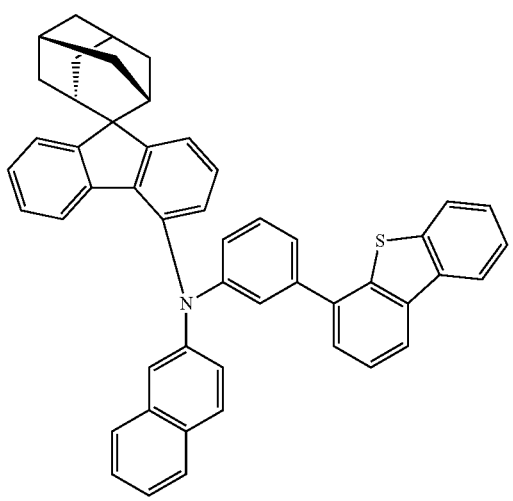
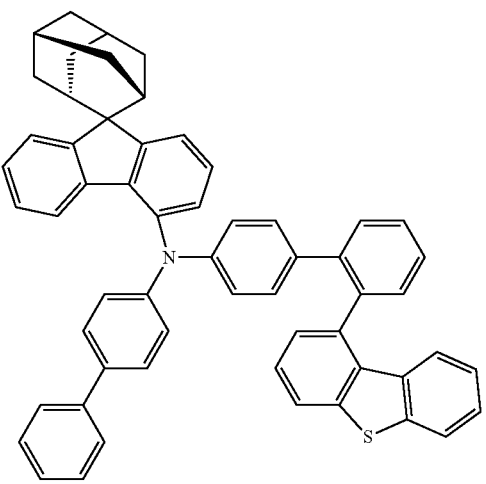

197
-continued
198
-continued
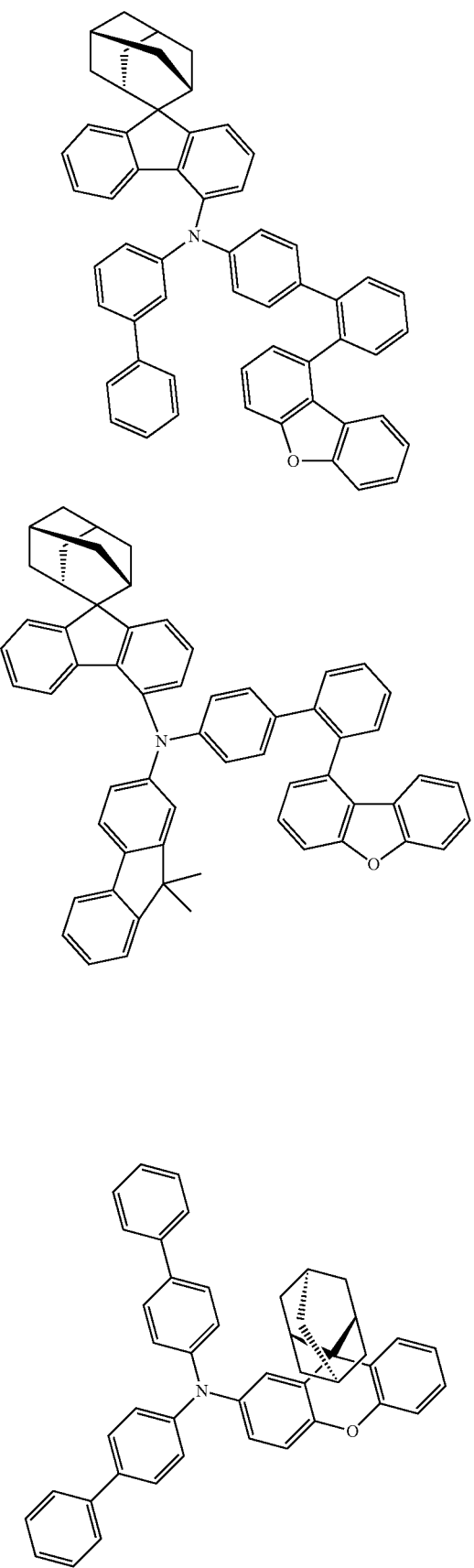
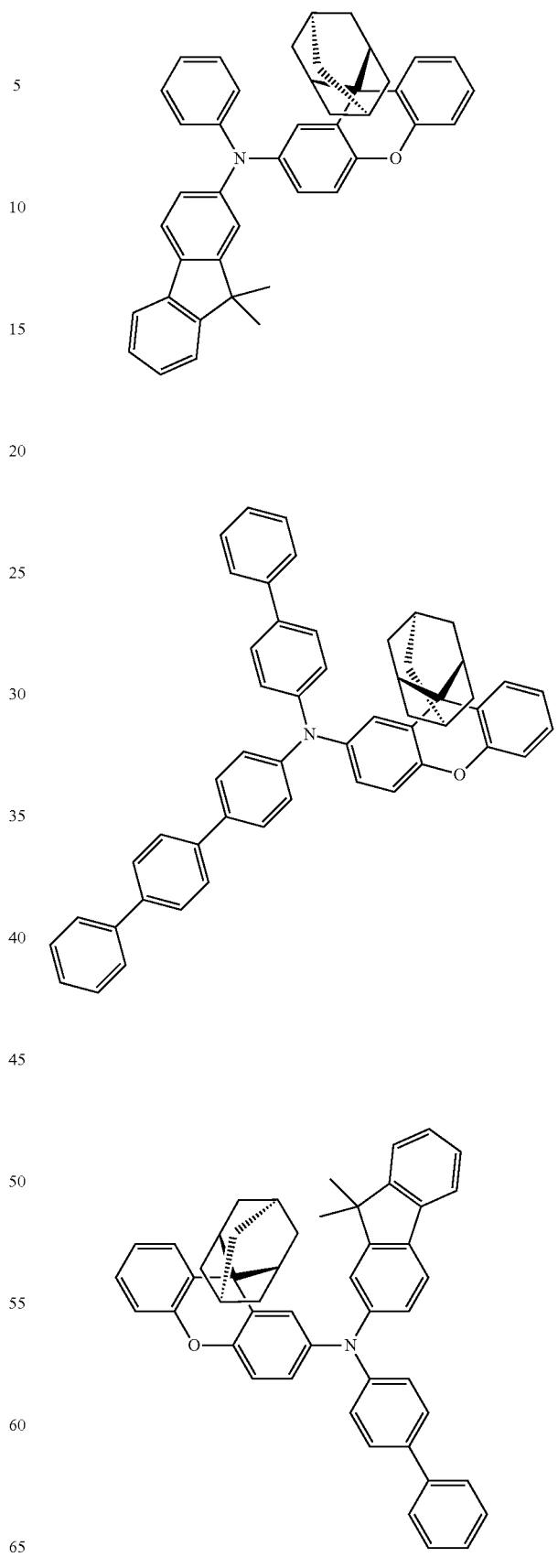

199
-continued
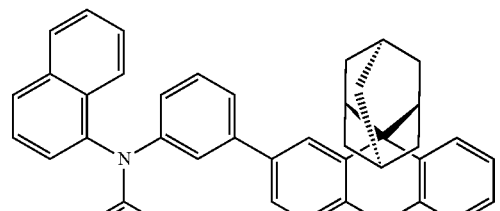
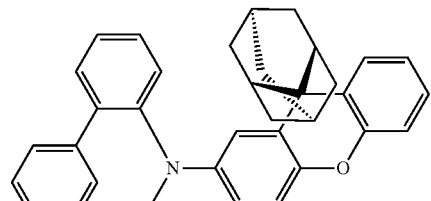
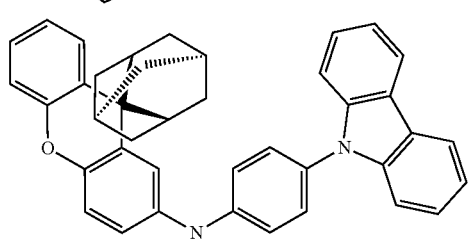
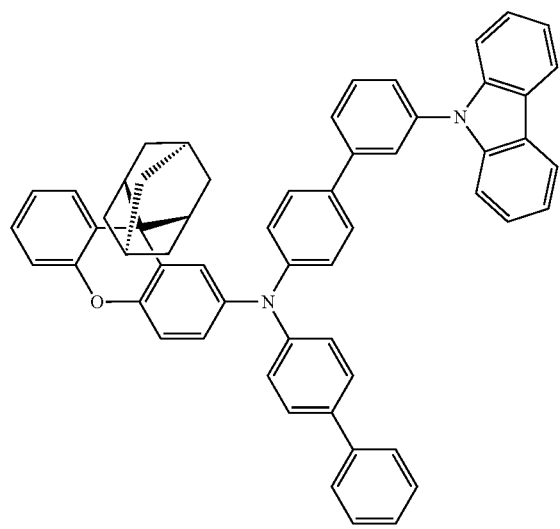
200
-continued
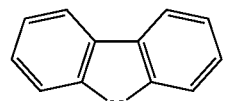
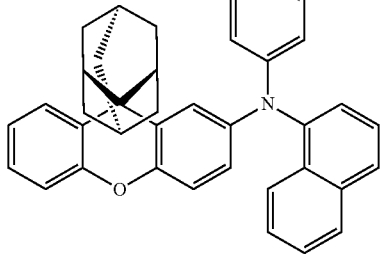
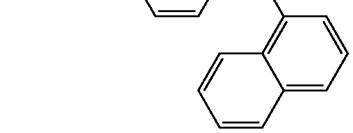

201
-continued
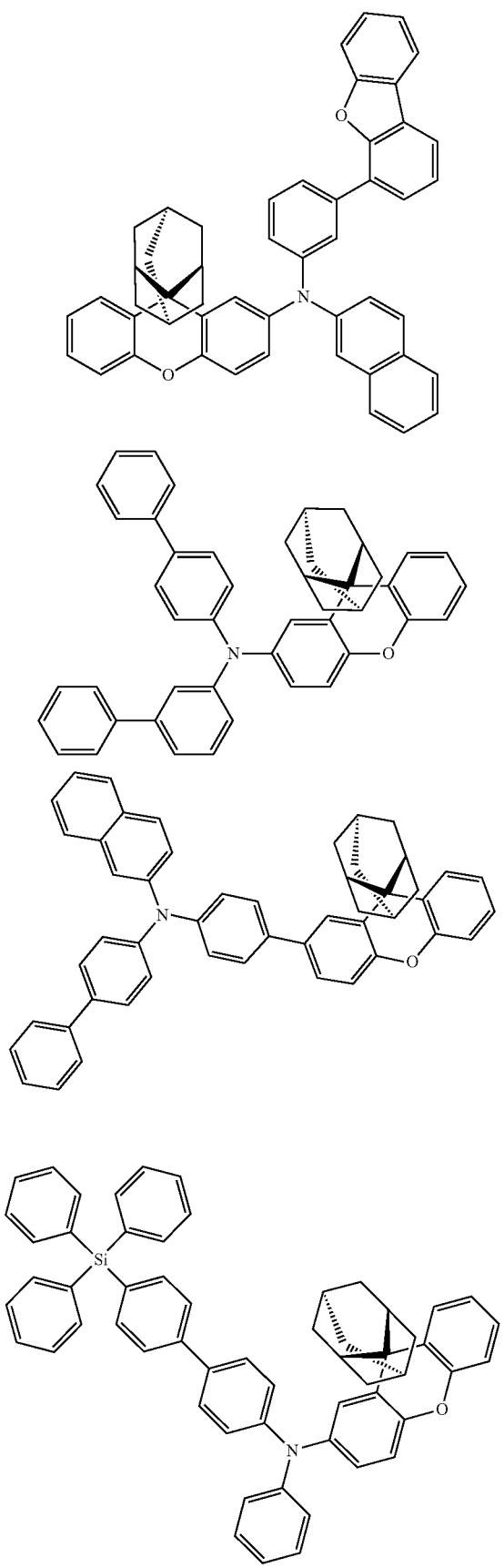
202
-continued
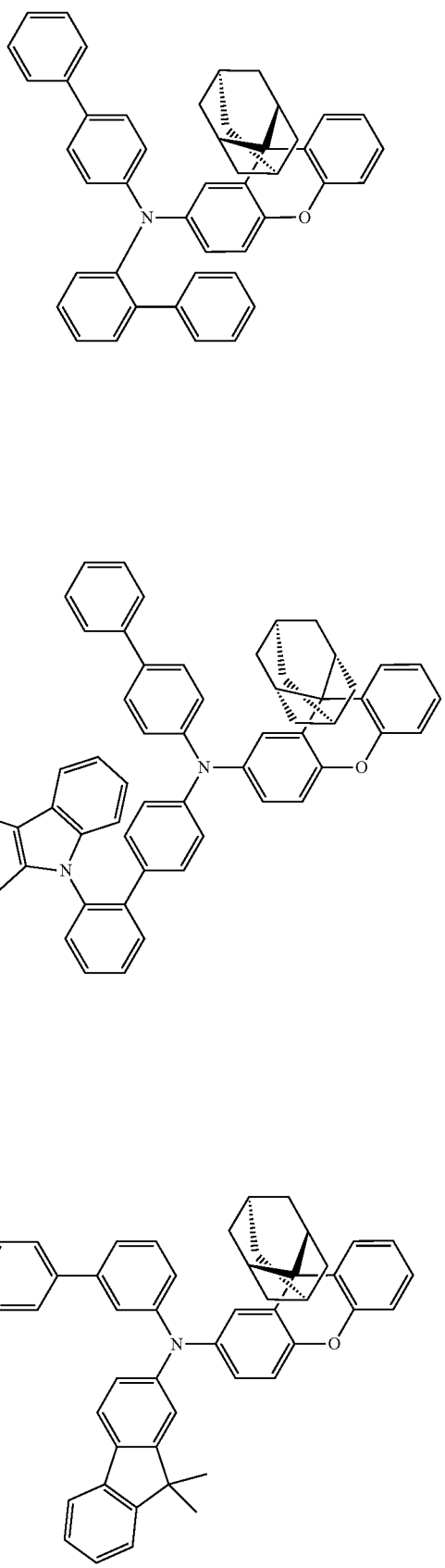

203
-continued
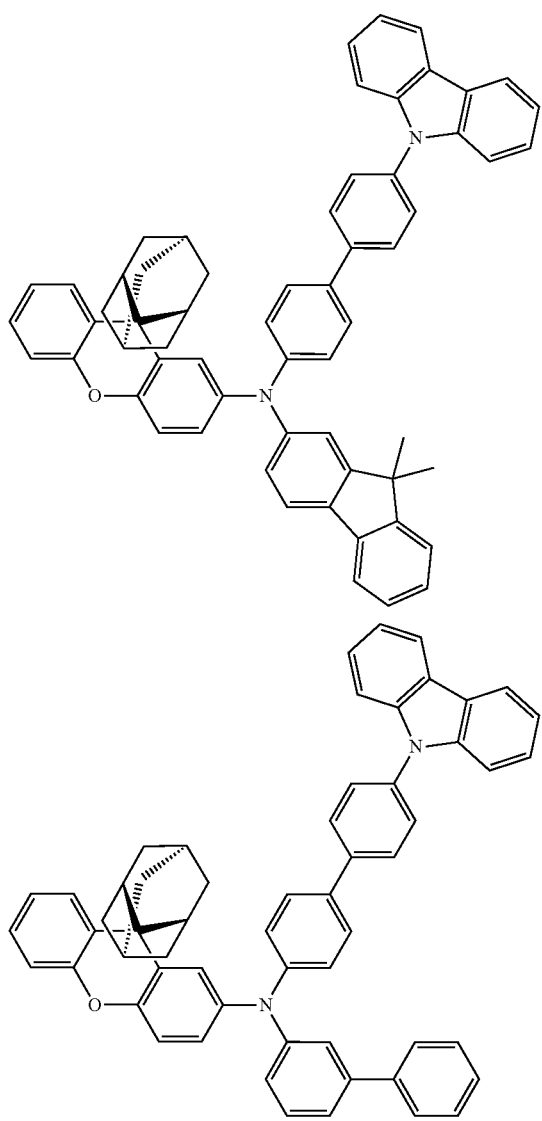
204
-continued
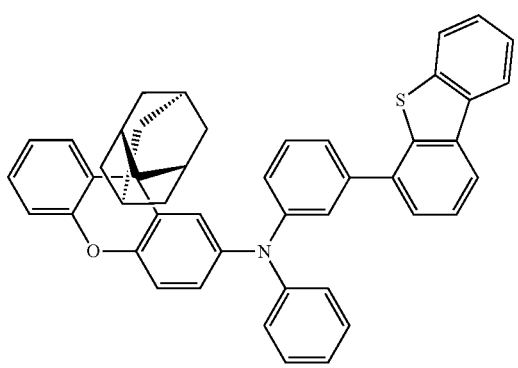
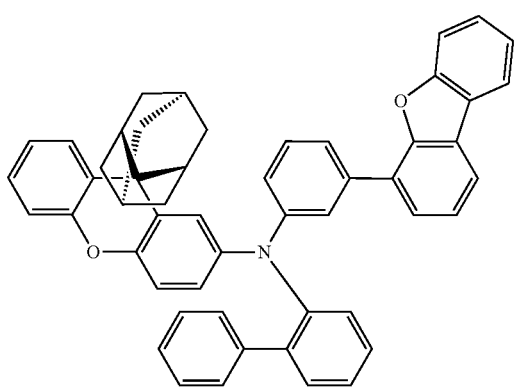
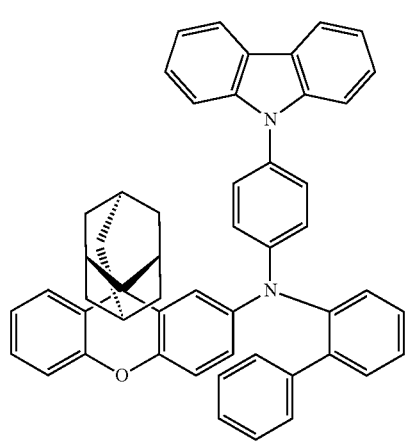
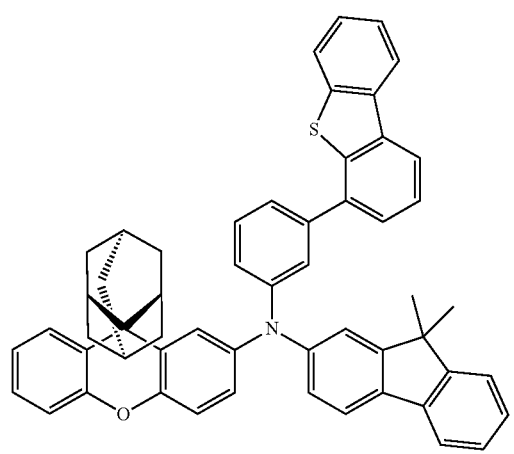

205
-continued
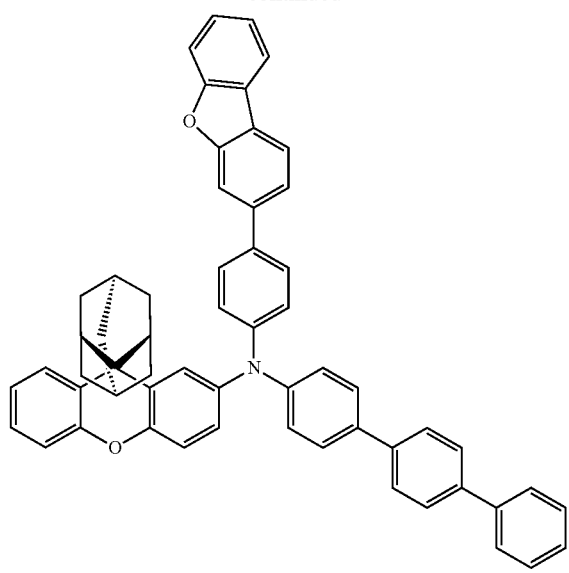
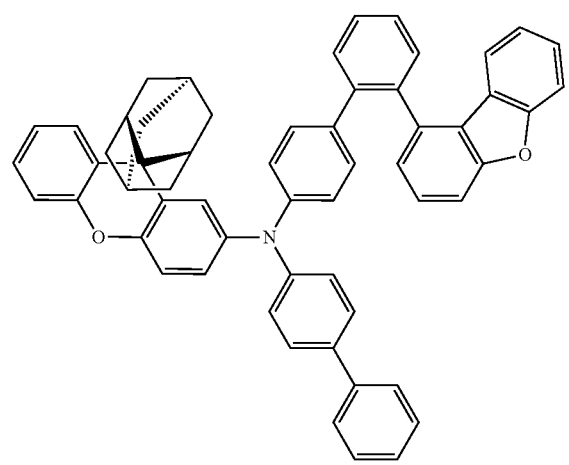
206
-continued
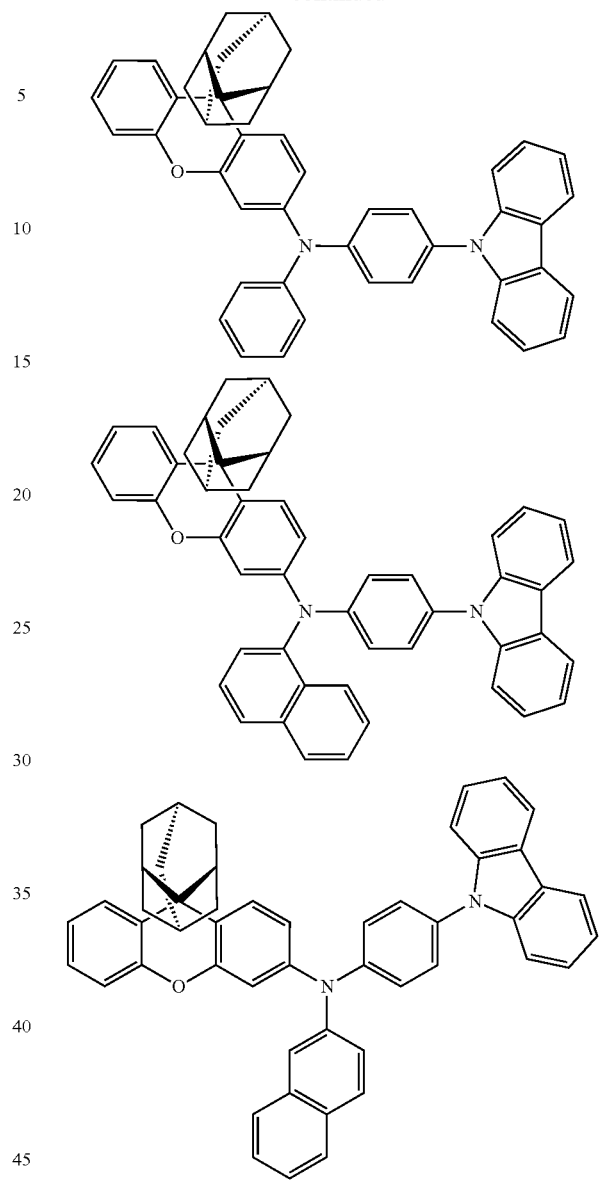
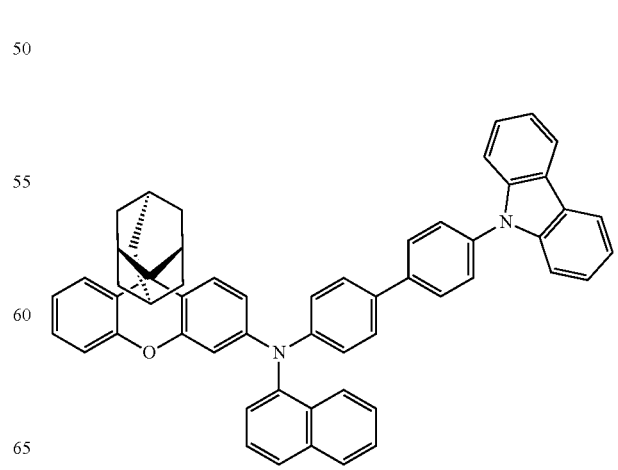

207
-continued
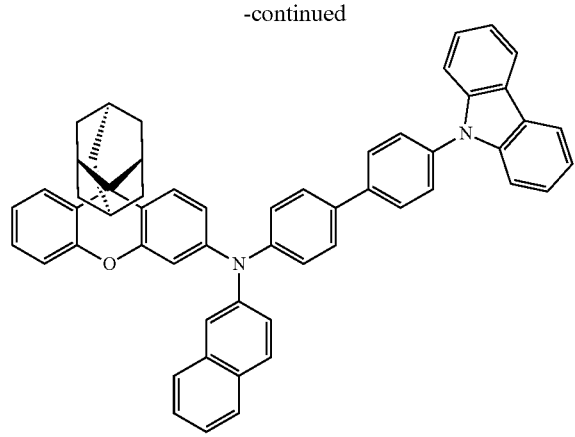
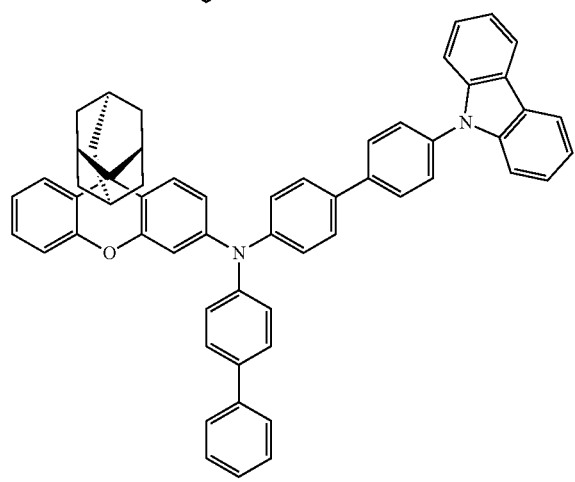
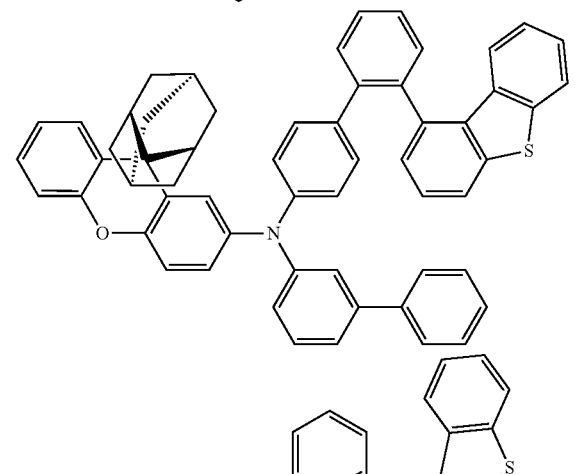
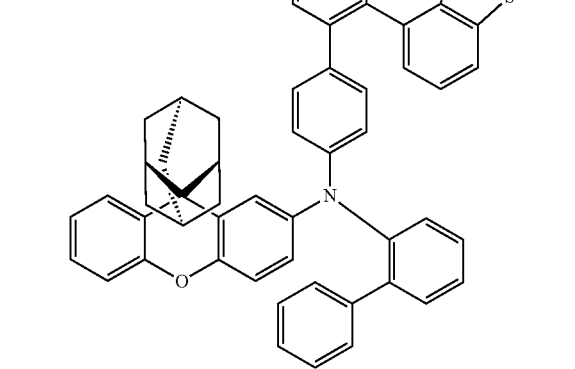
208
-continued
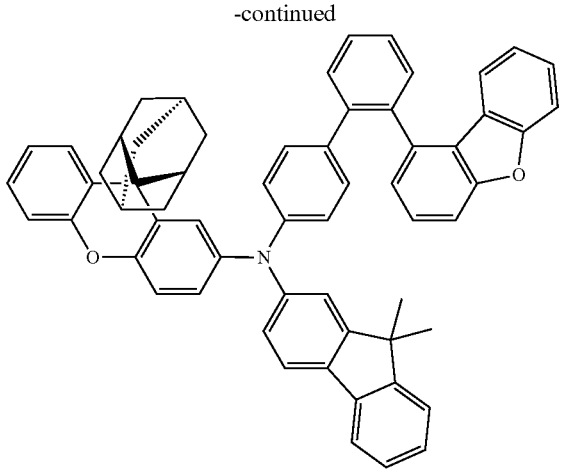
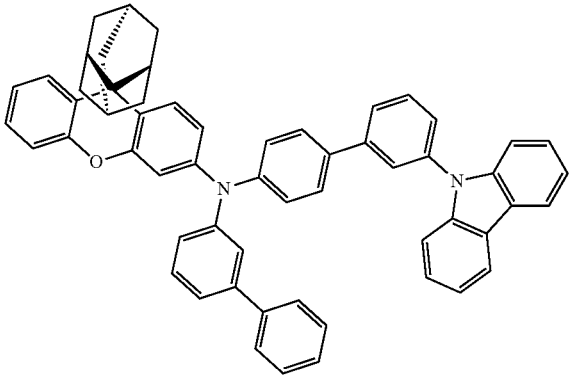
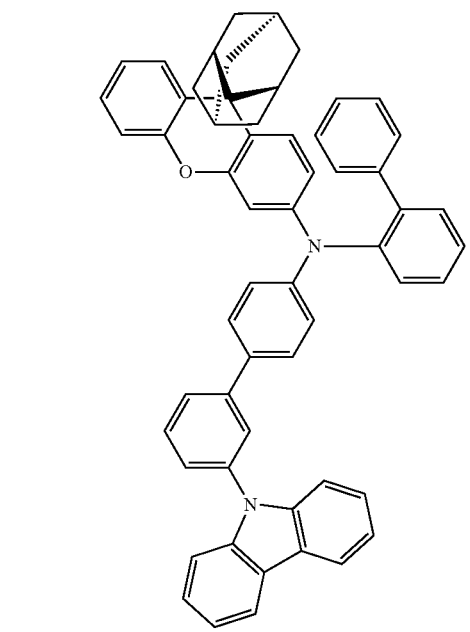

209
-continued
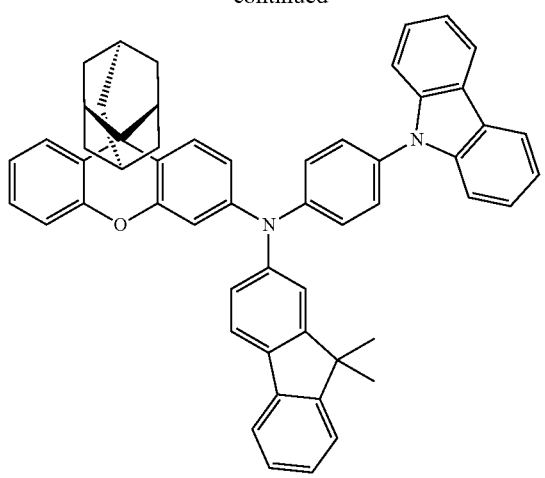
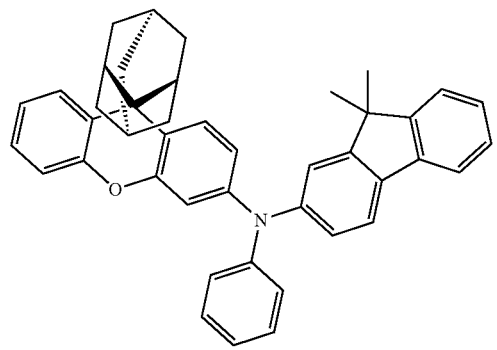
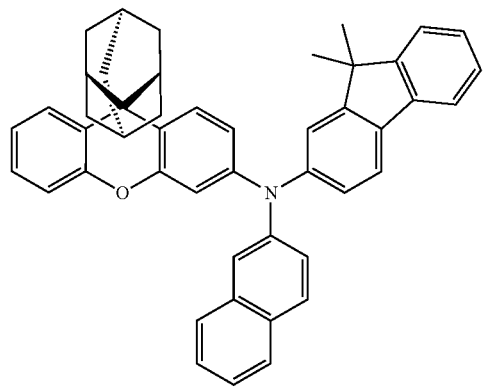
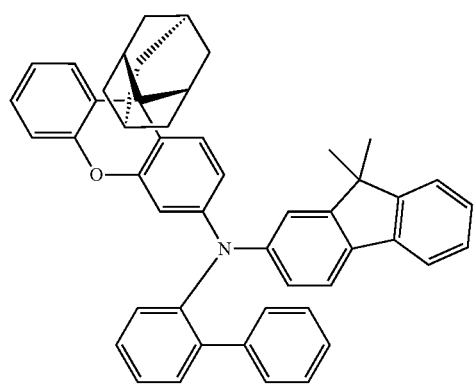
210
-continued
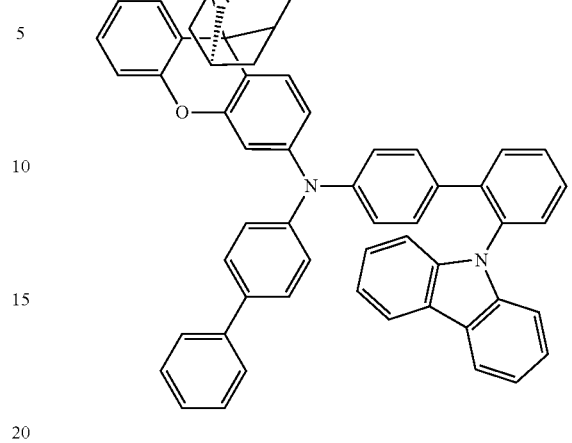
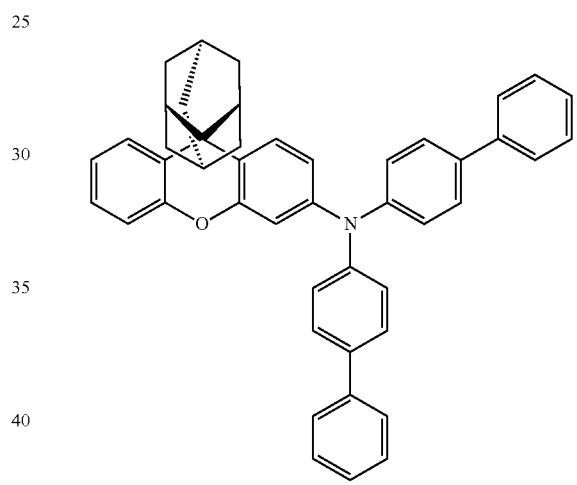
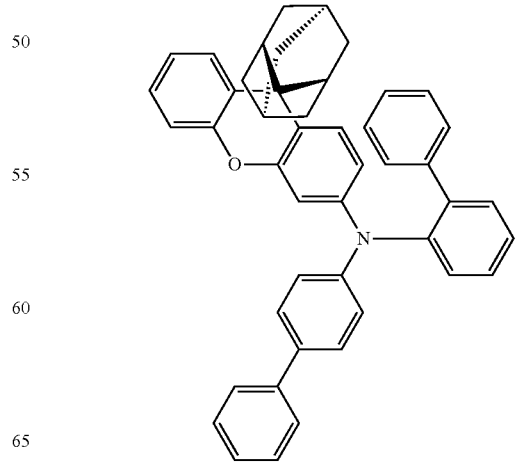

211
-continued
212
-continued
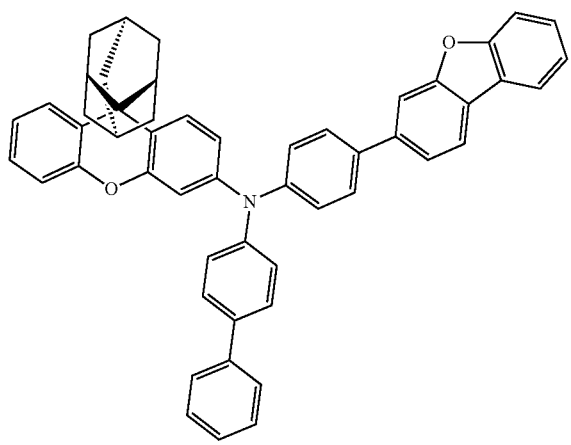
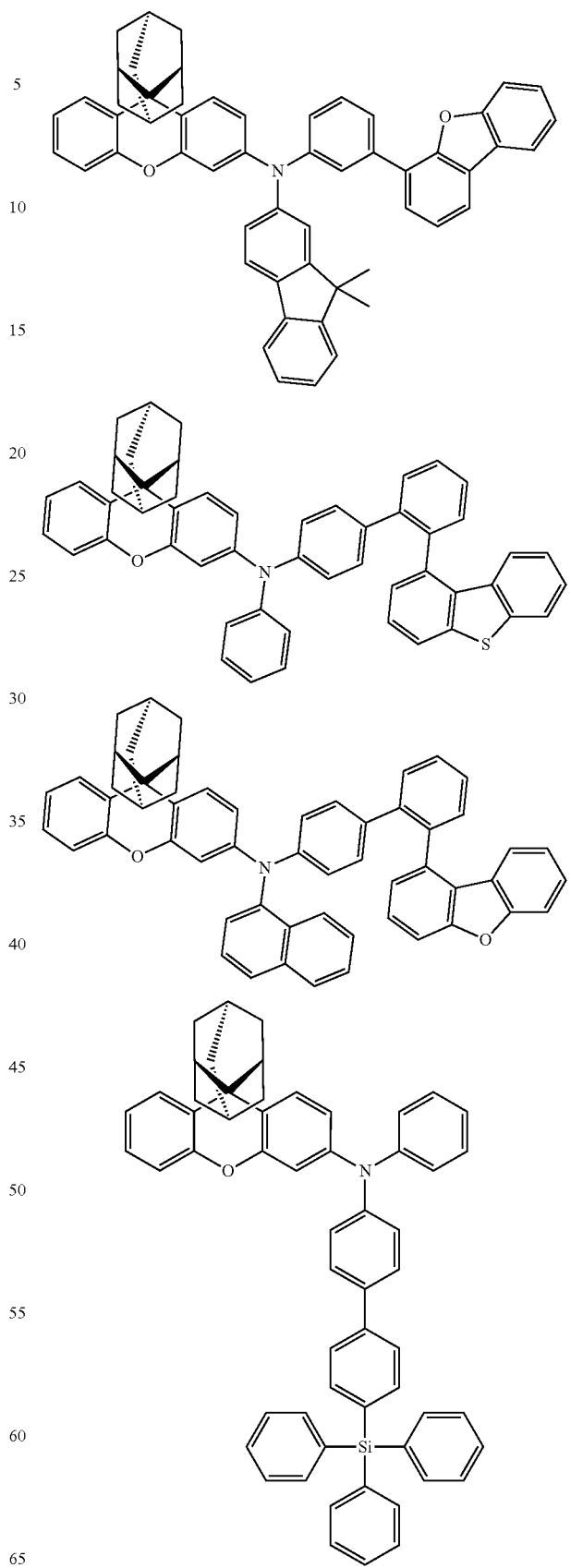

213
-continued
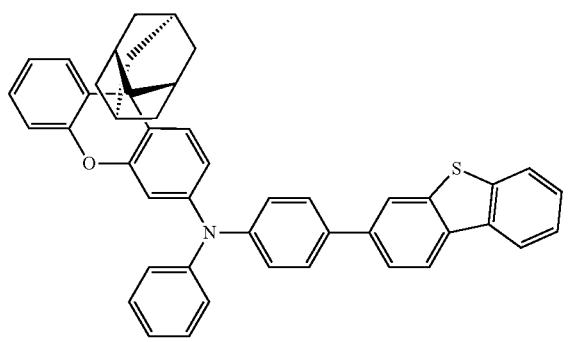
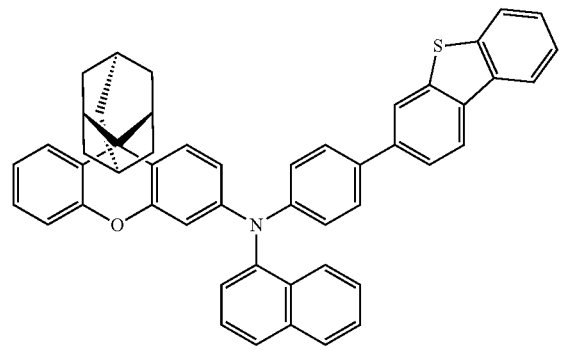
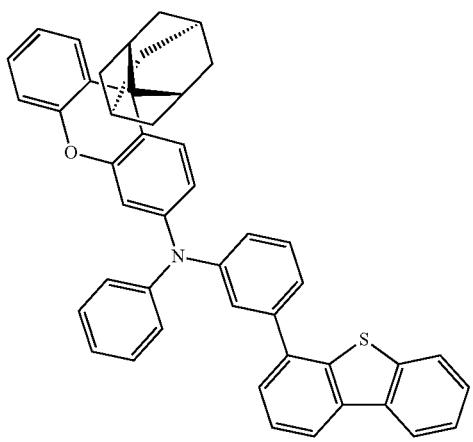
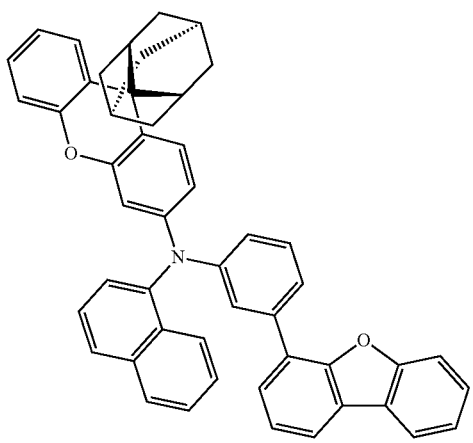
214
-continued
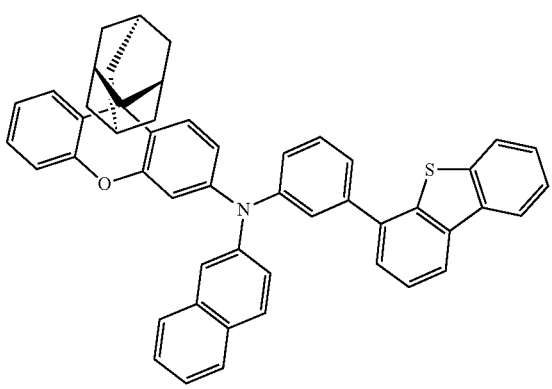
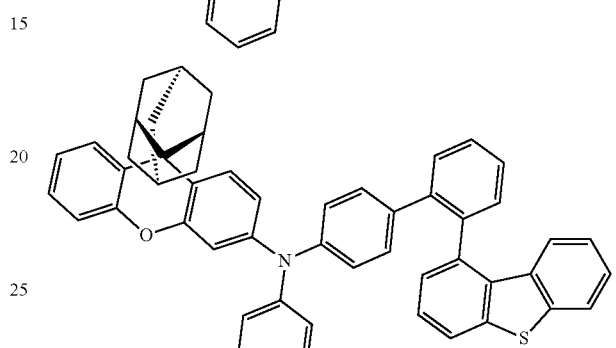
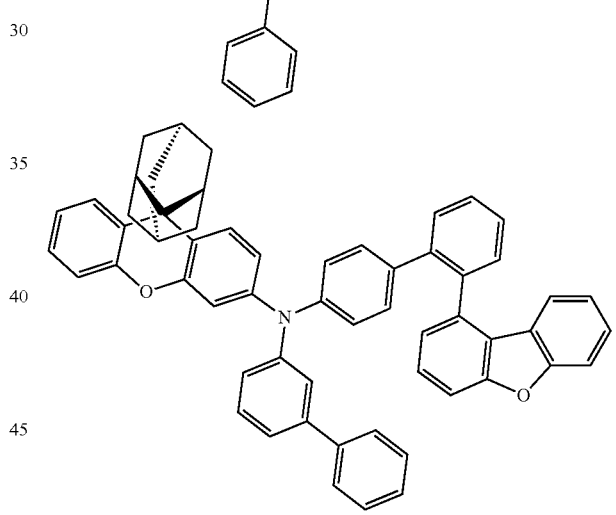
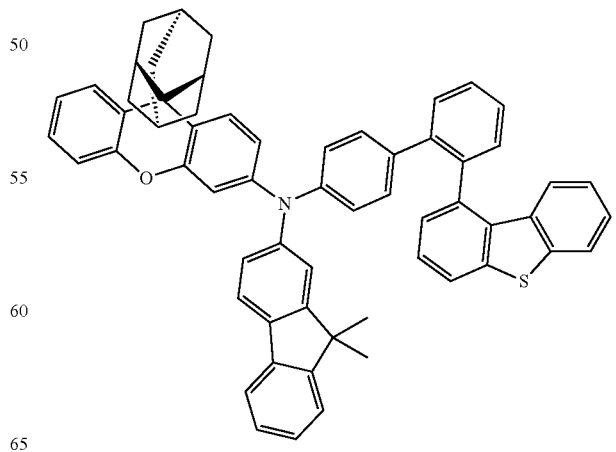

215
-continued
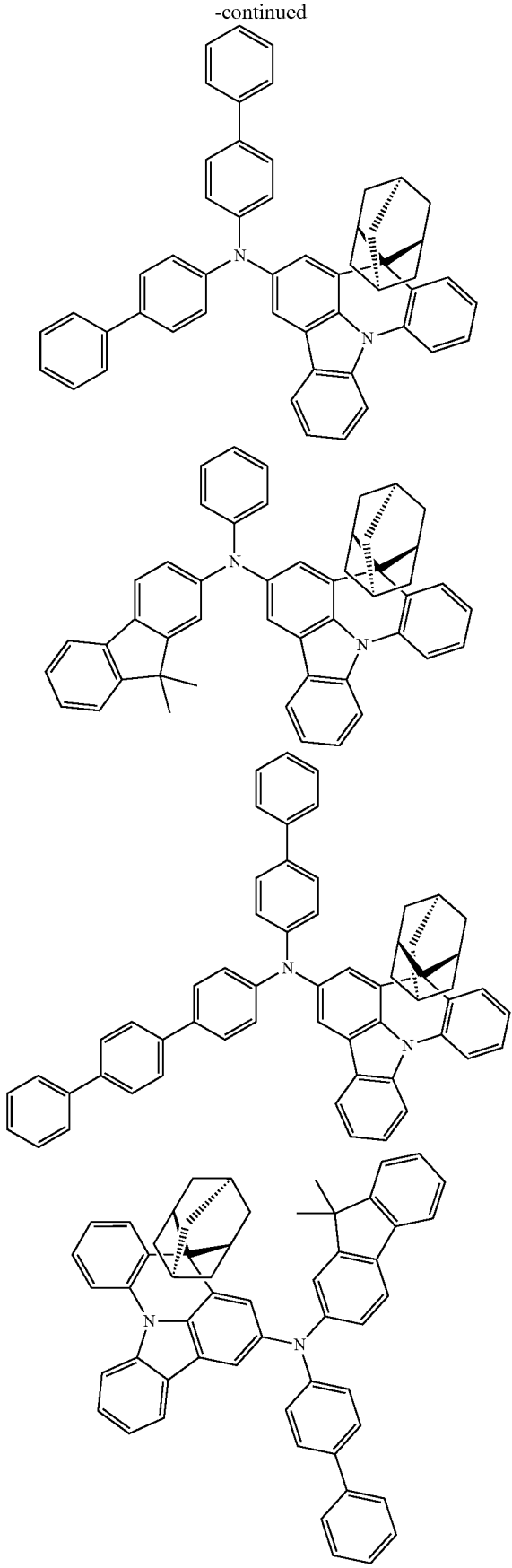
216
-continued
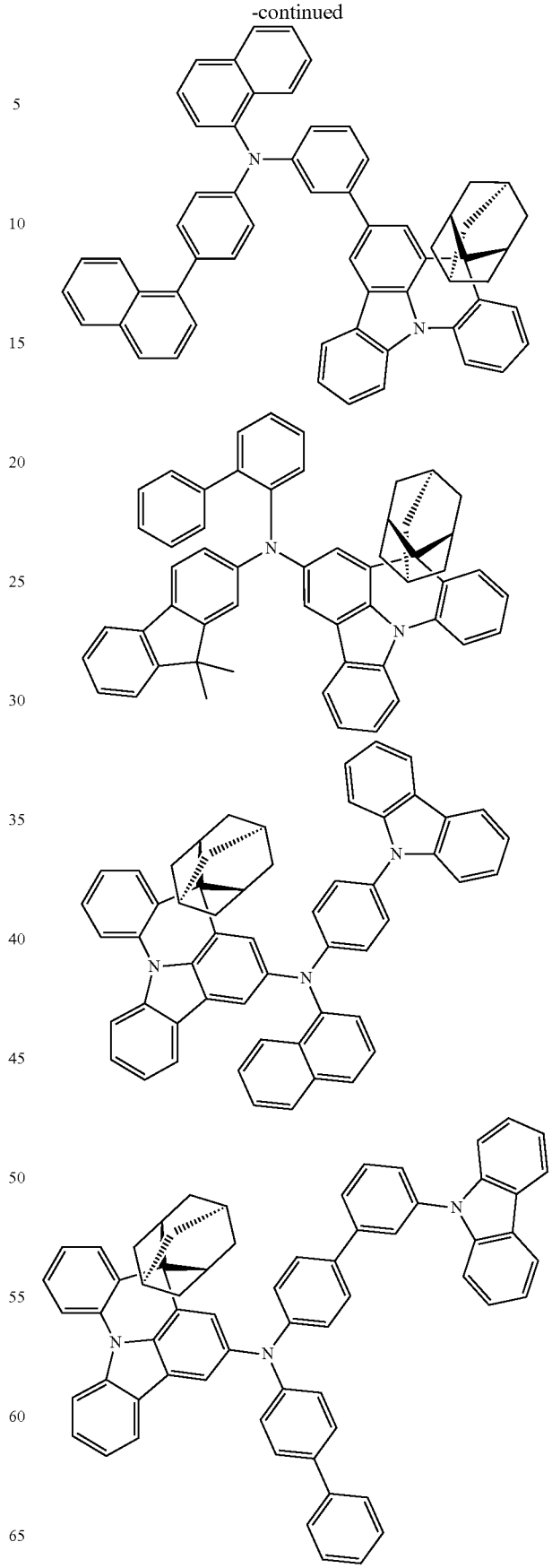

217
-continued
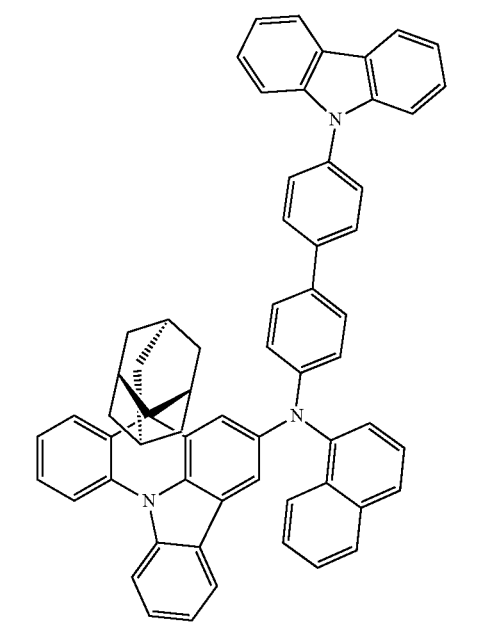
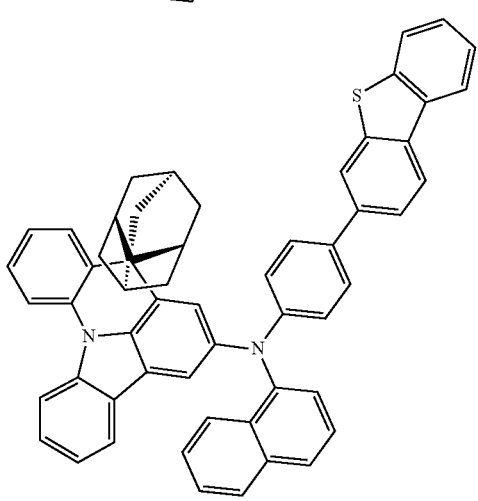
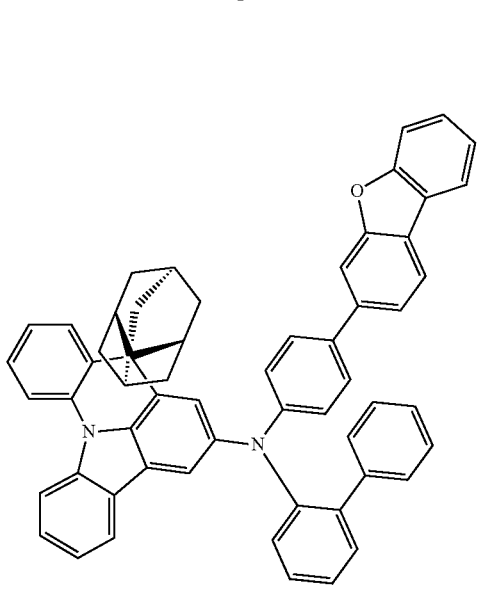
218
-continued
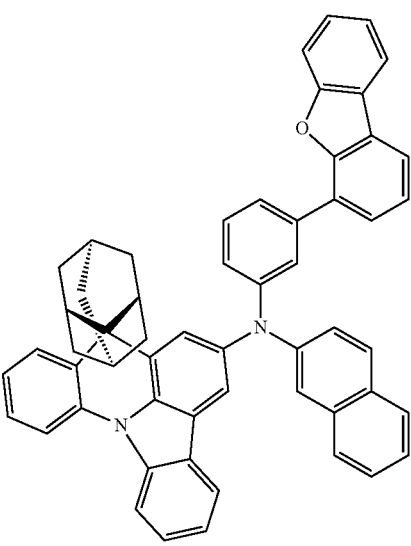 [SMILES: c1cc(-c2cccc3c2oc2ccccc23)cc(N(c2ccc3ccccc3c2)c2cc3c4c(c2)c2ccccc2n4-c2ccccc2C32[C@H]3C[C@@H]4C[C@@H](C[C@H]2C4)C3)c1]
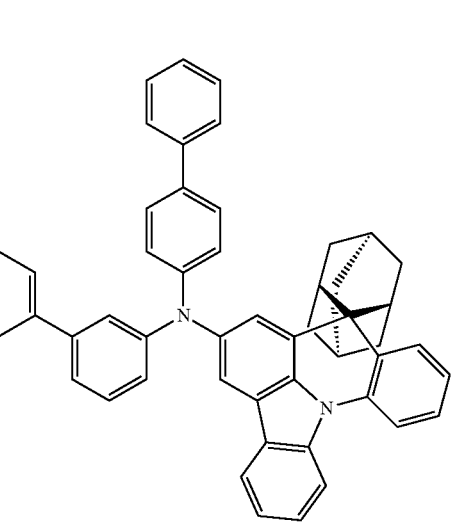

219
-continued
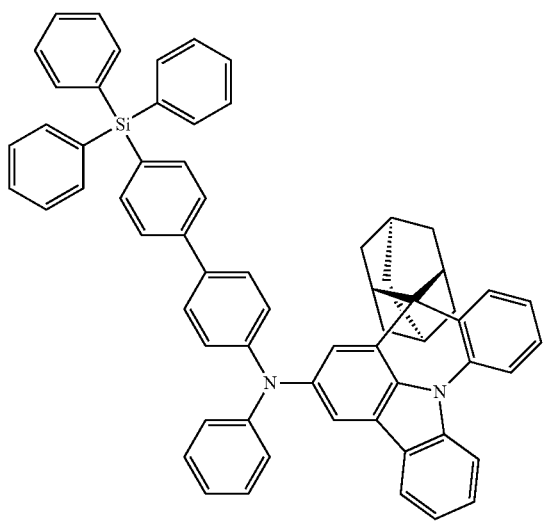
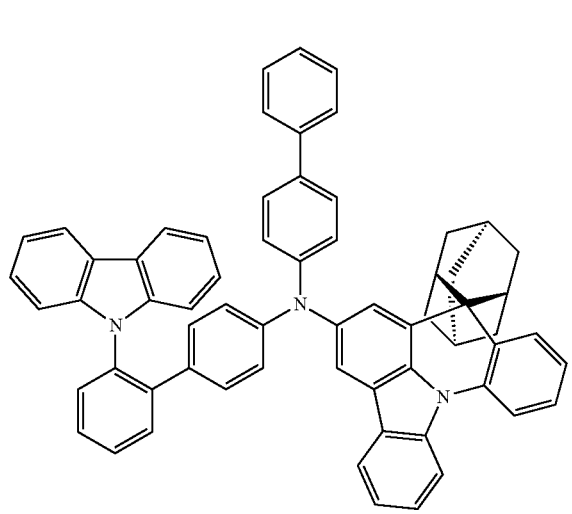
220
-continued
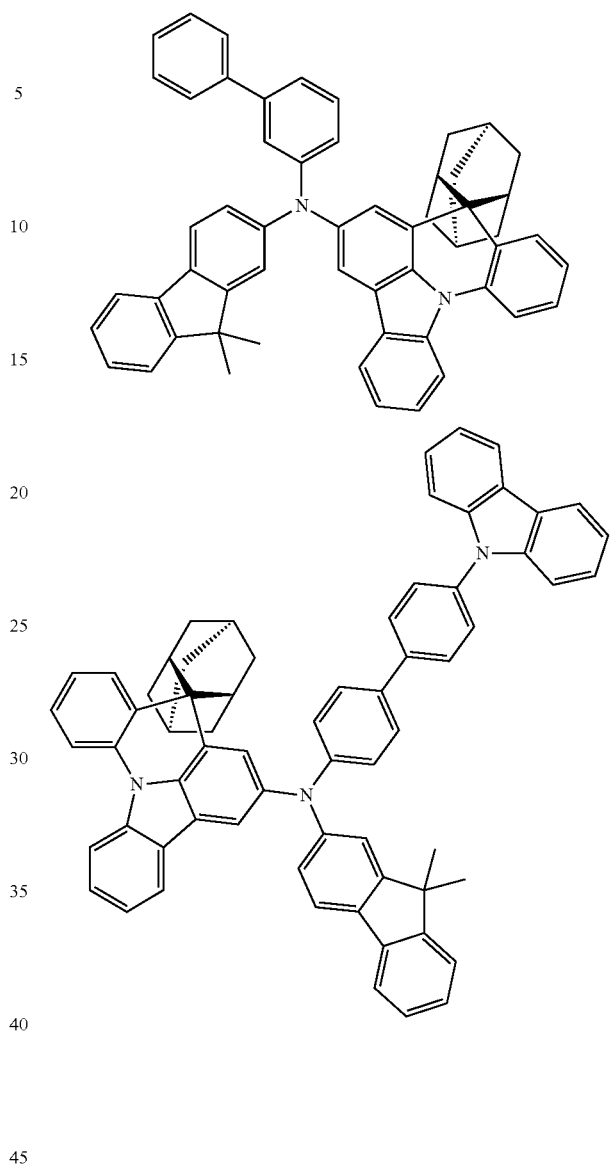
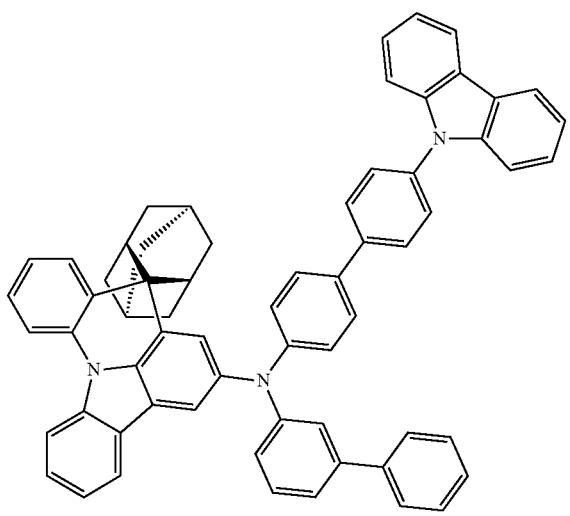

221
-continued
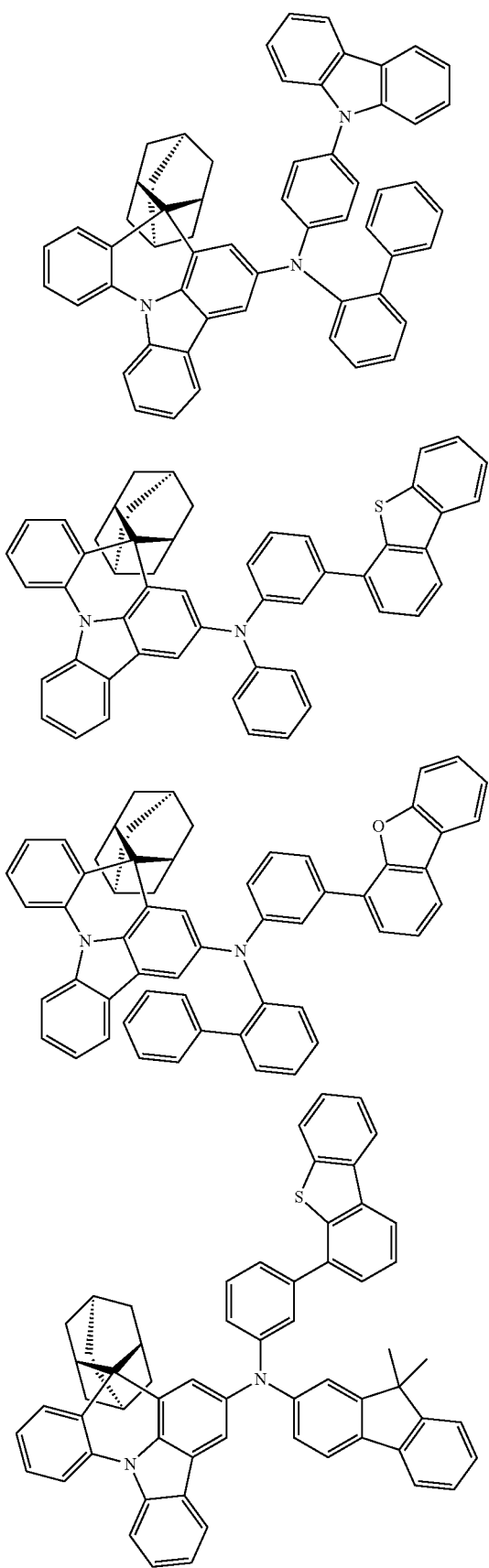
222
-continued
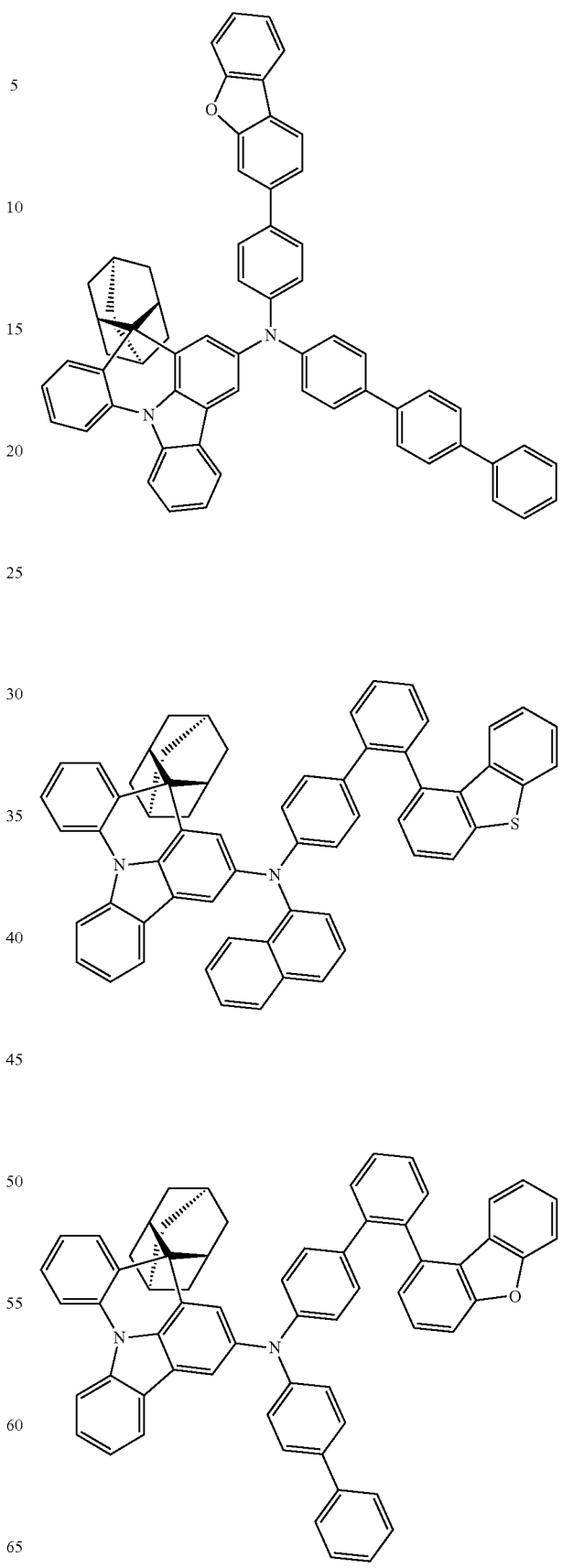

223
-continued
224
-continued
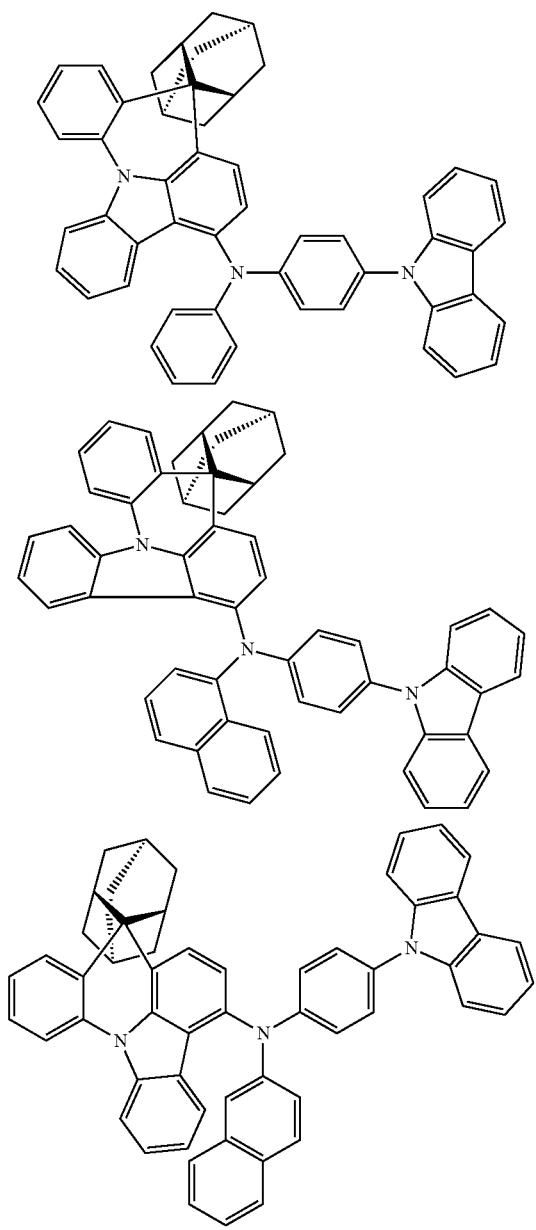
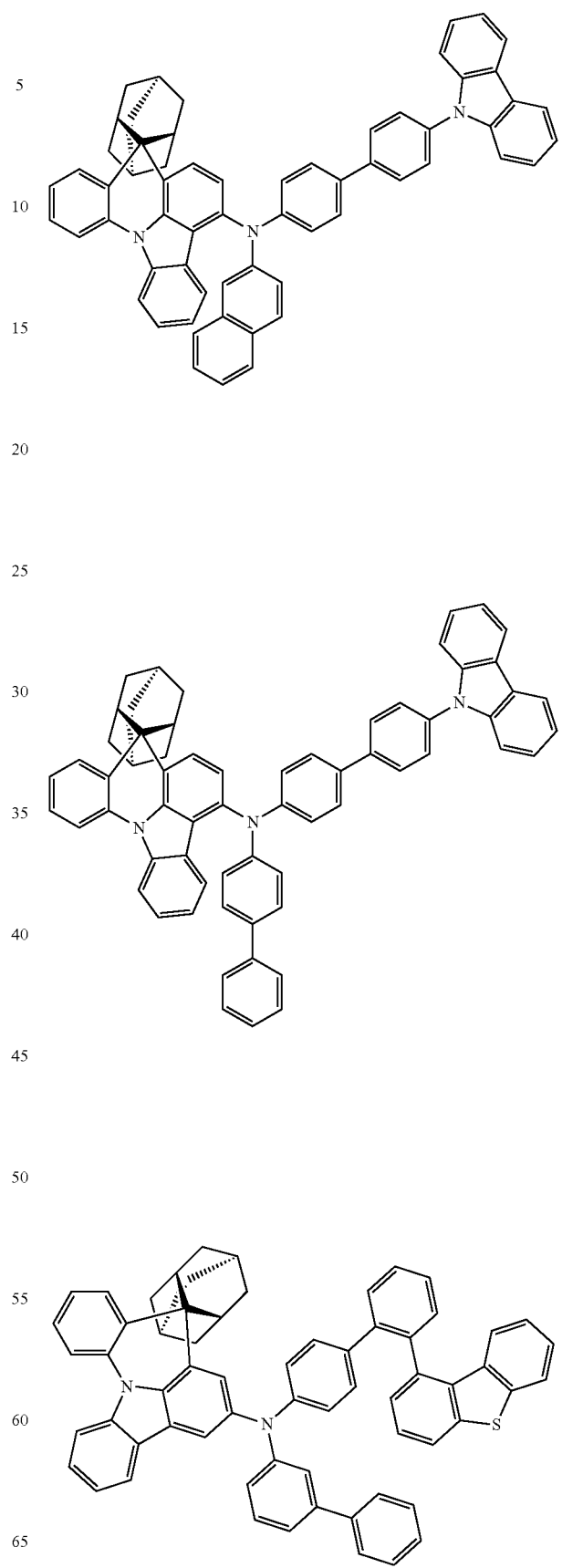

225
-continued
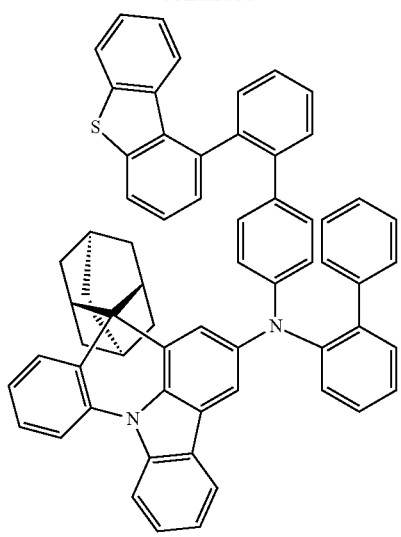
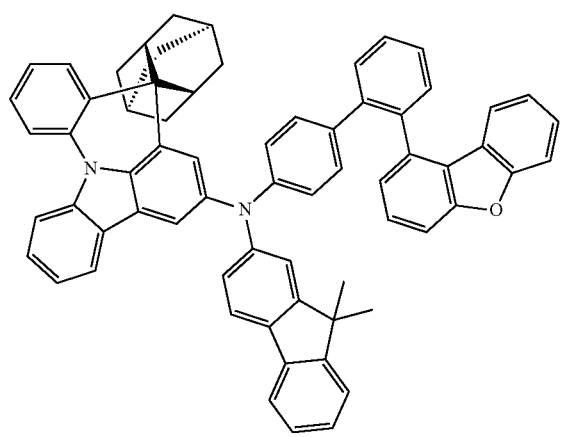
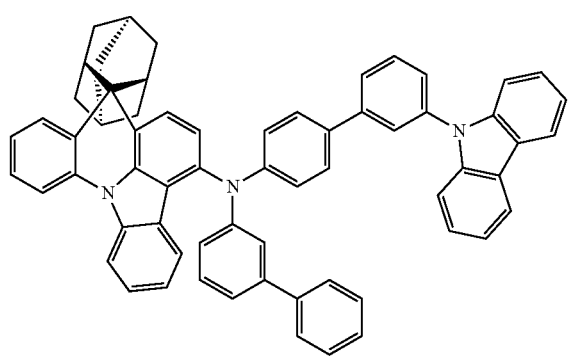
226
-continued
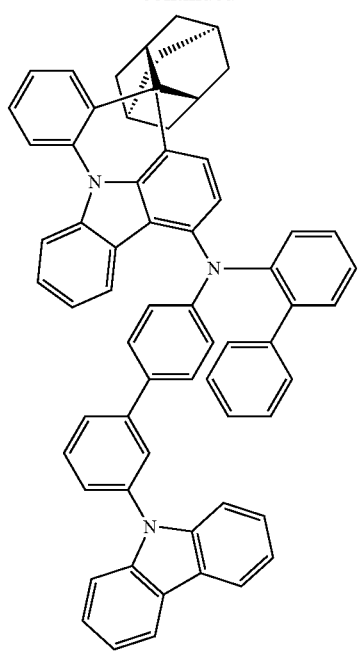
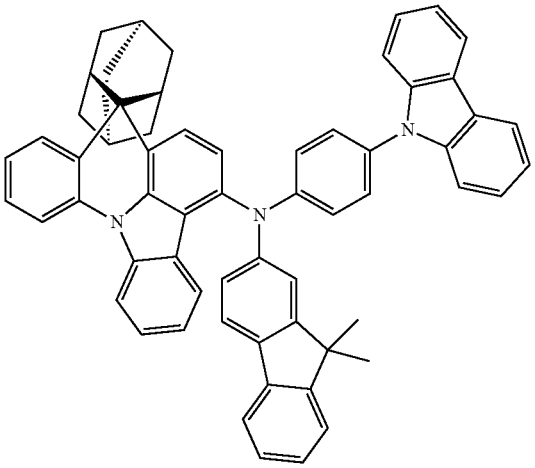
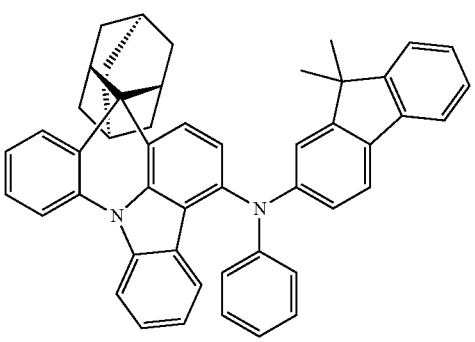

227
-continued
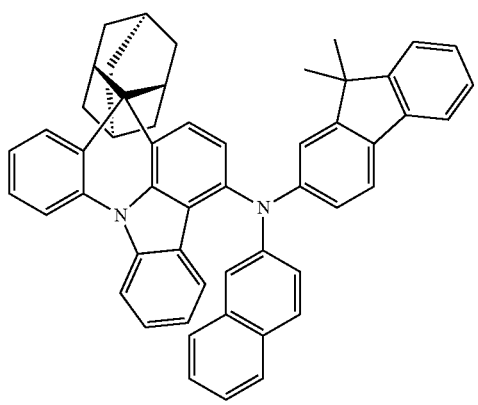
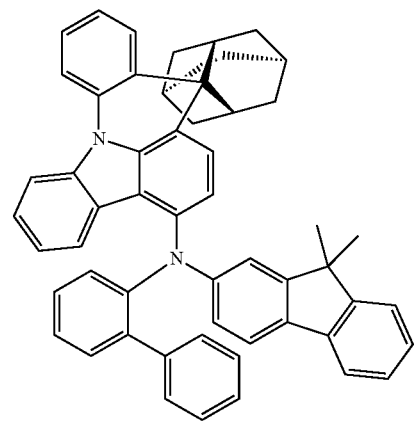
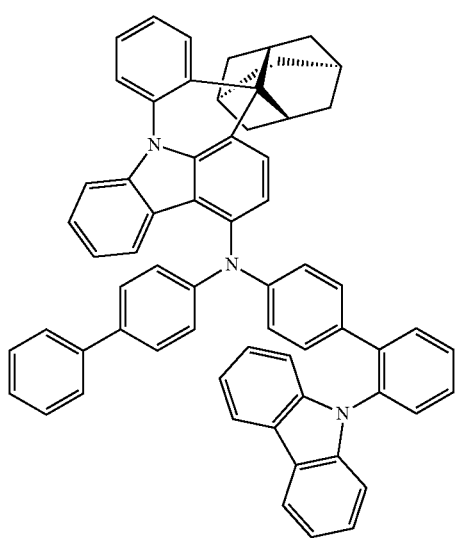
228
-continued
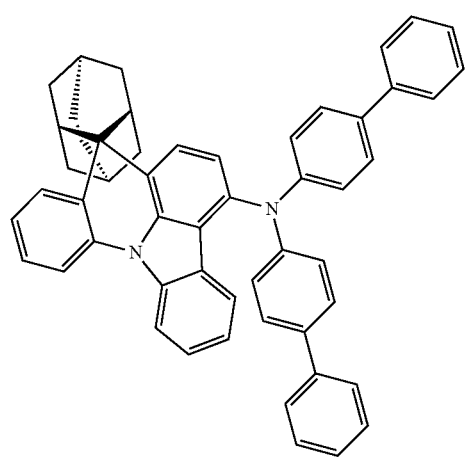
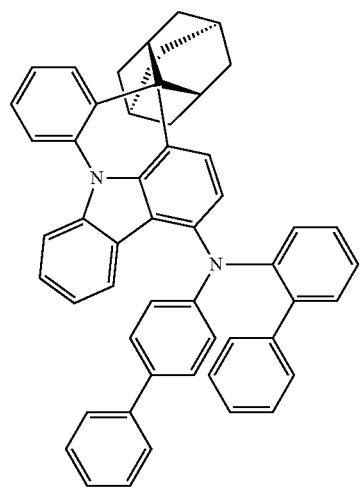
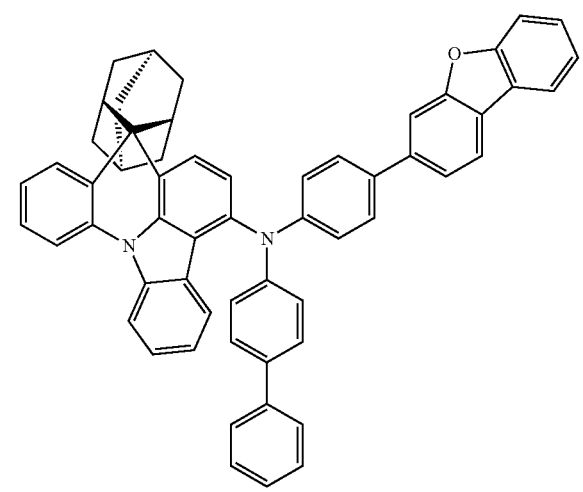

229
-continued
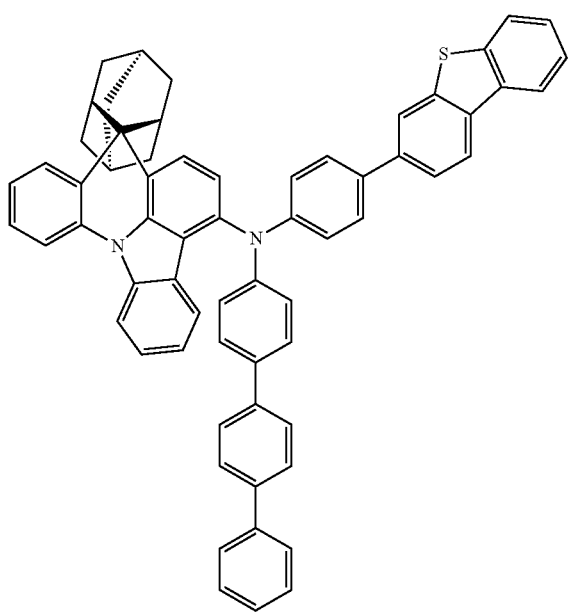
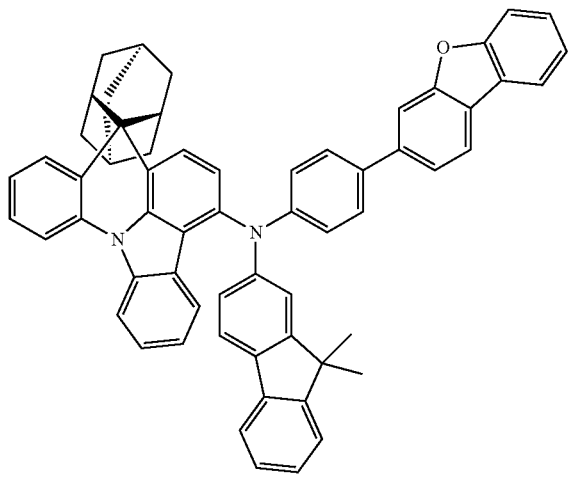
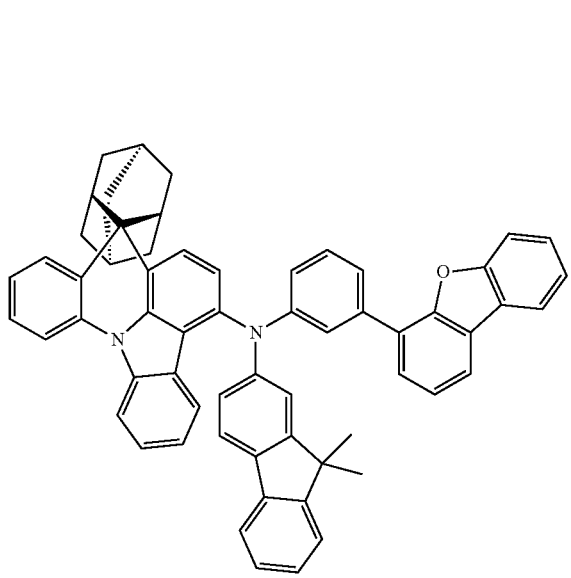
230
-continued
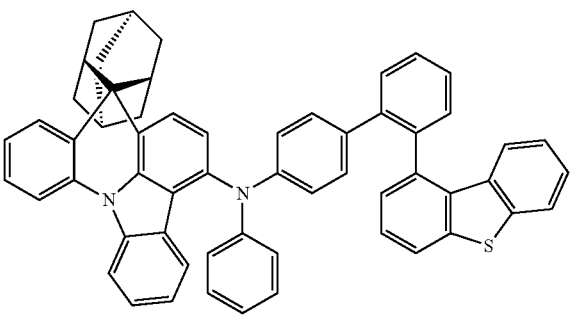
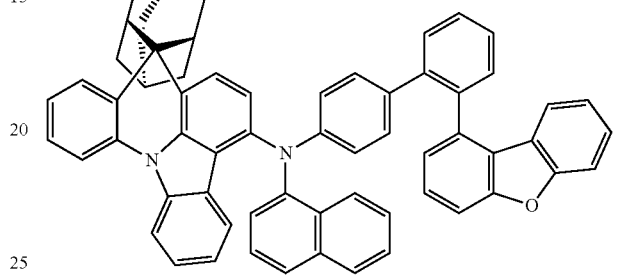
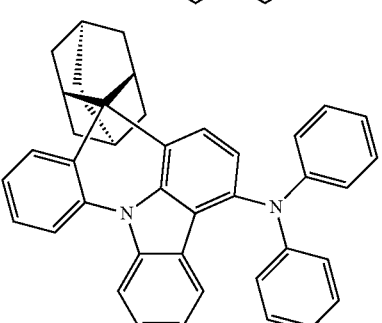
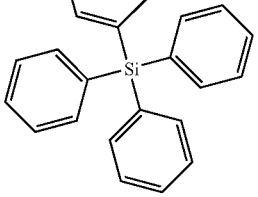
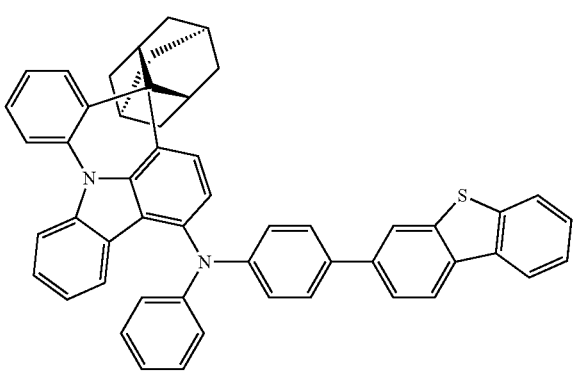

231
-continued
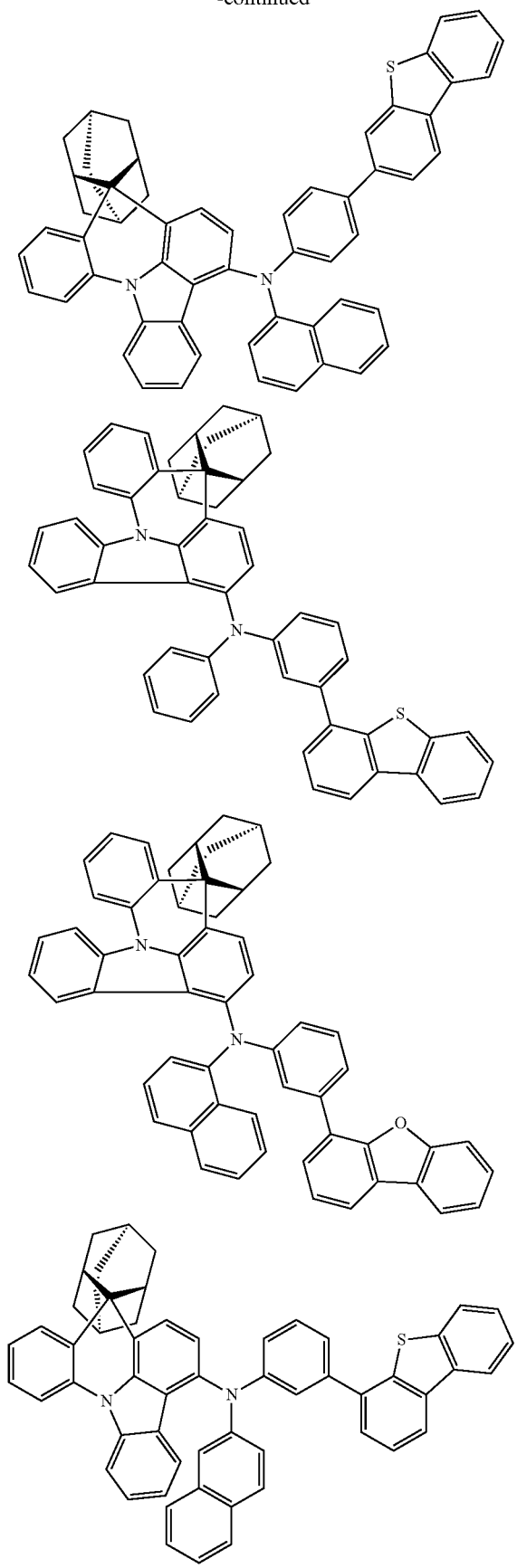
232
-continued
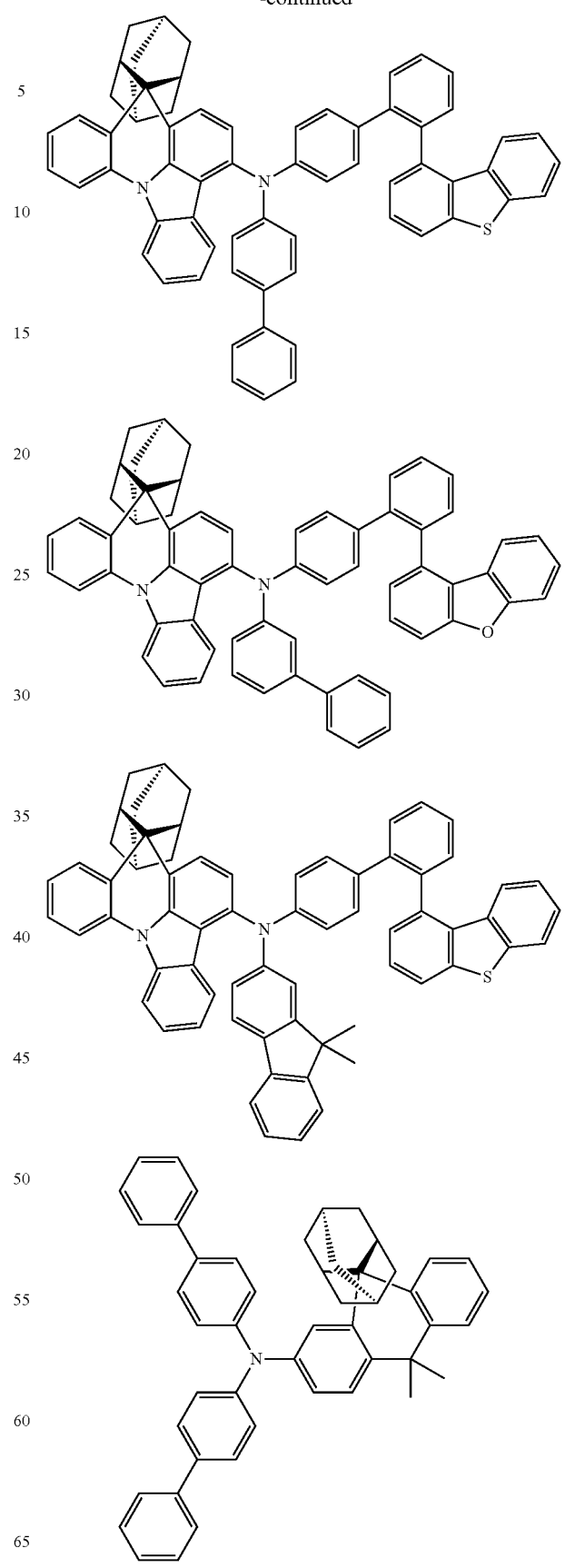

233
-continued
234
-continued
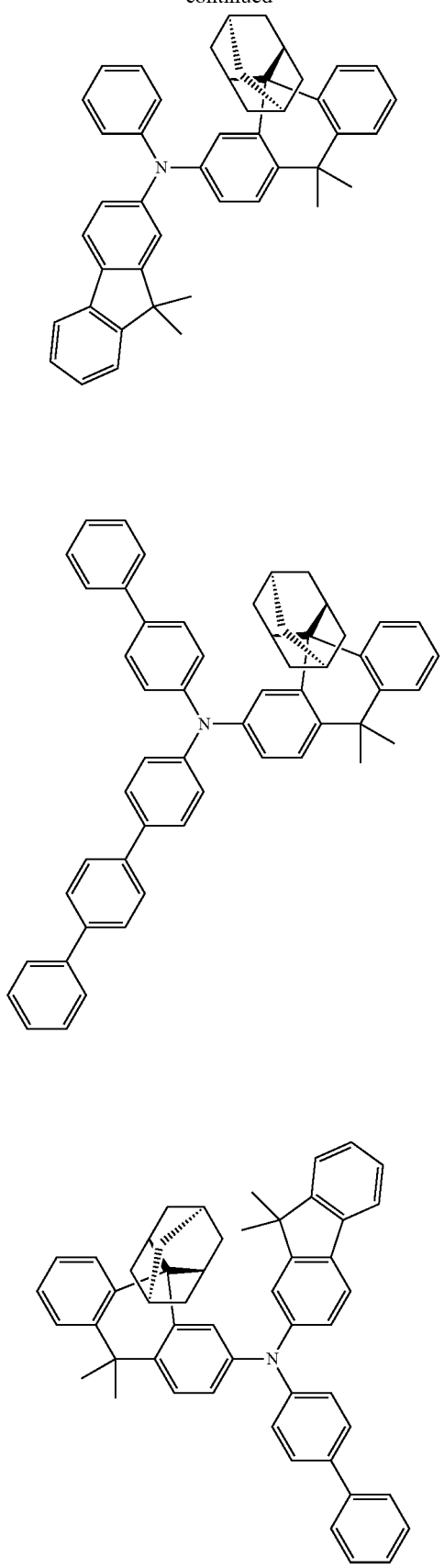

235
-continued
236
-continued
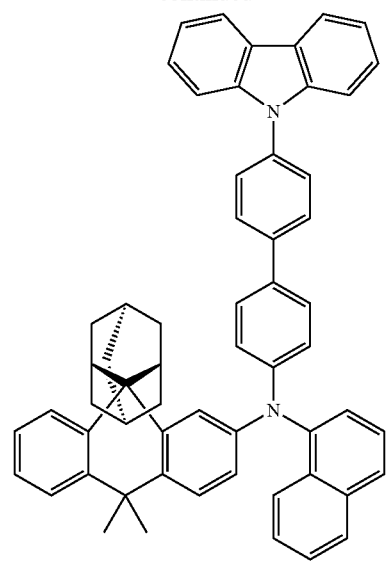
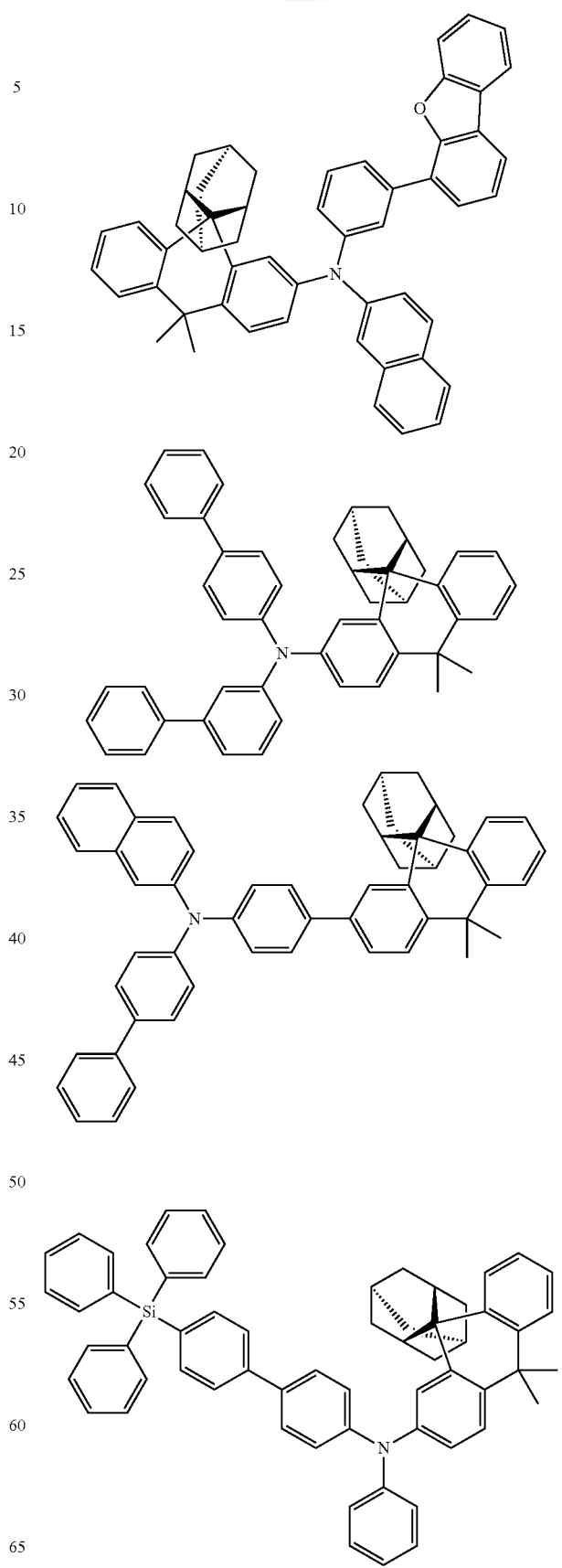

237
-continued
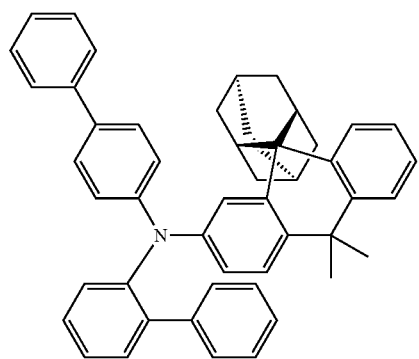
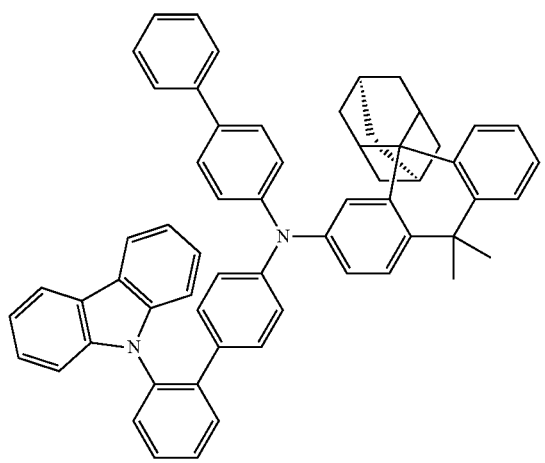
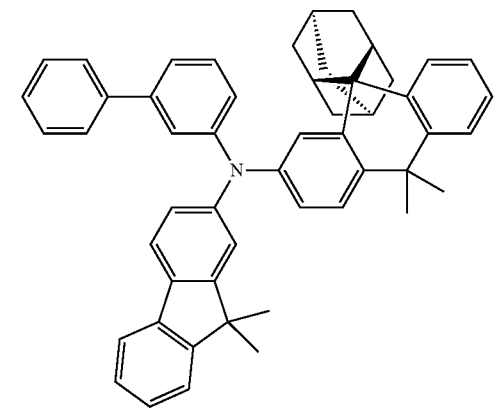
238
-continued
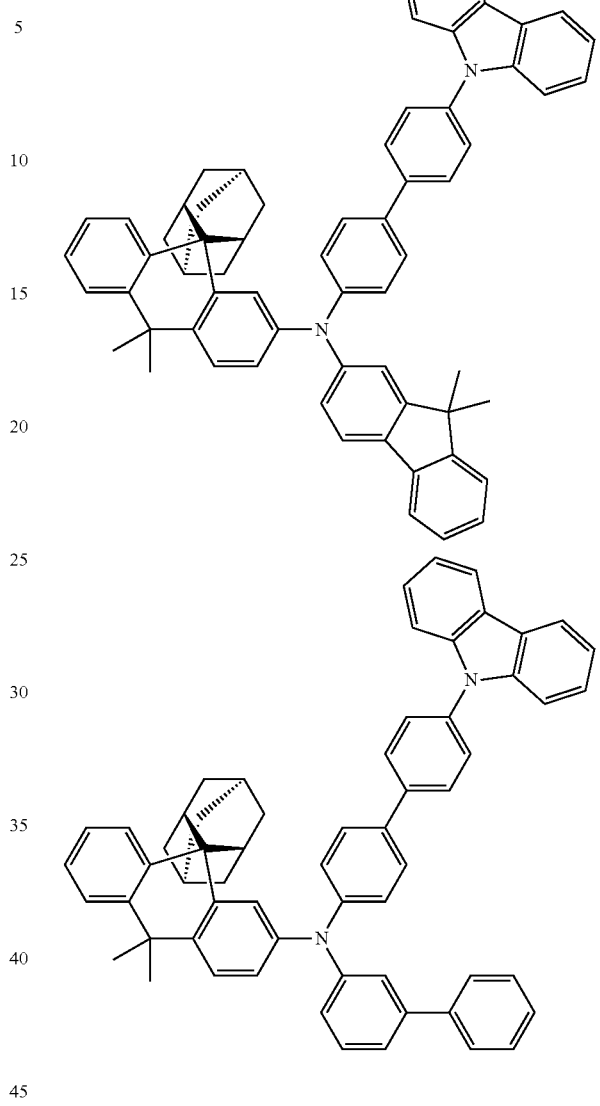
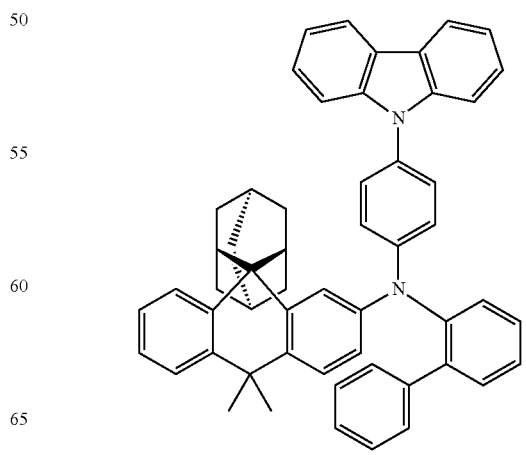

239
-continued
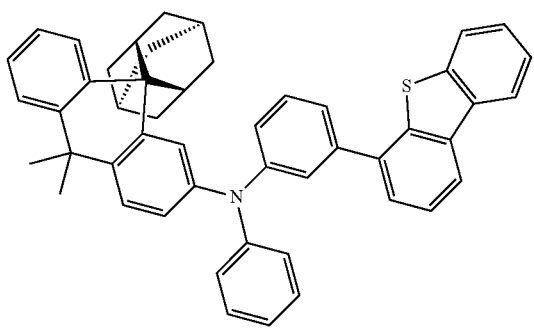
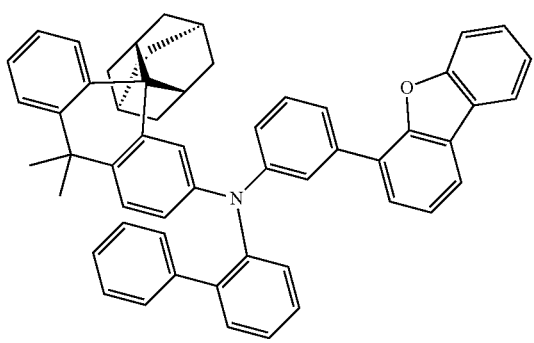
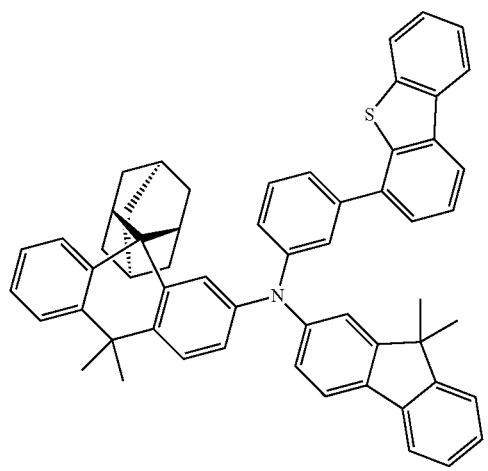
240
-continued
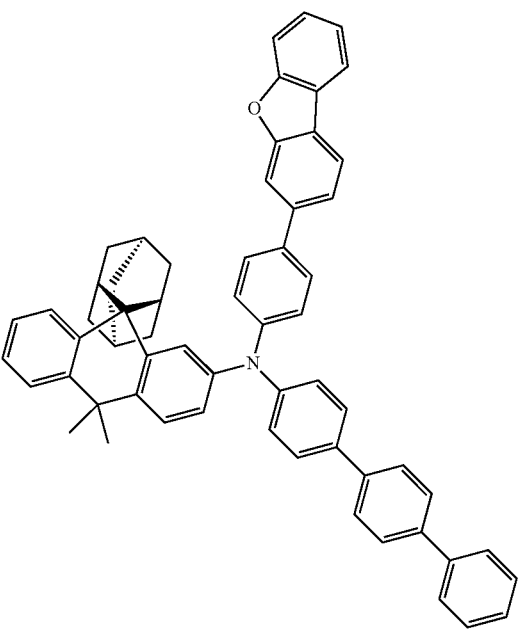
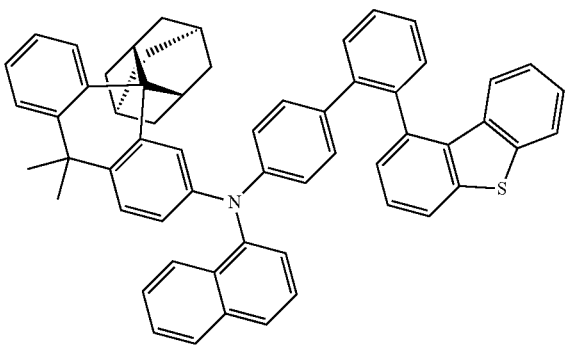
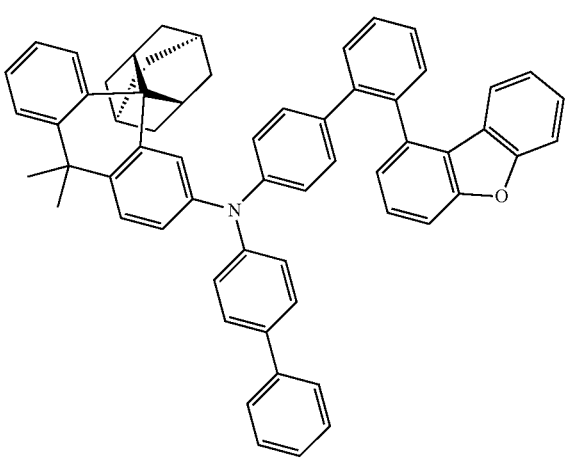

241
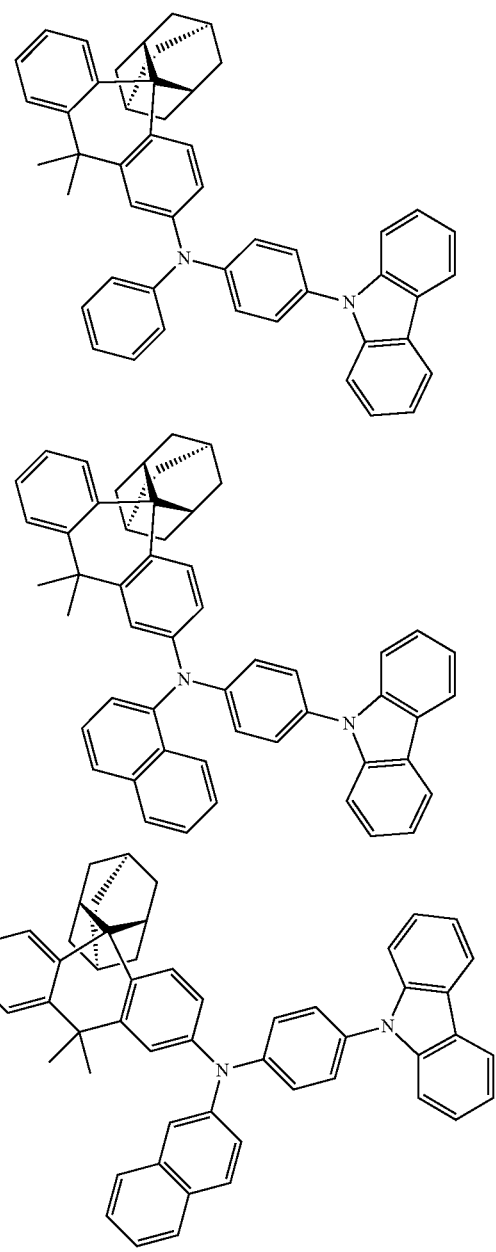
242
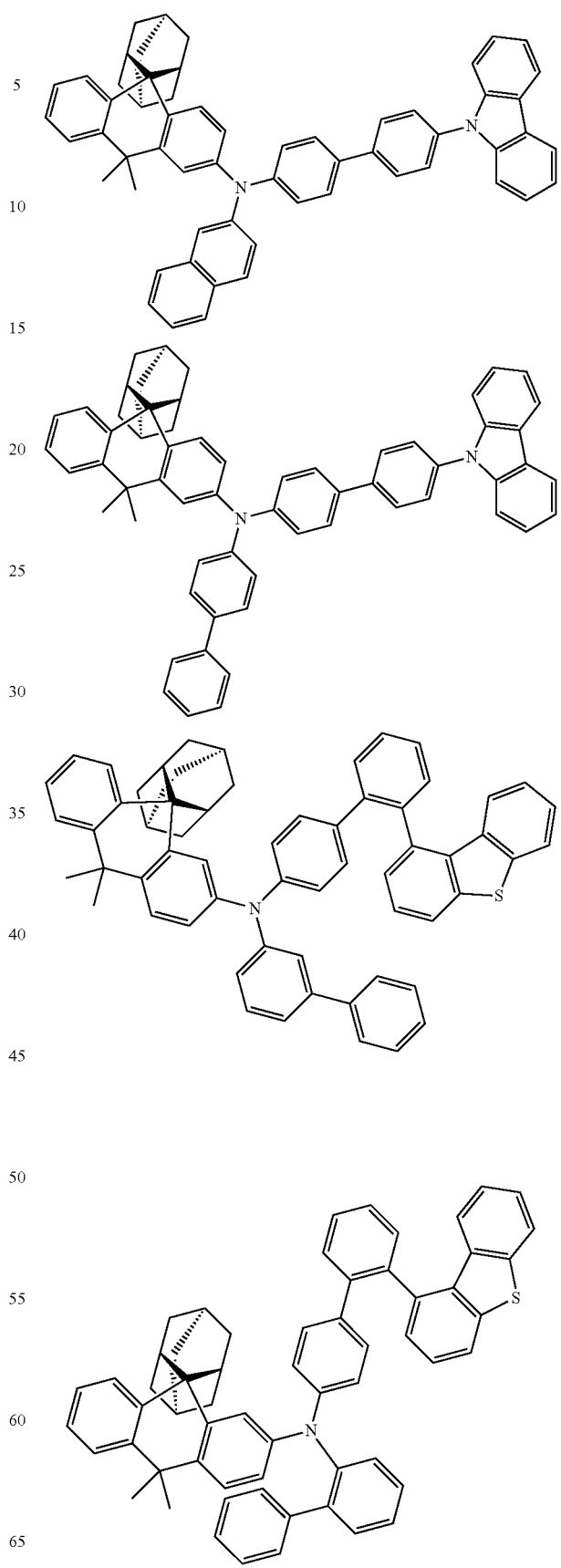

243
-continued
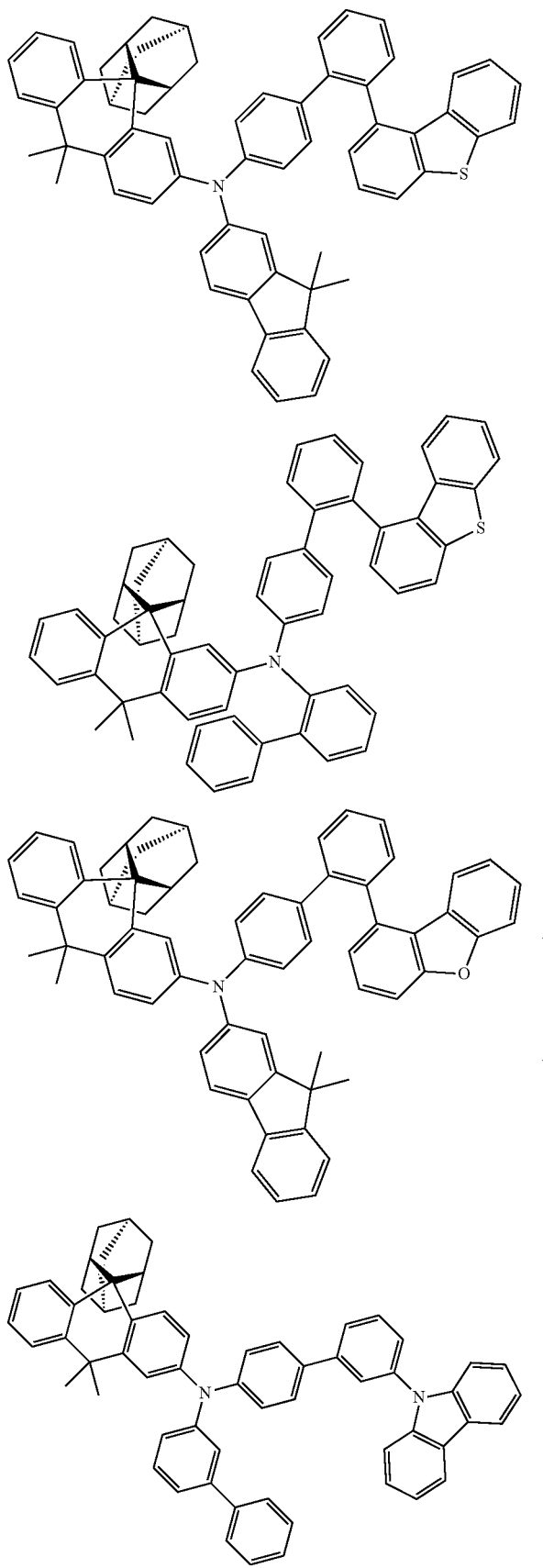
244
-continued
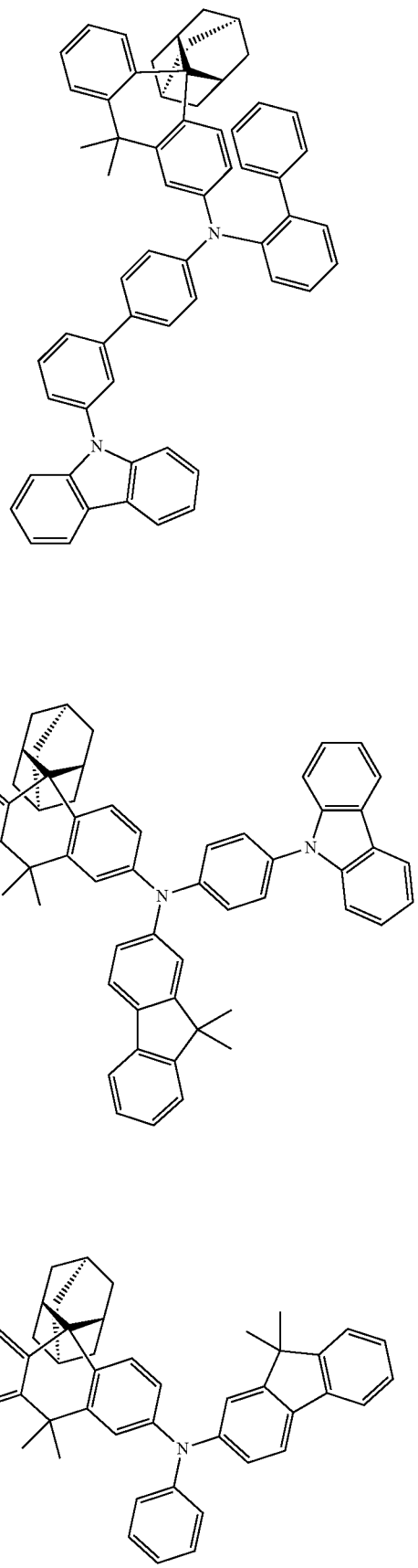

245
-continued
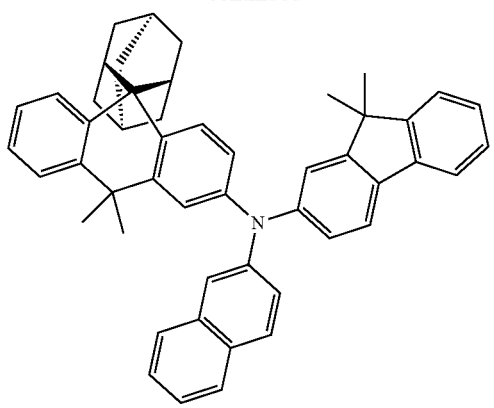
246
-continued
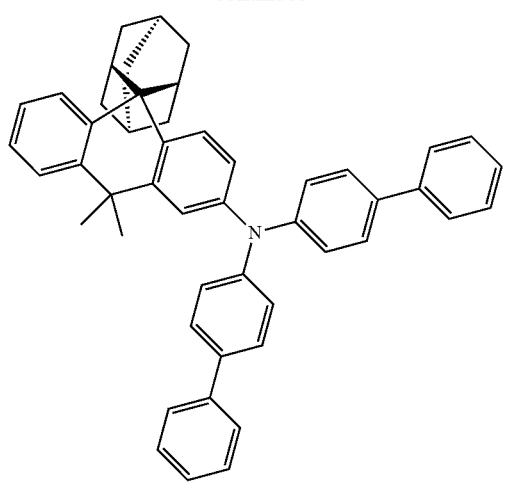
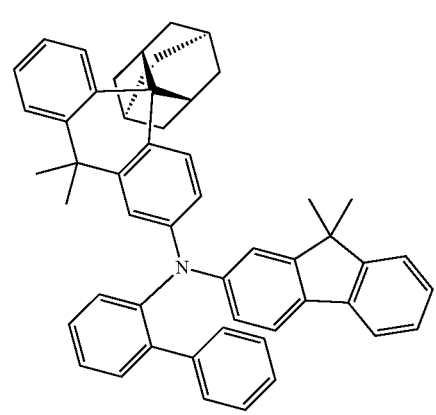
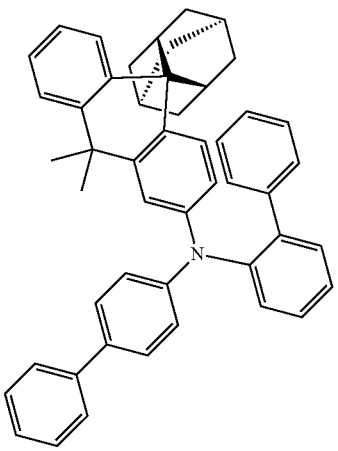
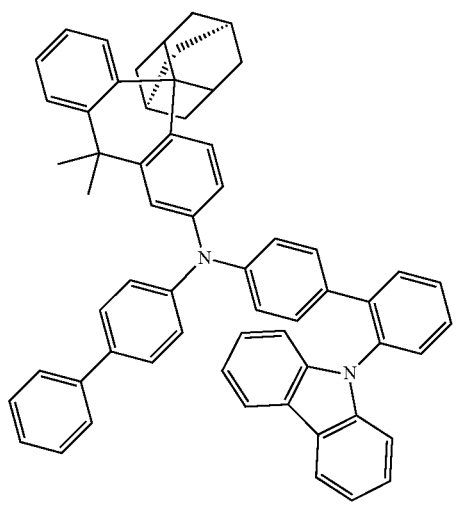
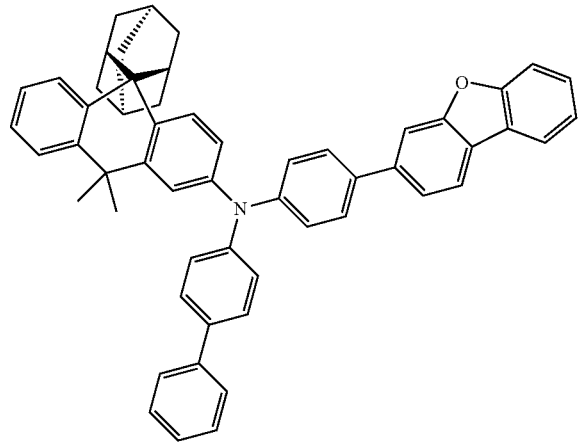

247
-continued
248
-continued
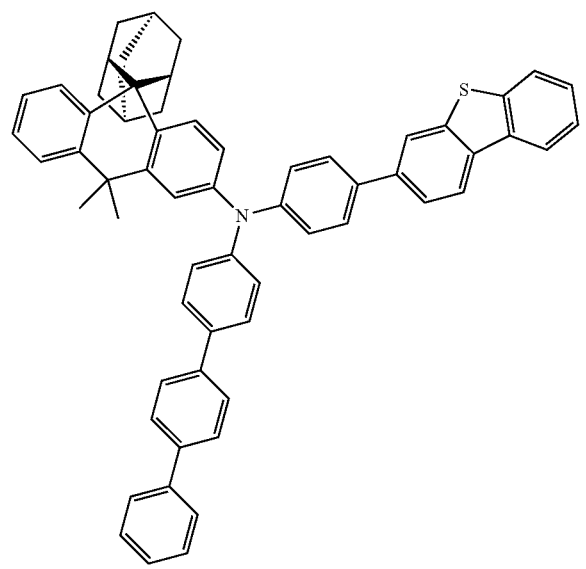
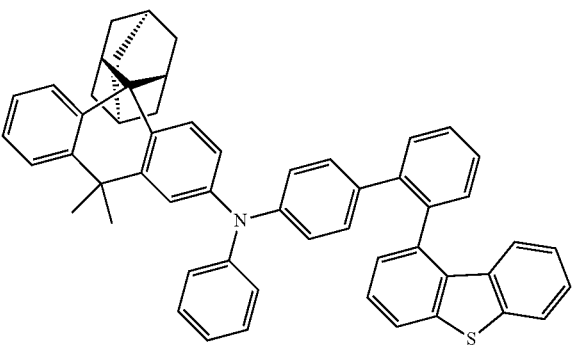
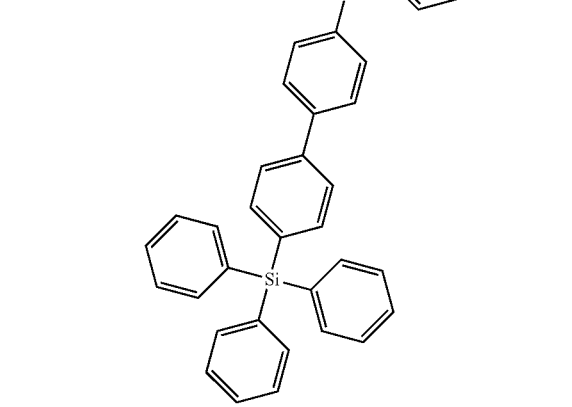
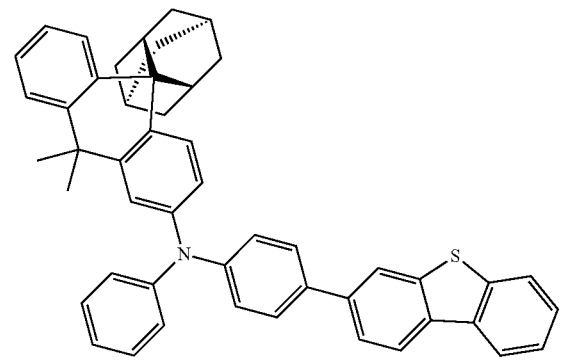

249
-continued
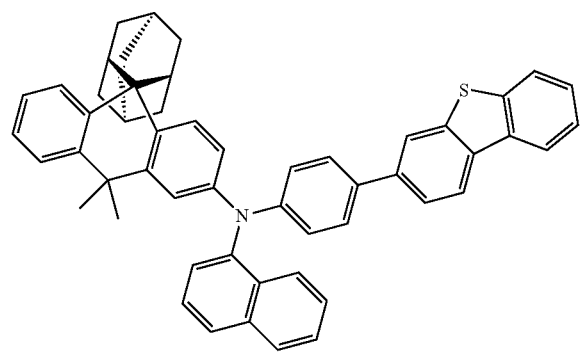
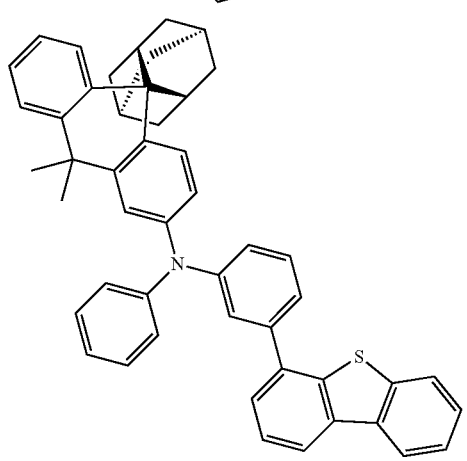
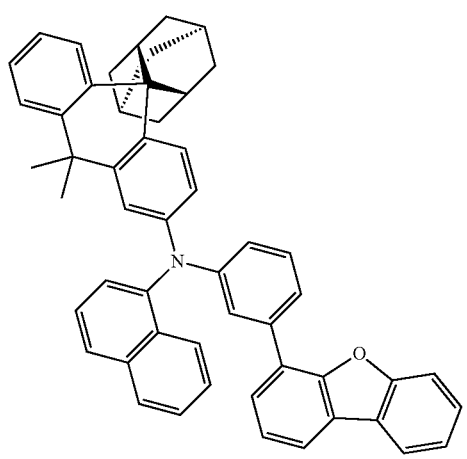
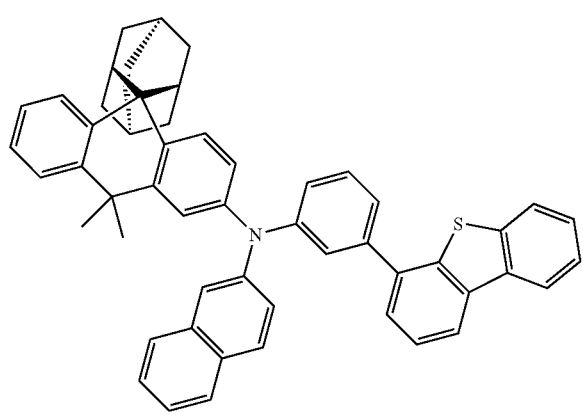
250
-continued
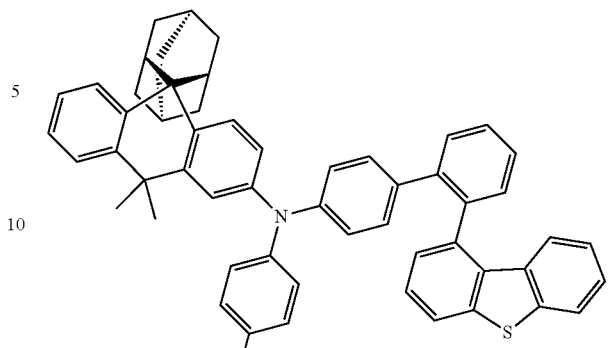
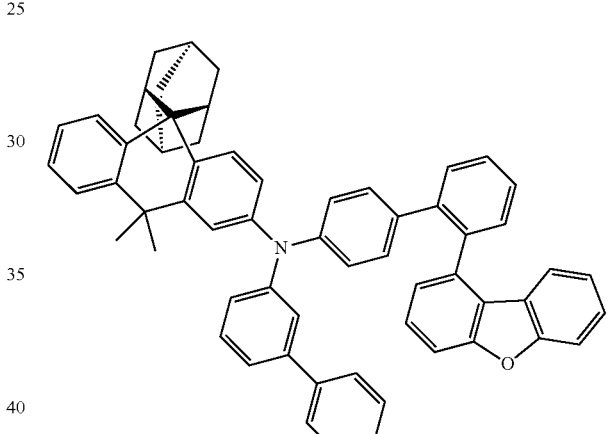
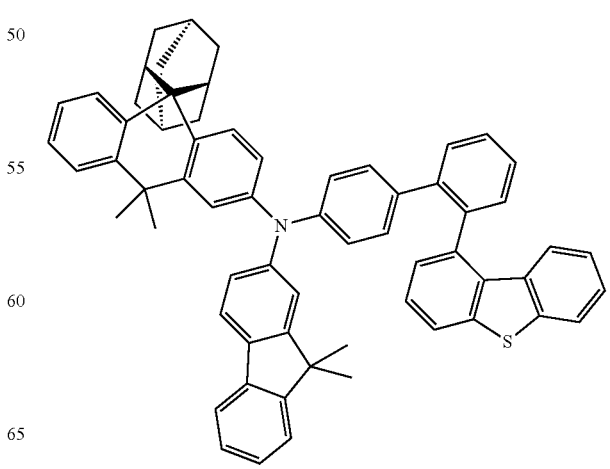

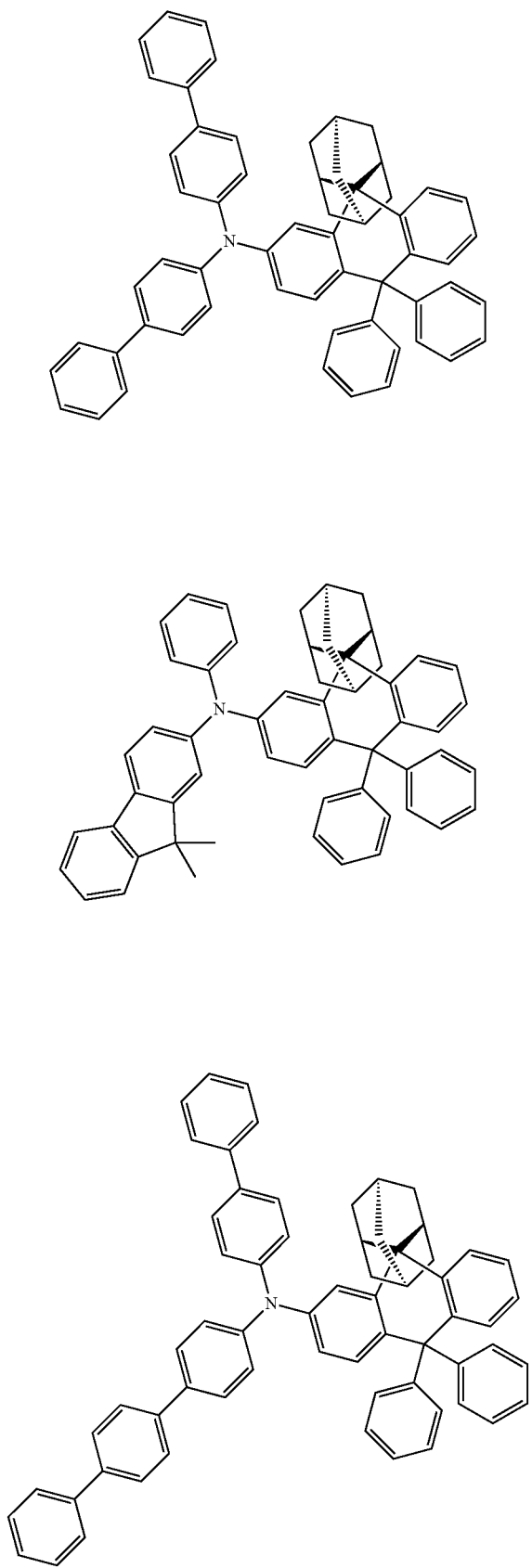
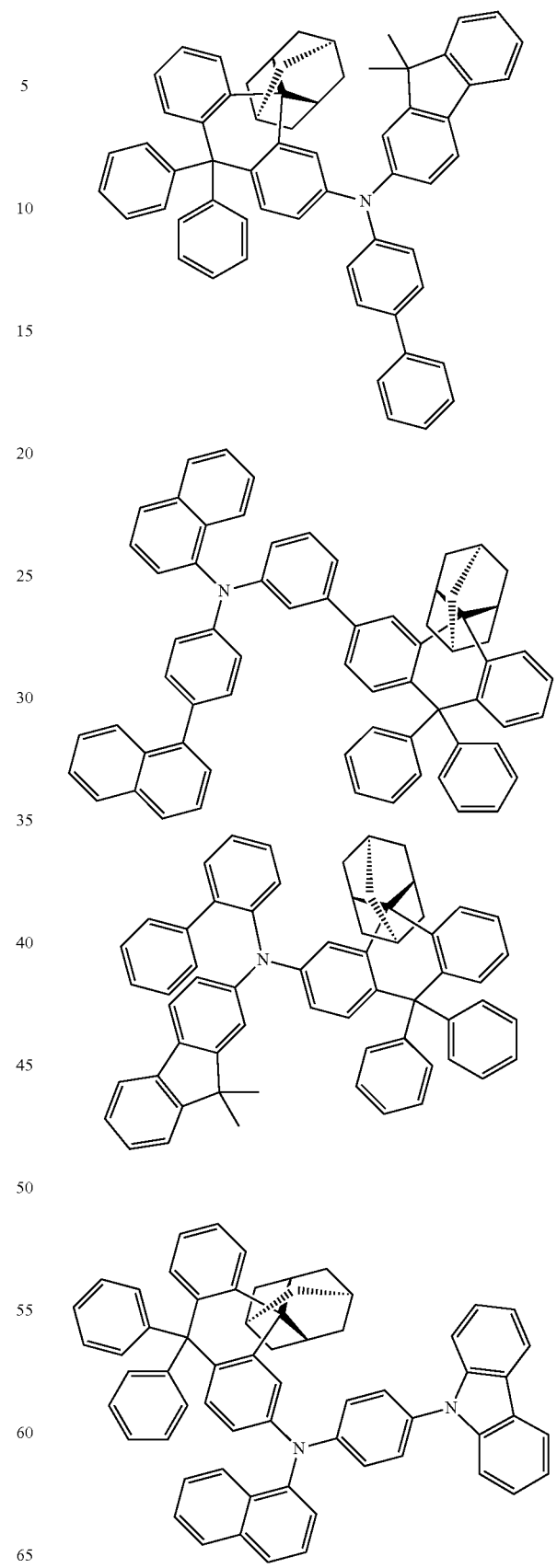

253
-continued
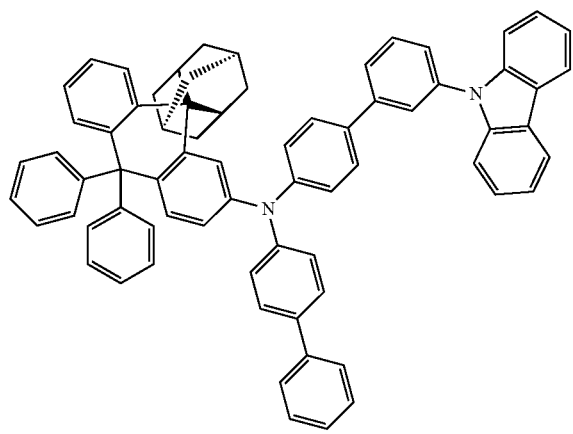
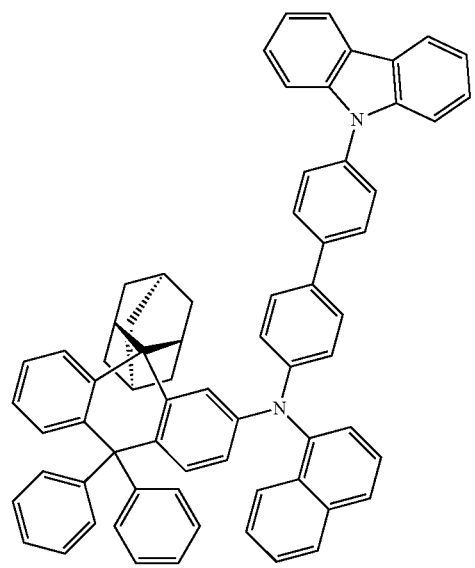
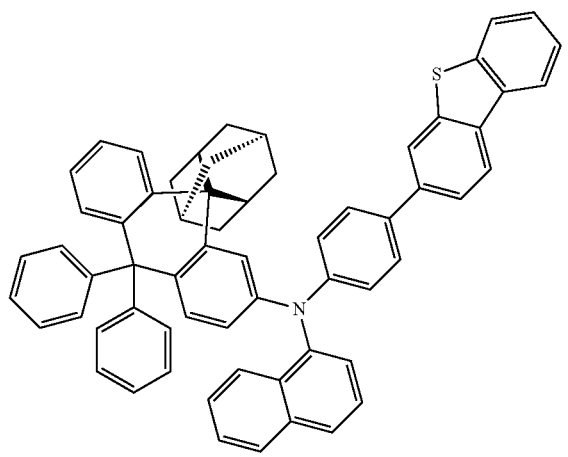
254
-continued
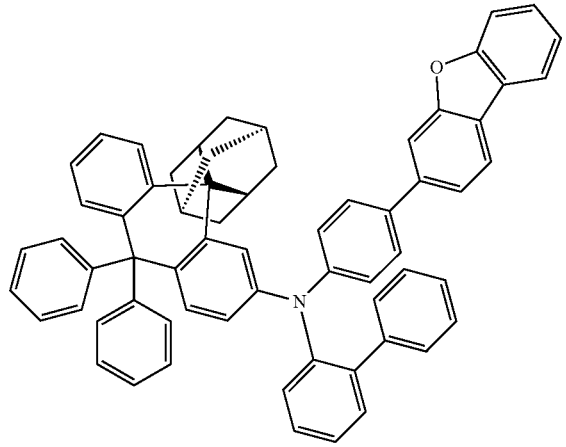
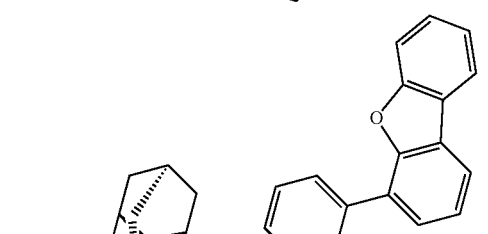
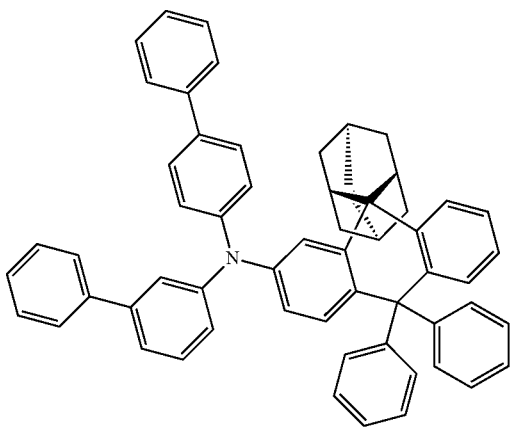
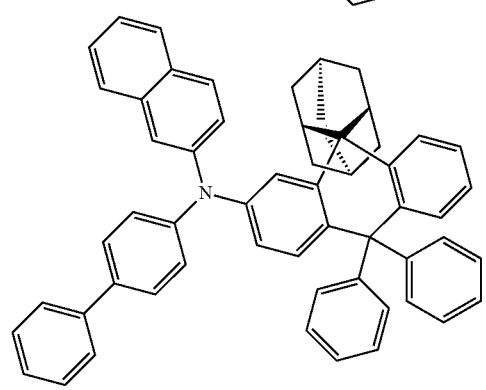

255
-continued
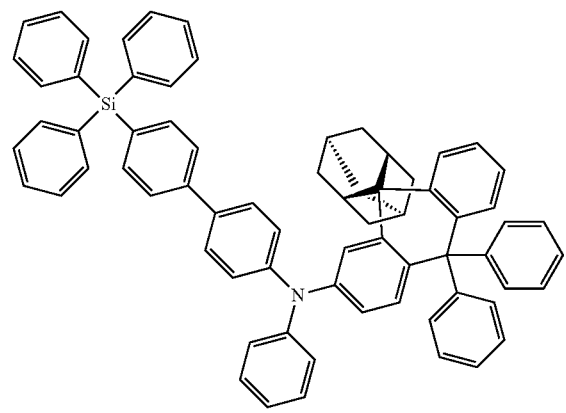
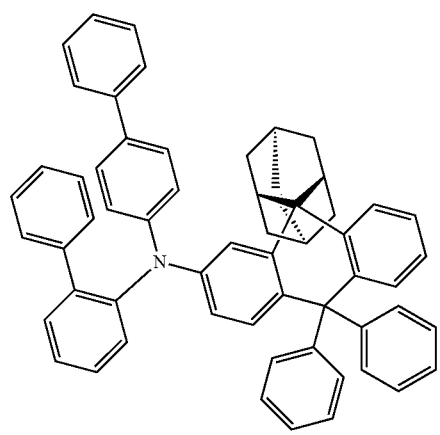
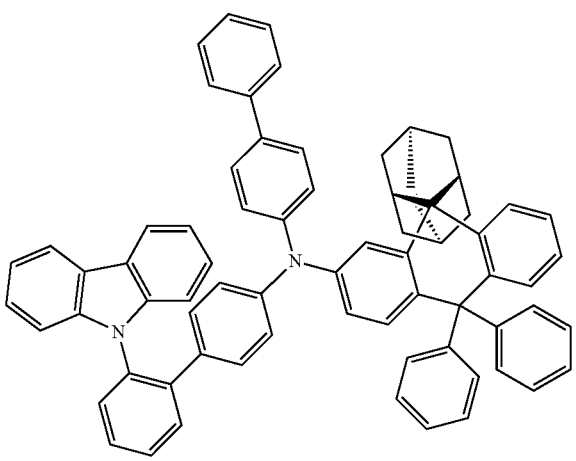
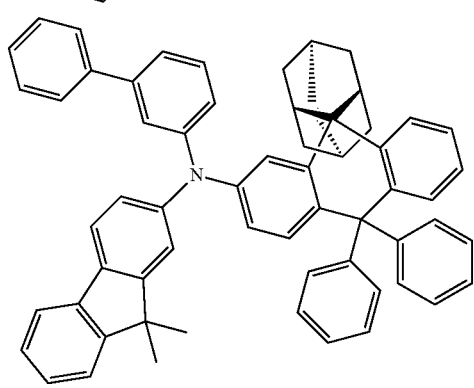
256
-continued
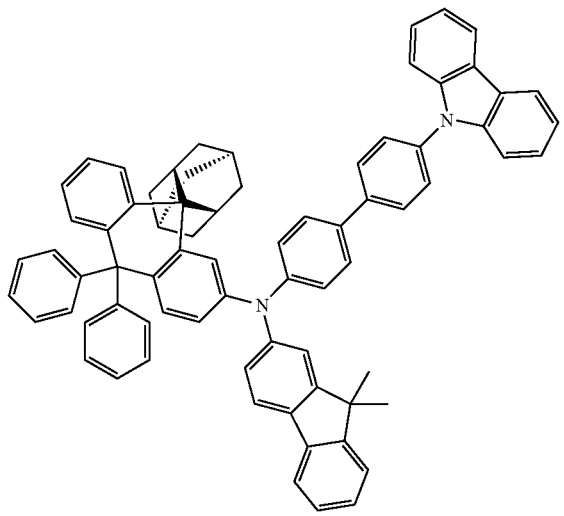
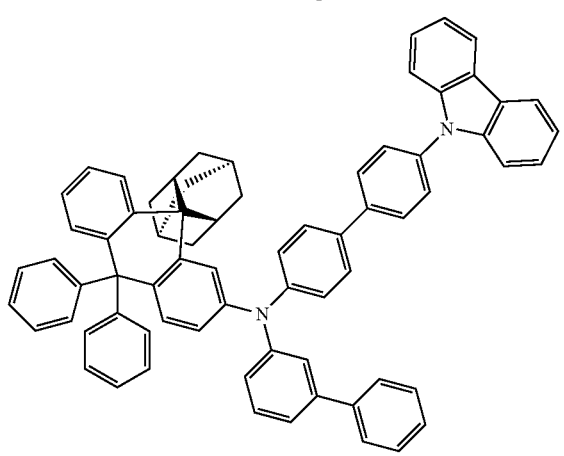
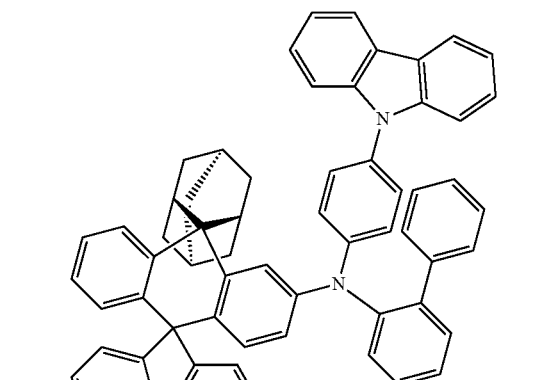
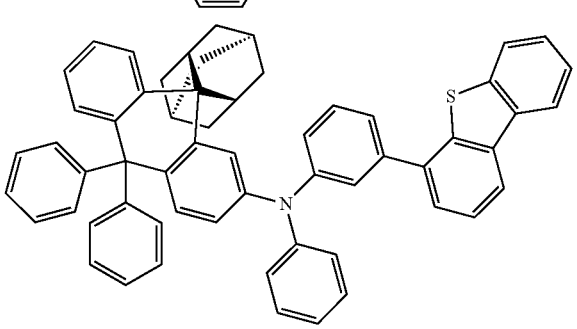

257
-continued
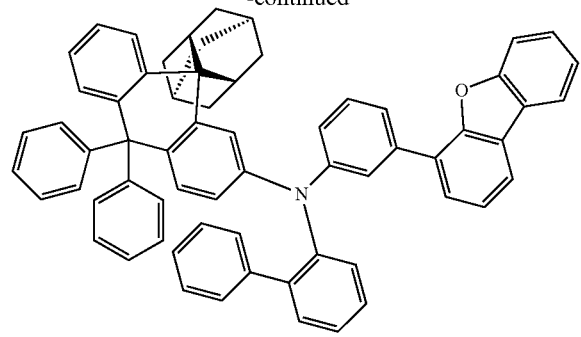
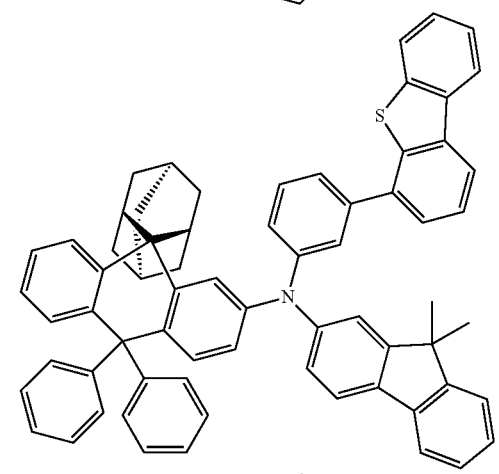
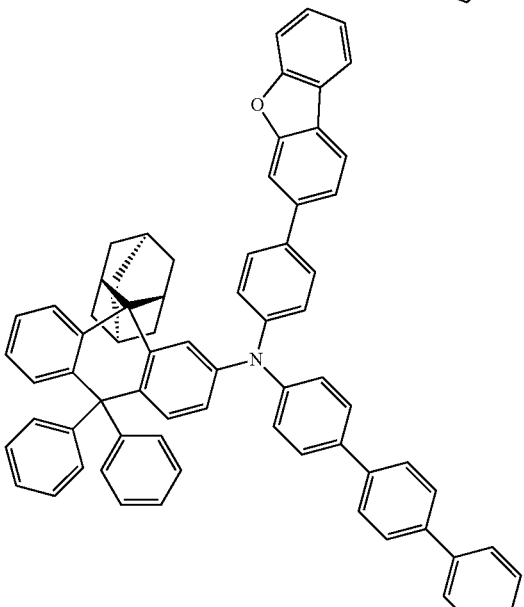
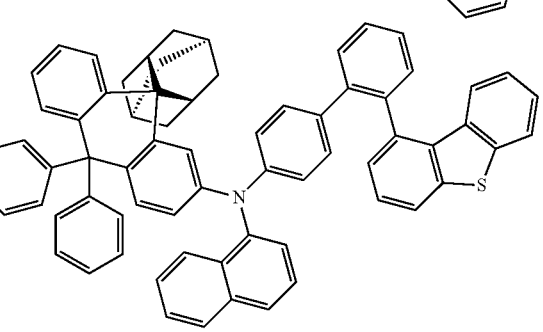
258
-continued
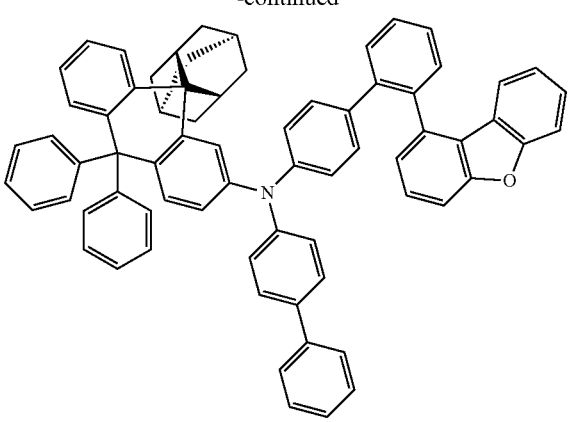
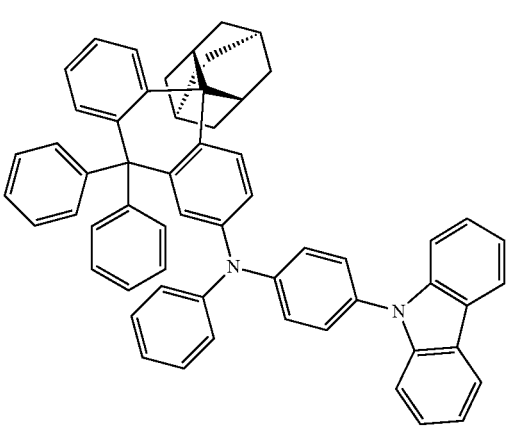
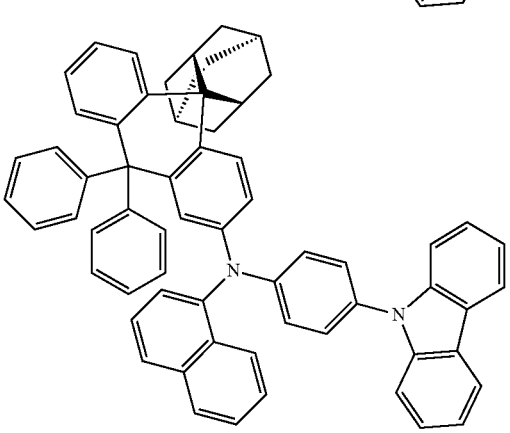
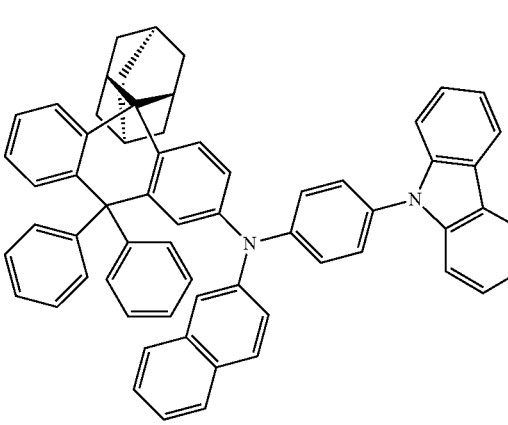

259
-continued
260
-continued
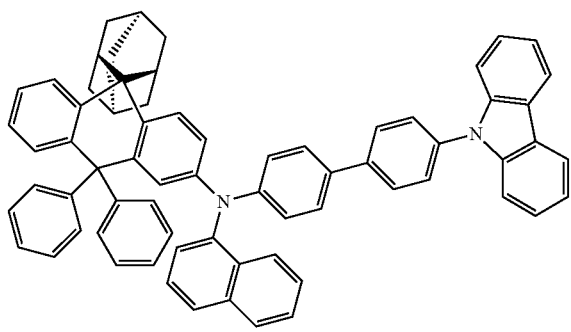
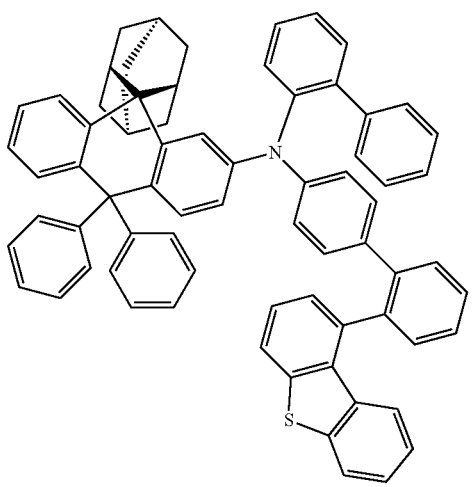
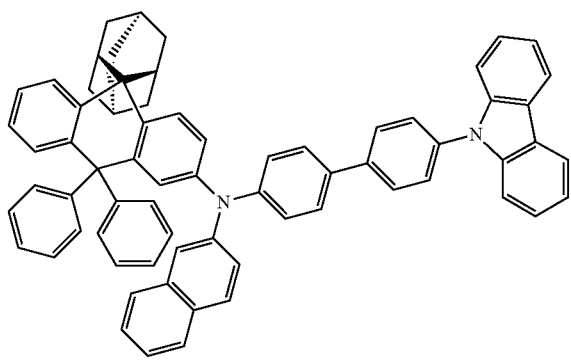
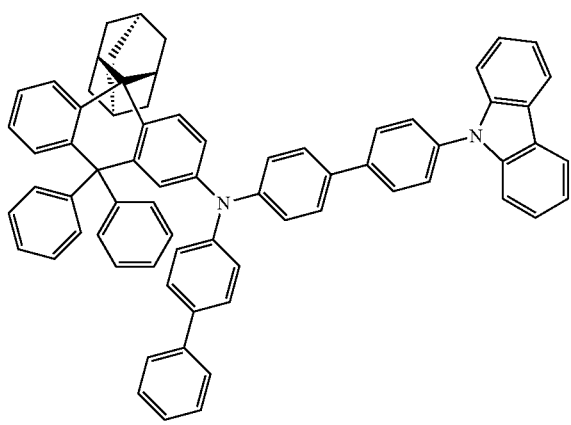
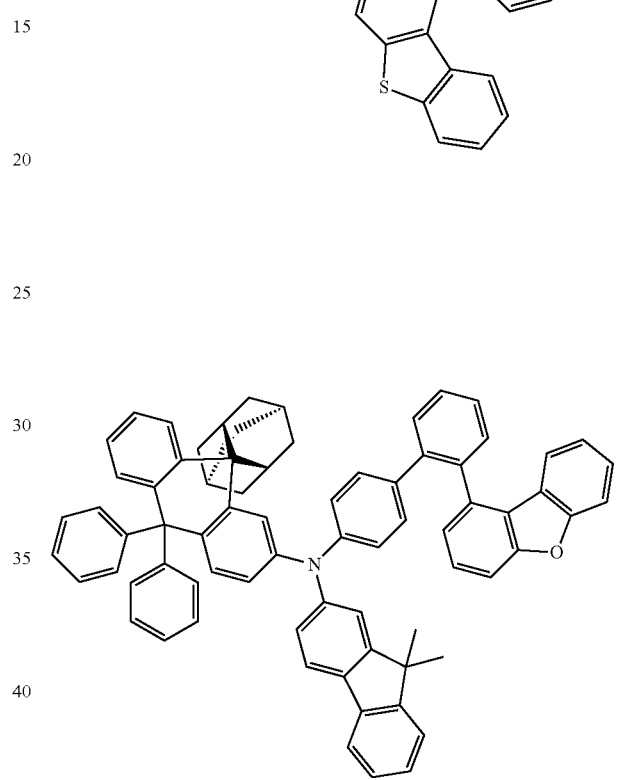
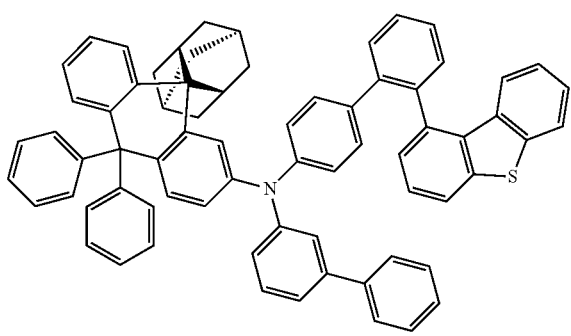
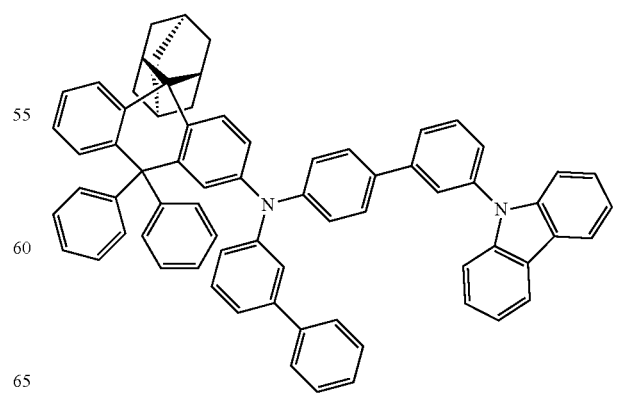

261
-continued
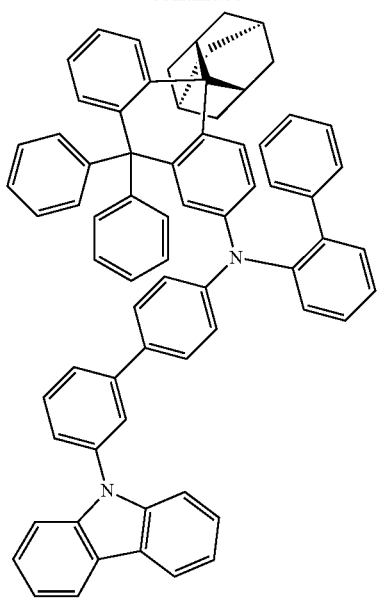
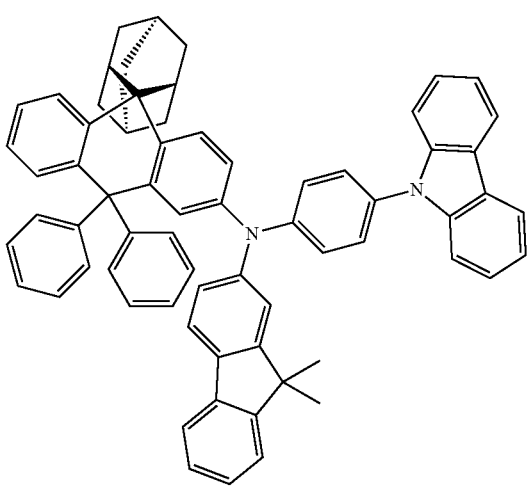
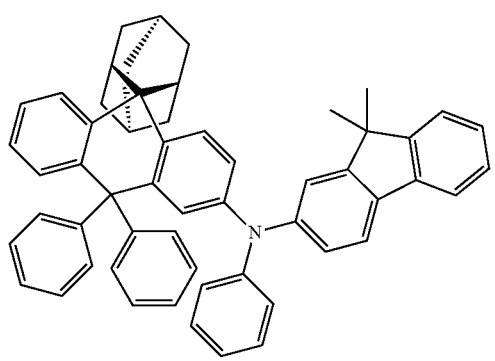
262
-continued
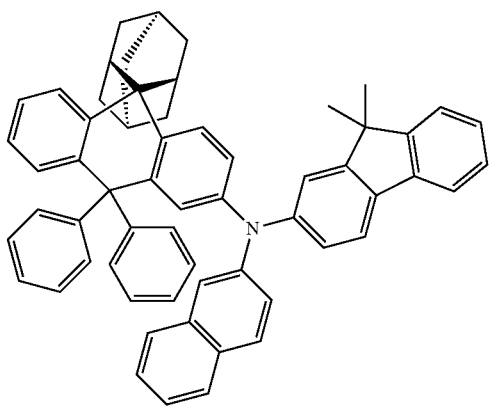
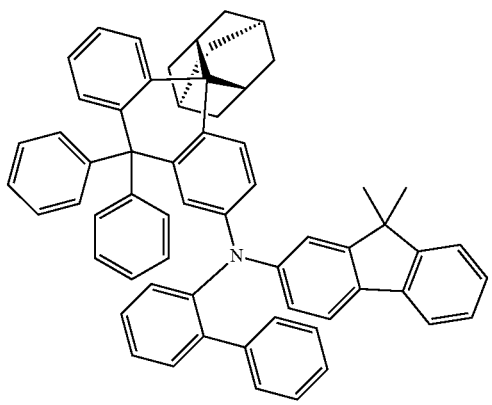
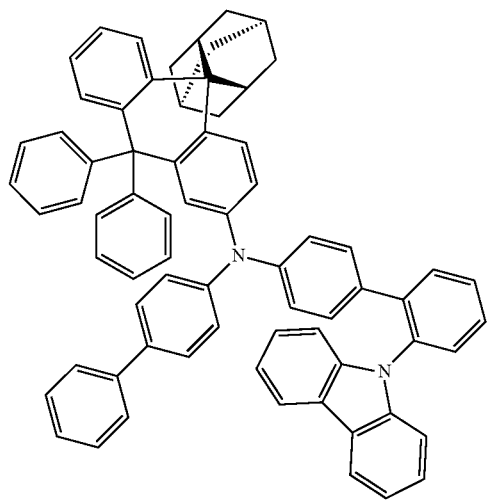

263
-continued
264
-continued
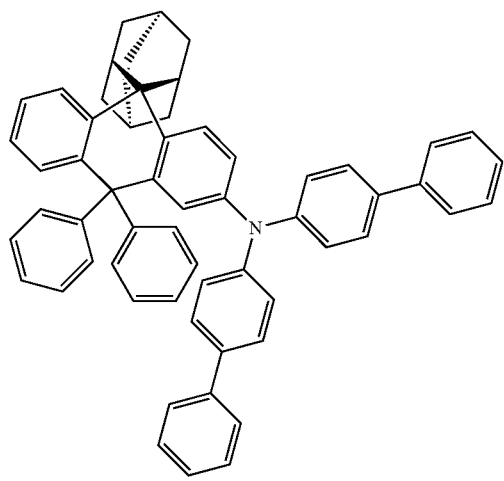
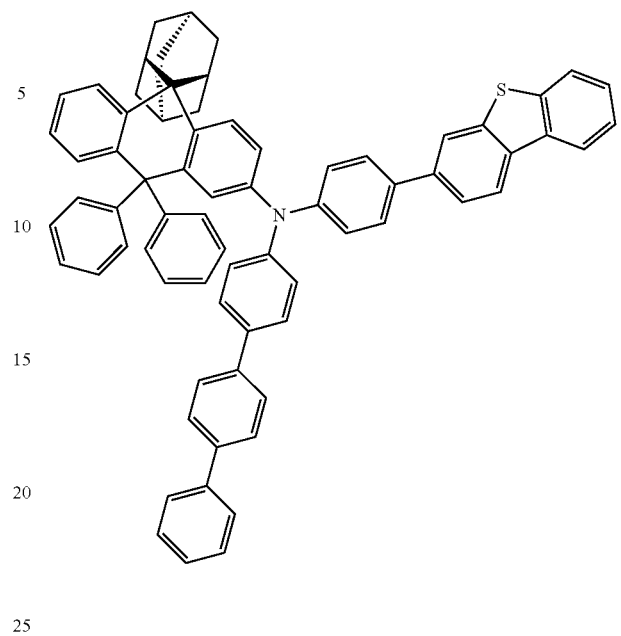
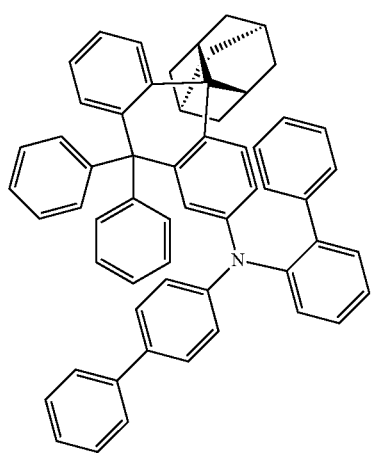
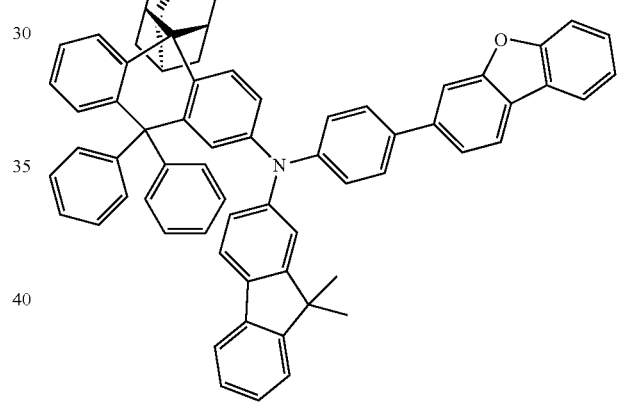
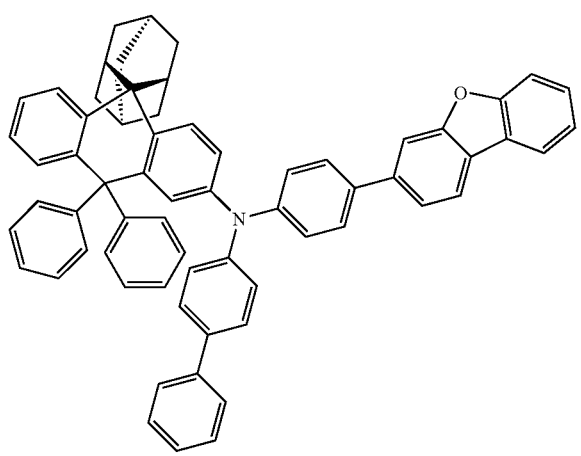
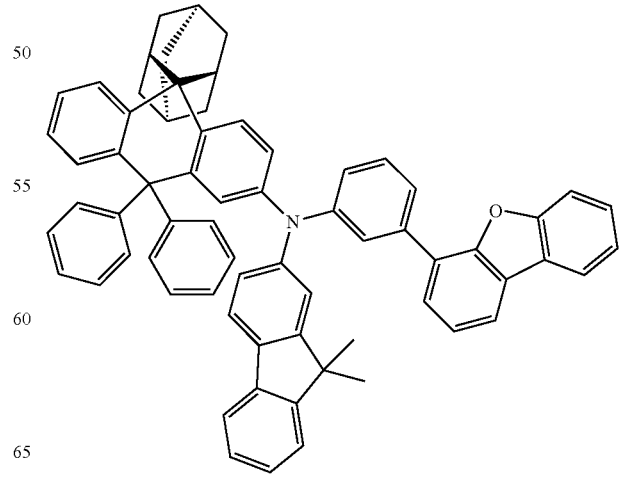

265
-continued
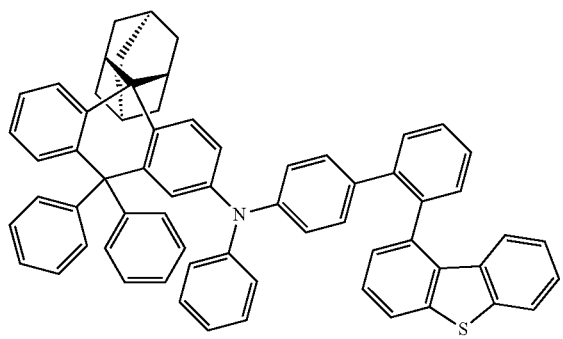
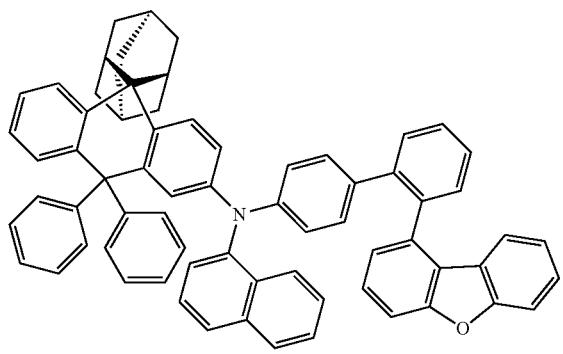
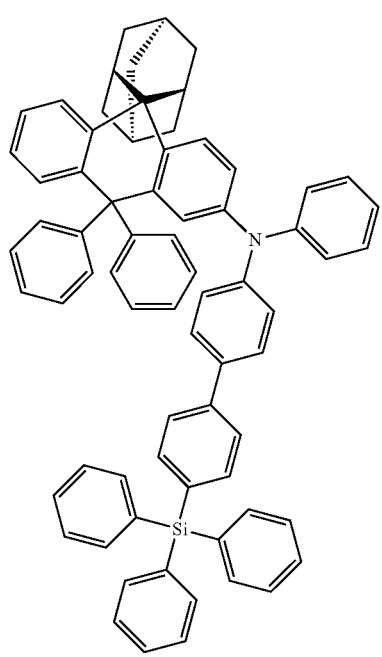
266
-continued
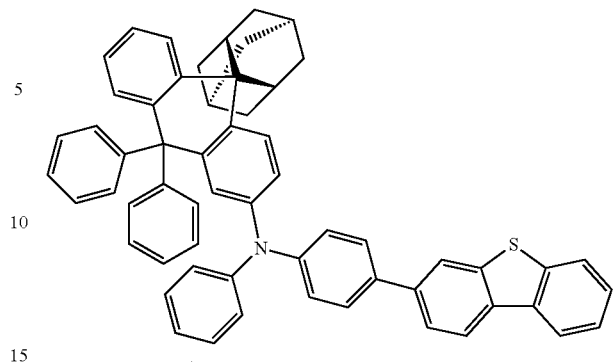
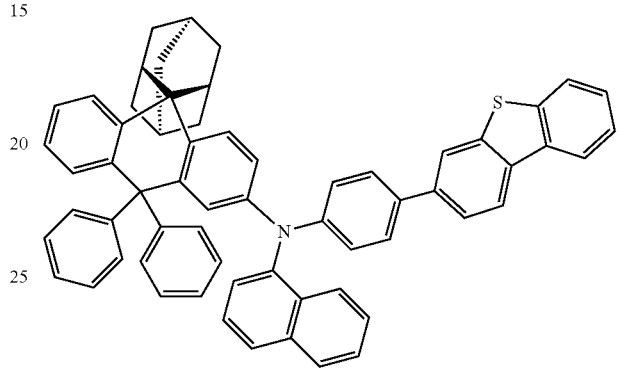
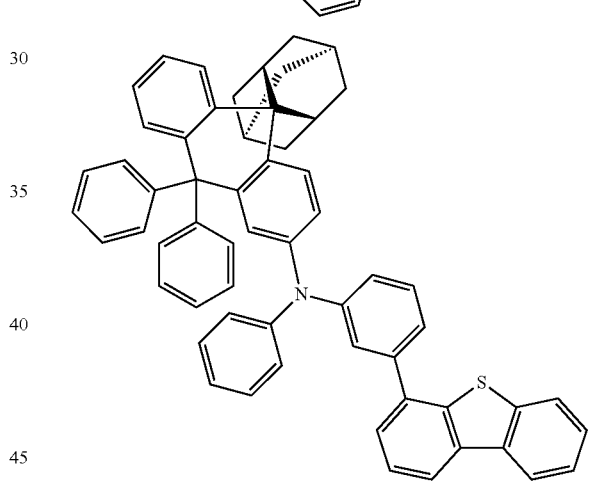
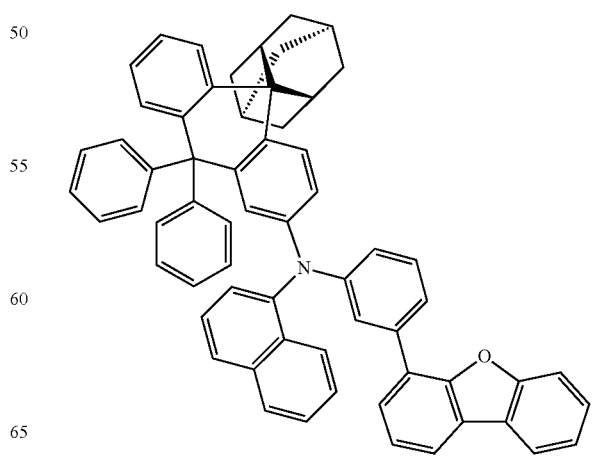

267
-continued
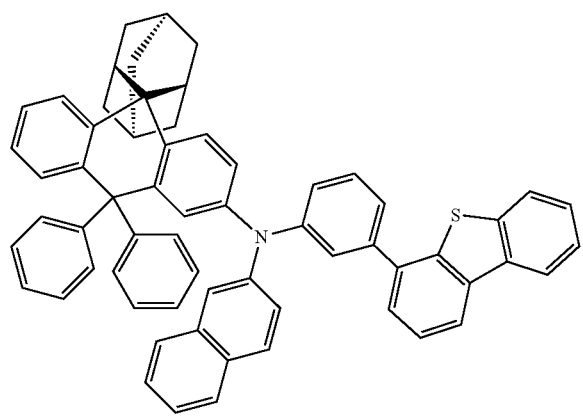
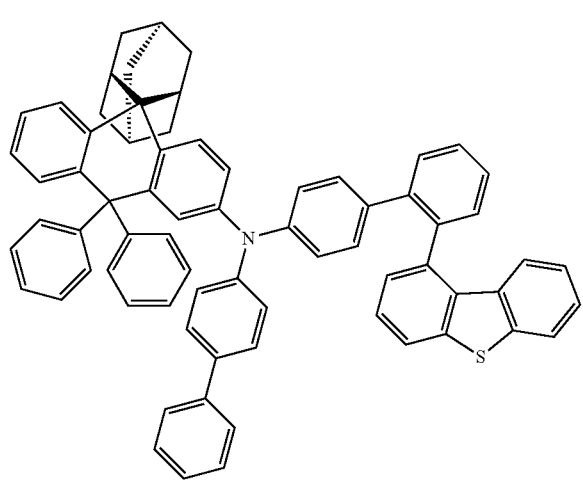
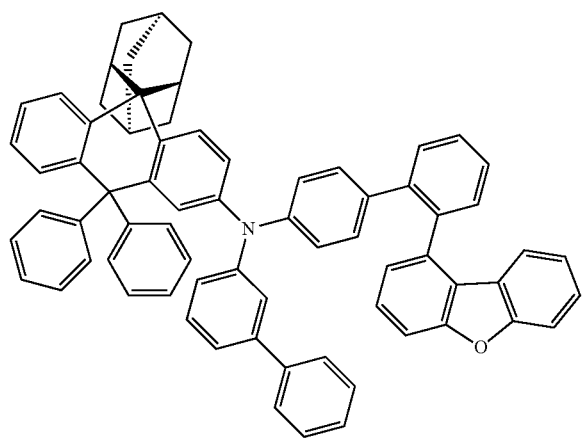
268
-continued
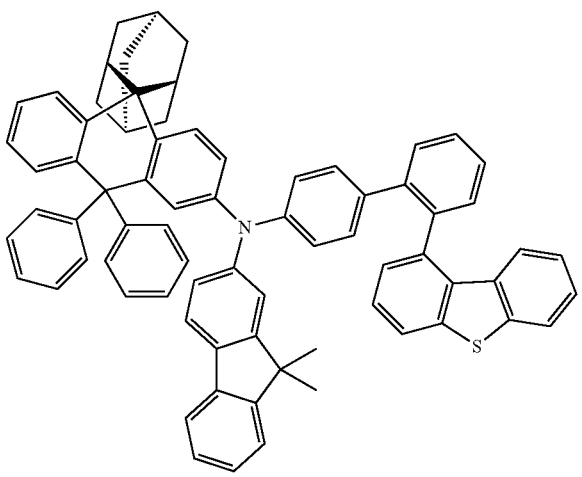
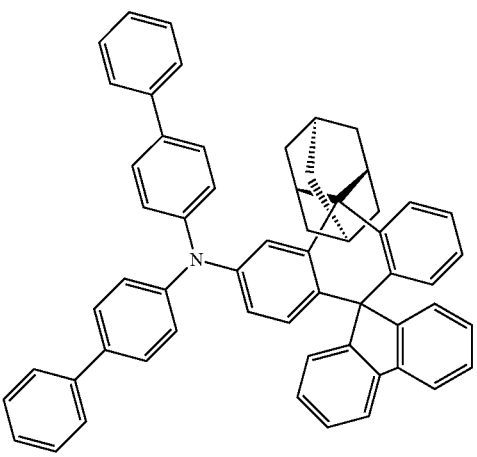
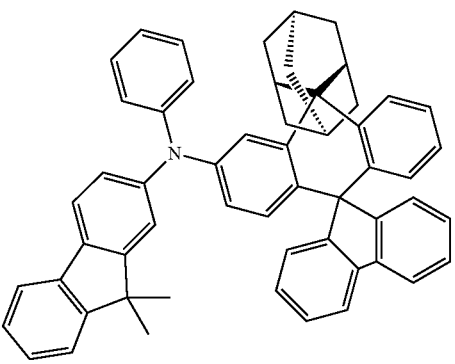

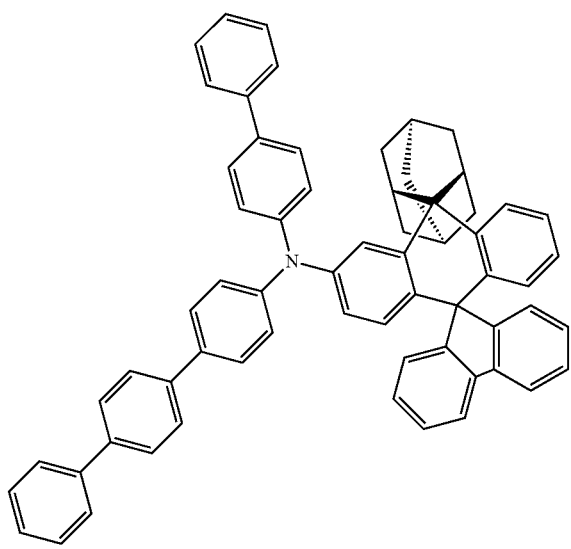
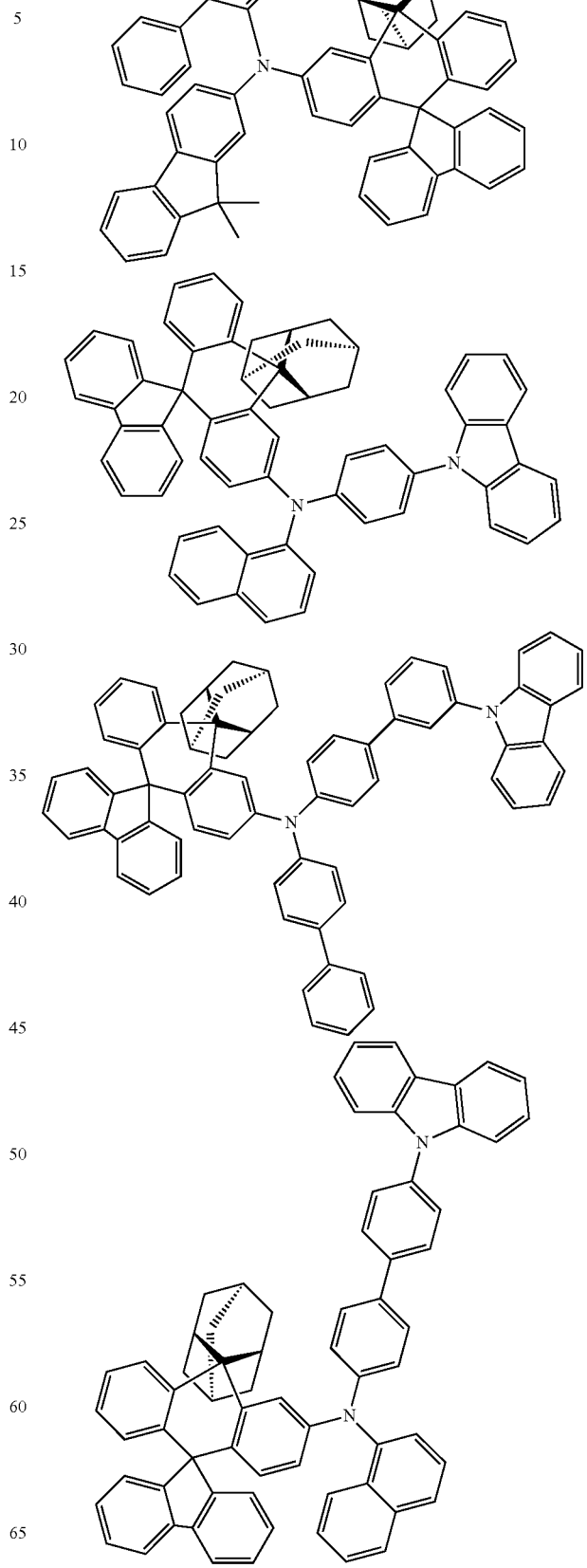

271
-continued
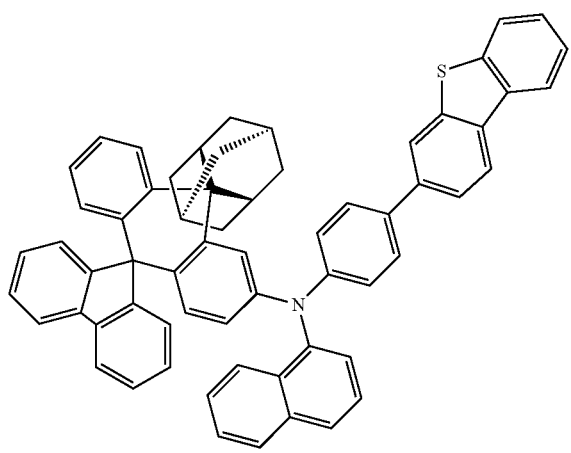
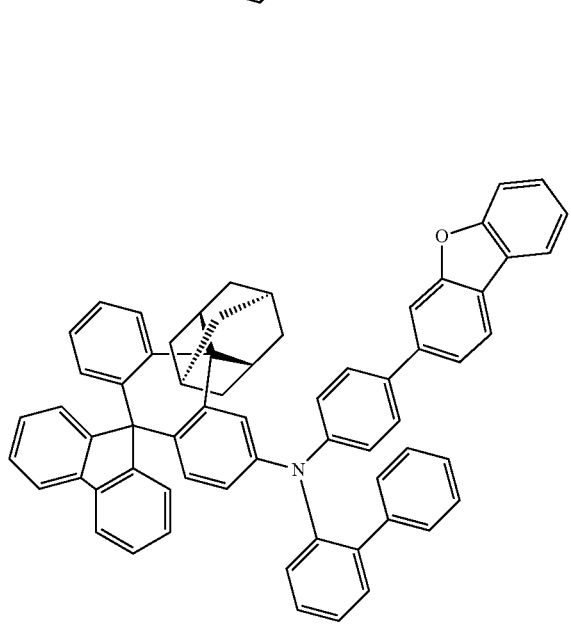
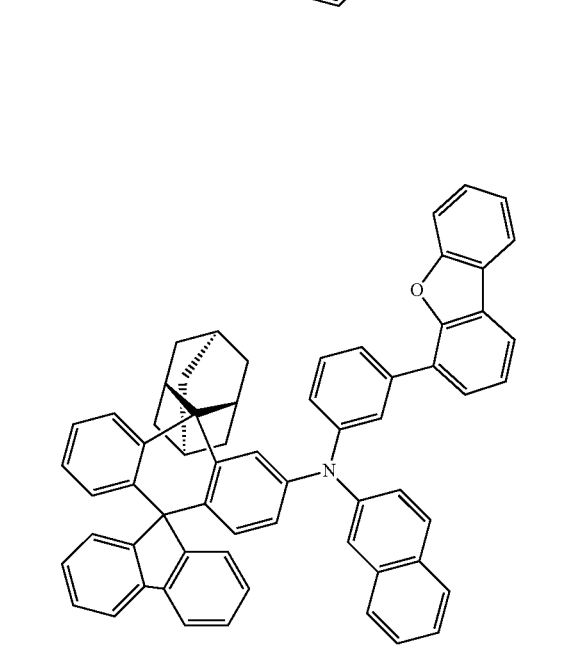
272
-continued
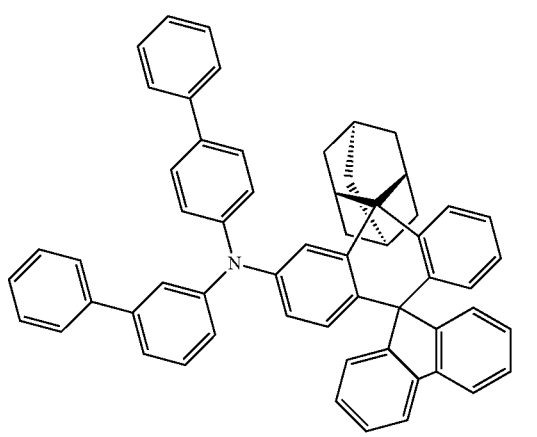
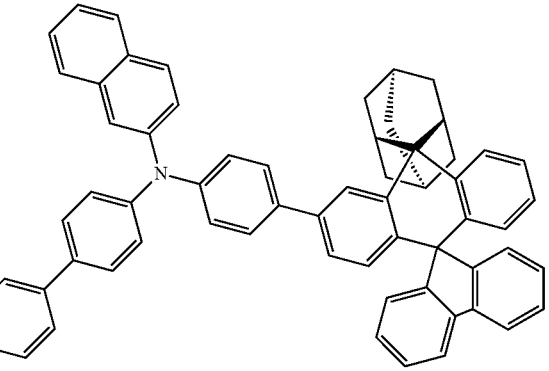
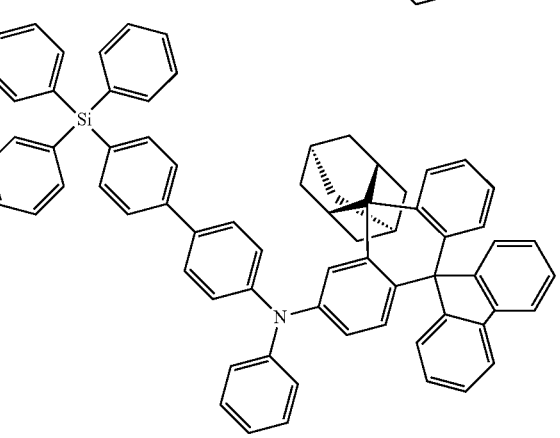
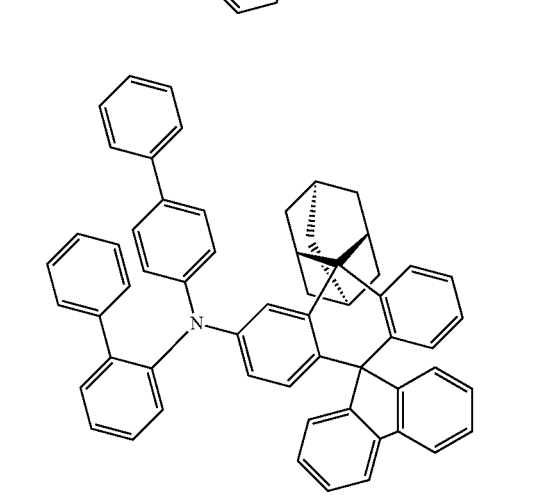

273
-continued
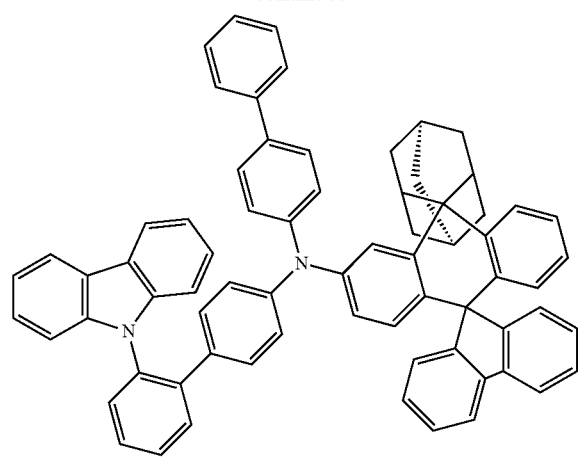
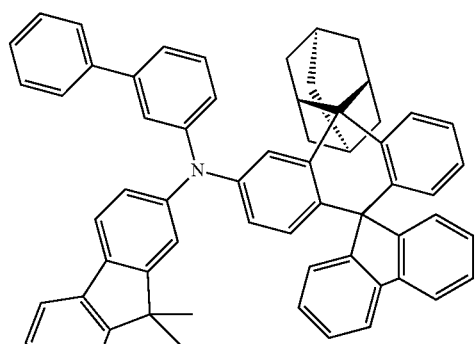
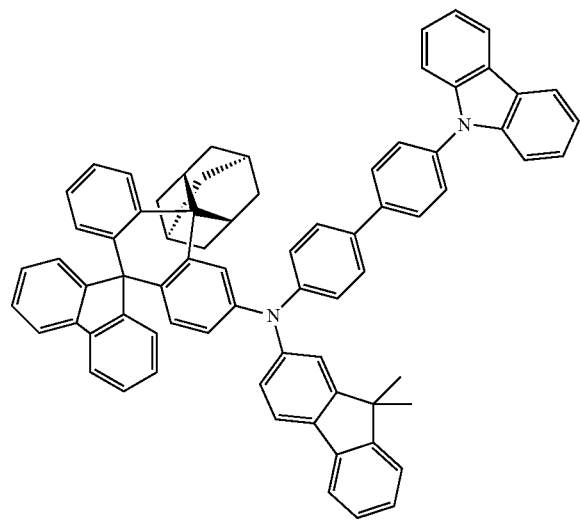
274
-continued
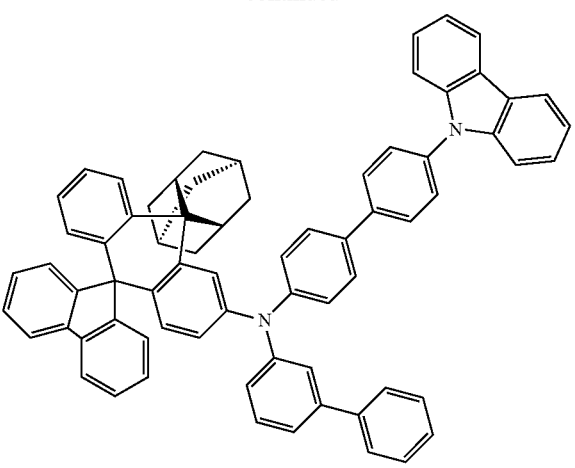
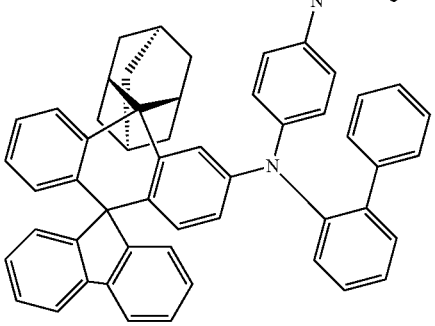
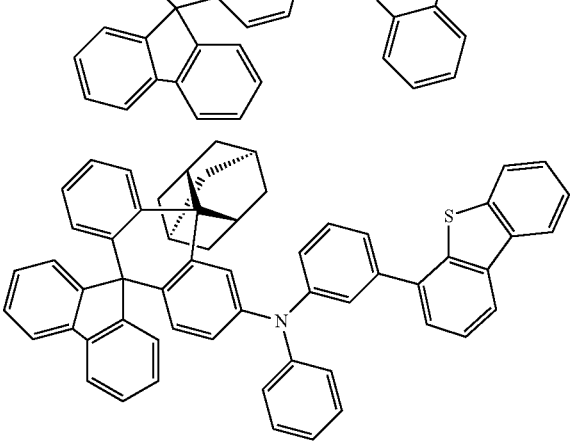
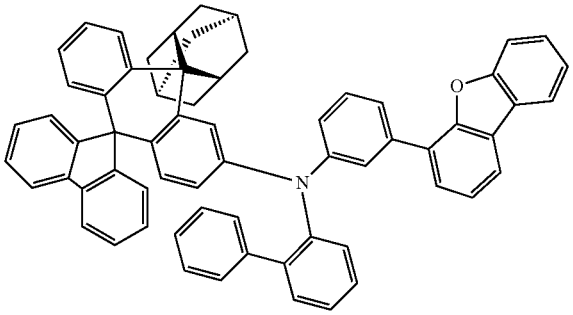

275
-continued
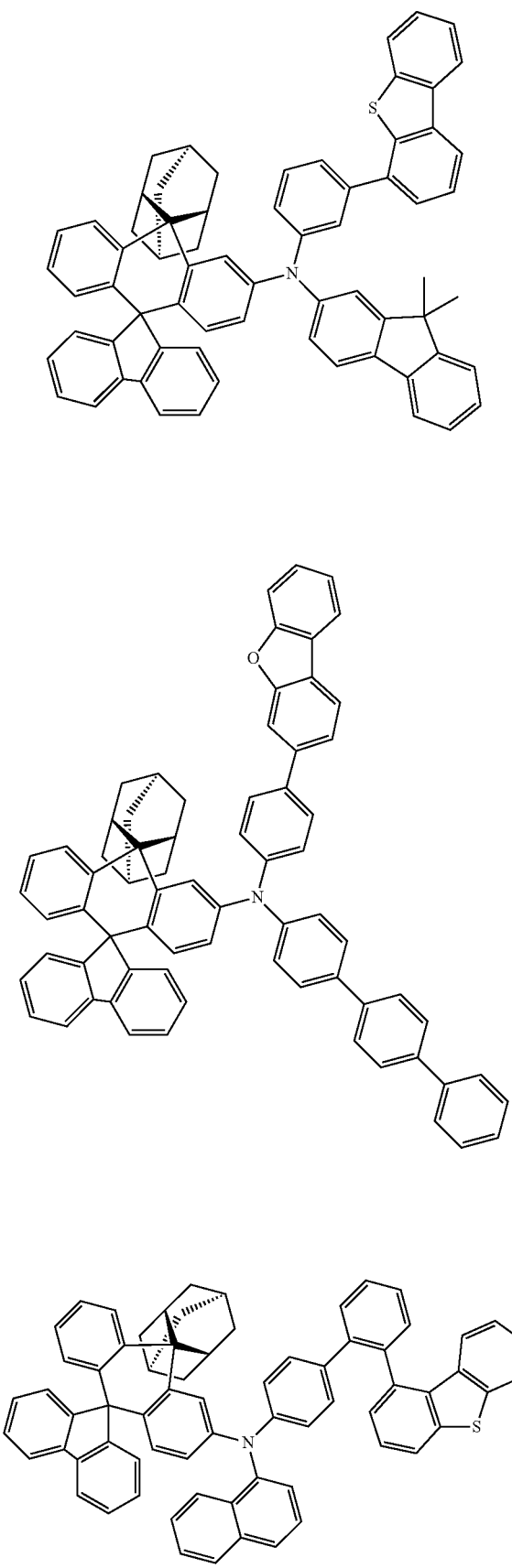
276
-continued
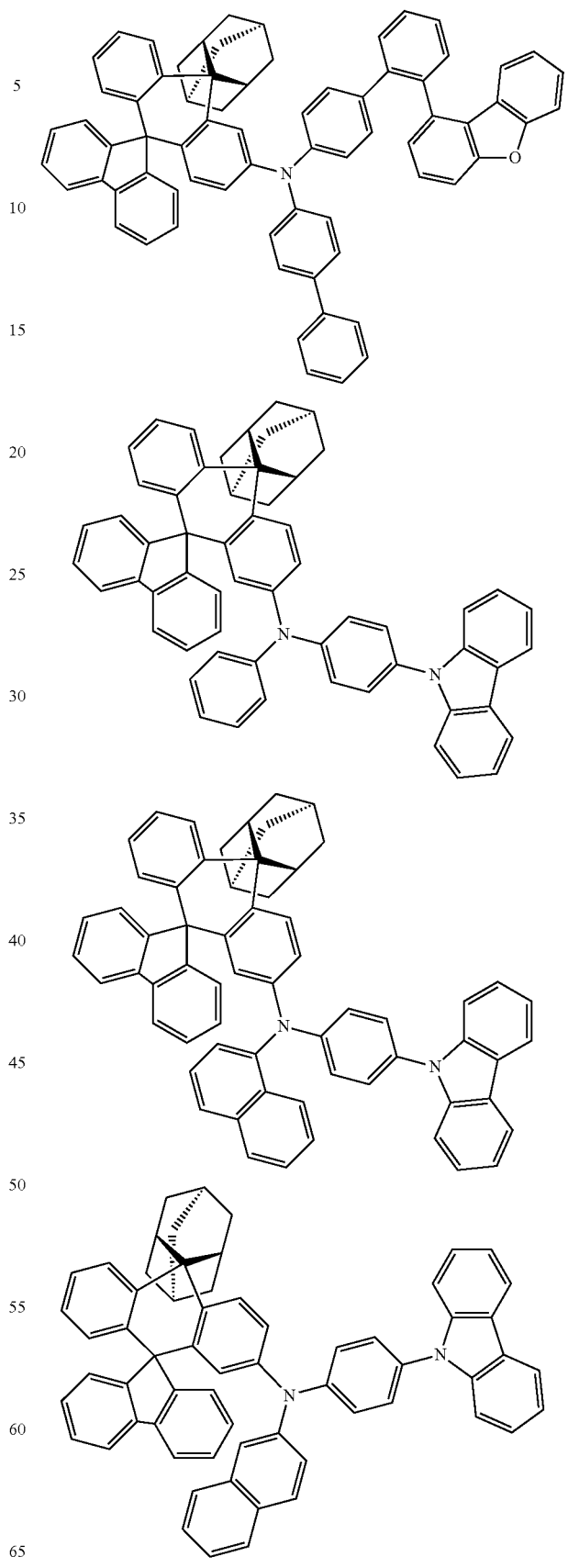

277
-continued
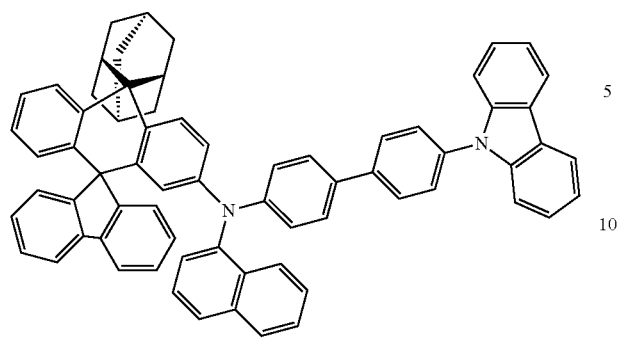
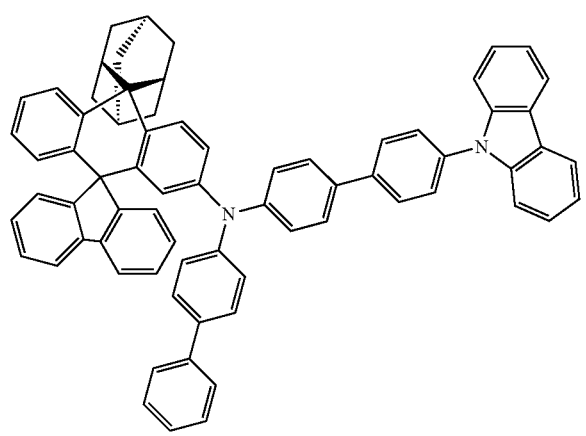
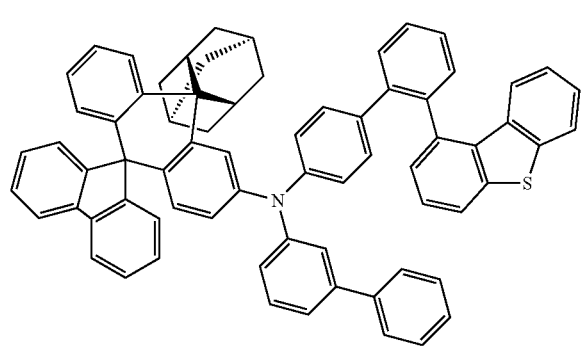
278
-continued
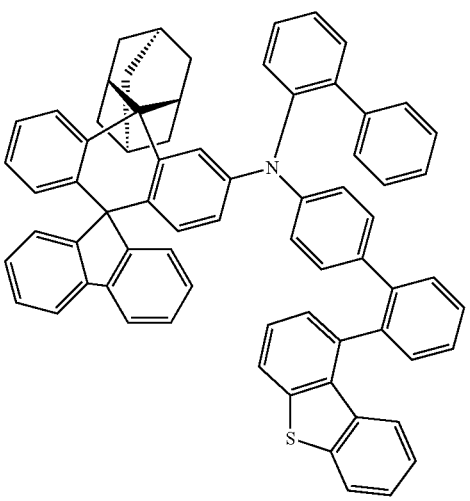
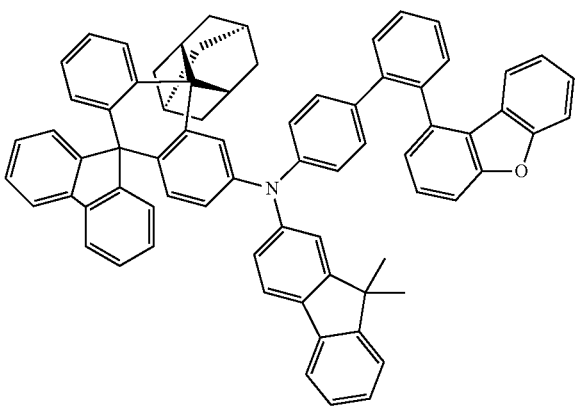
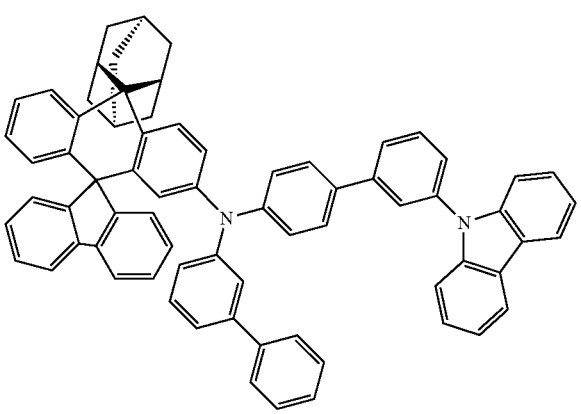

279
-continued
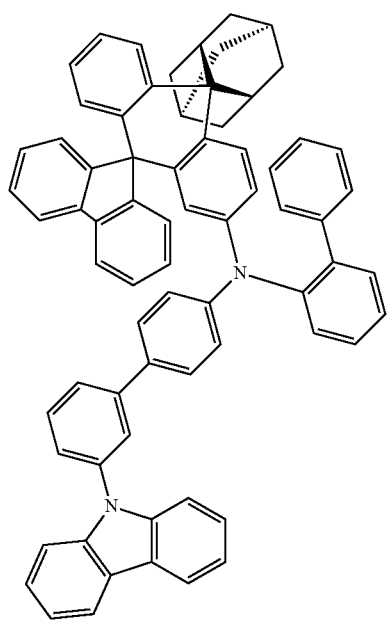
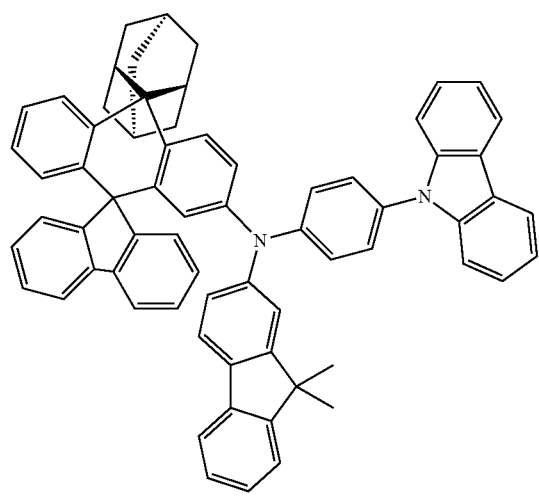
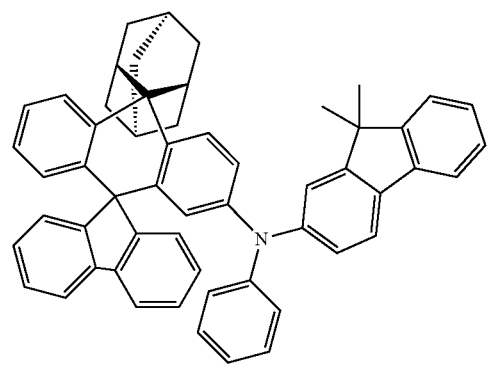
280
-continued
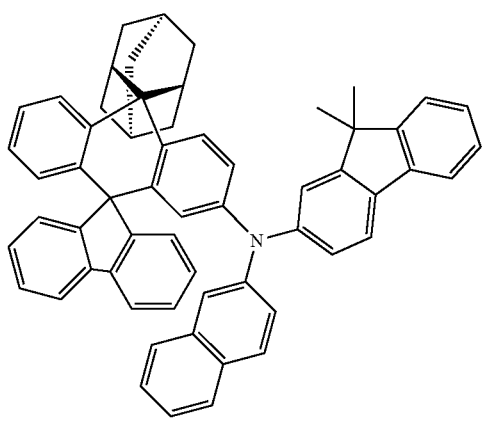
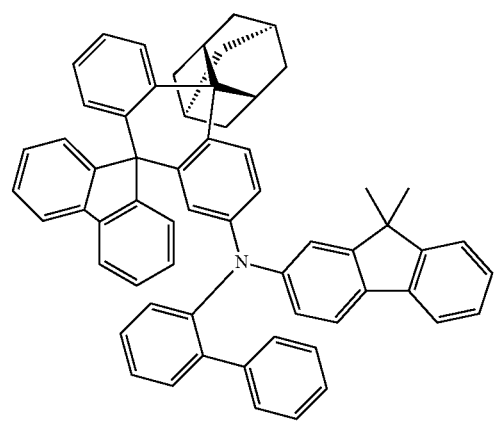
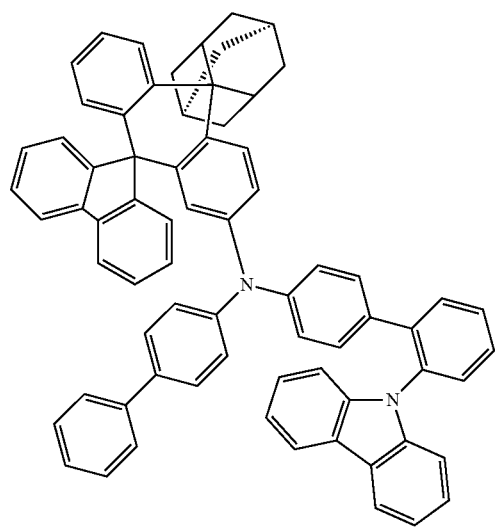

281
-continued
282
-continued
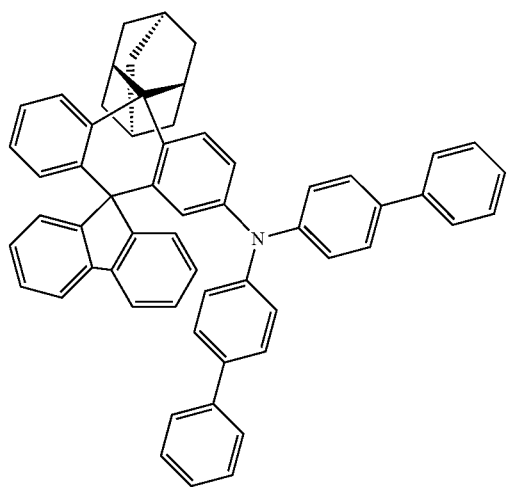
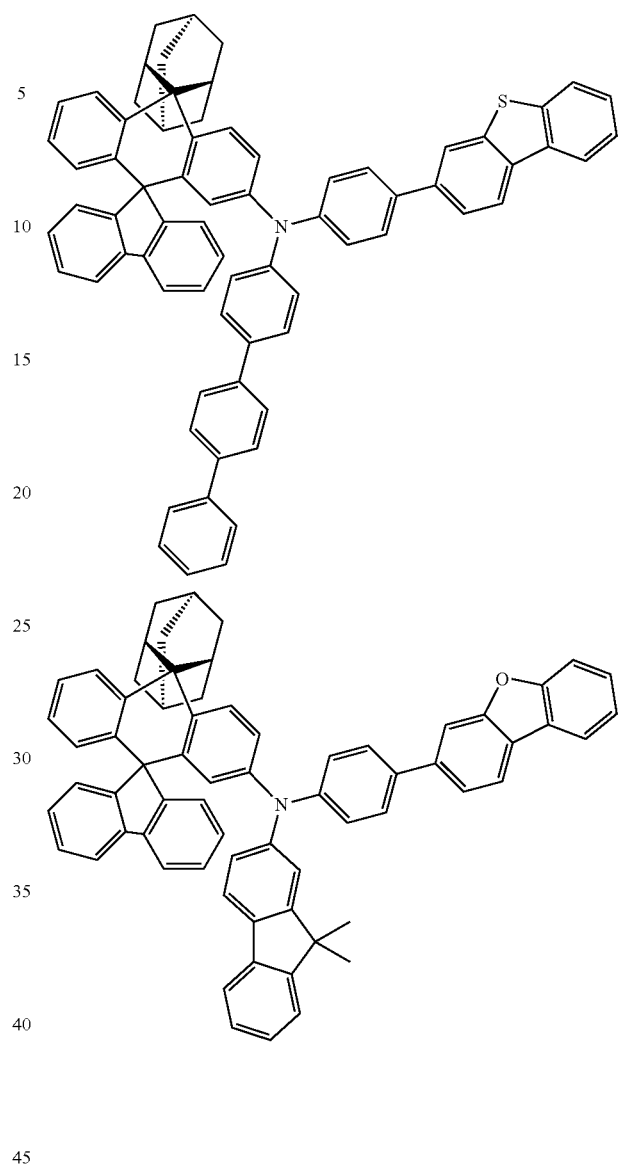
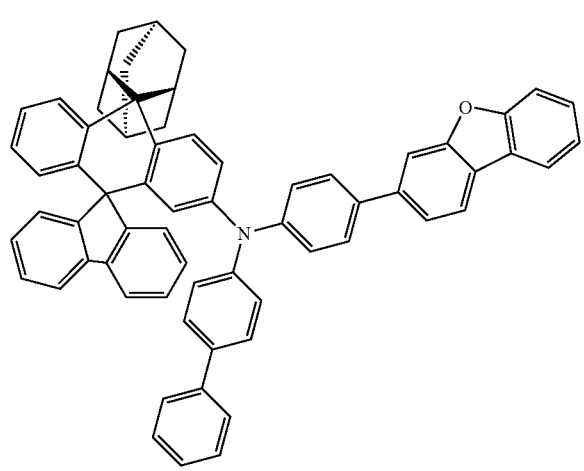
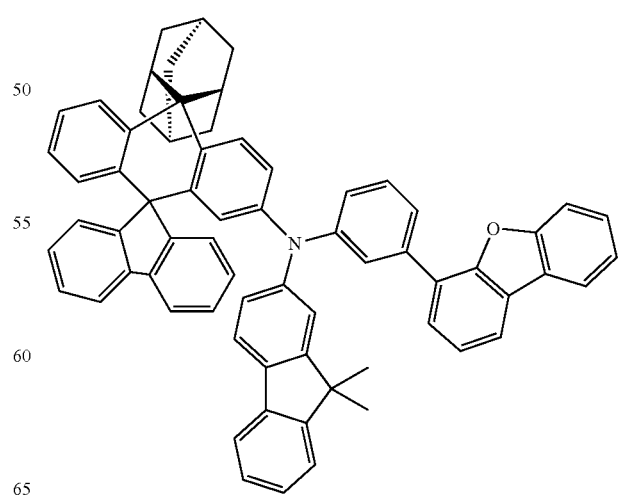

283
-continued
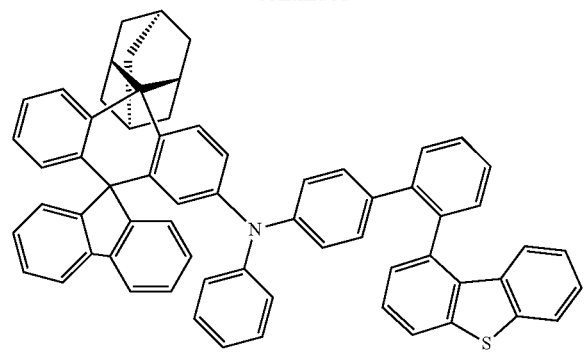
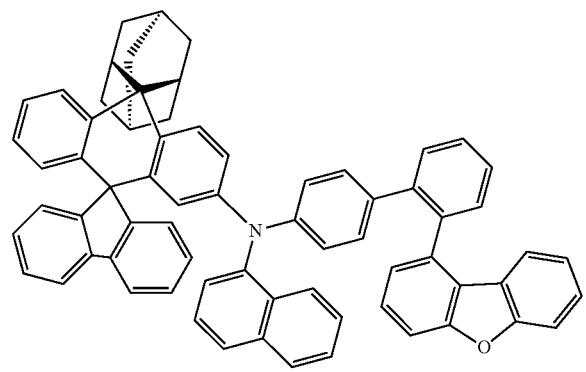
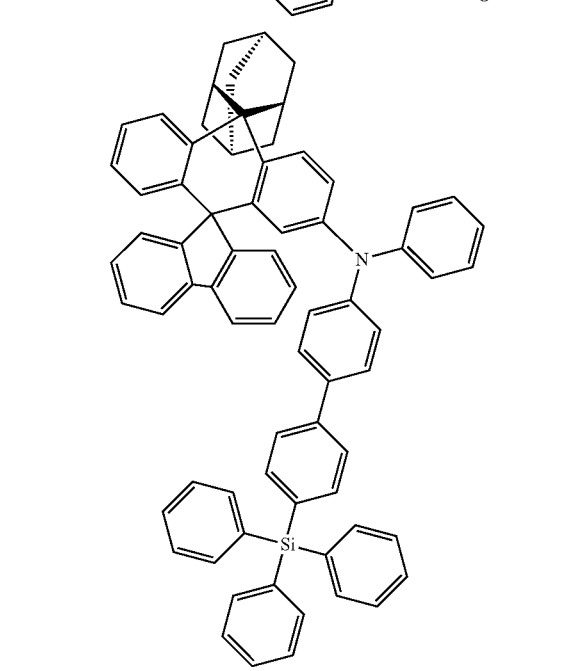
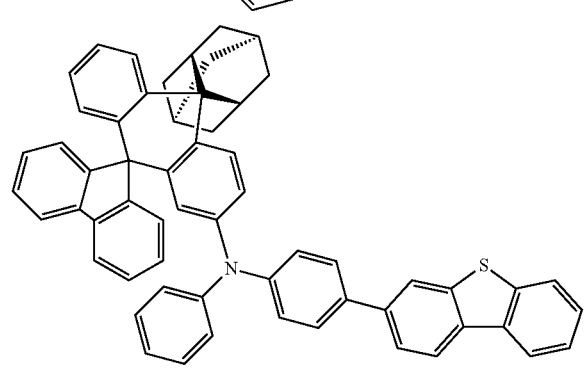
284
-continued
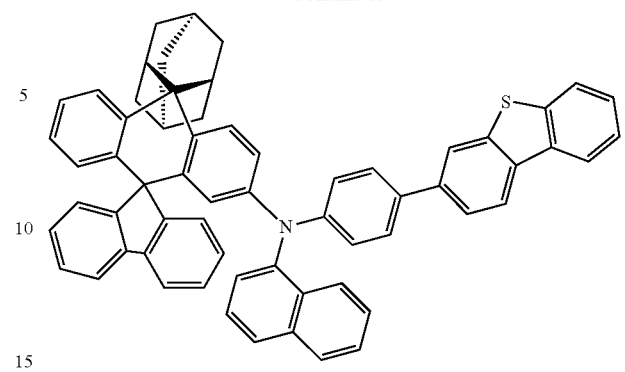
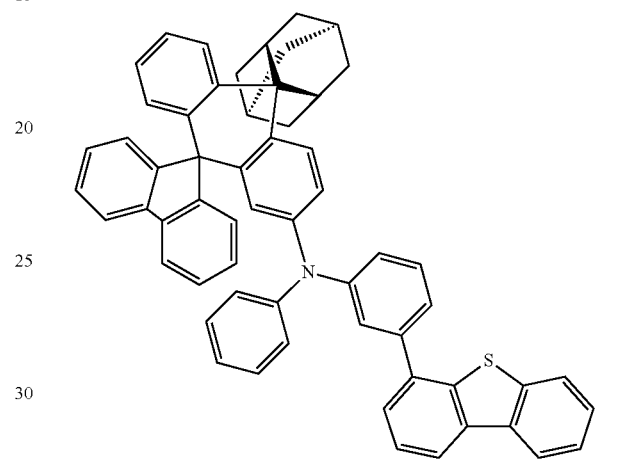
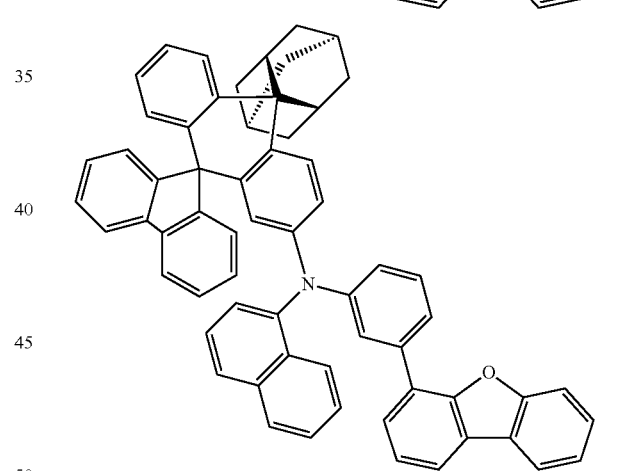
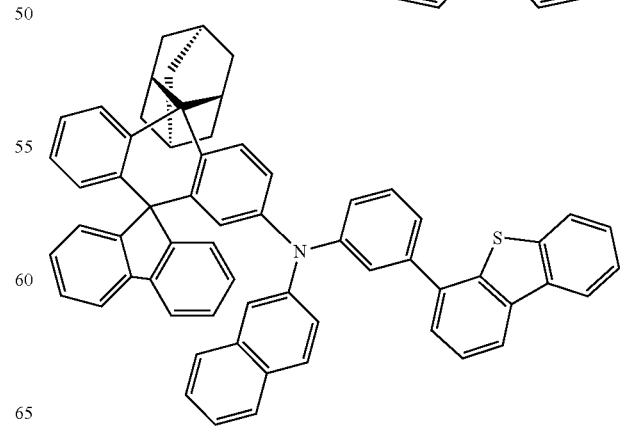

285
-continued
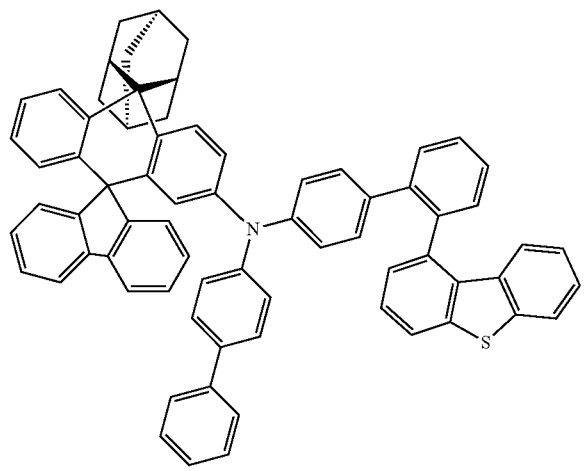
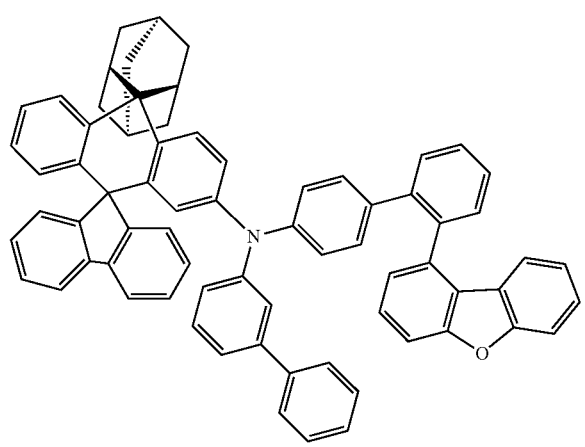
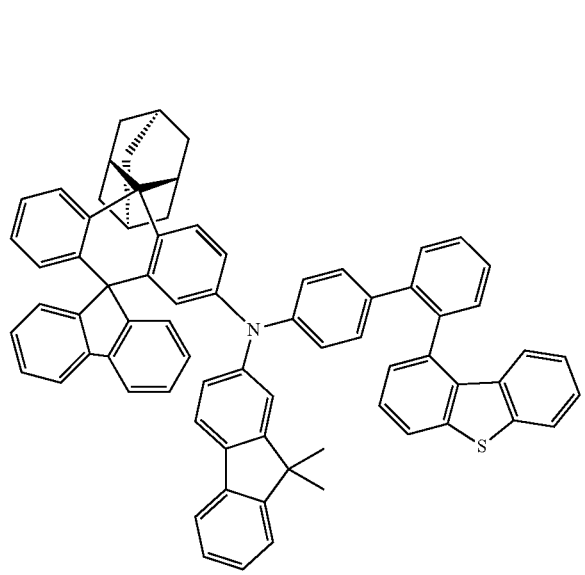
286
-continued
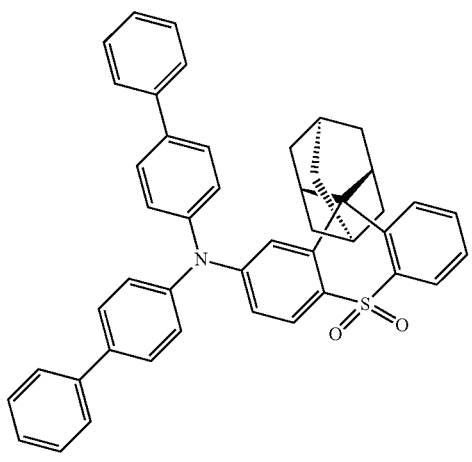
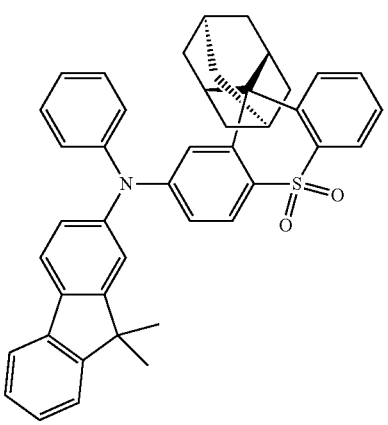
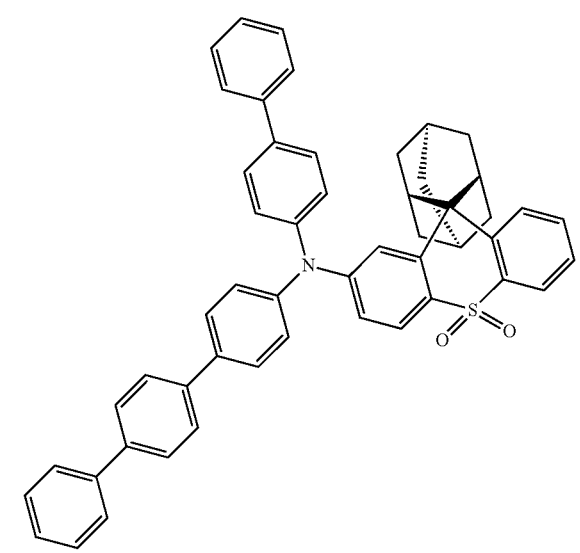

287
-continued
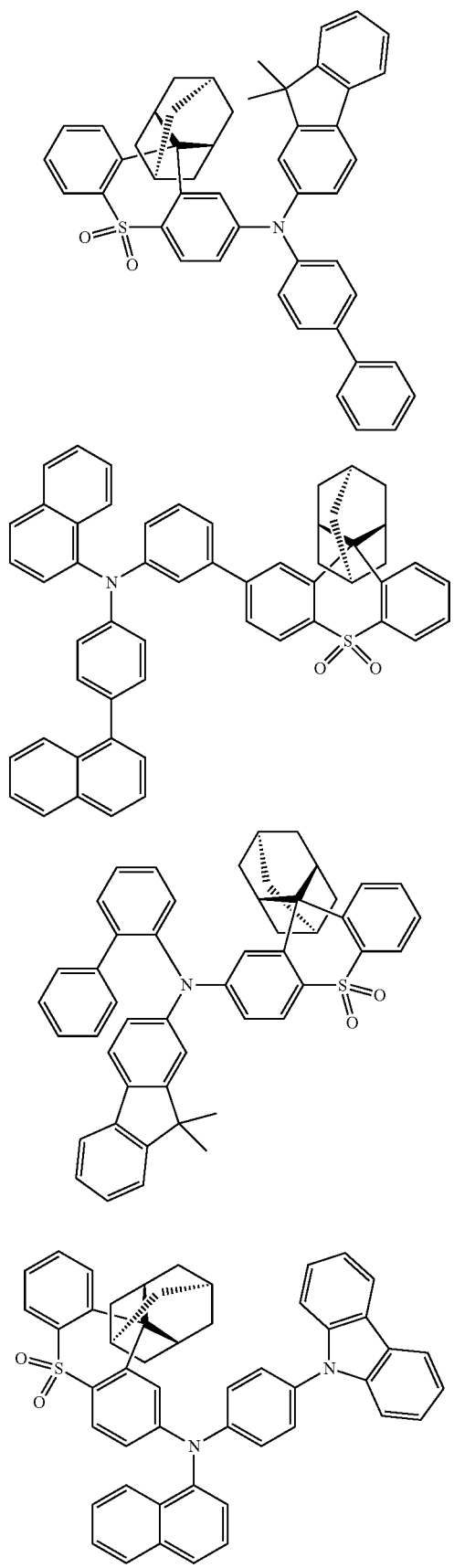
288
-continued
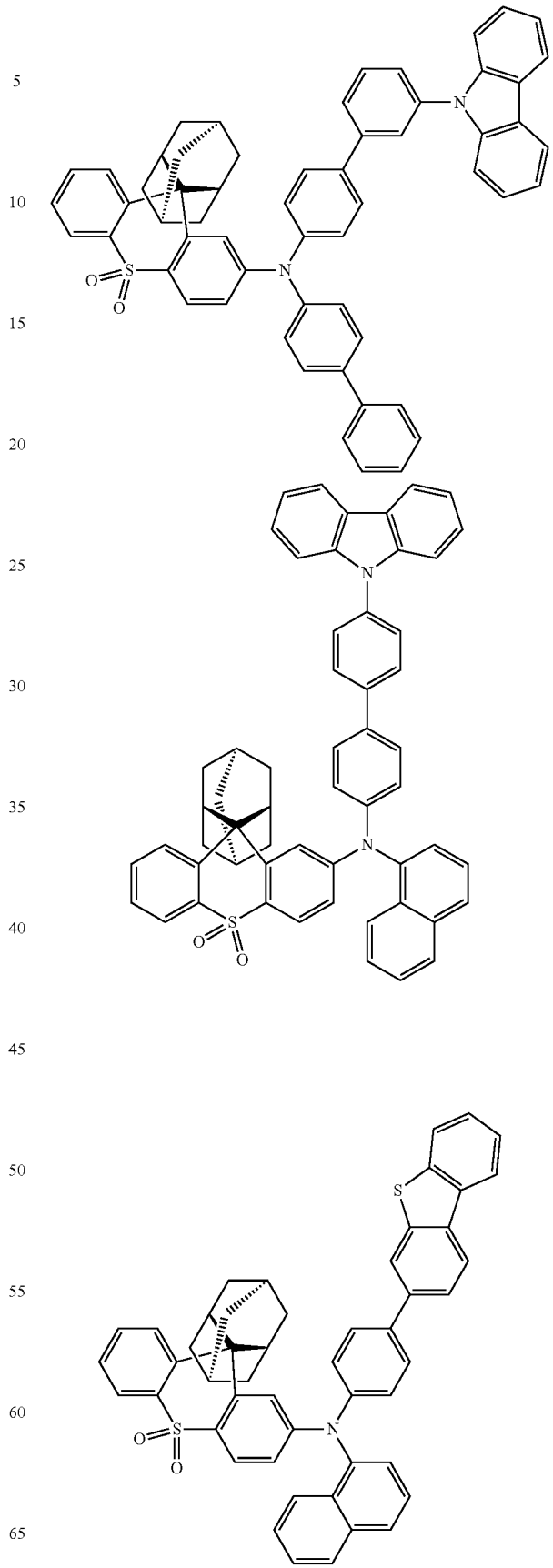

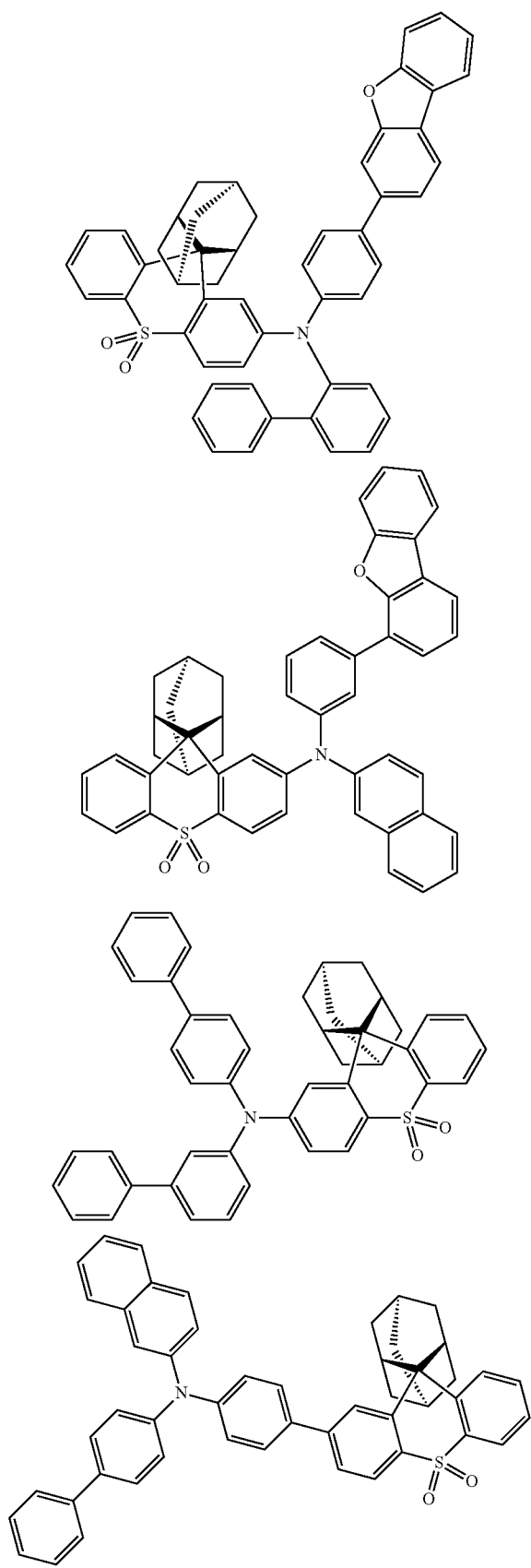
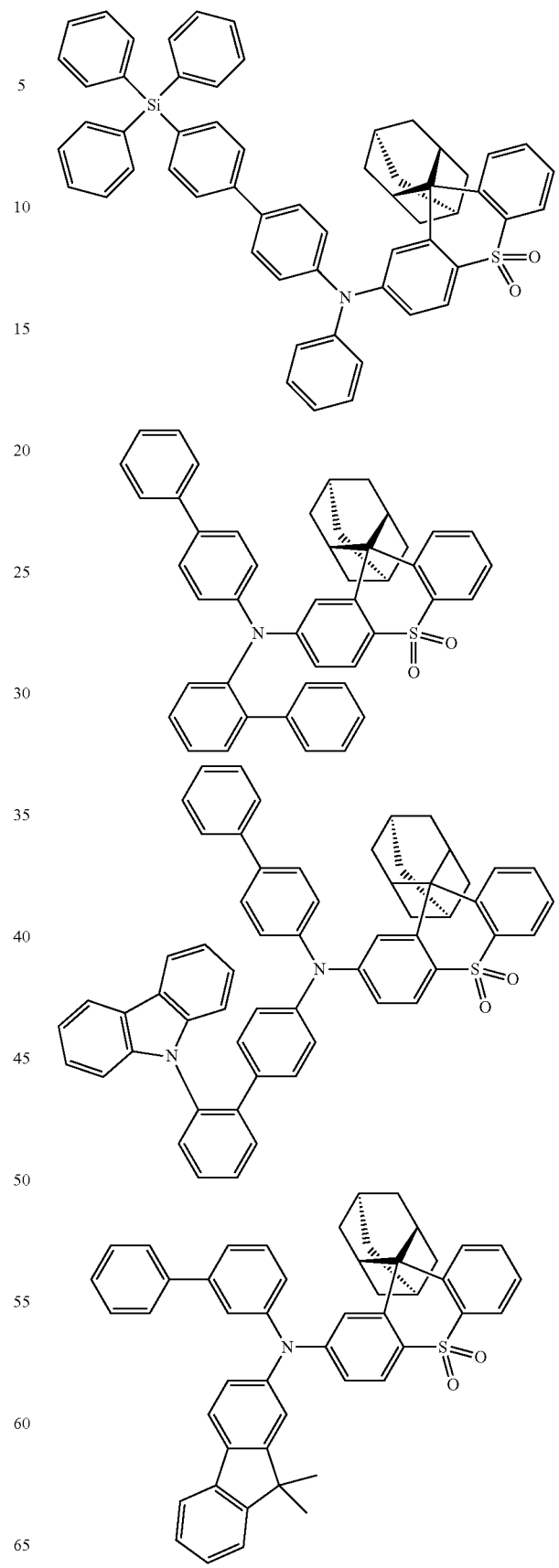

291
-continued
292
-continued
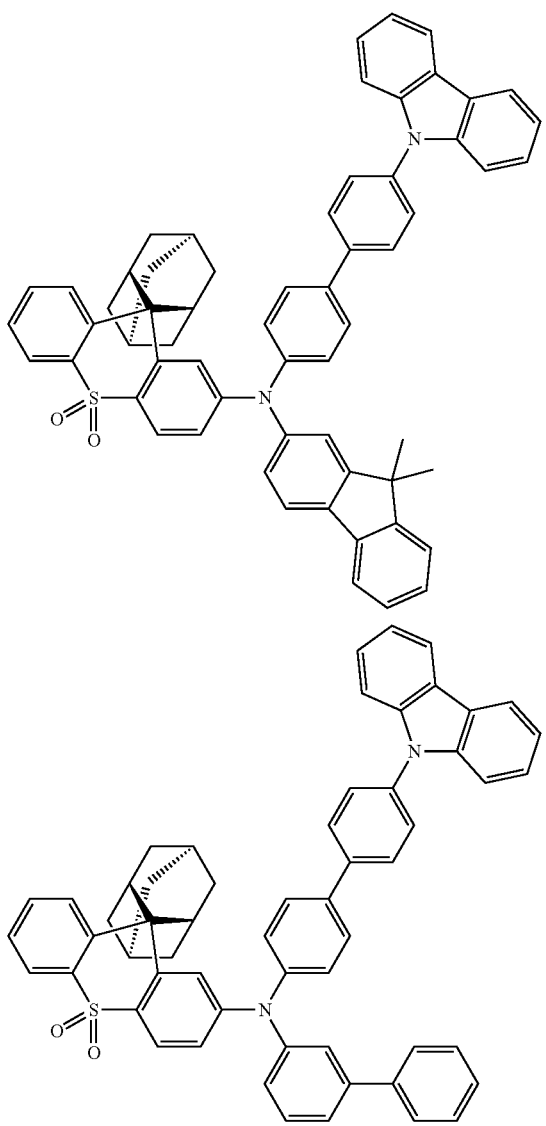
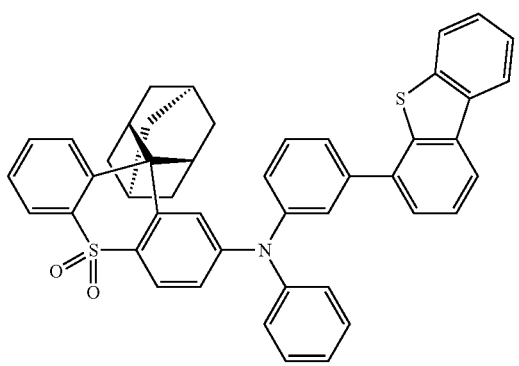
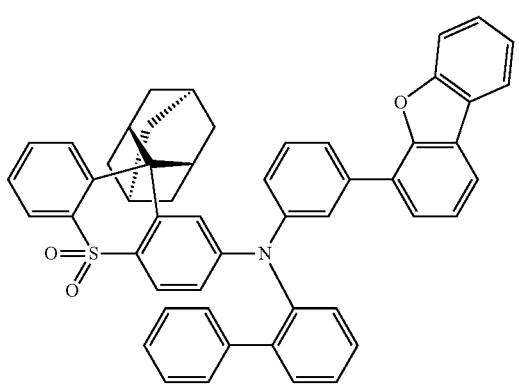
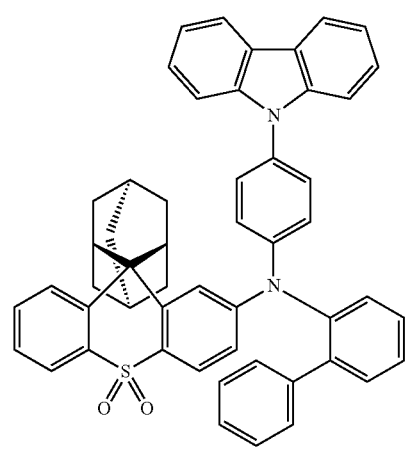
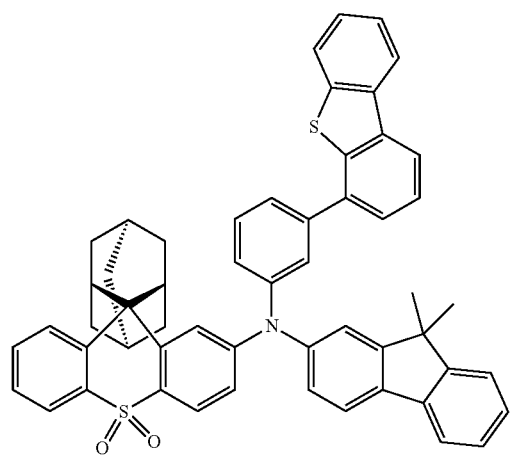

293
-continued
294
-continued
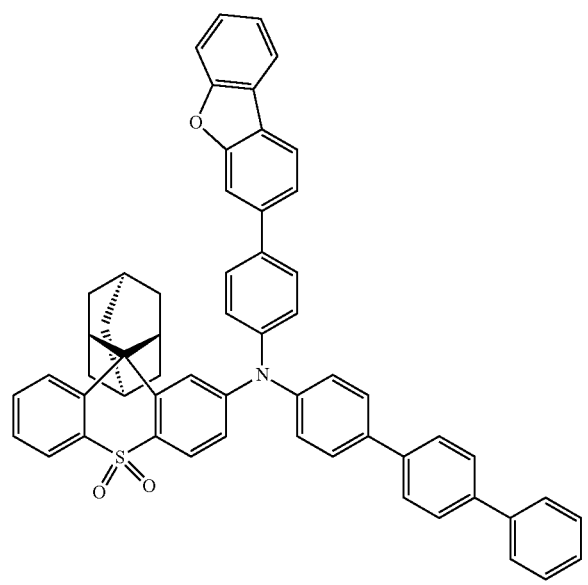
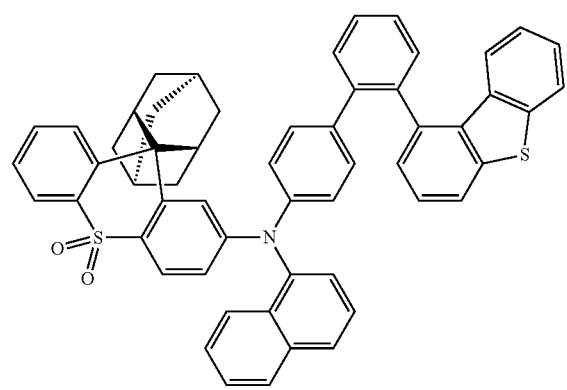
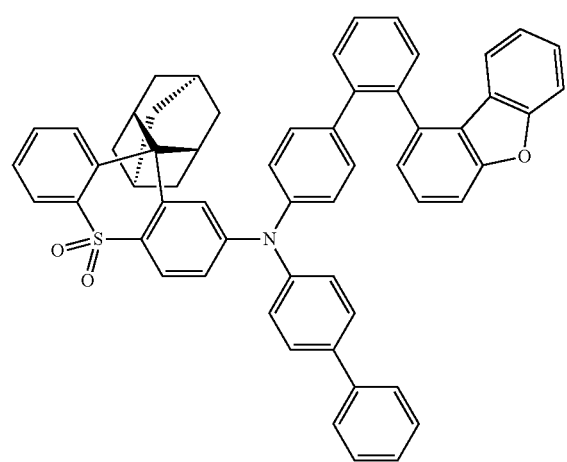
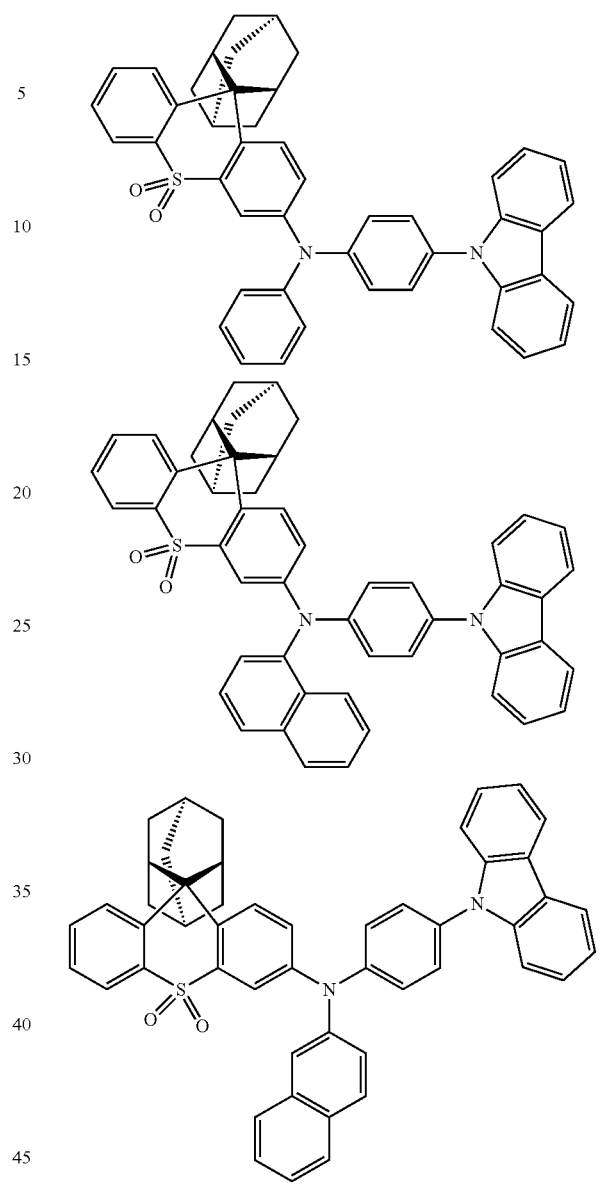
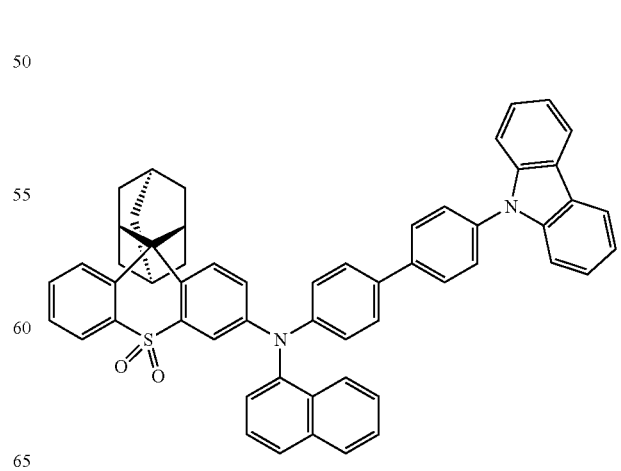

295
-continued
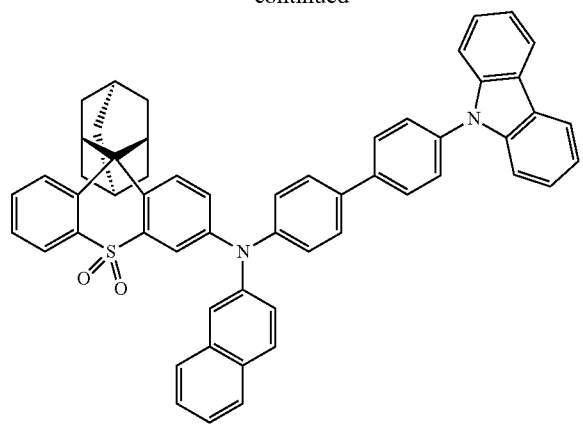
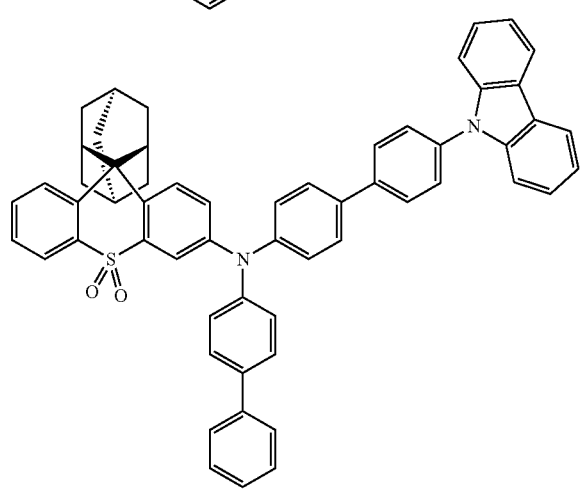
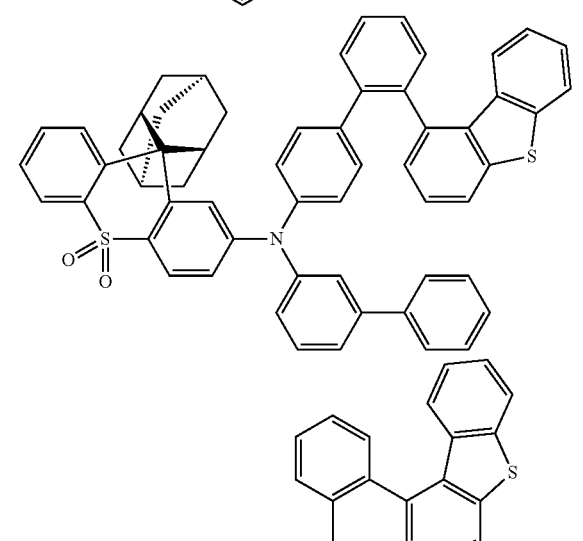
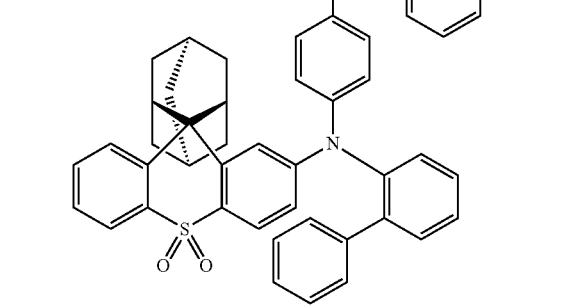
296
-continued
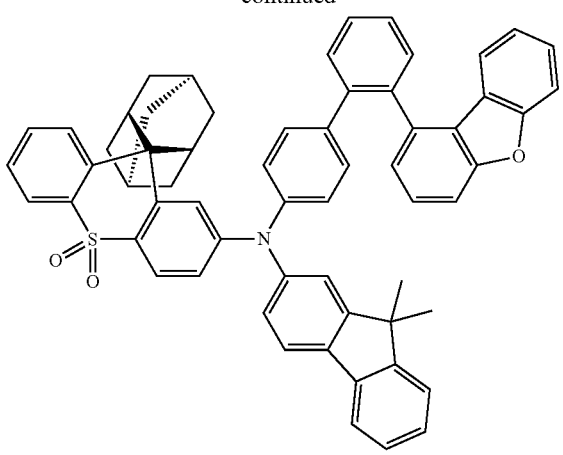
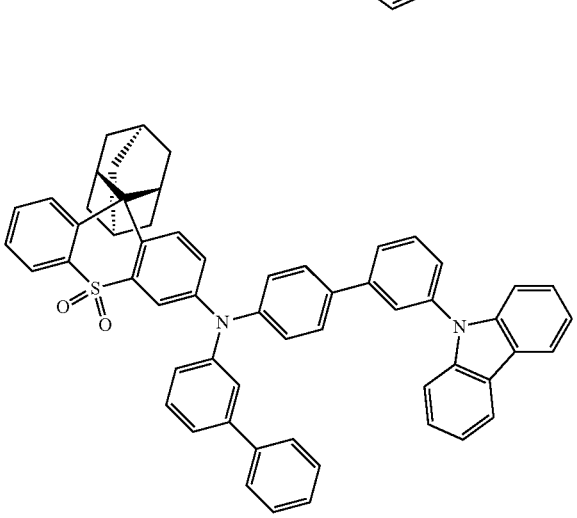
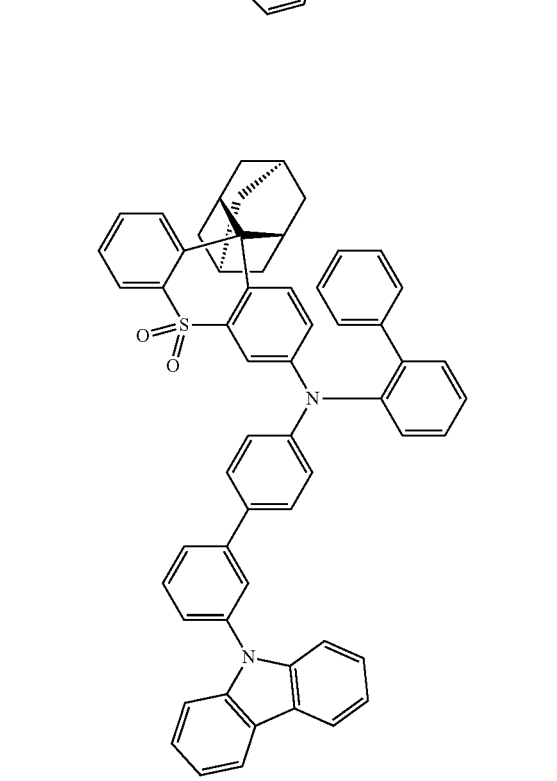

297
-continued
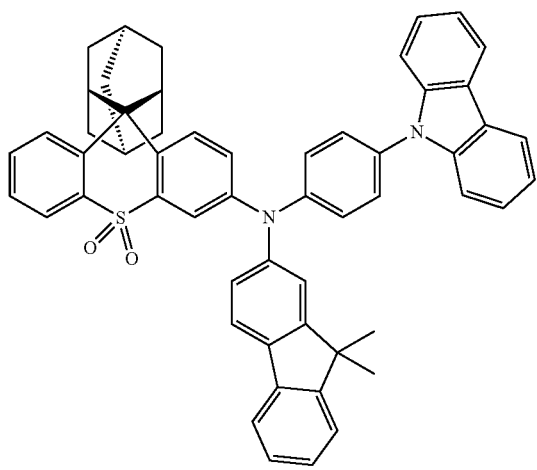
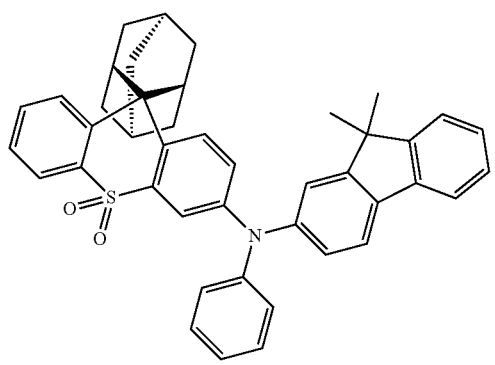
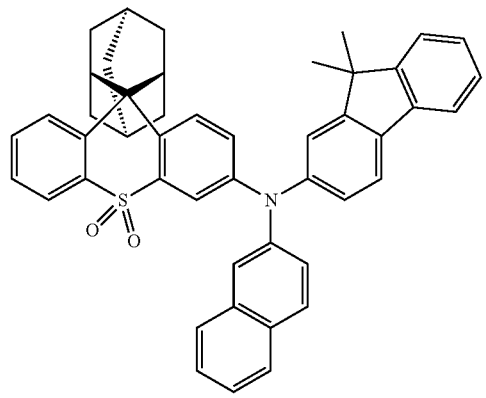
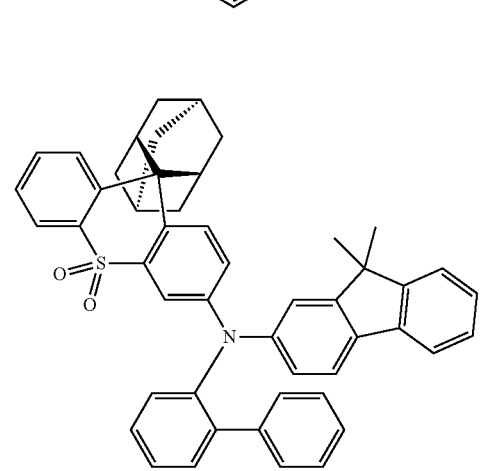
298
-continued
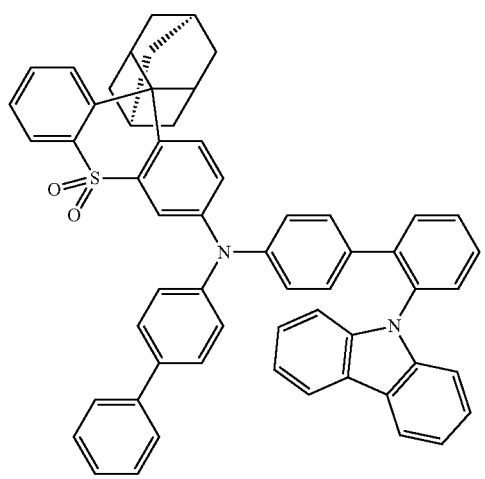
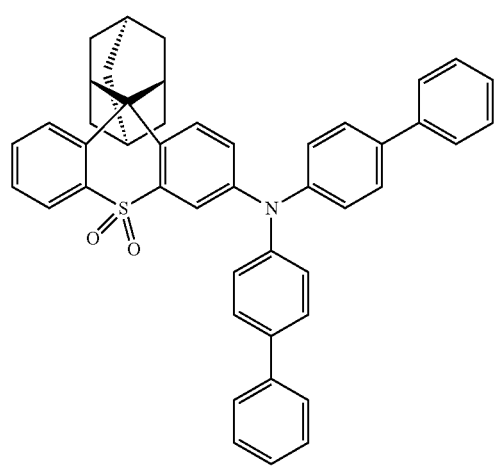
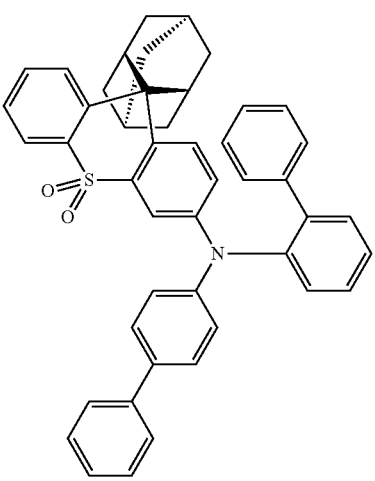

299
-continued
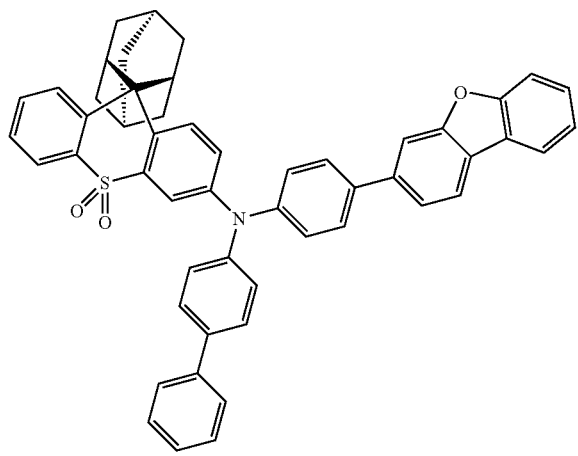
300
-continued
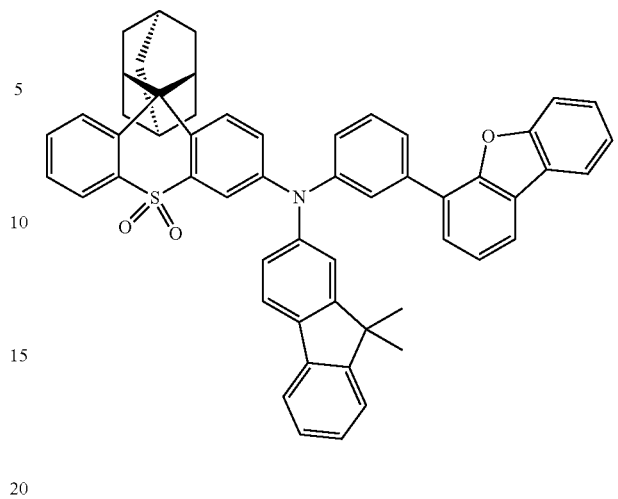
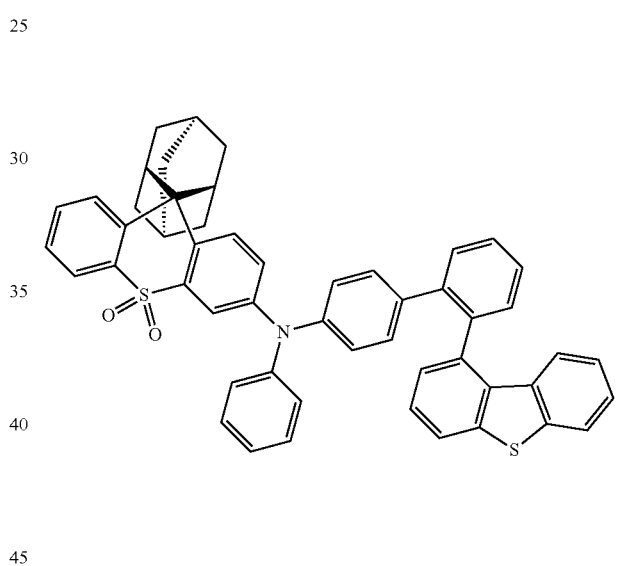
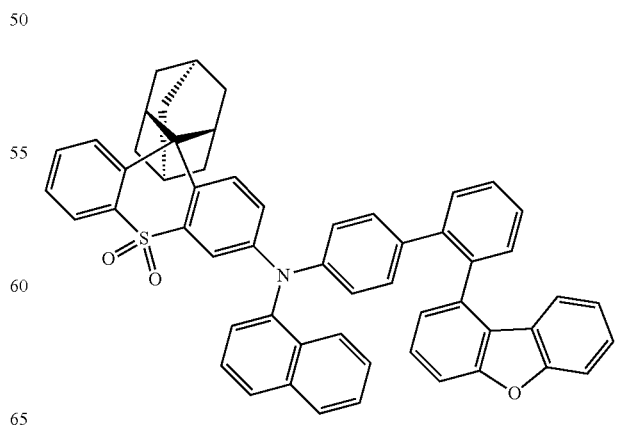

301
-continued
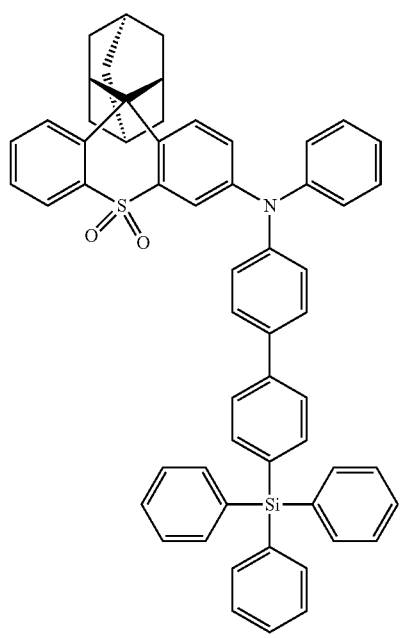
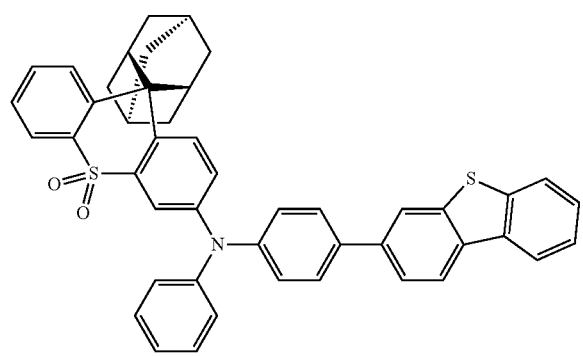
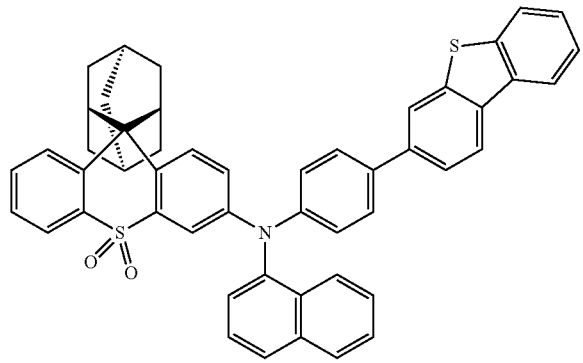
302
-continued
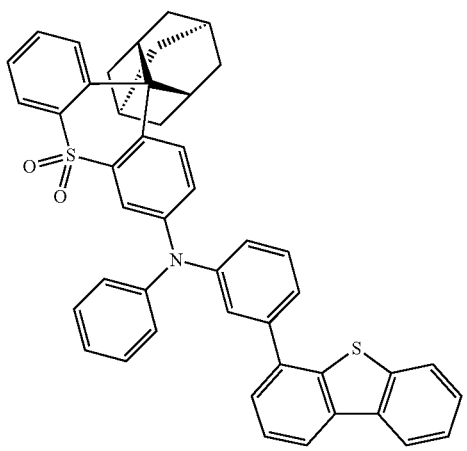
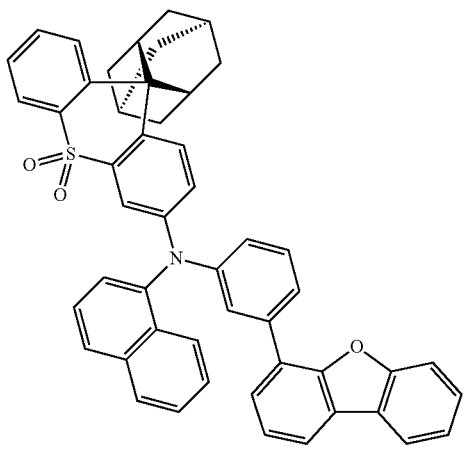
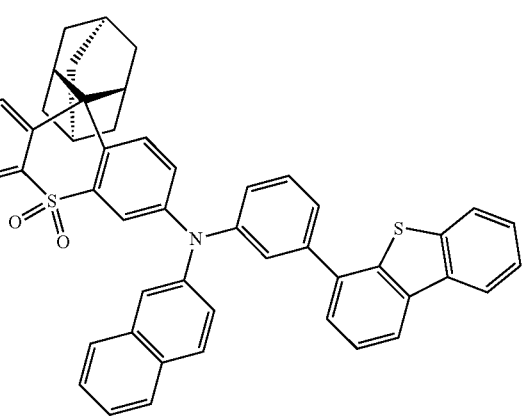

303
-continued

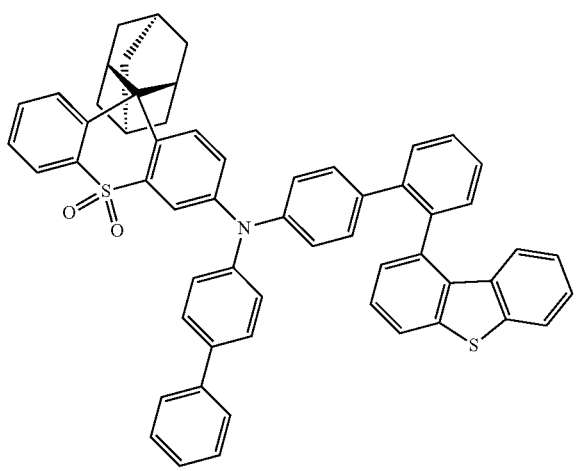

304
-continued

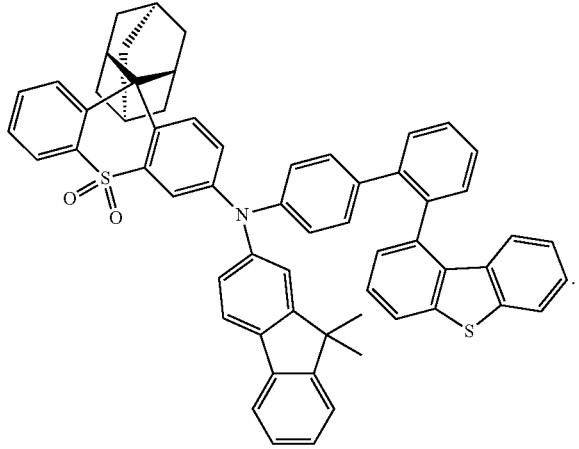

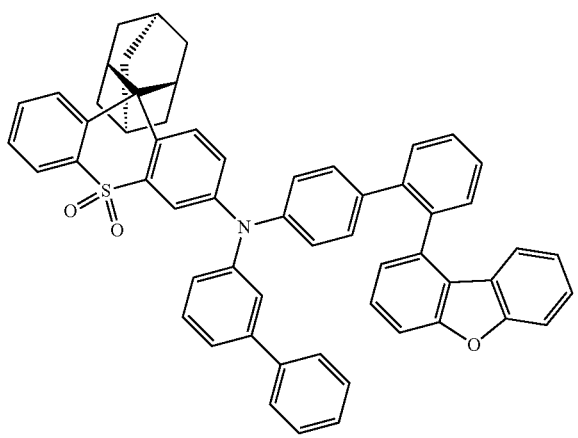

8. An organic light emitting device comprising: a first electrode; a second electrode that is provided opposite to the first electrode; and one or more organic material layers that are provided between the first electrode and the second electrode, wherein one or more layers of the organic material layers include Compound According to claim 1.

9. The compound of claim 1,
wherein X is a substituent group represented by the following Chemical Formula 2,

[Chemical Formula 2]

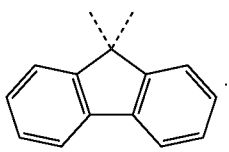

* * * * *